United States Patent
Kaplan et al.

(10) Patent No.: US 9,650,349 B2
(45) Date of Patent: May 16, 2017

(54) THERAPEUTIC ISOXAZOLE COMPOUNDS

(71) Applicant: Dart Neuroscience (Cayman) Ltd., Grand Cayman (KY)

(72) Inventors: Alan Kaplan, San Diego, CA (US); Terence Keenan, San Diego, CA (US); Andrew McRiner, Melrose, MA (US)

(73) Assignee: Dart NeuroScience (Cayman) Ltd. (KY)

( * ) Notice: Subject to any disclaimer, the term of this patent is extended or adjusted under 35 U.S.C. 154(b) by 0 days.

(21) Appl. No.: 14/709,206

(22) Filed: May 11, 2015

(65) Prior Publication Data

US 2015/0336941 A1 Nov. 26, 2015

Related U.S. Application Data

(60) Continuation of application No. 13/542,358, filed on Jul. 5, 2012, now Pat. No. 9,029,397, which is a division of application No. 12/198,686, filed on Aug. 26, 2008, now Pat. No. 8,222,243.

(60) Provisional application No. 60/968,205, filed on Aug. 27, 2007.

(51) Int. Cl.
| | |
|---|---|
| *A61K 31/4525* | (2006.01) |
| *A61K 31/4535* | (2006.01) |
| *A61K 31/454* | (2006.01) |
| *C07D 261/08* | (2006.01) |
| *C07D 413/04* | (2006.01) |
| *C07D 413/14* | (2006.01) |
| *C07D 453/02* | (2006.01) |
| *C07D 487/04* | (2006.01) |
| *C07D 491/044* | (2006.01) |

(52) U.S. Cl.
CPC .......... *C07D 261/08* (2013.01); *A61K 31/454* (2013.01); *A61K 31/4525* (2013.01); *A61K 31/4535* (2013.01); *C07D 413/04* (2013.01); *C07D 413/14* (2013.01); *C07D 453/02* (2013.01); *C07D 487/04* (2013.01); *C07D 491/044* (2013.01)

(58) Field of Classification Search
None
See application file for complete search history.

(56) References Cited

U.S. PATENT DOCUMENTS

| | | |
|---|---|---|
| 3,270,029 A | 8/1966 | Palazzo |
| 3,995,048 A | 11/1976 | Nadelson |
| 4,871,387 A | 10/1989 | Sasse et al. |
| 4,938,949 A | 7/1990 | Borch et al. |
| 5,047,554 A | 9/1991 | Ehrgott et al. |
| 5,204,482 A | 4/1993 | Gassner et al. |
| 5,246,914 A | 9/1993 | Vogelbacher et al. |
| 6,492,368 B1 | 12/2002 | Dorsch et al. |
| 6,495,578 B1 | 12/2002 | Watanabe et al. |
| 6,720,343 B2 | 4/2004 | Yoshioka et al. |
| 6,897,232 B2 | 5/2005 | Schindler et al. |
| 7,223,791 B2 | 5/2007 | Maekawa et al. |
| 7,229,987 B2 | 6/2007 | Ammenn et al. |
| 7,300,950 B2 | 11/2007 | Schindler et al. |
| 7,338,967 B2 | 3/2008 | Lee et al. |
| 7,622,464 B2 | 11/2009 | Ancliff et al. |
| 7,919,626 B2 | 4/2011 | Zhou et al. |
| 8,389,550 B2 | 3/2013 | Buettelmann |
| 8,507,480 B2 | 8/2013 | Drysdale et al. |
| 2002/0049213 A1 | 4/2002 | Weidner-Wells et al. |
| 2005/0038087 A1 | 2/2005 | Chabrier De Lassauniere et al. |
| 2005/0176799 A1 | 8/2005 | Schindler et al. |
| 2005/0256118 A1 | 11/2005 | Altenbach et al. |
| 2006/0041006 A1 | 2/2006 | Ibrahim et al. |
| 2006/0142214 A1 | 6/2006 | Or et al. |
| 2006/0241106 A1 | 10/2006 | Drysdale et al. |
| 2006/0287341 A1 | 12/2006 | Wu et al. |
| 2007/0010556 A1 | 1/2007 | Ashwell et al. |
| 2007/0203154 A1 | 8/2007 | Zhou et al. |
| 2010/0317648 A1 | 12/2010 | Zhou et al. |
| 2011/0160248 A1 | 6/2011 | Zhou et al. |

FOREIGN PATENT DOCUMENTS

| | | |
|---|---|---|
| CA | 2075586 C | 12/2002 |
| CA | 2521199 | 10/2004 |

(Continued)

OTHER PUBLICATIONS

Chang et al., "Status and Progress of Treatment of Mild Cognitive Impairment," *J Contemp Neurol Tech Neuro.*, (Dec. 2006) 6(6): 485-488.

Korbonits et al.,"Ring transformation of 3-(2-aminoaryl)-1,2,4-oxadiazoles into 3-acylaminoindazoles; Extension of the Boulton-Katritzy scheme", J.C.S. Perkin I (1982) 3: 759-766.

Stanovnik et al., "Syntheses and Transformations of 4-amino-2-methylthio- and 4-amino-2-methoxypyrimidine-5-carboxamide Oximes", Heterocycles (1985) 23(11): 2819-2828.

Vernin et al., Studies in the heterocyclic radical series: Part XIV. 3,4-Dimethylisoxazol-5-yl radicals. Reactivity in the aromatic and heteroaromatic series: new route to the preparation of 3,4-dimethylisoxazoles C(5)-substituted by aryl and heteroaryl groups, Helvetica Chimica Acta, (1976) 59(5): 1705-1724.

(Continued)

*Primary Examiner* — Samantha Shterengarts
(74) *Attorney, Agent, or Firm* — Knobbe Martens Olson & Bear LLP

(57) ABSTRACT

The invention provides a compound of formula I:

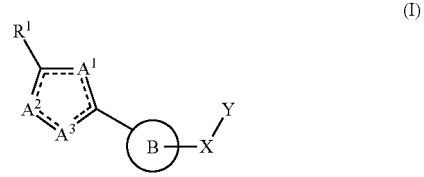

wherein $A^1$, $A^2$, $A^3$, $R^1$, X, Y, and B have any of the values described herein, as well as salts of such compounds, compositions comprising such compounds, and therapeutic methods that comprise the administration of such compounds. The compounds are inhibitors of monoamine oxidase B (MAO-B) enzyme function and are useful for improving cognitive function and for treating psychiatric disorders in animals.

18 Claims, No Drawings

(56) References Cited

FOREIGN PATENT DOCUMENTS

| | | |
|---|---|---|
| DE | 3929233 A1 | 3/1991 |
| EP | 0393936 | 10/1990 |
| EP | 0527378 A1 | 2/1993 |
| EP | 1024138 | 8/2000 |
| GB | 935523 | 8/1963 |
| GB | 2 265 371 A | 9/1993 |
| JP | 61-083181 A | 4/1986 |
| JP | 11-139975 A | 5/1999 |
| JP | 11-240832 | 9/1999 |
| JP | 2001-316378 A | 11/2001 |
| JP | 2006-316054 A | 11/2006 |
| WO | WO 96/25405 A1 | 8/1996 |
| WO | WO 97/46530 A1 | 12/1997 |
| WO | WO 98/37068 A1 | 8/1998 |
| WO | WO 98/38171 A1 | 9/1998 |
| WO | WO 98/46605 A1 | 10/1998 |
| WO | WO 00/45799 A2 | 8/2000 |
| WO | WO 01/25200 | 4/2001 |
| WO | WO 01/70753 A1 | 9/2001 |
| WO | WO 02/15662 | 2/2002 |
| WO | WO 02/16355 | 2/2002 |
| WO | WO 02/17358 | 2/2002 |
| WO | WO 02/22610 | 3/2002 |
| WO | WO 02/068417 A2 | 9/2002 |
| WO | WO 03/004027 | 1/2003 |
| WO | WO 03/018585 | 3/2003 |
| WO | WO 03/080573 A1 | 10/2003 |
| WO | WO 03/089013 A1 | 10/2003 |
| WO | WO 03/097047 A1 | 11/2003 |
| WO | WO 2004/013130 A1 | 2/2004 |
| WO | WO 2004/016227 | 2/2004 |
| WO | WO 2004/060882 | 7/2004 |
| WO | WO 2004/072050 A1 | 8/2004 |
| WO | WO 2004/076418 | 9/2004 |
| WO | WO 2004/085401 A1 | 10/2004 |
| WO | WO 2004/089367 | 10/2004 |
| WO | WO 2005/032468 | 4/2005 |
| WO | WO 2005/040121 A2 | 5/2005 |
| WO | WO 2005/040144 A1 | 5/2005 |
| WO | WO 2005/058808 A1 | 6/2005 |
| WO | WO 2005/066163 | 7/2005 |
| WO | WO 2005/090330 | 9/2005 |
| WO | WO 2005/113551 A1 | 12/2005 |
| WO | WO 2005/120584 A2 | 12/2005 |
| WO | WO 2006/008133 A2 | 1/2006 |
| WO | WO 2006/018260 A1 | 2/2006 |
| WO | WO 2006/046916 | 5/2006 |
| WO | WO 2006/078287 A2 | 7/2006 |
| WO | WO 2006/078577 A1 | 7/2006 |
| WO | WO 2006/090177 | 8/2006 |
| WO | WO 2006/134481 A1 | 12/2006 |
| WO | WO 2007/002559 | 1/2007 |
| WO | WO 2007/030574 | 3/2007 |
| WO | WO 2007/041634 A1 | 4/2007 |
| WO | WO 2007/043400 A1 | 4/2007 |
| WO | WO 2007/093827 A1 | 8/2007 |
| WO | WO 2007/100851 A1 | 9/2007 |
| WO | WO 2008/023248 A2 | 2/2008 |
| WO | WO 2008/073942 A2 | 6/2008 |
| WO | WO 2008/121670 A1 | 10/2008 |
| WO | WO 2009/029632 A1 | 3/2009 |

OTHER PUBLICATIONS

Andrianov, et al., "Rearrangements of 1-oxa-2-azoles. 4.* Synthesis and rearrangement of isoxazole- and 4,5-dihydroisoxazole-3-carboxylic acids amidoximes," *Inst. Org. Sint., Riga*, 226006, (1991), 651-656 (translated from Khimiya Geterotsiklicheskikh Soedinenii (6): 827-832 (1991).

Bach et al., "cDNA cloning of human liver monoamine oxidase A and B: molecular basis of differences in enzymatic properties," *Proc. Natl. Acad. Sci.*, 85(13): 4934-4938 (1988).
Bentue-Ferrer et al., "Monoamine oxydase B inhibitors: Current Status and Future Potential," *CNS Drugs*, 6(3): 217-236 (1996).
Brahma, S. et al., "A simple approach to azirines containing an aldehyde functionality and their stabilization as palladium (II) complexes," *Tetrahedron Letters*, 46(38): 6575-6578 (2005).
Chen et al., "Clinical Pharmacology of Rasagiline: A Novel, Second-Generation Propargylamine for the Treatment of Parkinson Disease," *J. Clin. Pharmacol.*, 45(8): 878-894 (2005).
Database Registry Chemical Abstracts Service, Columbus, Ohio, Accession No. RN 215319-08-7, RN 215319-09-8, Entered STN: Dec. 9, 1998.
Database Registry Chemical Abstracts Service, Columbus, Ohio, Accession No. RN 187812-15-3, Entered STN: Mar. 28, 1997.
Emilsson et al., "Increased monoamine oxidase messenger RNA expression levels in frontal cortex of Alzheimer's disease patients", *Neuroscience Letters*, vol. 326(1): 56-60 (2002).
Ettmayer, et al., "Lessons Learned from Marketed and Investigational Prodrugs," *J. Med. Chem.*, 47(10): 2394-2404 (2004).
Fowler et al., "The effect of Age on the Activity and Molecular Properties of Human Brain Monoamine Oxidase," *J. Neural Transm.*, 49(1-2): 1-20 (1980).
Goddard "5-Heteroaryl-2-Thiophenecarboxylic Acids: Oxazoles and Oxadiazoles," *J. Heterocyclic Chem.*, 28(1): 17-28 (1991).
Habeeb, A. G. et al., "Design and syntheses of diarylisoxazoles: novel inhibitors of cyclooxygenase-2 (COX-2) with analgesic-antiinflammatory activity," *Drug Development Research*, 51(4): 273-286 (2000).
Habeeb, A. G., et al., "Design and synthesis of 4,5-diphenyl-4-isoxazolines: novel inhibitors of cyclooxygenase-2 with analgesic and anti-inflammatory activity," *J. Med. Chem.*, 44(18): 2921-2927 (2001).
Majo, V. J. et al., "A general method for the synthesis of aryl [11C]methylsufones: potential PET probes for imaging cyclooxygenase-2 expression," *Bioorganic & Medicinal Chemistry Letters*, 15(19): 4268-4271 (2005).
Marzinzik, A. L., et al., "Solid support synthesis of highly functionalized pyrazoles and isoxazoles; Scaffolds for molecular diversity," *Tetrahedron Letters*, 37(7): 1003-1006 (1996).
Saura et al., "Molecular Neuroanatomy of Human Monoamine Oxidases A and B Revealed by Quantitative Enzyme Radioautography and in Situ Hybridization Histochemistry," *Neuroscience*, 70(3): 755-774 (1996).
Shang, Y. et al., "One-pot synthesis of isoxazolines and isoxazoles using soluble polymer-supported aldehyde," *Journal of Chemical Research*, vol. 5, pp. 336-338 (2004).
Stella, V. J., "Prodrugs as therapeutics," *Expert Opin. Ther. Patents*, 14(3): 277-280 (2004).
Strolin Benedetti et al., "Monoamine oxidase, brain ageing and degenerative diseases," *Biochem. Pharmacol.*, 38(4): 555-561 (1989).
Testa, B., "Prodrug Research: futile or fertile?" *Biochem. Pharmacol.*, 68(11): 2097-2106 (2004).
Wolff, M.E. ed., Burger's Medicinal Chemistry, 5th Ed., vol. 1: Principles and Practice, pp. 975-977, (1994), Wiley-Interscience; New York.
Yoshimi et al. "Novel Monoamine Oxidase Inhibitors, 3-(2-Aminoethoxyl)-1,2-benzisoxazole Derivatives, and Their Differential Reversibility", *Jpn. J. Parmacol.*, 88(2): 174-182 (2002).
International Search Report mailed Nov. 21, 2008 for corresponding PCT Application No. PCT/US2008/074353 filed Aug. 26, 2008.
International Written Opinion mailed Nov. 21, 2008 for corresponding PCT Application No. PCT/US2008/074353 filed Aug. 26, 2008.
Salvino et al., "Polymer-supported tetrafluorophenol: A new activated resin for chemical library synthesis", J Comb Chem. (2000) 2(6): 691-697.
Thomas et al., "The rationale and use of hypomethylation agents in adult acute myeloid leukemia", Exp Op Drug Disc. (2009) 4(2): 195-205.

THERAPEUTIC ISOXAZOLE COMPOUNDS

RELATED APPLICATIONS

Any and all priority claims identified in the Application Data Sheet, or any correction thereto, are hereby incorporated by reference under 37 CFR 1.57. For example, this application is a continuation of U.S. patent application Ser. No. 13/542,358, filed Jul. 5, 2012, assigned U.S. Pat. No. 9,029,397 which is a divisional of U.S. patent application Ser. No. 12/198,686, filed Aug. 26, 2008, now U.S. Pat. No. 8,222,243 which claims priority under 35 U.S.C. §119(e) to U.S. Provisional Application No. 60/968,205, filed Aug. 27, 2007; the disclosures of which are incorporated herein by reference in their entireties.

BACKGROUND OF THE INVENTION

Monoamine oxidase (MAO, EC 1.4.3.4) is a flavin-dependent metabolic enzyme responsible for the oxidative deamination of both endogenous, aminergic neurotransmitters and xenobiotic amines. There are two reported isoforms of MAO, MAO-A and MAO-B, which arise from two independent genes (Bach, et. al., *Proc. Natl. Acad. Sci.,* 1988, 85, 4934-4938). Both forms of MAO are distributed in a variety of tissues in varying amounts throughout the body; in the human brain, MAO-B is present to a greater extent then MAO-A (Saura, et. al., *Neuroscience,* 1996, 70, 755-774).

MAO-A has greater selectivity for serotonin and adrenalin while MAO-B is selective for tyramine and phenethyl amine while both isoforms will metabolize dopamine. Studies have shown that the level of MAO-B activity in the brain increases with age (Fowler, et. al., *J. Neural Transm.,* 1980, 49, 1-20). The process of oxidative deamination, which produces both peroxide and aldehydes as byproducts, has also been associated with an increase in oxidative damage in the brain, especially to dopaminergic neurons, potentially exacerbating the neuronal degeneration associated with diseases such as Alzheimer's Disease and Parkinson's Disease. There are also reports that the level of MAO-B activity present is greater in patients with Alzheimer's disease which may be linked to the increased cognitive impairment of Alzheimer patients (Dostert, et. al, *Biochem. Pharmacol.,* 1989, 38, 555-561; and Emilsson, et. al., *Neuroscience Letters,* 2002, 326, 56-60). This link between oxidative stress and progression of neuronal damage suggests that inhibition of MAO-B will minimize the degenerative effects of both of these diseases, presumably by preventing the metabolism of monoamines in the brain. Furthermore, the relative increase in dopamine levels, due to inhibition of its metabolism, may have effects on downstream regulation of plasticity-associated cognitive function, which may help repair, not just impede the progression of these diseases.

The use of selective MAO-B inhibitors for neurological diseases has been known for some time (Bentue-Ferrer, et. al., *CNS Drugs,* 1996, 6, 217-236). Most early MAO inhibitors for the treatment of depression were irreversible inhibitors with minimal selectivity for MAO-B versus MAO-A. This can be problematic due to potential side effects associated with both the subsequent inability of the irreversibly inhibited enzyme to effectively metabolize dietary amines associated with cardiovascular events (the "cheese effect") and the potential for drug-drug interactions with other drugs that are metabolized by MAO-B. More recent drugs, including selegiline and rasagiline, while still irreversible inhibitors, have greater selectivity for MAO-B, and have better side-effect profiles (Chen & Swope, *J Clin Pharmacol.* 2005 45, 878-94). There is currently a need for compounds that are useful for enhancing cognitive function and for treating cognitive deterioration in Parkinson's Disease and Alzheimer's Disease, as well as compounds that can generally improve cognition in normal, diseased, and aging subjects. Preferably, such agents will have higher potency and/or fewer side-effects than current therapies.

SUMMARY OF THE INVENTION

The invention provides MAO-B inhibiting compounds that are useful, for example, for enhancing cognitive function in animals (e.g. humans). Accordingly, the invention provides a method for inhibiting one or more MAO enzymes in an animal comprising administering to the animal an effective MAO inhibiting amount of a compound of formula I.

EMBODIMENTS, ASPECTS AND VARIATIONS OF THE INVENTION

The present disclosure provides the following embodiments, aspects and variations: One embodiment provides a compound of formula I:

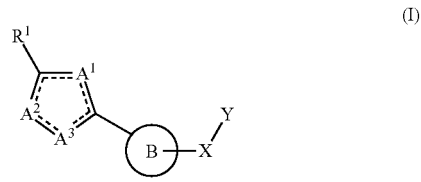

(I)

or a pharmaceutically acceptable salt or prodrug ester thereof, wherein:

$R^1$ is H (hydrogen), or is selected from the group consisting of aryl and $(C_1-C_6)$alkyl, each optionally substituted with one or more $R_h$;

each $R_h$ is independently selected from the group consisting of halo, cyano, nitro, —C(O)OH, $(C_1-C_6)$alkyl, $(C_3-C_8)$cycloalkyl, —$(CH_2)_n$OH, $(C_1-C_6)$alkoxy, halo$(C_1-C_6)$alkoxy, $(C_1-C_6)$C(O)—, $(C_1-C_6)$OC(O)—, and $(C_1-C_6)$C(O)O—;

$A^1$ is N (nitrogen), or $CR^2$;

$R^2$ is H (hydrogen), $(C_1-C_6)$alkyl, aryl$(C_1-C_6)$alkyl, $(C_2-C_6)$alkenyl, $(C_2-C_6)$alkynyl, or aryl optionally substituted with one or more halo;

$A^2$ and $A^3$ are each independently O (oxygen) or N (nitrogen) with the proviso that when $A^2$ is O (oxygen), $A^3$ is N (nitrogen) and when $A^2$ is N (nitrogen), $A^3$ is O (oxygen);

B is aryl or heteroaryl, each optionally substituted with one or more $R^3$;

X is —C(=O)—, —C(=S)—, —C($R^4$)$_2$—, or —S(O)$_z$—;

each n is independently an integer selected from 0, 1, and 2;

each z is independently an integer selected from 0, 1, and 2;

Y is $R^4$, —N($R^4$)$_2$, —O$R^4$, —S$R^4$, or —C($R^4$)$_3$, each optionally substituted with one or more $R_d$;

each $R^4$ is independently selected from the group consisting of hydrogen, —OH, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, (C₃-C₈)cycloalkyl, —(CH₂)ₙ(C₃-C₈)cycloalkyl, heteroaryl, aryl, aryl(C₁-C₆)alkyl, heterocycle, heterocycle(C₁-C₆)alkyl, heterocycle(C₁-C₆)alkanoyl and NR$_a$R$_b$; or when Y is —N(R⁴)₂, then two R⁴ groups are optionally taken together with the nitrogen to which they are attached to form a 3-8 membered monocyclic or a 7-12 membered bicyclic ring system, each optionally comprising one or more additional heteroatom groups selected from O (oxygen), S(O)$_z$, and NR$_c$ wherein each ring system is optionally substituted with one or more R$_d$;

each R$_a$ and R$_b$ is independently hydrogen or (C₁-C₆) alkyl, or R$_a$ and R$_b$ are optionally taken together with the nitrogen to which they are attached to form a 3-8 membered monocyclic or a 7-12 membered bicyclic ring system, each optionally substituted with one or more C₁-C₆alkyl groups;

each R$_c$ is independently selected from the group consisting of hydrogen, (C₁-C₆)alkyl, aryl, heteroaryl, (C₁-C₆)alkylsulfonyl, arylsulfonyl, (C₁-C₆)alkylC(O)—, arylC(O)—, hydroxy(C₁-C₆)alkyl, alkoxy(C₁-C₆) alkyl, heterocycle, (C₁-C₆)alkylOC(O)—, (C₁-C₆) alkylaminocarbonyl, and arylaminocarbonyl;

each R$_d$ is independently halo, cyano, nitro, oxo, R$_f$R$_g$N (C₁-C₆)alkyl, —(CH₂)ₙNR$_f$R$_g$, —C(O)NR$_f$R$_g$, —NR$_e$C(O)R$_g$, arylC(O)NR$_f$R$_g$, —C(O)OH, (C₁-C₆) alkyl, (C₃-C₈)cycloalkyl, —(CH₂)ₙOH, (C₁-C₆)alkoxy, halo(C₁-C₆)alkoxy, (C₁-C₆)C(O)—, (C₁-C₆)OC(O)—, (C₁-C₆)C(O)O—, heterocycle, aryl, heterocycle(C₁-C₆)alkyl, aryl(C₁-C₆)alkyl, —NR$_e$S(O)$_z$(C₁-C₆)alkyl, —NR$_e$S(O)$_z$aryl, —NR$_e$C(O)NR$_f$R$_g$, —NR$_e$C(O)OR$_f$, or —OC(O)NR$_f$R$_g$;

each R$_e$ is independently hydrogen, (C₁-C₆)alkyl, aryl or heteroaryl;

each R$_f$ and R$_g$ is independently hydrogen, (C₁-C₆)alkyl, aryl or heteroaryl, or R$_f$ and R$_g$ are optionally taken together with the nitrogen to which they are attached to form a 3-8 membered monocyclic or a 7-12 membered bicyclic ring system, each optionally comprising one or more additional heteroatom groups selected from O (oxygen), S(O)$_z$, and NR$_c$ wherein each ring system is optionally substituted with one or more R$_q$;

each R$_q$ is independently halo, cyano, nitro, oxo, R$_i$R$_j$N (C₁-C₆)alkyl, —(CH₂)ₙNR$_i$R$_j$, —C(O)NR$_i$R$_j$, —NR$_k$C (O)R$_j$, arylC(O)NR$_i$R$_j$, —C(O)OH, (C₁-C₆)alkyl, (C₃-C₈)cycloalkyl, —(CH₂)ₙOH, (C₁-C₆)alkoxy, halo(C₁-C₆)alkoxy, (C₁-C₆)C(O)—, (C₁-C₆)OC(O)—, (C₁-C₆) C(O)O—, heterocycle, aryl, heterocycle(C₁-C₆)alkyl, aryl(C₁-C₆)alkyl, —NR$_e$S(O)$_z$(C₁-C₆)alkyl, —NR$_k$S (O)$_z$aryl, —NR$_k$C(O)NR$_i$R$_j$, —NR$_k$C(O)OR$_j$, or —OC (O)NR$_i$R$_j$;

each R$_k$ is independently hydrogen, (C₁-C₆)alkyl, aryl or heteroaryl;

each R$_i$ and R$_j$ is independently hydrogen, (C₁-C₆)alkyl, aryl or heteroaryl;

each R³ is (C₁-C₆)alkyl, —NR$_i$R$_j$, —C(O)NR$_i$R$_j$, or aryl (C₁-C₆)alkyl; and the dashed line represents an optional double bond wherein the ring comprising A¹, A², and A³ is heteroaromatic;

with the proviso that the compound of formula I is not selected from the group consisting of:

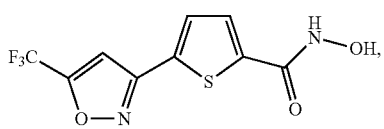

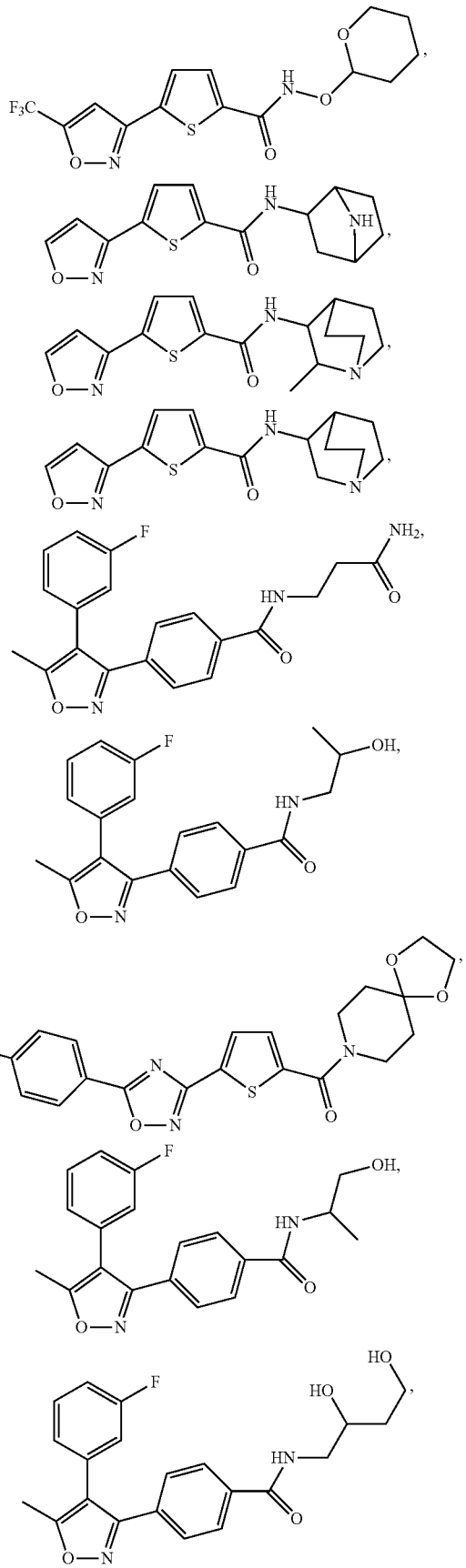

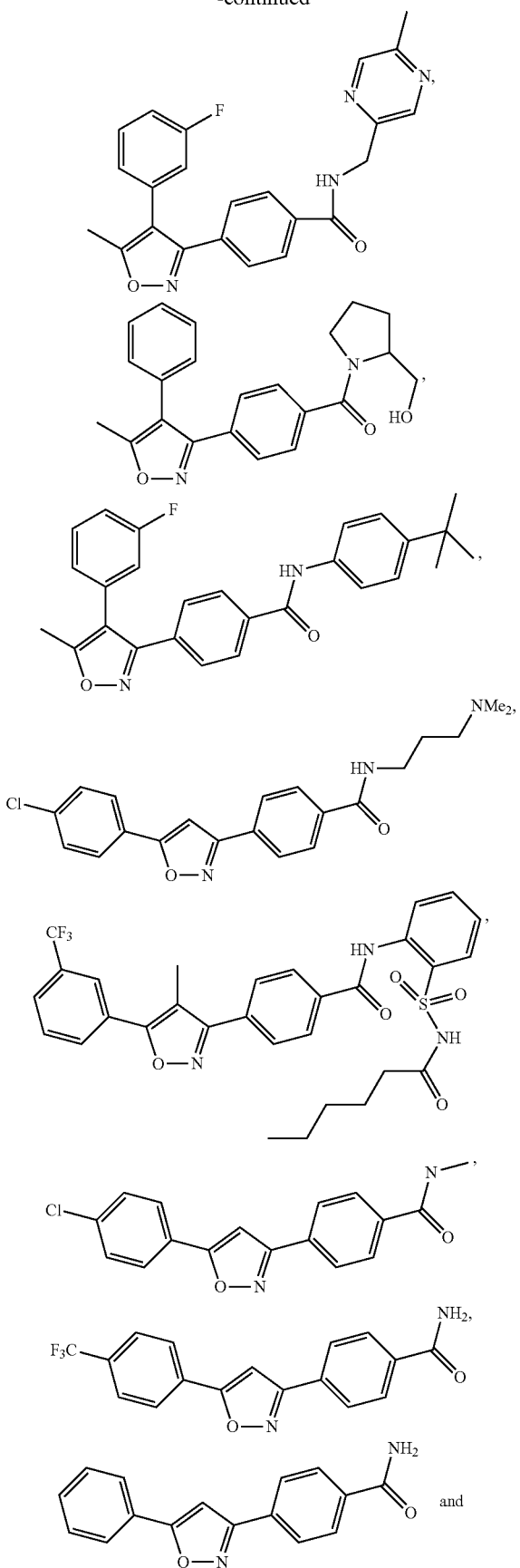

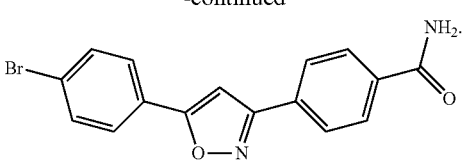

Another embodiment includes a compound having the formula:

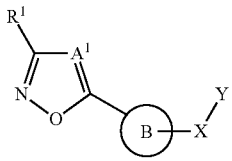

or a pharmaceutically acceptable salt or prodrug ester thereof, wherein the variables are defined according to the definitions for the compound of formula I. Another embodiment includes the compound of formula I, wherein each $R^3$ can be independently $(C_1-C_6)$alkyl, or aryl$(C_1-C_6)$alkyl. Another embodiment includes the compound of formula I, wherein each $R_h$ can be halo, cyano, nitro, —OH, or $(C_1-C_6)$alkyl. In some embodiments $R_h$ can be fluoro.

Another embodiment includes a compound having the formula:

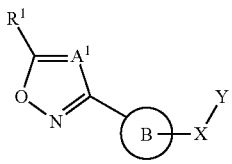

or a pharmaceutically acceptable salt or prodrug ester thereof, wherein the variables are defined according to the definitions for the compound of formula I.

Another embodiment includes the compound of formula I with the proviso that when B is a 5-membered ring and Y is —N(R$^4$)$_2$, then $R^4$ is not a 7-azabicyclo[2.2.1]heptane or 1-azabicyclo[2.2.2]octane, each optionally substituted with $(C_1-C_6)$alkyl. Another embodiment includes the compound of formula I with the proviso that when B is a 5-membered ring, then $R^3$ is not —C(O)NR$_i$R$_j$.

Another embodiment includes the compound of formula I with the proviso that when B is thiophene and not substituted with $R^3$, X is —C(=O)—, Y is —N(R$^4$)$_2$, and one $R^4$ is H, then the other $R^4$ is not —OH; and when B is thiophene and not substituted with $R^3$, and X is —C(=O)—, then Y is not —OH, or —O($C_1-C_6$)alkyl.

Another embodiment includes the compound of formula I having formula Ia:

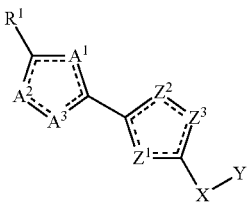

(Ia)

or a pharmaceutically acceptable salt or prodrug ester thereof,
wherein:
$Z^1$, $Z^2$, and $Z^3$ are each independently O (oxygen), N (nitrogen), S (sulfur), or $CR^5$ O (oxygen), N (nitrogen), S (sulfur), or $CR^5$ with the proviso that at least one of $Z^1$, $Z^2$, and $Z^3$ is not $CR^5$;
each $R^5$ is independently H (hydrogen), $(C_1-C_6)$alkyl, $-NR_fR_g$, $-C(O)NR_fR_g$, or aryl$(C_1-C_6)$alkyl;
each $R_f$ and $R_g$ is independently hydrogen, $(C_1-C_6)$alkyl, aryl or heteroaryl, or $R_f$ and $R_g$ are optionally taken together with the nitrogen to which they are attached to form a 3-8 membered monocyclic or a 7-12 membered bicyclic ring system, each optionally comprising one or more additional heteroatom groups selected from O (oxygen), $S(O)_z$, and $NR_c$ wherein each ring system is optionally substituted with one or more $R_q$;
each $R_q$ is independently halo, hydroxy, cyano, nitro, oxo, COOH, $-NR_iR_j$, $R_iR_jN(C_1-C_6)$alkyl, $-(CH_2)_nNR_iR_j$, $-C(O)NR_iR_j$, $-NR_kC(O)R_j$, aryl$C(O)NR_iR_j$, $-C(O)$ OH, $(C_1-C_6)$alkyl, $(C_3-C_8)$cycloalkyl, $-(CH_2)_nOH$, $(C_1-C_6)$alkoxy, halo$(C_1-C_6)$alkoxy, $(C_1-C_6)C(O)-$, $(C_1-C_6)OC(O)-$, $(C_1-C_6)C(O)O-$, heterocycle, aryl, heterocycle$(C_1-C_6)$alkyl, aryl$(C_1-C_6)$alkyl, $-NR_eS(O)_z(C_1-C_6)$alkyl, $-NR_kS(O)_z$aryl, $-NR_kC(O)NR_iR_j$, $-NR_kC(O)OR_i$, or $-OC(O)NR_iR_j$;
each $R_c$ is independently selected from the group consisting of hydrogen, $(C_1-C_6)$alkyl, aryl, heteroaryl, $(C_1-C_6)$alkylsulfonyl, arylsulfonyl, $(C_1-C_6)$alkylC(O)—, arylC(O)—, hydroxy$(C_1-C_6)$alkyl, alkoxy$(C_1-C_6)$alkyl, heterocycle, $(C_1-C_6)$alkylOC(O)—, $(C_1-C_6)$alkylaminocarbonyl, and arylaminocarbonyl;
each n is independently an integer selected from 0, 1, and 2;
each z is independently an integer selected from 0, 1, and 2;
each $R_k$ is independently hydrogen, $(C_1-C_6)$alkyl, aryl or heteroaryl;
each $R_i$ and $R_j$ is independently hydrogen, $(C_1-C_6)$alkyl, aryl or heteroaryl;
$R^1$, $A^1$, $A^2$, $A^3$, X and Y are defined according to the definitions for the compound of formula I; and
the dashed line represents an optional double bond wherein the ring comprising $Z^1$, $Z^2$, and $Z^3$ is heteroaromatic.

In some embodiments $Z^1$ can be O (oxygen), N (nitrogen) or S (sulfur). In some embodiments $Z^2$ can be O (oxygen), N (nitrogen) S (sulfur), or $CR^5$. In some embodiments $Z^3$ can be O (oxygen), N (nitrogen) S (sulfur), or $CR^5$.

Another embodiment includes a compound of formula Ia with the proviso that when $Z^1$ is O (oxygen), N (nitrogen) or S (sulfur) and Y is $-N(R^4)_2$, then $R^4$ is not a 7-azabicyclo[2.2.1]heptane or 1-azabicyclo[2.2.2]octane, each optionally substituted with $(C_1-C_6)$alkyl. Another embodiment includes a compound of formula Ia with the proviso that when $Z^1$ is S (sulfur), then $Z^3$ is not $CR^5$ where $R^5$ is $-C(O)NR_iR_j$.

Another embodiment includes a compound of formula Ia, wherein $Z^1$ is S (sulfur). Another embodiment includes a compound of formula Ia, wherein X is $-C(=O)$. Another embodiment includes the compound of formula Ia, wherein each $R_h$ can be halo, cyano, nitro, —OH, or $(C_1-C_6)$alkyl. In some embodiments $R_h$ can be fluoro.

Another embodiment includes the compound of formula Ia with the proviso that when $Z^1$ is S (sulfur) and $Z^2$ and $Z^3$ are both $CR^5$ where each $R^5$ is H (hydrogen), X is $-C(=O)-$, Y is $-N(R^4)_2$, and one $R^4$ is H, then the other $R^4$ is not —OH; and when $Z^1$ is S (sulfur) and $Z^2$ and $Z^3$ are both $CR^5$ where each $R^5$ is H, and X is $-C(=O)-$, then Y is not —OH, or $-O(C_1-C_6)$alkyl. Another embodiment includes the compound of formula Ia with the proviso that when $Z^1$ is S (sulfur) and $Z^2$ is $CR^5$ where $R^5$ is H (hydrogen), X is $-C(=O)-$, Y is $-N(R^4)_2$, and one $R^4$ is H, then the other $R^4$ is not —OH; and when $Z^1$ is S (sulfur) and $Z^2$ is $CR^5$ where $R^5$ is H, and X is $-C(=O)-$, then Y is not —OH, or $-O(C_1-C_6)$alkyl. Another embodiment includes the compound of formula Ia with the proviso that when $Z^1$ is S (sulfur) and $Z^3$ is $CR^5$ where $R^5$ is H (hydrogen), X is $-C(=O)-$, Y is $-N(R^4)_2$, and one $R^4$ is H, then the other $R^4$ is not —OH; and when $Z^1$ is S (sulfur) and $Z^3$ is $CR^5$ where $R^5$ is H, and X is $-C(=O)-$, then Y is not —OH, or $-O(C_1-C_6)$alkyl.

Another embodiment includes the compound of formula Ia, wherein Y is $-N(R^4)_2$. In some embodiments, $-N(R^4)_2$ is piperidinyl optionally substituted with one or more $R_d$.

Another embodiment includes a compound having the formula:

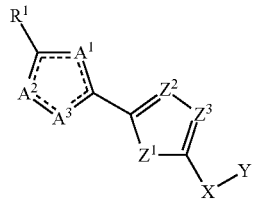

or a pharmaceutically acceptable salt or prodrug ester thereof,
wherein the variables are defined according to the definitions for the compound of formula Ia.

Another embodiment includes a compound having the formula:

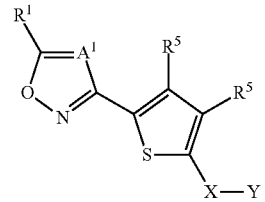

or a pharmaceutically acceptable salt or prodrug ester thereof,
wherein the variables are defined according to the definitions for the compound of formula Ia.

Another embodiment includes a compound having the formula:

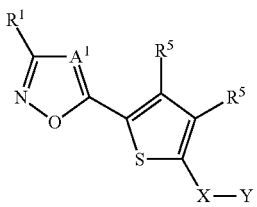

or a pharmaceutically acceptable salt or prodrug ester thereof, wherein the variables are defined according to the definitions for the compound of formula Ia.

Another embodiment includes the compound of formula I having the formula IIa:

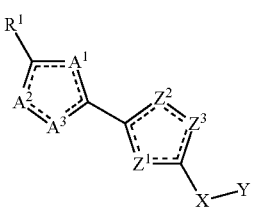

(IIa)

or a pharmaceutically acceptable salt or prodrug ester thereof, wherein:
- $R^1$ is H (hydrogen), or is selected from the group consisting of aryl and $(C_1-C_6)$alkyl, each optionally substituted with one or more $R_h$;
- each $R_h$ is independently selected from the group consisting of halo, cyano, nitro, —C(O)OH, $(C_1-C_6)$alkyl, $(C_3-C_8)$cycloalkyl, —$(CH_2)_n$OH, $(C_1-C_6)$alkoxy, halo$(C_1-C_6)$alkoxy, $(C_1-C_6)$C(O)—, $(C_1-C_6)$OC(O)—, and $(C_1-C_6)$C(O)O—;
- $A^1$ is N (nitrogen), or $CR^2$;
- $R^2$ is H (hydrogen), $(C_1-C_6)$alkyl, aryl$(C_1-C_6)$alkyl, $(C_2-C_6)$alkenyl, $(C_2-C_6)$alkynyl, or aryl optionally substituted with one or more halo;
- $A^2$ and $A^3$ are each independently O (oxygen) or N (nitrogen) with the proviso that when $A^2$ is O (oxygen), $A^3$ is N (nitrogen) and when $A^2$ is N (nitrogen), $A^3$ is O (oxygen);
- $Z^1$, $Z^2$, and $Z^3$ are each independently O (oxygen), N (nitrogen), S (sulfur), or $CR^5$ with the proviso that at least one of $Z^1$, $Z^2$, and $Z^3$ is not $CR^5$;
- each $R^5$ is independently H (hydrogen), $(C_1-C_6)$alkyl, —$NR_iR_j$, —$C(O)NR_iR_j$, or aryl$(C_1-C_6)$alkyl;
- X is —C(=O)—, —C(=S)—, —$C(R^4)_2$—, or —$S(O)_z$—;
- each n is independently an integer selected from 0, 1, and 2;
- each z is independently an integer selected from 0, 1, and 2;
- Y is —$N(R^4)_2$ optionally substituted with one or more $R_d$;
- each $R^4$ is independently selected from the group consisting of hydrogen, —OH, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_3-C_8)$cycloalkyl, —$(CH_2)_n(C_3-C_8)$cycloalkyl, heteroaryl, aryl, aryl$(C_1-C_6)$alkyl, heterocycle, heterocycle$(C_1-C_6)$alkyl, heterocycle$(C_1-C_6)$alkanoyl and $NR_aR_b$; or two $R^4$ groups are optionally taken together with the nitrogen to which they are attached to form a 3-8 membered monocyclic or a 7-12 membered bicyclic ring system, each optionally comprising one or more additional heteroatom groups selected from O (oxygen), $S(O)_z$, and $NR_c$ wherein each ring system is optionally substituted with one or more $R_d$;
- each $R_a$ and $R_b$ is independently hydrogen or $(C_1-C_6)$alkyl, or $R_a$ and $R_b$ are optionally taken together with the nitrogen to which they are attached to form a 3-8 membered monocyclic or a 7-12 membered bicyclic ring system, each optionally substituted with one or more $C_1-C_6$alkyl groups;
- each $R_c$ is independently selected from the group consisting of hydrogen, $(C_1-C_6)$alkyl, aryl, heteroaryl, $(C_1-C_6)$alkylsulfonyl, arylsulfonyl, $(C_1-C_6)$alkylC(O)—, arylC(O)—, hydroxy$(C_1-C_6)$alkyl, alkoxy$(C_1-C_6)$alkyl, heterocycle, $(C_1-C_6)$alkylOC(O)—, $(C_1-C_6)$alkylaminocarbonyl, and arylaminocarbonyl;
- each $R_d$ is independently halo, cyano, nitro, oxo, $R_fR_gN(C_1-C_6)$alkyl, —$(CH_2)_nNR_fR_g$, —$C(O)NR_fR_g$, —$NR_eC(O)R_g$, arylC(O)$NR_fR_g$, —C(O)OH, $(C_1-C_6)$alkyl, $(C_3-C_8)$cycloalkyl, —$(CH_2)_n$OH, $(C_1-C_6)$alkoxy, halo$(C_1-C_6)$alkoxy, $(C_1-C_6)$C(O)—, $(C_1-C_6)$OC(O)—, $(C_1-C_6)$C(O)O—, heterocycle, aryl, heterocycle$(C_1-C_6)$alkyl, aryl$(C_1-C_6)$alkyl, —$NR_eS(O)_z(C_1-C_6)$alkyl, —$NR_eS(O)_z$aryl, —$NR_eC(O)NR_fR_g$, —$NR_eC(O)OR_f$, or —$OC(O)NR_fR_g$;
- each $R_e$ is independently hydrogen, $(C_1-C_6)$alkyl, aryl or heteroaryl;
- each $R_f$ and $R_g$ is independently hydrogen, $(C_1-C_6)$alkyl, aryl or heteroaryl, or $R_f$ and $R_g$ are optionally taken together with the nitrogen to which they are attached to form a 3-8 membered monocyclic or a 7-12 membered bicyclic ring system, each optionally comprising one or more additional heteroatom groups selected from O (oxygen), $S(O)_z$, and $NR_c$ wherein each ring system is optionally substituted with one or more $R_q$;
- each $R_q$ is independently halo, cyano, nitro, oxo, $R_iR_jN(C_1-C_6)$alkyl, —$(CH_2)_nNR_iR_j$, —$C(O)NR_iR_j$, —$NR_kC(O)R_j$, arylC(O)$NR_iR_j$, —C(O)OH, $(C_1-C_6)$alkyl, $(C_3-C_8)$cycloalkyl, —$(CH_2)_n$OH, $(C_1-C_6)$alkoxy, halo$(C_1-C_6)$alkoxy, $(C_1-C_6)$C(O)—, $(C_1-C_6)$OC(O)—, $(C_1-C_6)C(O)O$—, heterocycle, aryl, heterocycle$(C_1-C_6)$alkyl, aryl$(C_1-C_6)$alkyl, —$NR_eS(O)_z(C_1-C_6)$alkyl, —$NR_kS(O)_z$aryl, —$NR_kC(O)NR_iR_j$, —$NR_kC(O)OR_i$, or —$OC(O)NR_iR_j$;
- each $R_k$ is independently hydrogen, $(C_1-C_6)$alkyl, aryl or heteroaryl;
- each $R_i$ and $R_j$ is independently hydrogen, $(C_1-C_6)$alkyl, aryl or heteroaryl; and
- the dashed line represents an optional double bond wherein the ring comprising $A^1$, $A^2$, and $A^3$ is heteroaromatic and the ring comprising $Z^1$, $Z^2$, and $Z^3$ is heteroaromatic;
- with the proviso that the compound of formula IIa is not selected from the group consisting of:

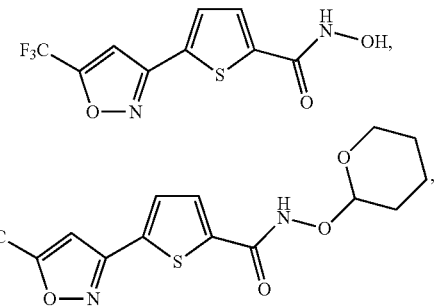

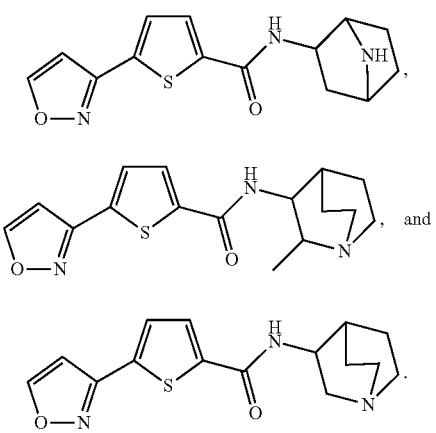

In some embodiments $Z^1$ can be O (oxygen), N (nitrogen) or S (sulfur). In some embodiments $Z^2$ can be O (oxygen), N (nitrogen) S (sulfur), or $CR^5$. In some embodiments $Z^3$ can be O (oxygen), N (nitrogen) S (sulfur), or $CR^5$. In a typical embodiment, $Z^1$ can be S (sulfur), $Z^2$ can be $CR^5$ and $Z^3$ can be $CR^5$.

Another embodiment includes the compound of formula IIa with the proviso that when $Z^1$ is O (oxygen), N (nitrogen) or S (sulfur), then $R^4$ is not a 7-azabicyclo[2.2.1]heptane or 1-azabicyclo[2.2.2]octane, each optionally substituted with $(C_1\text{-}C_6)$alkyl. Another embodiment includes the compound of formula IIa with the proviso that, $Z^3$ is not $CR^5$ where $R^5$ is $-C(O)NR_iR_j$. Another embodiment includes the compound of formula IIa with the proviso that when $Z^1$ is S (sulfur) and $Z^2$ and $Z^3$ are both $CR^5$ where each $R^5$ is H, X is $-C(=O)-$, Y is $-N(R^4)_2$, and one $R^4$ is H, then the other $R^4$ is not $-OH$; and when $Z^1$ is S (sulfur) and $Z^2$ and $Z^3$ are both $CR^5$ where each $R^5$ is H, and X is $-C(=O)-$, then Y is not $-OH$, or $-O(C_1\text{-}C_6)$alkyl. Another embodiment includes the compound of formula IIa wherein $-N(R^4)_2$ is piperidinyl optionally substituted with one or more $R_d$. Another embodiment includes the compound of formula IIa, wherein each $R_h$ can be halo, cyano, nitro, $-OH$, or $(C_1\text{-}C_6)$alkyl. In some embodiments $R_h$ can be fluoro.

Another embodiment includes a compound having the formula:

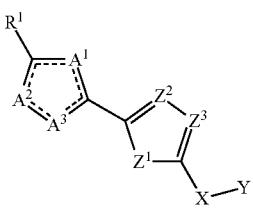

or a pharmaceutically acceptable salt or prodrug ester thereof, wherein the variables are defined according to the definitions for the compound of formula IIa.

Another embodiment includes a compound having the formula:

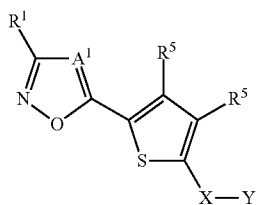

or a pharmaceutically acceptable salt or prodrug ester thereof, wherein the variables are defined according to the definitions for the compound of formula IIa.

Another embodiment includes a compound having the formula:

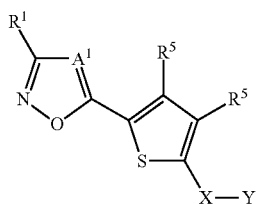

or a pharmaceutically acceptable salt or prodrug ester thereof, wherein the variables are defined according to the definitions for the compound of formula IIa.

Another embodiment includes the compound of formula IIa selected from the group consisting of:

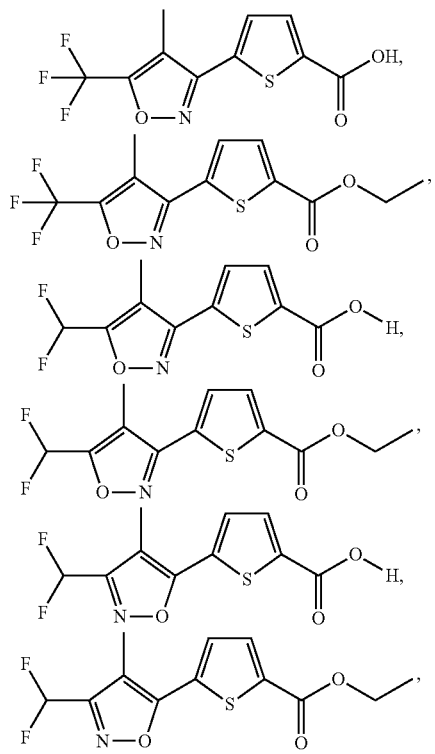

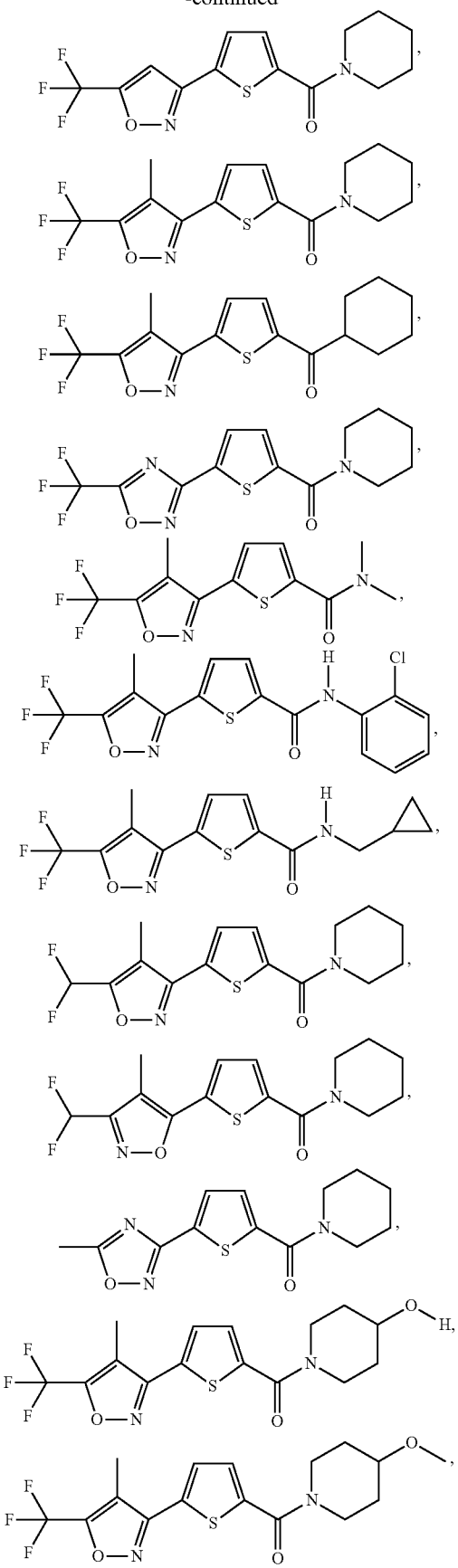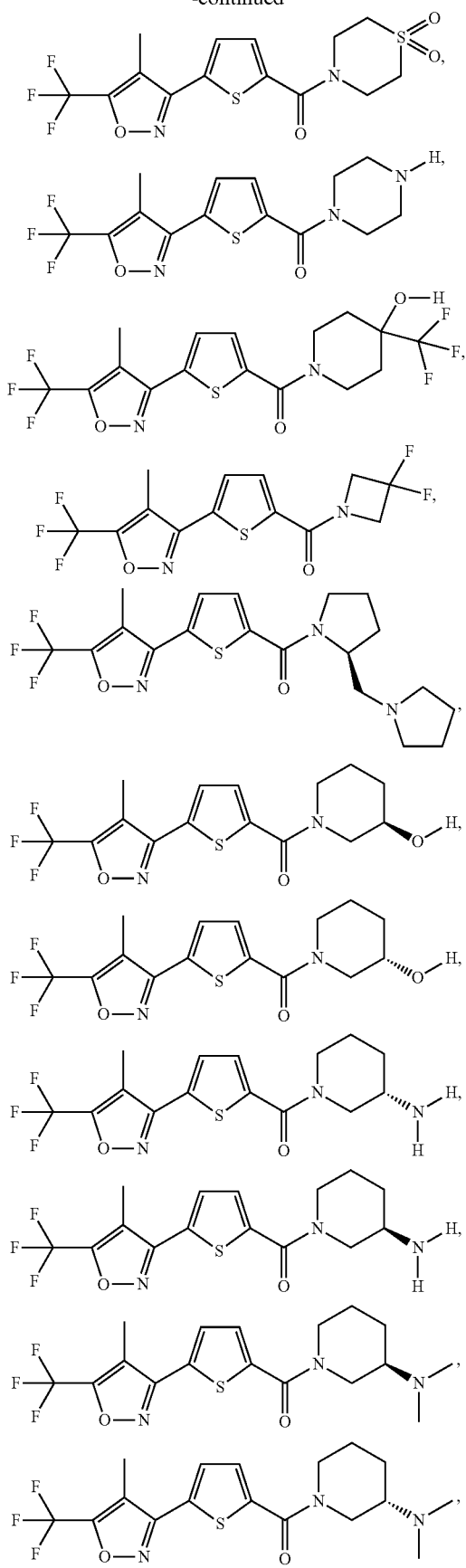

-continued
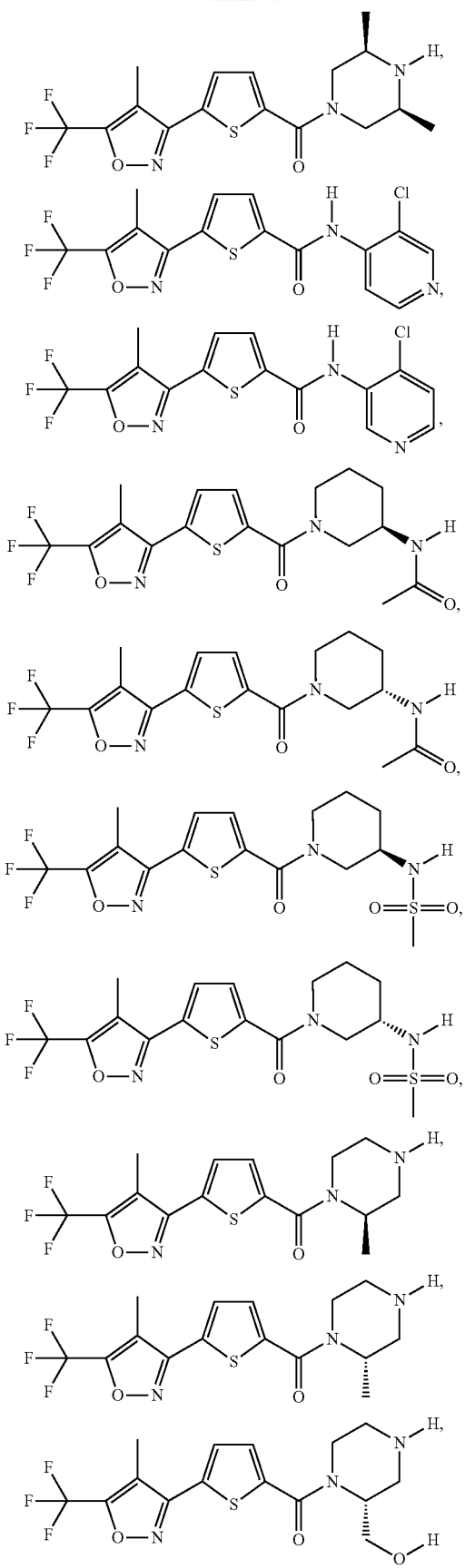
-continued
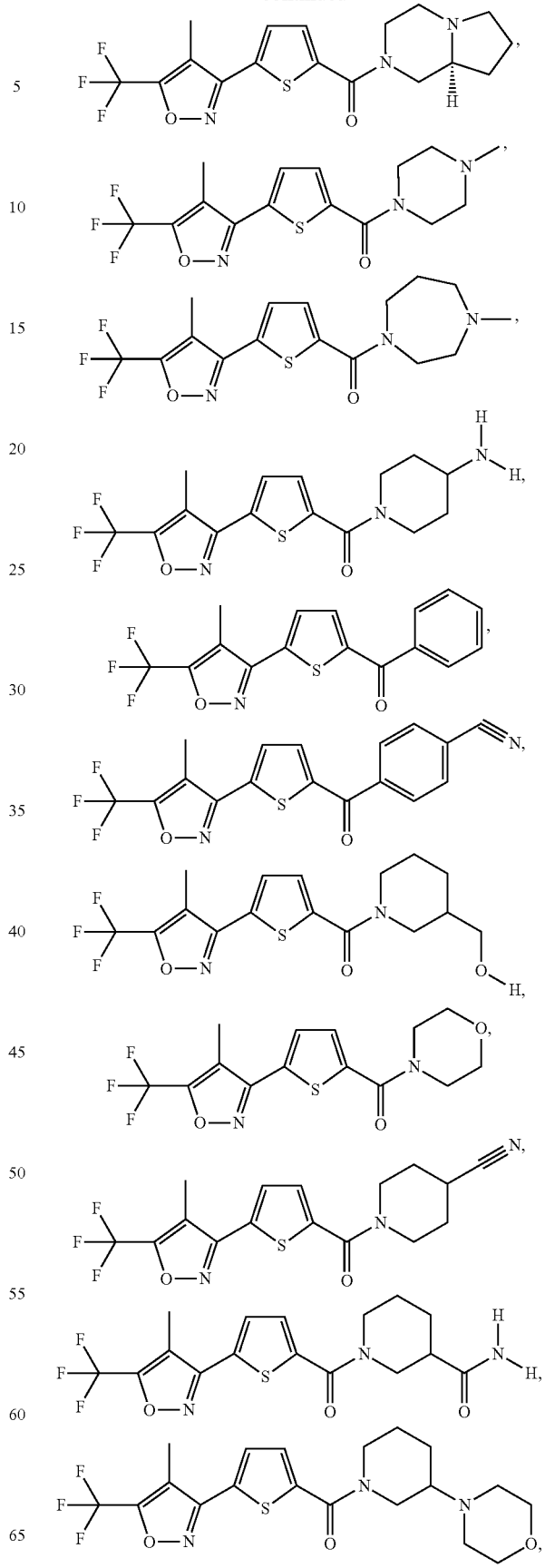

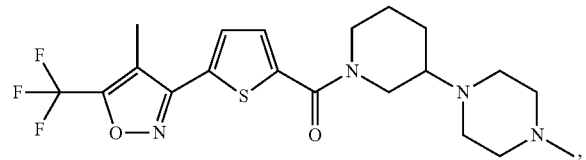
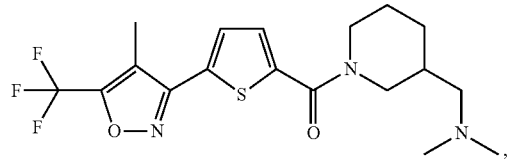
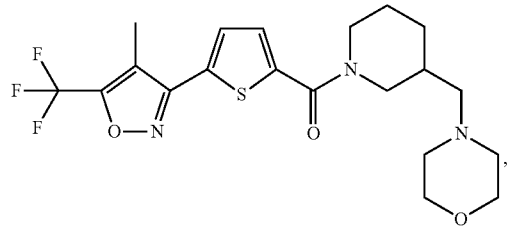
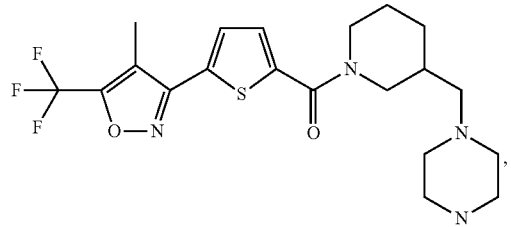
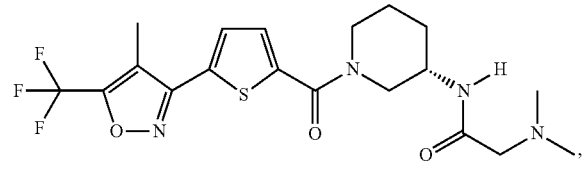
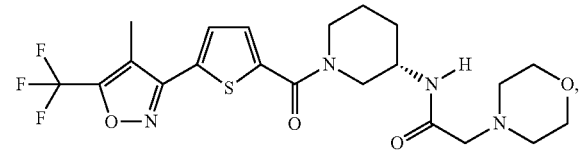
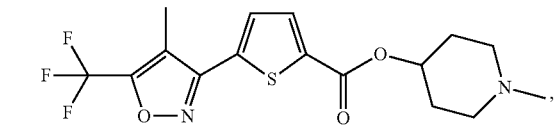
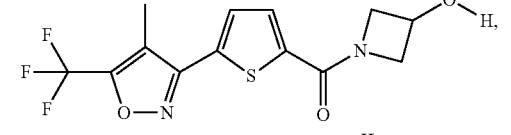
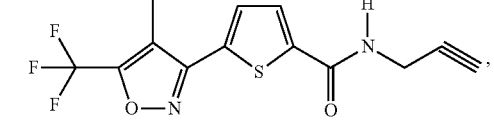
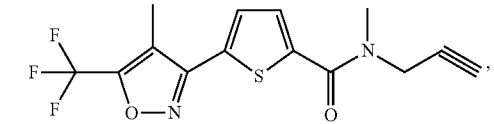
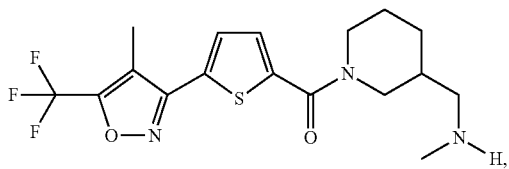
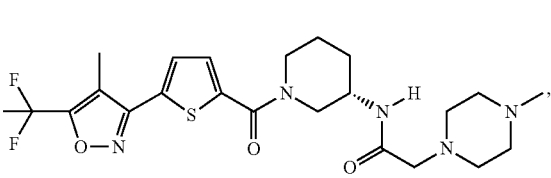
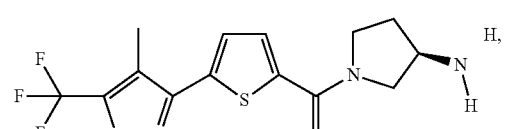
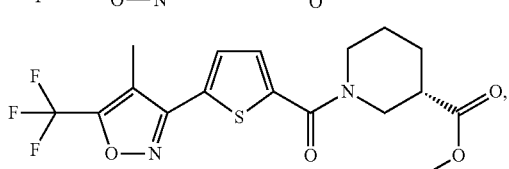
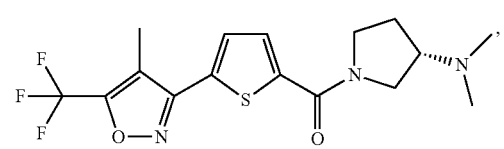
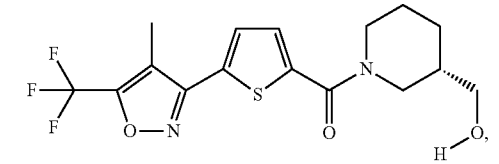
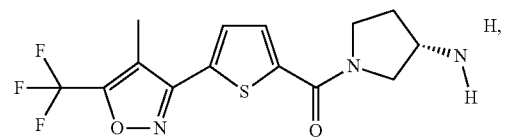
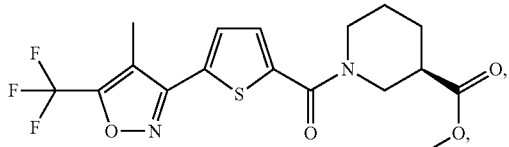
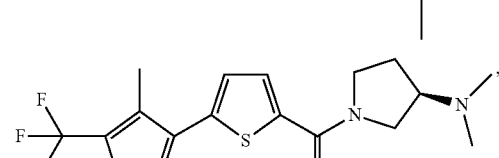
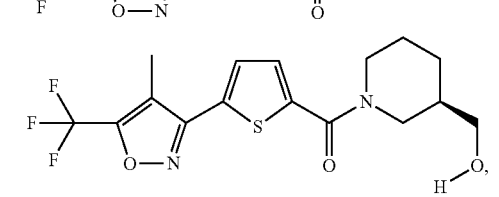

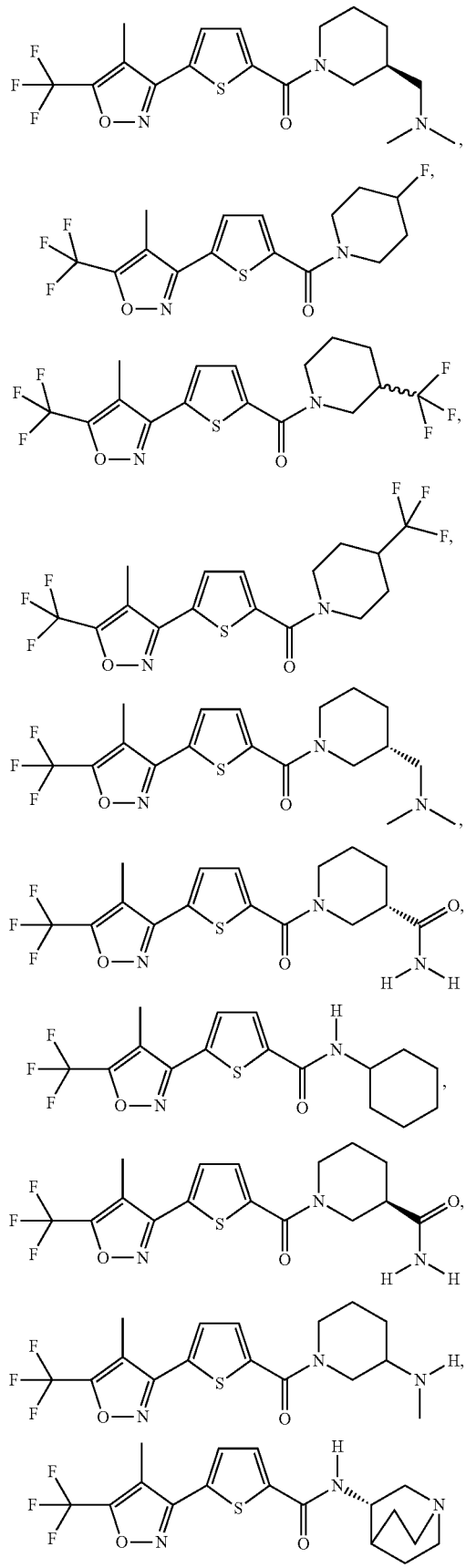
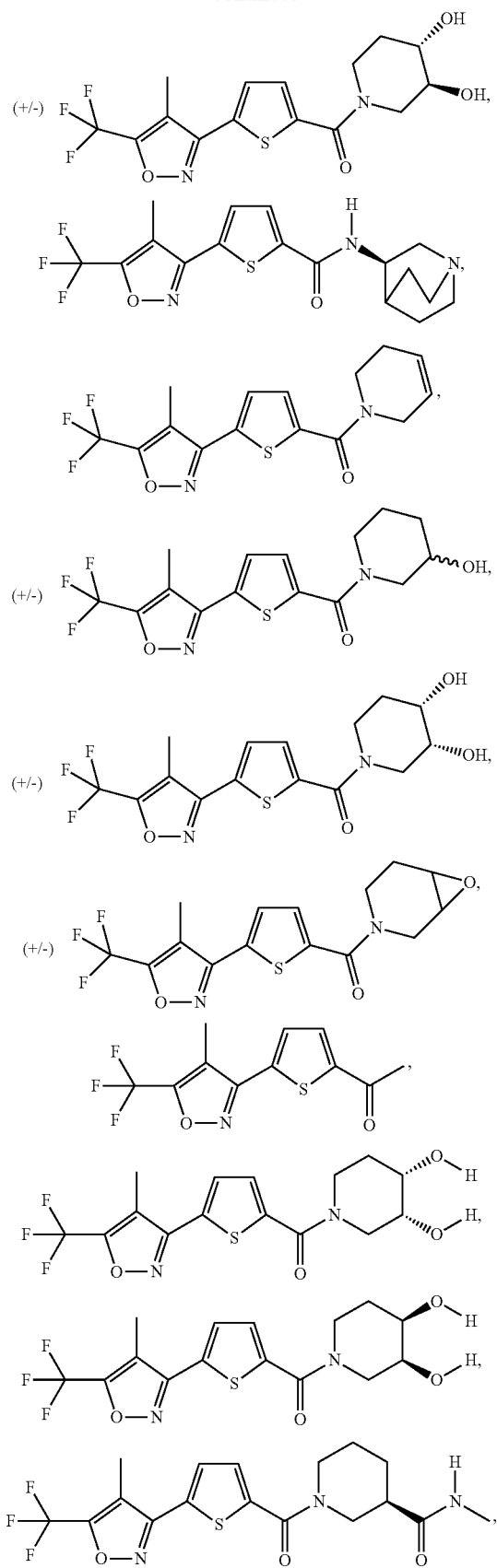

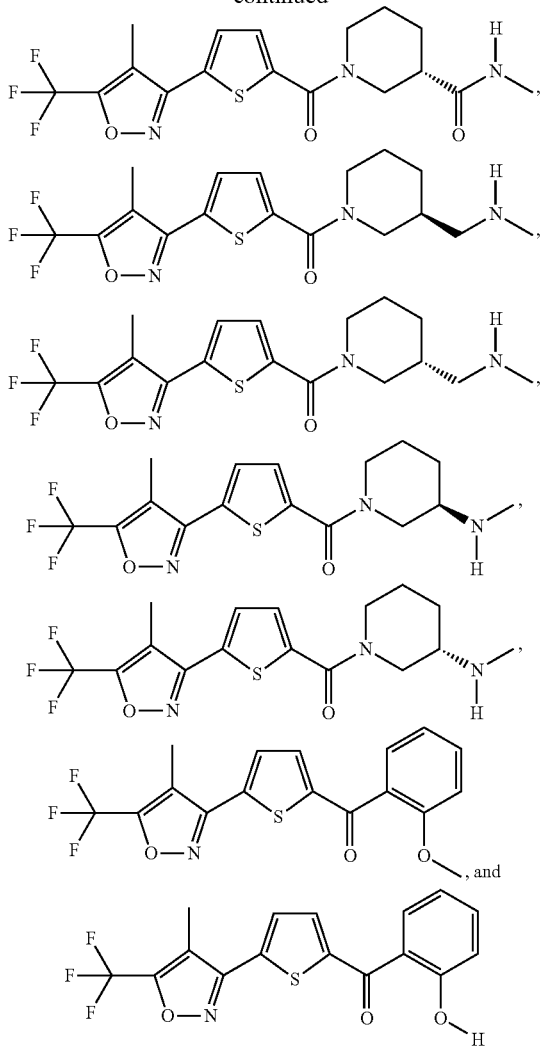

or a pharmaceutically acceptable salt or prodrug ester thereof.

Another embodiment includes the compound of formula I having the formula Id:

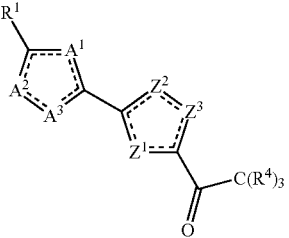

(Id)

or a pharmaceutically acceptable salt or prodrug ester thereof,
wherein:
$R^1$ is H (hydrogen), or is selected from the group consisting of aryl and $(C_1\text{-}C_6)$alkyl, each optionally substituted with one or more $R_h$;
each $R_h$ is independently selected from the group consisting of halo, cyano, nitro, —C(O)OH, $(C_1\text{-}C_6)$alkyl, $(C_3\text{-}C_8)$cycloalkyl, —$(CH_2)_n$OH, $(C_1\text{-}C_6)$alkoxy, halo$(C_1\text{-}C_6)$alkoxy, $(C_1\text{-}C_6)C(O)$—, $(C_1\text{-}C_6)OC(O)$—, and $(C_1\text{-}C_6)C(O)O$—;

$A^1$ is N (nitrogen), or $CR^2$;
$R^2$ is H (hydrogen), $(C_1\text{-}C_6)$alkyl, aryl$(C_1\text{-}C_6)$alkyl, $(C_2\text{-}C_6)$alkenyl, $(C_2\text{-}C_6)$alkynyl, or aryl optionally substituted with one or more halo;
$A^2$ and $A^3$ are each independently O (oxygen) or N (nitrogen) with the proviso that when $A^2$ is O (oxygen), $A^3$ is N (nitrogen) and when $A^2$ is N (nitrogen), $A^3$ is O (oxygen);
$Z^1$, $Z^2$, and $Z^3$ are each independently is O (oxygen), N (nitrogen), S (sulfur), or $CR^5$ with the proviso that at least one of $Z^1$, $Z^2$, and $Z^3$ is not $CR^5$;
$Z^2$ is O, N (nitrogen), S (sulfur), or $CR^5$;
$Z^3$ is O, N (nitrogen), S (sulfur), or $CR^5$;
each $R^5$ is independently H (hydrogen), $(C_1\text{-}C_6)$alkyl, —$NR_iR_j$, —$C(O)NR_iR_j$, or aryl$(C_1\text{-}C_6)$alkyl;
each $R^4$ is independently selected from the group consisting of hydrogen, —OH, $(C_1\text{-}C_6)$alkyl, $(C_2\text{-}C_6)$alkenyl, $(C_2\text{-}C_6)$alkynyl, $(C_1\text{-}C_6)$alkanoyl, $(C_1\text{-}C_6)$alkoxycarbonyl, $(C_3\text{-}C_8)$cycloalkyl, —$(CH_2)_n(C_3\text{-}C_8)$cycloalkyl, heteroaryl, aryl, aryl$(C_1\text{-}C_6)$alkyl, heterocycle, heterocycle$(C_1\text{-}C_6)$alkyl, heterocycle$(C_1\text{-}C_6)$alkanoyl and $NR_aR_b$, each optionally substituted with one or more $R_d$;
each $R_a$ and $R_b$ is independently hydrogen or $(C_1\text{-}C_6)$alkyl, or $R_a$ and $R_b$ are optionally taken together with the nitrogen to which they are attached to form a 3-8 membered monocyclic or a 7-12 membered bicyclic ring system, each optionally substituted with one or more $C_1\text{-}C_6$alkyl groups;
each $R_d$ is independently halo, cyano, nitro, oxo, $R_fR_gN$ $(C_1\text{-}C_6)$alkyl, —$(CH_2)_nNR_fR_g$, —$C(O)NR_fR_g$, —$NR_eC(O)R_g$, arylC(O)$NR_fR_g$, —C(O)OH, $(C_1\text{-}C_6)$alkyl, $(C_3\text{-}C_8)$cycloalkyl, —$(CH_2)_n$OH, $(C_1\text{-}C_6)$alkoxy, halo$(C_1\text{-}C_6)$alkoxy, $(C_1\text{-}C_6)C(O)$—, $(C_1\text{-}C_6)OC(O)$—, $(C_1\text{-}C_6)C(O)O$—, heterocycle, aryl, heterocycle$(C_1\text{-}C_6)$alkyl, aryl$(C_1\text{-}C_6)$alkyl, —$NR_eS(O)_z(C_1\text{-}C_6)$alkyl, —$NR_eS(O)_z$aryl, —$NR_eC(O)NR_fR_g$, —$NR_eC(O)OR_f$, or —$OC(O)NR_fR_g$;
each n is independently an integer selected from 0, 1, and 2;
each z is independently an integer selected from 0, 1, and 2;
each $R_e$ is independently hydrogen, $(C_1\text{-}C_6)$alkyl, aryl or heteroaryl;
each $R_f$ and $R_g$ is independently hydrogen, $(C_1\text{-}C_6)$alkyl, aryl or heteroaryl, or $R_f$ and $R_g$ are optionally taken together with the nitrogen to which they are attached to form a 3-8 membered monocyclic or a 7-12 membered bicyclic ring system, each optionally comprising one or more additional heteroatom groups selected from O (oxygen), $S(O)_z$, and $NR_c$ wherein each ring system is optionally substituted with one or more $R_q$;
each $R_q$ is independently halo, cyano, nitro, oxo, $R_iR_jN$ $(C_1\text{-}C_6)$alkyl, —$(CH_2)_nNR_iR_j$, —$C(O)NR_iR_j$, —$NR_kC$ $(O)R_j$, arylC(O)$NR_iR_j$, —C(O)OH, $(C_1\text{-}C_6)$alkyl, $(C_3\text{-}C_8)$cycloalkyl, —$(CH_2)_n$OH, $(C_1\text{-}C_6)$alkoxy, halo$(C_1\text{-}C_6)$alkoxy, $(C_1\text{-}C_6)C(O)$—, $(C_1\text{-}C_6)OC(O)$—, $(C_1\text{-}C_6)$ C(O)O—, heterocycle, aryl, heterocycle$(C_1\text{-}C_6)$alkyl, aryl$(C_1\text{-}C_6)$alkyl, —$NR_eS(O)_z(C_1\text{-}C_6)$alkyl, —$NR_kS$ $(O)_z$aryl, —$NR_kC(O)NR_iR_j$, —$NR_kC(O)OR_i$, or —OC $(O)NR_iR_j$;
each $R_k$ is independently hydrogen, $(C_1\text{-}C_6)$alkyl, aryl or heteroaryl;

each $R_i$ and $R_j$ is independently hydrogen, $(C_1-C_6)$alkyl, aryl or heteroaryl; and the dashed line represents an optional double bond wherein the ring comprising $A^1$, $A^2$, and $A^3$ is heteroaromatic and the ring comprising $Z^1$, $Z^2$, and $Z^3$ is heteroaromatic.

In some embodiments $Z^1$ can be O (oxygen), N (nitrogen) or S (sulfur). In some embodiments $Z^2$ can be O (oxygen), N (nitrogen) S (sulfur), or $CR^5$. In some embodiments $Z^3$ can be O (oxygen), N (nitrogen) S (sulfur), or $CR^5$. In a typical embodiment, $Z^1$ can be S (sulfur), $Z^2$ can be $CR^5$ and $Z^3$ can be $CR^5$. Another embodiment includes the compound of formula Id, wherein each $R_h$ can be halo, cyano, nitro, —OH, or $(C_1-C_6)$alkyl. In some embodiments $R_h$ can be fluoro.

Another embodiment includes a compound having the formula:

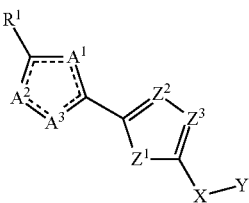

or a pharmaceutically acceptable salt or prodrug ester thereof,
wherein the variables are defined according to the definitions for the compound of formula Ia.

Another embodiment includes a compound having the formula:

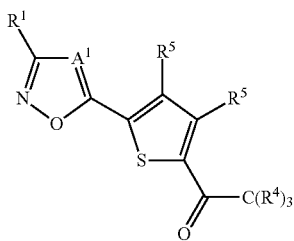

or a pharmaceutically acceptable salt or prodrug ester thereof,
wherein the variables are defined according to the definitions for the compound of formula Id.

Another embodiment includes a compound having the formula:

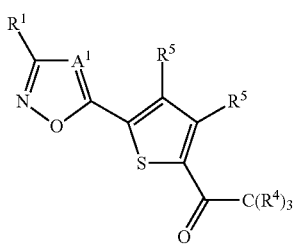

or a pharmaceutically acceptable salt or prodrug ester thereof,
wherein the variables are defined according to the definitions for the compound of formula Id.

Another embodiment includes the compound of formula I having the formula Ie:

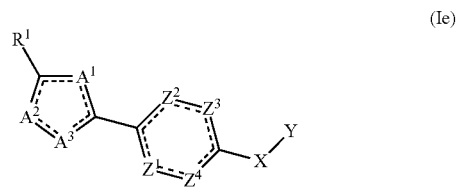

or a pharmaceutically acceptable salt or prodrug ester thereof,
wherein:
$R^1$ is H (hydrogen), or is selected from the group consisting of $(C_1-C_6)$alkyl and aryl, each optionally substituted with one or more $R_h$;
each $R_h$ is independently selected from the group consisting of halo, cyano, nitro, —C(O)OH, $(C_1-C_6)$alkyl, $(C_3-C_8)$cycloalkyl, —$(CH_2)_n$OH, $(C_1-C_6)$alkoxy, halo $(C_1-C_6)$alkoxy, $(C_1-C_6)$C(O)—, $(C_1-C_6)$OC(O)—, and $(C_1-C_6)$C(O)O—;
$A^1$ is N (nitrogen), or $CR^2$;
$R^2$ is H (hydrogen), $(C_1-C_6)$alkyl, aryl$(C_1-C_6)$alkyl, $(C_2-C_6)$alkenyl, $(C_2-C_6)$alkynyl, or aryl optionally substituted with one or more halo;
$A^2$ and $A^3$ are each independently O (oxygen) or N (nitrogen) with the proviso that when $A^2$ is O (oxygen), $A^3$ is N (nitrogen) and when $A^2$ is N (nitrogen), $A^3$ is O (oxygen);
$Z^1$ is N (nitrogen), or $CR^5$;
$Z^2$ is N (nitrogen), or $CR^5$;
$Z^3$ is N (nitrogen), or $CR^5$;
$Z^4$ is N (nitrogen), or $CR^5$;
each $R^5$ is independently H, $(C_1-C_6)$alkyl, —$NR_iR_j$, —$C(O)NR_iR_j$, or aryl$(C_1-C_6)$alkyl;
X is —C(=O)—, —C(=S)—, —$C(R^4)_2$—, or —$S(O)_z$—; each n is independently an integer selected from 0, 1, and 2;
each z is independently an integer selected from 0, 1, and 2;
Y is $R^4$, —$N(R^4)_2$, —$OR^4$, —$SR^4$, or —$C(R^4)_3$, each optionally substituted with one or more $R_d$;
each $R^4$ is independently selected from the group consisting of hydrogen, —OH, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $(C_3-C_8)$cycloalkyl, —$(CH_2)_n(C_3-C_8)$cycloalkyl, heteroaryl, aryl, aryl$(C_1-C_6)$alkyl, heterocycle, heterocycle$(C_1-C_6)$alkyl, heterocycle$(C_1-C_6)$alkanoyl and $NR_aR_b$; or when Y is —$N(R^4)_2$, then two $R^4$ groups are optionally taken together with the nitrogen to which they are attached to form a 3-8 membered monocyclic or a 7-12 membered bicyclic ring system, each optionally comprising one or more additional heteroatom groups selected from O (oxygen), $S(O)_z$, and $NR_c$ wherein each ring system is optionally substituted with one or more $R_d$;
each $R_a$ and $R_b$ is independently hydrogen or $(C_1-C_6)$ alkyl, or $R_a$ and $R_b$ are optionally taken together with the nitrogen to which they are attached to form a 3-8 membered monocyclic or a 7-12 membered bicyclic ring system, each optionally substituted with one or more $C_1-C_6$alkyl groups;

each $R_c$ is independently selected from the group consisting of hydrogen, $(C_1\text{-}C_6)$alkyl, aryl, heteroaryl, $(C_1\text{-}C_6)$alkylsulfonyl, arylsulfonyl, $(C_1\text{-}C_6)$alkylC(O)—, arylC(O)—, hydroxy$(C_1\text{-}C_6)$alkyl, alkoxy$(C_1\text{-}C_6)$alkyl, heterocycle, $(C_1\text{-}C_6)$alkylOC(O)—, $(C_1\text{-}C_6)$alkylaminocarbonyl, and arylaminocarbonyl;

each $R_d$ is independently halo, cyano, nitro, oxo, $R_fR_gN(C_1\text{-}C_6)$alkyl, —$(CH_2)_nNR_fR_g$, —$C(O)NR_fR_g$, —$NR_eC(O)R_g$, arylC(O)$NR_fR_g$, —C(O)OH, $(C_1\text{-}C_6)$alkyl, $(C_3\text{-}C_8)$cycloalkyl, —$(CH_2)_nOH$, $(C_1\text{-}C_6)$alkoxy, halo$(C_1\text{-}C_6)$alkoxy, $(C_1\text{-}C_6)$C(O)—, $(C_1\text{-}C_6)$OC(O)—, $(C_1\text{-}C_6)$C(O)O—, heterocycle, aryl, heterocycle$(C_1\text{-}C_6)$alkyl, aryl$(C_1\text{-}C_6)$alkyl, —$NR_eS(O)_z(C_1\text{-}C_6)$alkyl, —$NR_eS(O)_z$aryl, —$NR_eC(O)NR_fR_g$, —$NR_eC(O)OR_f$, or —$OC(O)NR_fR_g$;

each $R_e$ is independently hydrogen, $(C_1\text{-}C_6)$alkyl, aryl or heteroaryl;

each $R_f$ and $R_g$ is independently hydrogen, $(C_1\text{-}C_6)$alkyl, aryl or heteroaryl, or $R_f$ and $R_g$ are optionally taken together with the nitrogen to which they are attached to form a 3-8 membered monocyclic or a 7-12 membered bicyclic ring system, each optionally comprising one or more additional heteroatom groups selected from O (oxygen), $S(O)_z$, and $NR_c$ wherein each ring system is optionally substituted with one or more $R_q$;

each $R_q$ is independently halo, cyano, nitro, oxo, $R_iR_jN(C_1\text{-}C_6)$alkyl, —$(CH_2)_nNR_iR_j$, —$C(O)NR_iR_j$, —$NR_kC(O)R_j$, arylC(O)$NR_iR_j$, —C(O)OH, $(C_1\text{-}C_6)$alkyl, $(C_3\text{-}C_8)$cycloalkyl, —$(CH_2)_nOH$, $(C_1\text{-}C_6)$alkoxy, halo$(C_1\text{-}C_6)$alkoxy, $(C_1\text{-}C_6)$C(O)—, $(C_1\text{-}C_6)$OC(O)—, $(C_1\text{-}C_6)$C(O)O—, heterocycle, aryl, heterocycle$(C_1\text{-}C_6)$alkyl, aryl$(C_1\text{-}C_6)$alkyl, —$NR_eS(O)_z(C_1\text{-}C_6)$alkyl, —$NR_kS(O)_z$aryl, —$NR_kC(O)NR_iR_j$, —$NR_kC(O)OR_i$, or —$OC(O)NR_iR_j$;

each $R_k$ is independently hydrogen, $(C_1\text{-}C_6)$alkyl, aryl or heteroaryl;

each $R_i$ and $R_j$ is independently hydrogen, $(C_1\text{-}C_6)$alkyl, aryl or heteroaryl; and the dashed line represents an optional double bond wherein the ring comprising $A^1$, $A^2$, and $A^3$ is heteroaromatic and the ring comprising $Z^1$, $Z^2$, $Z^3$ and $Z^4$ is aromatic or heteroaromatic with the proviso that the compound of Formula Ie is not selected from the group consisting of:

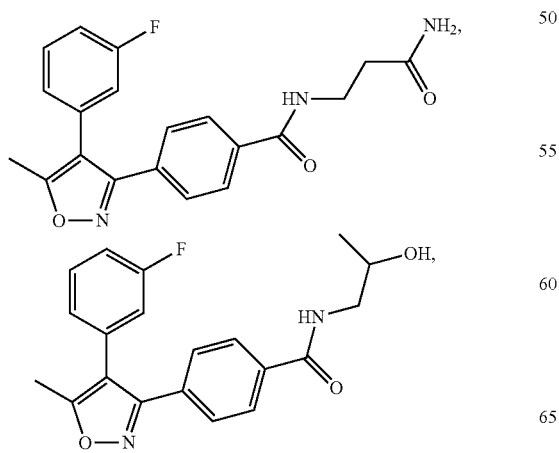

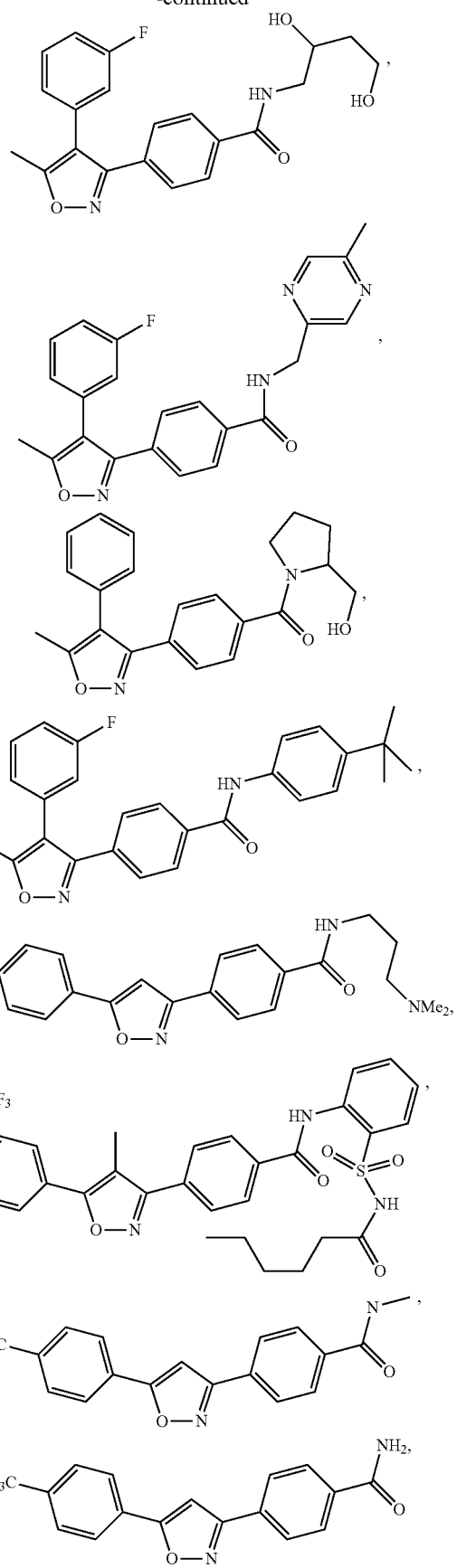

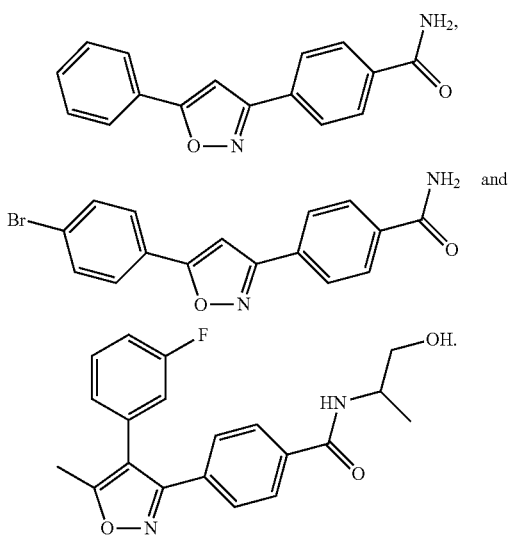

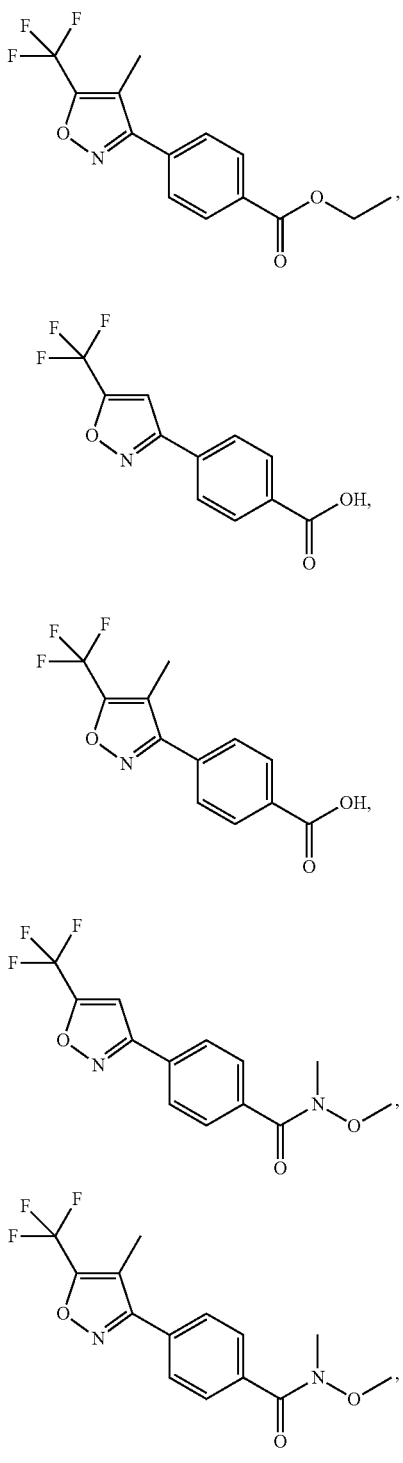

Another embodiment includes the compound of formula Ie wherein $Z^1$, $Z^2$, $Z^3$ and $Z^4$ can each be $CR^5$. Another embodiment includes the compound of formula Ie wherein Y can be $-N(R^4)_2$. Another embodiment includes the compound of formula Ie wherein $Z^1$, $Z^2$, $Z^3$ and $Z^4$ can each be $CR^5$ and Y can be $-N(R^4)_2$. Another embodiment includes the compound of formula Ie, wherein each $R_h$ can be halo, cyano, nitro, —OH, or $(C_1-C_6)$alkyl. In some embodiments $R_h$ can be fluoro.

Another embodiment includes a compound having the formula:

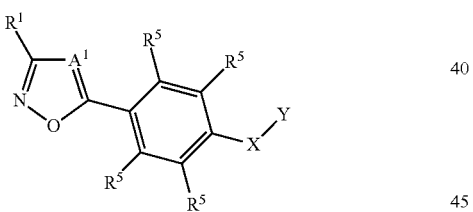

or a pharmaceutically acceptable salt or prodrug ester thereof, wherein the variables are defined according to the definitions for the compound of formula Ie.

Another embodiment includes the compound of formula Ie selected from the group consisting of

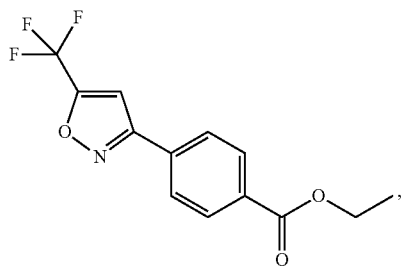

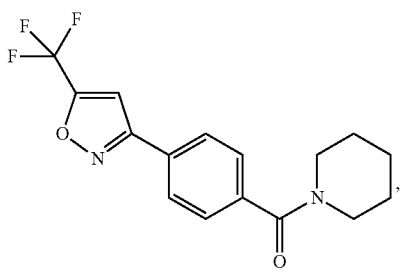

-continued

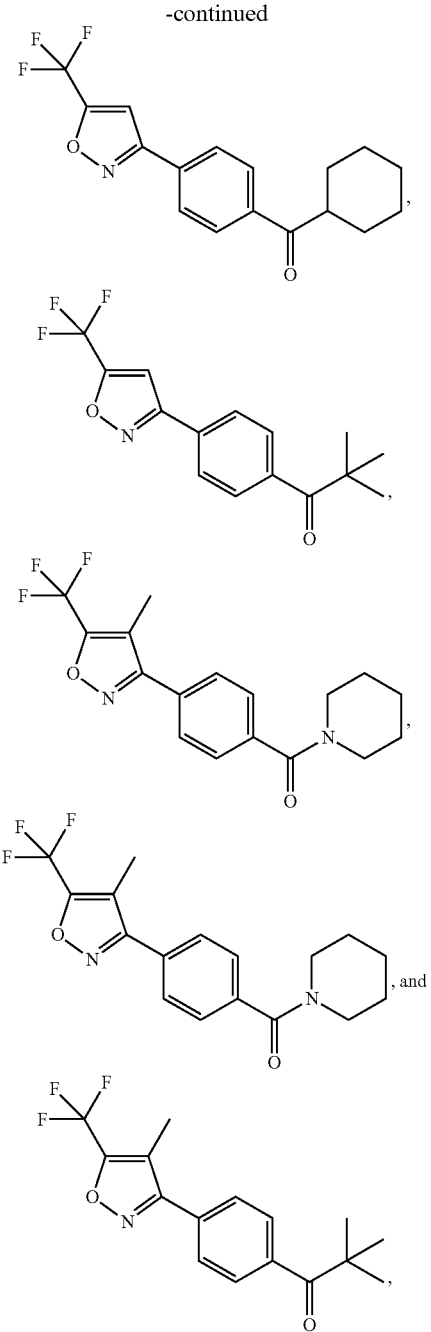

or a pharmaceutically acceptable salt or prodrug ester thereof.

Another embodiment includes a compound having the formula:

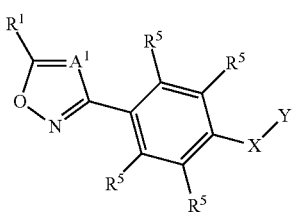

or a pharmaceutically acceptable salt or prodrug ester thereof, wherein the variables are defined according to the definitions for the compound of formula Ie. In some embodiments, Y can be —N(R⁴)₂ and X can be —C(=O)—. In some embodiments, $R^1$ can be $CF_3$ and $A^1$ can be $CR^2$.

Another embodiment includes the compound of formula Ie, wherein $Z^1$, $Z^2$, $Z^3$ and $Z^4$ can each be $CR^5$, Y can be —N(R⁴)₂, and X can be —C(=O)—. Another embodiment includes the compound of formula Ie, wherein Y can be —C(R⁴)₃ and X can be —C(=O)—. Another embodiment includes the compound of formula Ie wherein Y can be —C(R⁴)₃, X can be —C(=O)— and $Z^1$, $Z^2$, $Z^3$ and $Z^4$ can each be CR.

Another embodiment includes a compound having the formula:

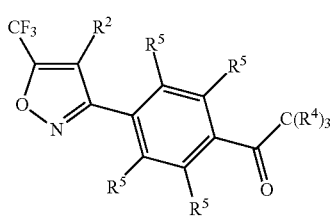

or a pharmaceutically acceptable salt or prodrug ester thereof, wherein the variables are defined according to the definitions for the compound of formula Ie.

One embodiment of the invention provides a pharmaceutical composition comprising:
 a) the compound of any of the embodiments and examples disclosed herein; and
 b) a pharmaceutically acceptable carrier.

The present embodiments provide for a method of preparing a pharmaceutically acceptable salt of the compound of any of the embodiments and examples disclosed herein, comprising:
 a) deprotecting a corresponding compound that comprises one or more protecting groups to provide the compound; and
 b) forming a pharmaceutically acceptable salt from the compound.

The present embodiments provide for a method of inhibiting one or more monoamine oxidase (MAO) enzymes in an animal comprising administering to the animal an effective amount of a compound of any of the embodiments and examples disclosed herein. In some embodiments, the animal is a healthy animal. In some embodiments, the animal is an aged animal.

The present embodiments provide for a method for improving cognitive function in an animal in need of such treatment comprising administering to the animal an effective amount of a compound of any of the embodiments and examples disclosed herein. In some embodiments, the animal can be a healthy animal. In some embodiments, the animal can be an aged animal.

The present embodiments provide for a method for activating the CREB pathway in an animal in need of such treatment, comprising administering to the animal an effective amount of a compound of compound of any of the embodiments and examples disclosed herein.

The present embodiments provide for a method for treating age-associated memory impairment, mild cognitive impairment, Alzheimer's disease or Parkinson's disease in an animal in need of such treatment comprising administering to the animal an effective amount of a compound of any of the embodiments and examples disclosed herein. In some embodiments, the animal can have a psychiatric disorder. In some embodiments, the psychiatric disorder can be a psychotic disorder, a neurological disorder, or a neurotic disorder. In some embodiments, the psychotic disorder can be schizophrenia. In some embodiments, the animal can have a disorder of the central nervous system. In some embodiments, the animal can have head trauma, brain trauma or cerebrovascular disease. In some embodiments, the cerebrovascular disease can be vascular dementia. In some embodiments, the animal can have attention deficit disorder. In some embodiments, the animal has an affective disorder the cerebrovascular disease is vascular dementia the mild cognitive impairment is associated with depression.

The present embodiments provide for a method for treating a psychiatric disorder in an animal comprising administering to an animal in need thereof an effective amount of a compound of any of the embodiments and examples disclosed herein. In some embodiments, the psychiatric disorder can be a disorder of the central nervous system. In some embodiments, the disorder of the central nervous system can be age-associated memory impairment, mild cognitive impairment, Alzheimer's disease or Parkinson's disease. In some embodiments, the psychiatric disorder can be associated with head trauma, brain trauma or cerebrovascular disease. In some embodiments, the psychiatric disorder can be attention deficit disorder. In some embodiments, the psychiatric disorder can be an affective disorder. In some embodiments, the cerebrovascular disease can be vascular dementia. In some embodiments, the psychiatric disorder can be depression.

The present embodiments provide for a use of a compound of any of compound of any of the embodiments and examples disclosed herein, or a pharmaceutically acceptable salt or prodrug ester thereof, for the manufacture of a medicament useful for improving cognitive function in an animal.

The present embodiments provide for a use of a compound of any of the embodiments and examples disclosed herein, or a pharmaceutically acceptable salt or prodrug ester thereof, for the manufacture of a medicament useful for inhibiting MAO receptors in an animal.

The present embodiments provide for a use of a compound of any of the embodiments and examples disclosed herein, or a pharmaceutically acceptable salt or prodrug ester thereof, for the manufacture of a medicament useful for activating the CREB pathway in an animal.

The present embodiments provide for a use of a compound of any of the embodiments and examples disclosed herein, or a pharmaceutically acceptable salt or prodrug ester thereof, for the manufacture of a medicament useful for treating a psychiatric disorder in an animal.

DETAILED DESCRIPTION OF THE INVENTION

Definitions

As used herein, common organic abbreviations are defined as follows:
Ac Acetyl
aq. Aqueous
Bu n-Butyl
cat. Catalytic
CDI 1,1'-carbonyldiimidazole
° C. Temperature in degrees Centigrade
Dowtherm® eutectic mixture of diphenyl ether and biphenyl
DBN 1,5-Diazabicyclo[4.3.0]non-5-ene
DBU 1,8-Diazabicyclo[5.4.0]undec-7-ene
DIEA Diisopropylethylamine
DMA Dimethylacetamide
DMF N,N'-Dimethylformamide
DMSO Dimethylsulfoxide
Et Ethyl
g Gram(s)
h Hour (hours)
HPLC High performance liquid chromatography
iPr or isopr Isopropyl
LCMS Liquid chromatography-mass spectrometry
Me Methyl
MeOH Methanol
mL Milliliter(s)
Pd/C Palladium on activated carbon
ppt Precipitate
rt Room temperature
TEA Triethylamine
Tert, t tertiary
THF tetrahydrofuran
μL Microliter(s)

The term "halo" used herein refers to fluoro, chloro, bromo, or iodo. As used herein, the term "alkyl" refers to an aliphatic hydrocarbon group. The alkyl moiety may or may not be a "saturated alkyl" group, i.e., one that does not contain any alkene or alkyne moieties. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety may be branched, straight chain, or cyclic. Examples of branched alkyl groups include, but are not limited to, isopropyl, sec-butyl, t-butyl and the like. Examples of straight chain alkyl groups include, but are not limited to, methyl, ethyl, propyl, butyl, pentyl, hexyl, heptyl, and the like. Examples of cycloalkyl groups include, but are not limited to, cyclopropyl, cyclobutyl, cyclopentyl, cyclohexyl, cycloheptyl, and the like.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "alkoxycarbonyl" used herein refers to an alkoxy radical covalently bonded to the parent molecule through a carbonyl linkage. Examples of alkoxycarbonyl groups include, but are not limited to, methylOC(O)—, ethylOC(O)—, propylOC(O)—, isopropylOC(O)—, butylOC(O)—, n-butylOC(O)—, sec-butylOC(O)—, t-butylOC(O)— and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

The term "aryl" used herein refers to homocyclic aromatic radical whether one ring or multiple fused rings. Moreover, the term "aryl" includes fused ring systems wherein at least two aryl rings, or at least one aryl and an ortho-fused bicyclic carbocyclic radical having about nine to ten ring atoms in which at least one ring is aromatic share at least one chemical bond. Examples of "aryl" rings include, but are not limited to, optionally substituted phenyl, biphenyl, naphthalenyl, phenanthrenyl, anthracenyl, tetralinyl, fluorenyl, indenyl, and indanyl.

The term, "heterocycle" or "heterocycle group" used herein refers to an optionally substituted monocyclic, bicyclic, or tricyclic ring system comprising at least one heteroatom in the ring system backbone. The heteroatoms are independently selected from oxygen, sulfur, and nitrogen. The term, "heterocycle" includes multiple fused ring systems. Moreover, the term "heterocycle" includes fused ring systems that may have any degree of saturation provided that at least one ring in the ring system is not aromatic. The monocyclic, bicyclic, or tricyclic ring system may be substituted or unsubstituted, and can be attached to other groups via any available valence, preferably any available carbon or nitrogen. Preferred monocyclic ring systems are of 3 to 8 members. Six membered monocyclic rings contain from up to three heteroatoms wherein each heteroatom is individually selected from oxygen, sulfur, and nitrogen, and wherein when the ring is five membered, preferably it has one or two heteroatoms wherein each heteroatom is individually selected from oxygen, sulfur, and nitrogen. Preferred bicyclic cyclic ring systems are of 7 to 12 members and include spirocycles. An example of an optional substituent includes, but is not limited to, oxo (=O).

The term "heteroaryl" used herein refers to an aromatic heterocyclic group, whether one ring or multiple fused rings. In fused ring systems, the one or more heteroatoms may be present in only one of the rings, or in two or more rings. Examples of heteroaryl groups include, but are not limited to, benzothiazyl, benzoxazyl, quinazolinyl, quinolinyl, isoquinolinyl, quinoxalinyl, pyridyl, pyrrolyl, oxazolyl, indolyl, thienyl, and the like. The term "heterocycle" encompasses heteroaryl fused to a non-aromatic ring system.

The term "heteroatom" used herein refers to, for example, O (oxygen), S (sulfur) and N (nitrogen).

The term "heteroatom group" used herein refers to a radical containing a "heteroatom" optionally substituted with a substituent. The "heteroatom group" is covalently bonded to the parent molecule through the "heteroatom." Examples of a "heteroatom group" includes, but is not limited to, O (oxygen), S (sulfur), S(O), S(O)$_2$, NH and N (nitrogen) substituted with a group selected from, but are not limited to, (C$_1$-C$_6$)alkyl, aryl, heteroaryl, (C$_1$-C$_6$)alkylsulfonyl, arylsulfonyl, (C$_1$-C$_6$)alkylC(O)—, arylC(O)—, hydroxy(C$_1$-C$_6$)alkyl, alkoxy(C$_1$-C$_6$)alkyl, heterocycle, (C$_1$-C$_6$)alkylOC(O)—, (C$_1$-C$_6$)alkylaminocarbonyl, and arylaminocarbonyl. When the "heteroatom group" is incorporated as a part of a 3-8 membered monocyclic or a 7-12 membered bicyclic ring system, each "heteroatom" within the "heteroatom group" is covalently bonded twice as part of the ring system. For example, when O (oxygen) is incorporated in a ring system, the oxygen is covalently bonded twice to provide an ether type linkage, this type of ring system includes, but is not limited to, morpholinyl and the like. In another example, when N (nitrogen) substituted with (C$_1$-C$_6$)alkyl is incorporated in a ring system, the nitrogen is covalently bonded twice to provide an amine type linkage, this type of ring system includes, but is not limited to, N-methylpiperazinyl, N-ethylpiperazinyl, N-propylpiperazinyl, N-2-propylpiperazinyl, N-butylpiperazinyl, N-2-butylpiperazinyl, N-pentylpiperazinyl, N-hexylpiperazinyl, and the like. In some embodiments, a "heteroatom group" can be a "heteroatom." In other embodiments, a "heteroatom group" is a "heteroatom" with a substituent, for example the substituent can be another heteroatom or a group as disclosed herein.

The term "amino" used herein refers to a nitrogen radical substituted with hydrogen, alkyl, aryl, or combinations thereof. Examples of amino groups include, but are not limited to, —NHMethyl, —NH$_2$, —NMethyl$_2$, —NPhenylMethyl, —NHPhenyl, —NEthylMethyl, and the like. An "alkylamino" refers to a nitrogen radical substituted with at least one alkyl group. Examples of alkylamino groups include, but are not limited to, —NHMethyl, —NMethyl$_2$, —NPropylMethyl, —NHButyl, —NEthylMethyl, —NPhenylMethyl, and the like. An "arylamino" refers to a nitrogen radical substituted with at least one aryl group. Examples of alkylamino groups include, but are not limited to, —NPhenylMethyl, —NHPhenyl, and the like.

The term "alkylaminocarbonyl" used herein refers to an alkylamino radical covalently bonded to the parent molecule through the carbon of a "carbonyl" group. Examples of alkylaminocarbonyl groups include, but are not limited to, —C(O)NHMethyl, —C(O)NMethyl$_2$, —C(O)NPropylMethyl, —C(O)NHButyl, —C(O)NEthylMethyl, —C(O)NPhenylMethyl, and the like.

The term "arylaminocarbonyl" used herein refers to an alkylamino radical covalently bonded to the parent molecule through the carbon of a "carbonyl" group. Examples of arylaminocarbonyl groups include, but are not limited to, —C(O)NPhenylMethyl, —C(O)NHPhenyl, and the like.

The term "arylalkyl" used herein refers to one or more aryl groups appended to an alkyl radical. Examples of arylalkyl groups include, but are not limited to, benzyl, phenethyl, phenpropyl, phenbutyl, and the like.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S— linkage. Examples of alkylthio groups include, but are not limited to, methylsulfanyl, ethylsulfanyl, propylsulfanyl, isopropylsulfanyl, cyclopropylsulfanyl, butylsulfanyl, n-butylsulfanyl, sec-butylsulfanyl, t-butylsulfanyl, cyclobutylsulfanyl and the like.

The term "alkylsulfonyl" used herein refers to straight or branched chain alkyl radical covalently bonded to the parent molecule through an —S— linkage where the sulfur is substituted with two oxygen atoms. Examples of alkylsulfonyl groups include, but are not limited to, methylsulfonyl, ethylsulfonyl, propylsulfonyl, isopropylsulfonyl, cyclopropylsulfonyl, butylsulfonyl, n-butylsulfonyl, sec-butylsulfonyl, t-butylsulfonyl, cyclobutylsulfonyl and the like.

The term "arylsulfonyl" used herein refers to optionally substituted aryl radical covalently bonded to the parent molecule through an —S— linkage where the sulfur is substituted with two oxygen atoms. Examples of optionally substituted arylsulfonyl groups include, but are not limited to, phenylsulfonyl, trifluoromethylphenylsulfonyl, methoxyphenylsulfonyl, methylphenylsulfonyl, cyanophenylsulfonyl, fluorophenylsulfonyl, chlorophenylsulfonyl, bromophenylsulfonyl, biphenylsulfonyl, naphthalenylsulfonyl, phenanthrenylsulfonyl, anthracenylsulfonyl, tetralinylsulfonyl, fluorenylsulfonyl, indenylsulfonyl, and indanylsulfonyl propyl, isopropylsulfonyl, cyclopropylsulfonyl, butylsulfonyl, n-butylsulfonyl, sec-butylsulfonyl, t-butylsulfonyl, cyclobutylsulfonyl and the like.

The term "carbonyl" used herein refers to C=O (i.e. carbon double bonded to oxygen).

The term "oxo" used herein refers to =O (i.e. double bond to oxygen). For example, cyclohexane substituted with "oxo" is cyclohexanone.

The term "alkanoyl" used herein refers to a "carbonyl" substituted with an "alkyl" group, the "alkanoyl" group is covalently bonded to the parent molecule through the carbon of the "carbonyl" group. Examples of alkanoyl groups include, but are not limited to, methanoyl, ethanoyl, propanoyl, and the like. Methanoyl is commonly known as acetyl.

The term, "heterocyclealkanoyl" used herein refers to a "alkanoyl" substituted with an "heterocycle" group, the "heterocycle" group is covalently bonded to the parent molecule through the carbonyl of the "alkanoyl" group. Examples of heterocyclealkanoyl groups include, but are not limited to, 2-(piperidin-1-yl)acetyl, 2-(morpholin-4-yl)acetyl, 2-(piperazin-1-yl)acetyl, 2-(4-methylpiperazin-1-yl)acetyl, 3-(piperidin-1-yl)propanoyl, 3-(morpholin-4-yl)propanoyl, 3-(piperazin-1-yl)propanoyl, 3-(4-methylpiperazin-1-yl)propanoyl, 3-(2,6-dimethylpiperidin-1-yl)propanoyl, 3-(3,5-dimethylmorpholin-4-yl)propanoyl, 3-(pyrrolidin-1-yl)propanoyl, 2-(pyrrolidin-1-yl)acetyl, 2-(azetidin-1-yl)acetyl, 3-(azetidin-1-yl)propanoyl, ethanoyl, propanoyl, and the like.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, a substituted group is derived from the unsubstituted parent structure in which there has been an exchange of one or more hydrogen atoms for another atom or group.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and pro-drug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound.

The term "pro-drug ester" refers to derivatives of the compounds disclosed herein formed by the addition of any of several ester-forming groups that are hydrolyzed under physiological conditions. Examples of pro-drug ester groups include, but are not limited to fatty acid esters, pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

Where a dashed line (----) appears in a structure, the dashed line represents a bond that is optionally present (in accordance with the rules of valency), indicating, together with the single bond to which it is adjacent, either a single or double bond. A dashed line encircling the inside of a ring indicates that the ring is optionally aromatic or heteroaromatic.

The term "animal" as used herein includes birds, reptiles, and mammals (e.g. domesticated mammals and humans).

The terms "individual," "host," "subject," and "patient" are used interchangeably herein, and refer to a mammal, including, but not limited to, murines, simians, humans, mammalian farm animals, mammalian sport animals, and mammalian pets.

The term "selectively inhibiting" as used herein means that a compound inhibits the activity of MAO-B to a greater extent than it inhibits the activity of MAO-A (in vitro or in vivo). In one embodiment of the invention, the compound of formula I inhibits the activity of MAO-B two times more than it inhibits the activity of MAO-A. In another embodiment of the invention, the compound of formula I inhibits the activity of MAO-B five times more than it inhibits the activity of MAO-A. In another embodiment of the invention, the compound of formula I inhibits the activity of MAO-B ten times more than it inhibits the activity of MAO-A. In another embodiment of the invention, the compound of formula I inhibits the activity of MAO-B one hundred times more than it inhibits the activity of MAO-A.

The term "psychiatric disorder" as used herein includes psychotic disorders, neurological disorders and neurotic disorders. The term includes schizophrenia, age-associated memory impairment (AAMI); mild cognitive impairment (MCI), delirium (acute confusional state); depression, dementia (sometimes further classified as Alzheimer's or non-Alzheimer's type dementia); Alzheimer's disease; Parkinson's disease; Huntington's disease (chorea); mental retardation; (e.g., Rubenstein-Taybi and Downs Syndrome); cerebrovascular disease (e.g., vascular dementia, post-cardiac surgery); affective disorders; psychotic disorders; autism (Kanner's Syndrome); neurotic disorders; attention deficit disorder (ADD); subdural hematoma; normal-pressure hydrocephalus; brain tumor; head trauma (postconcussional disorder) or brain trauma.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, stereoisomeric, or regioisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine MAO-B inhibiting activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

For example, $(C_1-C_6)$alkyl includes, but is not limited to, methyl, ethyl, propyl, isopropyl, butyl, iso-butyl, sec-butyl, pentyl, 3-pentyl, hexyl, and the like; $(C_2-C_6)$alkenyl includes, but is not limited to, vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, 5-hexenyl, and the like; $(C_2-C_6)$alkynyl includes, but is not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like; $(C_3-C_8)$cycloalkyl can be cyclopropyl, cyclobutyl, cyclopentyl, cyclohexyl, and the like; $(C_3-C_8)$cycloalkyl$(C_1-C_6)$alkyl includes, but is not limited to, cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl, and the like; $(C_1-C_6)$alkoxy includes, but is not limited to, methoxy, ethoxy, propoxy, isopropoxy, butoxy, iso-butoxy, sec-butoxy, pentoxy, 3-pentoxy, or hexyloxy; $(C_1-C_6)$alkyl optionally substituted with one or more cyano includes, but is not limited to, 2-cyanoethyl, 3-cyanopropyl, 2-cyanopropyl, 4-cyanobutyl, and the like; $(C_1-C_6)$alkylC(O)— includes, but is not limited to, acetyl, propanoyl butanoyl, and the like; $(C_1-C_6)$alkyl optionally substituted with one or more halo includes, but is not limited to, iodomethyl, bromomethyl, chloromethyl, fluoromethyl, trifluoromethyl, 2-chloroethyl, 2-fluoroethyl, 2,2,2-trifluoroethyl, pentafluoroethyl, and the like; $(C_1-C_6)$alkyl optionally substituted with one or more hydroxy includes, but is not limited to, hydroxymethyl, 2-hydroxyethyl, 2-hydroxypropyl, 2,4-hydroxybutyl, and the like; $(C_1-C_6)$alkylOC(O)— includes, but is not limited to, methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylC(O)O-includes, but is not limited to, acetoxy, propanoyloxy, butanoyloxy, isobutanoyloxy, pentanoyloxy, or hexanoyloxy; $(C_1-C_6)$alkoxy$(C_2-C_6)$alkyl includes, but is not limited to, 2-methoxyethyl, 2-ethoxyethyl, 2,2-dimethoxyethyl, 3-ethoxypropyl, 4,4-dimethoxybutyl; $(C_1-C_6)$alkylOC(O)$(C_1-C_6)$alkyl includes, but is not limited to, methoxycarbonylmethyl, ethoxycarbonylmethyl, methoxycarbonylethyl, or ethoxycarbonylethyl; aryl includes, but is not limited to, phenyl, indenyl, or naphthyl; and heteroaryl includes, but is not limited to, furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Processes for preparing compounds of formula I are provided as further embodiments of the invention and are illustrated by the following procedures in which the meanings of the generic radicals are as given above unless otherwise qualified.

Compounds of formula I can be prepared using the general synthetic schemes illustrated below.

Scheme 1

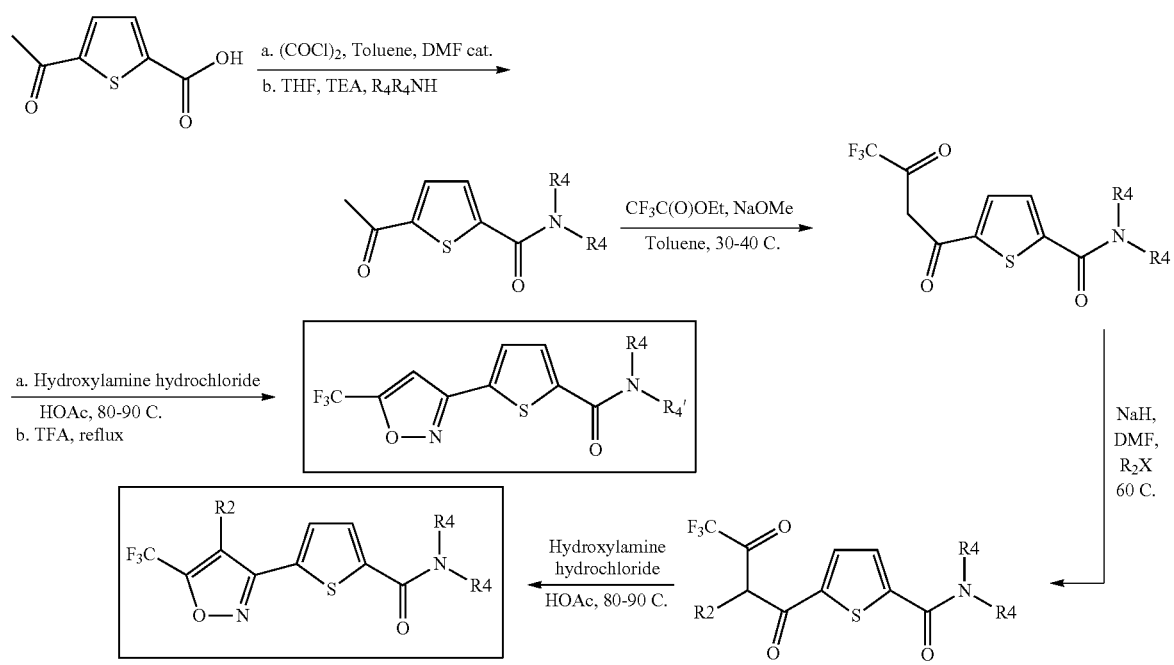

The thienyl carboxylic acid can be converted to an intermediate acid chloride followed by coupling with an appropriate amine to provide the desired product. The thienyl carboxylic acid can be treated with an appropriate chlorinating agent, with or without solvent, to provide an intermediate acid chloride which can be isolated or treated directly to provide the desired product. The thienyl carboxylic acid can be converted to an acid chloride using a chlorinating agent in the presence of solvent or neat. For example, the chlorinating agent can be selected from oxalyl chloride, thionyl chloride, phosphorus trichloride, phosphorus oxychloride, phosgene and phosgene equivalents, and the like. The solvent can be selected from methylene chloride, chloroform, benzene, toluene and the like. In a representative example, oxalyl chloride in the presence of catalytic DMF can convert the thienyl carboxylic acid to an acid chloride with toluene as the solvent.

The intermediate acid chloride can then be reacted with an amine in an appropriate solvent optionally in the presence of a base to provide the desired product. The solvent can be selected from methylene chloride, chloroform, benzene, toluene, THF, diethyl ether, dioxane, and the like. The base can be selected from triethylamine, diisopropylethyl amine, DBU, DBN, DMAP, pyridine, and the like and combinations thereof. In a representative example, the acid chloride can react with the appropriate amine in the presence of THF and triethylamine as a base to provide the desired product.

The amide can be condensed with ethyl trifluoroacetate in the presence of solvent and a base to provide a β-diketone. The solvent can be selected from methylene chloride, DMF, NMP, toluene and the like and combinations thereof. The base can be selected from sodium ethoxide, sodium methoxide, sodium tert-butoxide, potassium ethoxide, potassium methoxide, potassium tert-butoxide, sodium hydride, potassium hydride, and the like. In a representative example, the amide can react with ethyl trifluoroacetate in the presence of toluene and sodium ethoxide to provide the desired β-diketone.

The β-diketone can be converted to the isoxazole by reacting with hydroxylamine hydrochloride in an appropriate solvent, optionally, an additional step of refluxing with trifluoroacetic acid may be advantageous to complete the conversion. In a representative example, the β-diketone can react with hydroxylamine hydrochloride in the presence of acetic acid followed by reacting in the presence of trifluoroacetic acid at reflux to provide the desired isoxazole. In some embodiments a mixture of regioisomeric isoxazoles may form.

Alternatively, the β-diketone can be substituted at the α-position by an alkylation then converted to the isoxazole. The β-diketone can be reacted with an alkylating agent in an appropriate solvent and base to provide an α-substituted β-diketone. The alkylating agent can be selected from an optionally substituted alkylhalide, an optionally substituted alkylsulfonate and the like. The solvent can be selected from DMF, NMP, THF, dioxane, and the like and combinations thereof. The base can be selected from sodium ethoxide, sodium methoxide, sodium tert-butoxide, potassium ethoxide, potassium methoxide, potassium tert-butoxide, sodium hydride, potassium hydride, and the like. In a representative example, the β-diketone can react with an alkylhalide in DMF with sodium hydride as the base.

The α-substituted β-diketone can be converted to the isoxazole by reacting with hydroxylamine hydrochloride in an appropriate solvent. In a representative example, the α-substituted β-diketone can react with hydroxylamine hydrochloride in the presence of acetic acid. In some embodiments a mixture of regioisomeric isoxazoles may form.

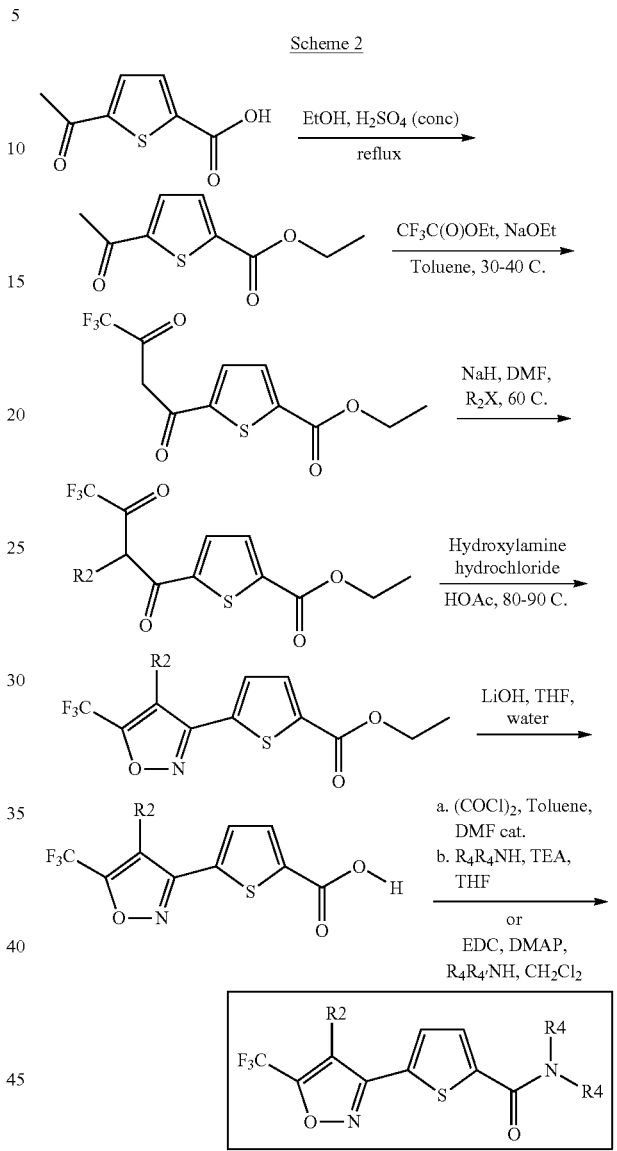

The thienyl carboxylic acid can be converted to an thienyl carboxylic ester by esterfication. For example the thienyl carboxylic acid can be converted to a thienyl carboxylic ester by treating the thienyl carboxylic acid with acid in the presence of an alcoholic solvent and heating. The acid can be hydrochloric acid, sulfuric acid and the like. The solvent can be methyl alcohol, ethyl alcohol, and the like. In a representative example, the thienyl carboxylic acid can react with ethyl alcohol at reflux in the presence of sulfuric acid to provide the thienyl carboxylic ester. The thienyl carboxylic ester can be condensed with ethyl trifluoroacetate in the presence of solvent and a base to provide a β-diketone. The solvent can be selected from methylene chloride, DMF, NMP, toluene and the like and combinations thereof. The base can be selected from sodium ethoxide, sodium methoxide, sodium tert-butoxide, potassium ethoxide, potassium methoxide, potassium tert-butoxide, sodium hydride, potassium hydride, and the like. In a representative example, the ester can react with ethyl trifluoroacetate in the presence of toluene and sodium ethoxide to provide the desired β-diketone ester.

The β-diketone ester can be substituted at the α-position by an alkylation then converted to the isoxazole. The β-diketone ester can be reacted with an alkylating agent in an appropriate solvent and base to provide an α-substituted β-diketone. The alkylating agent can be selected from an optionally substituted alkylhalide, an optionally substituted alkylsulfonate and the like. The solvent can be selected from DMF, NMP, THF, dioxane, and the like and combinations thereof. The base can be selected from sodium ethoxide, sodium methoxide, sodium tert-butoxide, potassium ethoxide, potassium methoxide, potassium tert-butoxide, sodium hydride, potassium hydride, and the like. In a representative example, the β-diketone ester can react with an alkylhalide in DMF with sodium hydride as the base at around 60° C.

The α-substituted β-diketone ester can be converted to the isoxazole by reacting with hydroxylamine hydrochloride in an appropriate solvent. In a representative example, the α-substituted β-diketone ester can react with hydroxylamine hydrochloride in the presence of acetic acid to provide the α-substituted isoxazole ester. The α-substituted isoxazole ester can be converted to the α-substituted isoxazole carboxylic acid by acid or base catalyzed hydrolysis. The base catalyzed hydrolysis can be accomplished treating the α-substituted isoxazole ester with a base in an appropriate solvent in the presence of water. The base can be selected from sodium hydroxide, potassium hydroxide, lithium hydroxide, and the like. The solvent can be selected from, ethyl alcohol, methyl alcohol, THF, dioxane, DMF, NMP, and the like and combinations thereof. In a representative example, the ester in THF can be hydrolyzed by reacting with lithium hydroxide in the presence of water to provide an α-substituted isoxazole carboxylic acid.

The α-substituted isoxazole carboxylic acid can be converted to an intermediate acid chloride followed by coupling with an appropriate amine to provide the desired product. The α-substituted isoxazole carboxylic acid can be treated with an appropriate chlorinating agent, with or without solvent, to provide an intermediate acid chloride which can be isolated or treated directly to provide the desired product. The α-substituted isoxazole carboxylic acid can be converted to an acid chloride using a chlorinating agent in the presence of solvent or neat. For example, the chlorinating agent can be selected from oxalyl chloride, thionyl chloride, phosphorus trichloride, phosphorus oxychloride, phosgene and phosgene equivalents, and the like. The solvent can be selected from methylene chloride, chloroform, benzene, toluene and the like. In a representative example, oxalyl chloride in the presence of catalytic DMF can convert the α-substituted isoxazole carboxylic acid to an acid chloride with toluene as the solvent. The intermediate acid chloride can then be reacted with an amine in an appropriate solvent optionally in the presence of a base to provide the desired product. The solvent can be selected from methylene chloride, chloroform, benzene, toluene, THF, diethyl ether, dioxane, and the like. The base can be selected from triethylamine, diisopropylethyl amine, DBU, DBN, DMAP, pyridine, and the like and combinations thereof. In a representative example, the acid chloride can react with the appropriate amine in the presence of THF and triethylamine as a base to provide the desired product.

Alternatively, the α-substituted isoxazole carboxylic acid can be converted to the desired product using a coupling reaction. The α-substituted isoxazole carboxylic acid can be reacted with a coupling agent in the presence of a catalyst and the appropriate amine in the presence of a solvent to provide the desired product. The reaction can be optionally run in the presence of a base. The coupling agent can be selected from dicyclohexylcarbodiimide (DCC), diisopropylcarbodiimide (DIC), 1-ethyl-3-(3-dimethylaminopropyl) carbodiimide hydrochloride (EDC), O-Benzotriazole-N,N,N',N'-tetramethyl-uronium-hexafluoro-phosphate (HBTU), O-(7-Azabenzotriazol-1-yl)-N,N,N',N'-tetramethyluronium hexafluorophosphate (HATU), O-(Benzotriazol-1-yl)-N,N,N',N'-tetramethyluronium tetrafluoroborate (TBTU), (Benzotriazol-1-yloxy)tripyrrolidinophosphonium hexafluorophosphate (PyBOP), Bromo-tris-pyrrolidinophosphonium hexafluorophosphate (PyBrOP), and the like. The catalyst can be selected from DMAP, 1-hydroxy-benzotriazole (HOBt), 1-hydroxy-7-aza-benzotriazole (HOAt) and the like. The solvent can be selected from methylene chloride, chloroform, DMF, NMP, THF, EtOAc, pyridine and the like. The base can be selected from triethylamine, diisopropylethylamine and the like. In a representative example, the α-substituted isoxazole carboxylic acid can react with the appropriate amine in the presence of methylene chloride using EDC as the coupling agent and DMAP as the catalyst.

Scheme 3

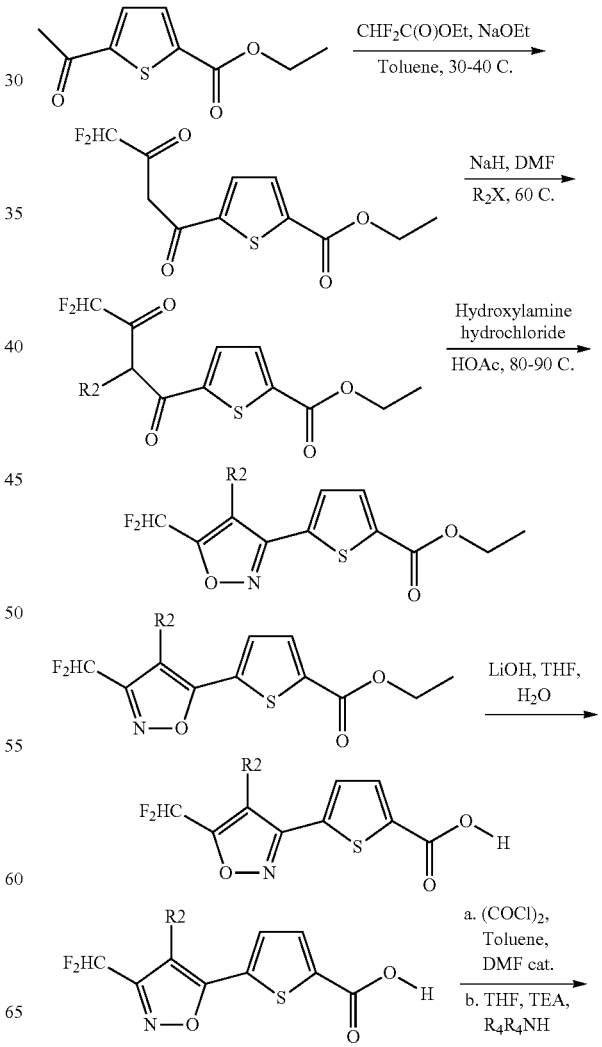

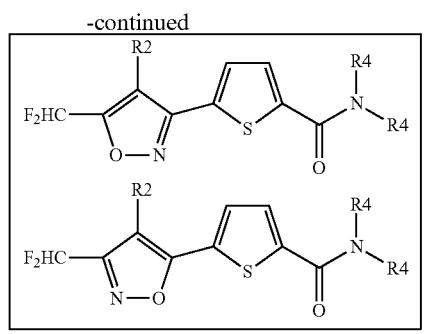

The thienyl carboxylic ester can be condensed with ethyl difluoroacetate in the presence of solvent and a base to provide a β-diketone. The solvent can be selected from methylene chloride, DMF, NMP, toluene and the like and combinations thereof. The base can be selected from sodium ethoxide, sodium methoxide, sodium tert-butoxide, potassium ethoxide, potassium methoxide, potassium tert-butoxide, sodium hydride, potassium hydride, and the like. In a representative example, the ester can react with ethyl difluoroacetate in the presence of toluene and sodium ethoxide to provide the desired β-diketone ester.

The β-diketone ester can be substituted at the α-position by an alkylation then converted to the isoxazole. The β-diketone ester can be reacted with an alkylating agent in an appropriate solvent and base to provide an α-substituted β-diketone. The alkylating agent can be selected from an optionally substituted alkylhalide, an optionally substituted alkylsulfonate and the like. The solvent can be selected from DMF, NMP, THF, dioxane, and the like and combinations thereof. The base can be selected from sodium ethoxide, sodium methoxide, sodium tert-butoxide, potassium ethoxide, potassium methoxide, potassium tert-butoxide, sodium hydride, potassium hydride, and the like. In a representative example, the β-diketone ester can react with an alkylhalide in DMF with sodium hydride as the base at around 60° C.

The α-substituted β-diketone ester can be converted to the isoxazole by reacting with hydroxylamine hydrochloride in an appropriate solvent. In a representative example, the α-substituted β-diketone ester can react with hydroxylamine hydrochloride in the presence of acetic acid to provide the α-substituted isoxazole ester. In some embodiments a mixture of regioisomeric isoxazoles may form. The regioisomeric isoxazoles may be separated and individually taken through the remaining steps or taken through the remaining steps as the mixture.

The α-substituted isoxazole ester can be converted to the α-substituted isoxazole carboxylic acid by acid or base catalyzed hydrolysis. The base catalyzed hydrolysis can be accomplished treating the α-substituted isoxazole ester with a base in an appropriate solvent in the presence of water. The base can be selected from sodium hydroxide, potassium hydroxide, lithium hydroxide, and the like. The solvent can be selected from, ethyl alcohol, methyl alcohol, THF, dioxane, DMF, NMP, and the like and combinations thereof. In a representative example, the ester in THF can be hydrolyzed by reacting with lithium hydroxide in the presence of water to provide an α-substituted isoxazole carboxylic acid.

The α-substituted isoxazole carboxylic acid can be converted to an intermediate acid chloride followed by coupling with an appropriate amine to provide the desired product. The α-substituted isoxazole carboxylic acid can be treated with an appropriate chlorinating agent, with or without solvent, to provide an intermediate acid chloride which can be isolated or treated directly to provide the desired product. The α-substituted isoxazole carboxylic acid can be converted to an acid chloride using a chlorinating agent in the presence of solvent or neat. For example, the chlorinating agent can be selected from oxalyl chloride, thionyl chloride, phosphorus trichloride, phosphorus oxychloride, phosgene and phosgene equivalents, and the like. The solvent can be selected from methylene chloride, chloroform, benzene, toluene and the like. In a representative example, oxalyl chloride in the presence of catalytic DMF can convert the α-substituted isoxazole carboxylic acid to an acid chloride with toluene as the solvent. The intermediate acid chloride can then be reacted with an amine in an appropriate solvent optionally in the presence of a base to provide the desired product. The solvent can be selected from methylene chloride, chloroform, benzene, toluene, THF, diethyl ether, dioxane, and the like. The base can be selected from triethylamine, diisopropylethyl amine, DBU, DBN, DMAP, pyridine, and the like and combinations thereof. In a representative example, the acid chloride can react with the appropriate amine in the presence of THF and triethylamine as a base to provide the desired product.

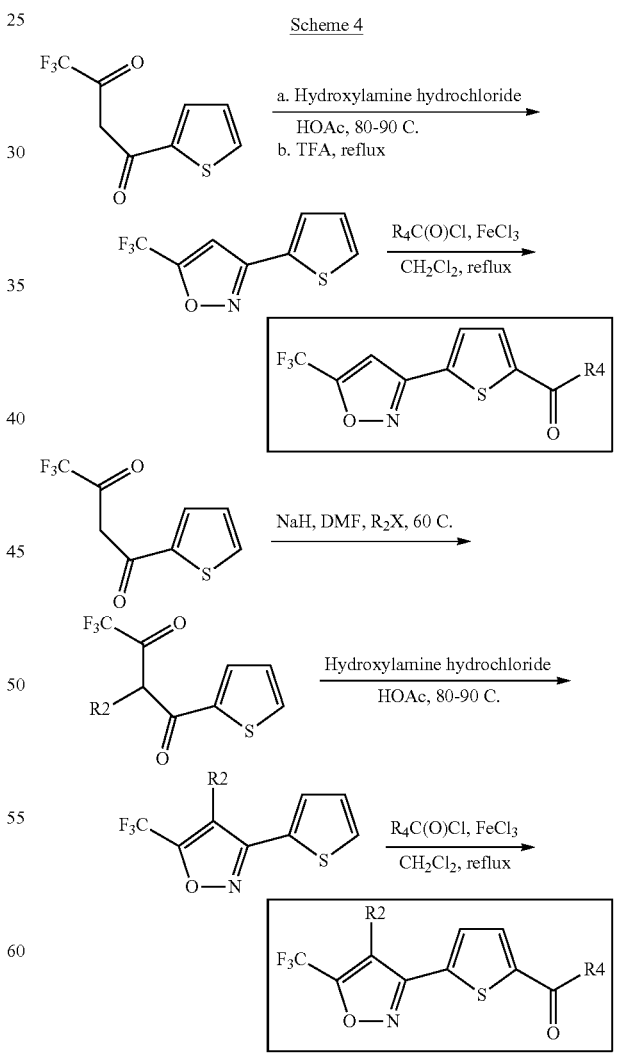

The thienyl β-diketone can be converted to the thienyl isoxazole by reacting with hydroxylamine hydrochloride in an appropriate solvent, optionally, an additional step of refluxing with trifluoroacetic acid may be advantageous to complete the conversion. In a representative example, the β-diketone can react with hydroxylamine hydrochloride in the presence of acetic acid followed by reacting in the presence of trifluoroacetic acid at reflux to provide the desired thienyl isoxazole.

The thienyl isoxazole can undergo a Friedel-Crafts acylation reaction with an acid chloride and a Lewis acid in an appropriate solvent. The Lewis acid can selected from AlCl₃, TiCl₄, FeCl₃ and the like. The solvent can be selected from methylene chloride, nitrobenzene carbon disulfide and the like. In a representative example, the thienyl isoxazole can react in methylene chloride with an acid chloride in the presence of FeCl₃ under reflux to provide the desired product.

The thienyl β-diketone can be substituted at the α-position by an alkylation then converted to the isoxazole. The thienyl β-diketone can be reacted with an alkylating agent in an appropriate solvent and base to provide an α-substituted thienyl β-diketone. The alkylating agent can be selected from an optionally substituted alkylhalide, an optionally substituted alkylsulfonate and the like. The solvent can be selected from DMF, NMP, THF, dioxane, and the like and combinations thereof. The base can be selected from sodium ethoxide, sodium methoxide, sodium tert-butoxide, potassium ethoxide, potassium methoxide, potassium tert-butoxide, sodium hydride, potassium hydride, and the like. In a representative example, the thienyl β-diketone ester can react with an alkylhalide in DMF with sodium hydride as the base at about 60° C.

The α-substituted thienyl β-diketone can be converted to the isoxazole by reacting with hydroxylamine hydrochloride in an appropriate solvent. In a representative example, the α-substituted thienyl β-diketone can react with hydroxylamine hydrochloride in the presence of acetic acid to provide the α-substituted thienyl isoxazole.

The α-substituted thienyl isoxazole can undergo a Friedel-Crafts acylation reaction with an acid chloride and a Lewis acid in an appropriate solvent. The Lewis acid can selected from AlCl₃, TiCl₄, FeCl₃ and the like. The solvent can be selected from methylene chloride, nitrobenzene carbon disulfide and the like. In a representative example, the α-substituted thienyl isoxazole can react in methylene chloride with an acid chloride in the presence of FeCl₃ under reflux to provide the desired α-substituted thienyl isoxazole ketone product.

Scheme 5

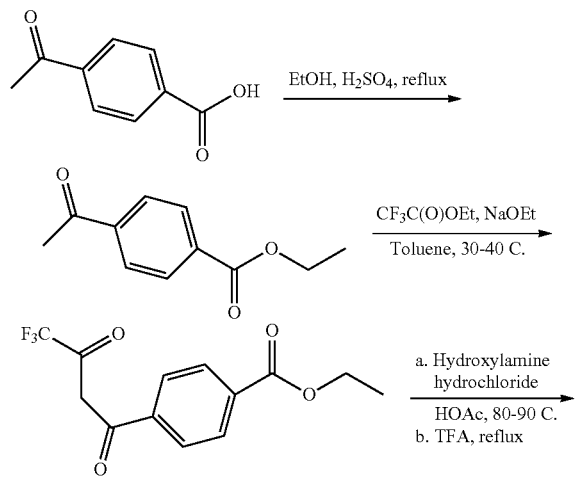

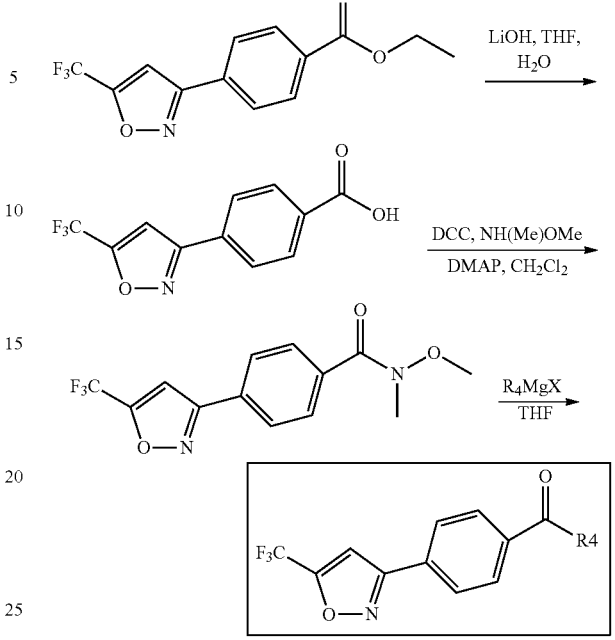

4-Acetylbenzoic acid can be converted to 4-acetylbenzoic ester by esterfication. For example the 4-acetylbenzoic acid can be converted to 4-acetylbenzoic ester by treating 4-acetylbenzoic acid with acid in the presence of an alcoholic solvent and heating. The acid can be hydrochloric acid, sulfuric acid and the like. The solvent can be methyl alcohol, ethyl alcohol, and the like. In a representative example, the 4-acetylbenzoic acid can react with ethyl alcohol at reflux in the presence of sulfuric acid to provide ethyl 4-acetylbenzoate.

The ethyl 4-acetylbenzoate can be condensed with a β-ketoester in the presence of solvent and a base to provide a β-diketone. The solvent can be selected from methylene chloride, DMF, NMP, toluene and the like and combinations thereof. The base can be selected from sodium ethoxide, sodium methoxide, sodium tert-butoxide, potassium ethoxide, potassium methoxide, potassium tert-butoxide, sodium hydride, potassium hydride, and the like. In a representative example, the amide can react with ethyl trifluoroacetate in the presence of toluene and sodium ethoxide to provide the desired β-diketone ester.

The β-diketone ester can be substituted at the α-position by an alkylation then converted to the isoxazole. The β-diketone ester can be reacted with an alkylating agent in an appropriate solvent and base to provide an α-substituted β-diketone. The alkylating agent can be selected from an optionally substituted alkylhalide, an optionally substituted alkylsulfonate and the like. The solvent can be selected from DMF, NMP, THF, dioxane, and the like and combinations thereof. The base can be selected from sodium ethoxide, sodium methoxide, sodium tert-butoxide, potassium ethoxide, potassium methoxide, potassium tert-butoxide, sodium hydride, potassium hydride, and the like.

If no substitution at the α-position is required, the β-diketone can be converted directly to the isoxazole by reacting with hydroxylamine hydrochloride in an appropriate solvent. Optionally, an additional step of refluxing with trifluoroacetic acid may be advantageous to complete the conversion. In a representative example, the β-diketone can react with hydroxylamine hydrochloride in the presence of acetic acid followed by reacting in the presence of trifluoroacetic acid at reflux to provide the desired isoxazole benzoic ester. In some embodiments a mixture of regioisomeric isoxazole benzoic esters may form.

The isoxazole benzoic ester can be converted to the isoxazole benzoic acid by acid or base catalyzed hydrolysis. The base catalyzed hydrolysis can be accomplished treating the isoxazole benzoic ester with a base in an appropriate solvent in the presence of water. The base can be selected from sodium hydroxide, potassium hydroxide, lithium hydroxide, and the like. The solvent can be selected from, ethyl alcohol, methyl alcohol, THF, dioxane, DMF, NMP, and the like and combinations thereof. In a representative example, the isoxazole benzoic ester in THF can be hydrolyzed by reacting with lithium hydroxide in the presence of water to provide an isoxazole benzoic acid.

The isoxazole benzoic acid can be converted to an intermediate isoxazole benzoic N,O-dimethylamide (i.e. Weinreb amide) followed by an organometallic reaction to provide an isoxazole ketone.

The isoxazole benzoic acid can be can be converted to the isoxazole benzoic N,O-dimethylamide using a coupling reaction. The isoxazole benzoic acid can be reacted with a coupling agent in the presence of a catalyst and N,O-Dimethylhydroxylamine hydrochloride in the presence of a solvent to provide the desired product. The reaction can be optionally run in the presence of a base. The coupling agent can be selected from dicyclohexylcarbodiimide (DCC), diisopropylcarbodiimide (DIC), 1-ethyl-3-(3-dimethylaminopropyl) carbodiimide hydrochloride (EDC), O-Benzotriazole-N,N,N',N'-tetramethyl-uronium-hexafluoro-phosphate (HBTU), O-(7-Azabenzotriazol-1-yl)-N,N,N',N'-tetramethyluronium hexafluorophosphate (HATU), O-(Benzotriazol-1-yl)-N,N,N',N'-tetramethyluronium tetrafluoroborate (TBTU), (Benzotriazol-1-yloxy)tripyrrolidinophosphonium hexafluorophosphate (PyBOP), Bromo-tris-pyrrolidinophosphonium hexafluorophosphate (PyBrOP), and the like. The catalyst can be selected from DMAP, 1-hydroxy-benzotriazole (HOBt), 1-hydroxy-7-aza-benzotriazole (HOAt) and the like. The solvent can be selected from methylene chloride, chloroform, DMF, NMP, THF, EtOAc, pyridine and the like. The base can be selected from triethylamine, diisopropylethylamine and the like. In a representative example, the isoxazole benzoic acid can react with N,O-Dimethylhydroxylamine hydrochloride in the presence of methylene chloride using DCC as the coupling agent and DMAP as the catalyst to provide the isoxazole benzoic N,O-dimethylamide.

The isoxazole benzoic N,O-dimethylamide can react with an organometallic reagent in an appropriate solvent to provide a isoxazole phenylketone. The organometetallic reagent can be a Grignard reagent, alkyl zinc and the like. The solvent can be THF, dioxane, diethyl ether and the like. In a representative example, the isoxazole benzoic N,O-dimethylamide can react with a Grignard reagent in THF to provide an isoxazole phenylketone.

Scheme 6

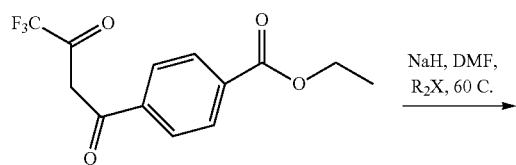

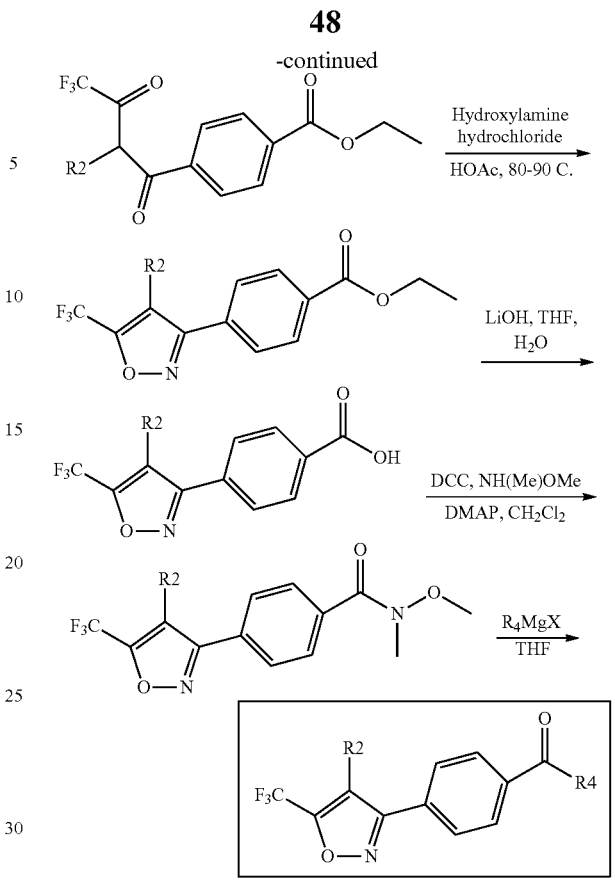

The β-diketone benzoic ester can be substituted at the α-position by an alkylation then converted to the isoxazole. The β-diketone benzoic ester can be reacted with an alkylating agent in an appropriate solvent and base to provide an α-substituted β-diketone benzoic ester. The alkylating agent can be selected from an optionally substituted alkylhalide, an optionally substituted alkylsulfonate and the like. The solvent can be selected from DMF, NMP, THF, dioxane, and the like and combinations thereof. The base can be selected from sodium ethoxide, sodium methoxide, sodium tert-butoxide, potassium ethoxide, potassium methoxide, potassium tert-butoxide, sodium hydride, potassium hydride, and the like.

The α-substituted β-diketone benzoic ester can be converted to the α-substituted isoxazole benzoic ester by reacting with hydroxylamine hydrochloride in an appropriate solvent. In a representative example, the α-substituted β-diketone ester can react with hydroxylamine hydrochloride in the presence of acetic acid to provide the substituted isoxazole benzoic ester. In some embodiments a mixture of regioisomeric isoxazoles may form.

The substituted isoxazole benzoic ester can be converted to the substituted isoxazole benzoic acid by acid or base catalyzed hydrolysis. The base catalyzed hydrolysis can be accomplished treating the substituted isoxazole benzoic ester with a base in an appropriate solvent in the presence of water. The base can be selected from sodium hydroxide, potassium hydroxide, lithium hydroxide, and the like. The solvent can be selected from, ethyl alcohol, methyl alcohol, THF, dioxane, DMF, NMP, and the like and combinations thereof. In a representative example, the ester in THF can be hydrolyzed by reacting with lithium hydroxide in the presence of water to provide a substituted isoxazole benzoic acid.

The substituted isoxazole benzoic acid can be converted to an intermediate substituted isoxazole benzoic N,O-dimethylamide (i.e. Weinreb amide) followed by an organometallic reaction to provide a substituted isoxazole ketone.

The substituted isoxazole benzoic acid can be can be converted to the substituted isoxazole benzoic N,O-dimethylamide using a coupling reaction. The substituted isoxazole benzoic acid can be reacted with a coupling agent in the presence of a catalyst and N,O-dimethylhydroxylamine hydrochloride in the presence of a solvent to provide the desired product. The reaction can be optionally run in the presence of a base. The coupling agent can be selected from dicyclohexylcarbodiimide (DCC), diisopropylcarbodiimide (DIC), 1-ethyl-3-(3-dimethylaminopropyl) carbodiimide hydrochloride (EDC), O-Benzotriazole-N,N,N',N'-tetramethyl-uronium-hexafluoro-phosphate (HBTU), O-(7-Azabenzotriazol-1-yl)-N,N,N',N'-tetramethyluronium hexafluorophosphate (HATU), O-(Benzotriazol-1-yl)-N,N,N',N'-tetramethyluronium tetrafluoroborate (TBTU), (Benzotriazol-1-yloxy)tripyrrolidinophosphonium hexafluorophosphate (PyBOP), Bromo-tris-pyrrolidinophosphonium hexafluorophosphate (PyBrOP), and the like. The catalyst can be selected from DMAP, 1-hydroxy-benzotriazole (HOBt), 1-hydroxy-7-aza-benzotriazole (HOAt) and the like. The solvent can be selected from methylene chloride, chloroform, DMF, NMP, THF, EtOAc, pyridine and the like. The base can be selected from triethylamine, diisopropylethylamine and the like. In a representative example, the isoxazole benzoic acid can react with N,O-Dimethylhydroxylamine hydrochloride in the presence of methylene chloride using DCC as the coupling agent and DMAP as the catalyst to provide the substituted isoxazole benzoic N,O-dimethylamide.

The substituted isoxazole benzoic N,O-dimethylamide can react with an organometallic reagent in an appropriate solvent to provide a isoxazole phenylketone. The organometetallic reagent can be a Grignard reagent, dialkyl zinc and the like. The solvent can be THF, dioxane, diethyl ether and the like. In a representative example, the substituted isoxazole benzoic N,O-dimethylamide can react with a Grignard reagent in THF to provide an substituted isoxazole phenylketone.

Scheme 7

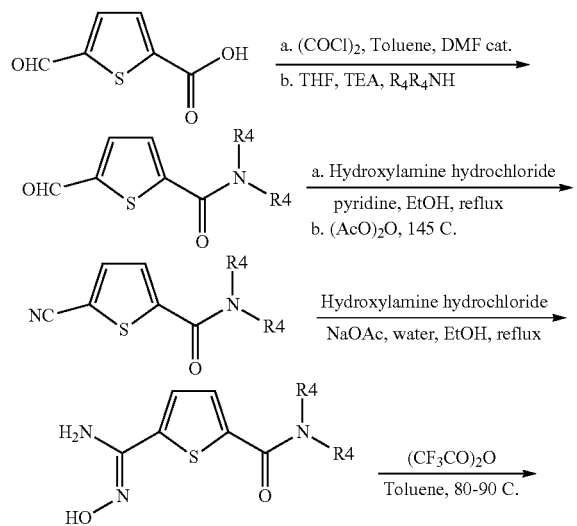

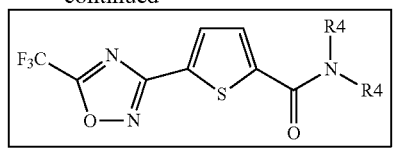

The thienyl carboxylic acid aldehyde can be converted to an intermediate thienyl acid chloride aldehyde followed by coupling with an appropriate amine to provide the desired product amide. The thienyl carboxylic acid can be treated with an appropriate chlorinating agent, with or without solvent, to provide an intermediate acid chloride which can be isolated or treated directly to provide the desired product. The thienyl carboxylic acid aldehyde can be converted to an acid chloride using a chlorinating agent in the presence of solvent or neat. For example, the chlorinating agent can be selected from oxalyl chloride, thionyl chloride, phosphorus trichloride, phosphorus oxychloride, phosgene and phosgene equivalents, and the like. The solvent can be selected from methylene chloride, chloroform, benzene, toluene and the like. In a representative example, oxalyl chloride in the presence of catalytic DMF can convert the thienyl carboxylic acid aldehyde to an thienyl carboxylic acid chloride aldehyde with toluene as the solvent.

The intermediate thienyl carboxylic acid chloride aldehyde can then be reacted with an amine in an appropriate solvent optionally in the presence of a base to provide the desired product amide. The solvent can be selected from methylene chloride, chloroform, benzene, toluene, THF, diethyl ether, dioxane, and the like. The base can be selected from triethylamine, diisopropylethyl amine, DBU, DBN, DMAP, pyridine, and the like and combinations thereof. In a representative example, the acid chloride can react with the appropriate amine in the presence of THF and triethylamine as a base to provide the desired product thienyl aldehyde amide.

The thienyl aldehyde amide can be converted to a thienyl nitrile amide in a two step process. The thienyl aldehyde amide can be reacted with hydroxylamine hydrochloride in an appropriate solvent in the presence of base followed by dehydration to provide a thienyl nitrile amide. In a representative example, the thienyl aldehyde amide can react with hydroxylamine hydrochloride in the presence of pyridine and ethyl alcohol under reflux to provide the intermediate thienyl hydroxyimine amide. The intermediate thienyl hydroxyimine amide can be dehydrated to provide the thienyl nitrile amide. The dehydrating reagent can be acetic anhydride and the like. In a representative example, the thienyl hydroxyimine amide can react with acetic anhydride at elevated temperature to provide the thienyl nitrile amide. The reaction temperature can be in the range of from about 80° C. to about 90° C.

The thienyl nitrile amide can be converted to the thienyl hydroxyamidine amide by reacting the thienyl nitrile amide with hydroxylamine hydrochloride under the appropriate conditions. The thienyl nitrile amide can be reacted with hydroxylamine hydrochloride, base, water and solvent to provide thienyl hydroxyamidine amide. The base can be sodium acetate, potassium acetate and the like. The solvent can be methyl alcohol, ethyl alcohol and the like. In a representative example, the thienyl nitrile amide can be reacted with hydroxylamine hydrochloride in the presence of sodium acetate, water and ethyl alcohol under reflux to provide the thienyl hydroxyamidine amide.

The thienyl hydroxyamidine amide can be converted to the azaisoxazole amide by reacting with trifluoroacetic anhydride in an appropriate solvent. In a representative example, the thienyl hydroxyamidine amide can be reacted with trifluoroacetic anhydride in the presence of toluene at elevated temperature. The reaction temperature can be in the range of from about 80° C. to about 90° C.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including but not limited to hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In certain aspects a prodrug form of the agent or compound may be administered to an individual in need thereof. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will often be in the range of from about 0.15 to about 100 mg/kg, e.g., from about 1 to about 75 mg/kg of body weight per day, such as 0.75 to about 50 mg per kilogram body weight of the recipient per day, preferably in the range of 1 to 90 mg/kg/day, most preferably in the range of 1 to 60 mg/kg/day.

The compound is conveniently administered in unit dosage form; for example, containing 1 to 1000 mg, conveniently 10 to 750 mg, most conveniently, 5 to 500 mg of active ingredient per unit dosage form.

Ideally, the active ingredient should be administered to achieve peak plasma concentrations of the active compound of from about 0.5 to about 7 µM, preferably, about 1 to 5 µM, most preferably, about 2 to about 3 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds of the invention can be administered to an animal for treatment of age-associated memory impairment, mild cognitive impairment, Alzheimer's disease, Parkinson's disease and related diseases. The compounds of the invention can be administered to a heathly animal or an aged animal to improve cognitative function in the animal. The compounds of the invention can be administered to an animal having a condition selected from schizophrenia, age-associated memory impairment (AAMI); mild cognitive impairment (MCI), delirium (acute confusional state); depression, dementia (sometimes further classified as Alzheimer's or non-Alzheimer's type dementia); Alzheimer's disease; Parkinson's disease; Huntington's disease (chorea); mental retardation; (e.g., Rubenstein-Taybi and Downs Syndrome); cerebrovascular disease (e.g., vascular dementia, post-cardiac surgery); affective disorders; psychotic disorders; autism (Kanner's Syndrome); neurotic disorders; attention deficit disorder (ADD); subdural hematoma; normal-pressure hydrocephalus; brain tumor; head trauma (postconcussional disorder), brain trauma (see DSM-IV, APA 1994) and the like.

The compounds of the invention can also optionally be administered in combination with one or more other therapeutic agents that are effective to improve cognition and/or one or more therapeutic agents that are effective to treat schizophrenia, age-associated memory impairment (AAMI); mild cognitive impairment (MCI), delirium (acute confusional state); depression, dementia (sometimes further classified as Alzheimer's or non-Alzheimer's type dementia); Alzheimer's disease; Parkinson's disease; Huntington's disease (chorea); mental retardation; (e.g., Rubenstein-Taybi and Downs Syndrome); cerebrovascular disease (e.g., vascular dementia, post-cardiac surgery); affective disorders; psychotic disorders; autism (Kanner's Syndrome); neurotic disorders; attention deficit disorder (ADD); subdural hematoma; normal-pressure hydrocephalus; brain tumor; head trauma (postconcussional disorder) or brain trauma (see DSM-IV, APA 1994).

The ability of a compound of the invention to act as an inhibitor of MAO-B can be determined using pharmacological models which are well known to the art, or using the following assay.

MAO Inhibition Assay

MAO enzymatic assay was performed according to the flurometric method described by Matsumoto and colleagues (Matsumoto, et. al., *Clin. Biochem.*, 1985 18, 126-129). with the following modifications. Human recombinant MAO-A and MAO-B expressed in insect cells were used. For both assays, test compound and/or vehicle was preincubated with purified enzyme in phosphate buffer pH 7.4 for 15 minutes at 37° C. The reaction was initiated by addition of 50 µM kynuramine. Following a 60 minute incubation period, the reaction was terminated by the addition of 6 N NaOH. The amount of 4-hydroxyquinoline formed was determined spectrofluorimetrically at 325 nm/465 nm. Results were converted to percent inhibition and $IC_{50}$'s were determined using the XLfit program from IDBS (ID Business Solutions Ltd., 2 Occam Court, Surrey Research Park, Guildford, Surrey, GU2 7QB UK). Representative compounds of the invention were evaluated in this assay. Typically, the compounds of the invention showed MAO-B inhibitory properties at a concentration of 10 µM. Preferred compounds also demonstrated selectivity for MAO-B over MAO-A.

In many embodiments, a subject compound shows MAO-B inhibitory properties at a concentration of less than about 50 µM, e.g., a subject compound shows MAO-B inhibitory properties at a concentration of less than about 40 µM, less than about 25 µM, less than about 10 µM, less than about 1 µM, less than about 100 nM, less than about 80 nM, less than about 60 nM, less than about 50 nM, less than about 25 nM, less than about 10 nM, or less than about 1 nM, or less.

A majority of the following compounds showed MAO-B inhibitory properties at a concentration of 10 µM or less:

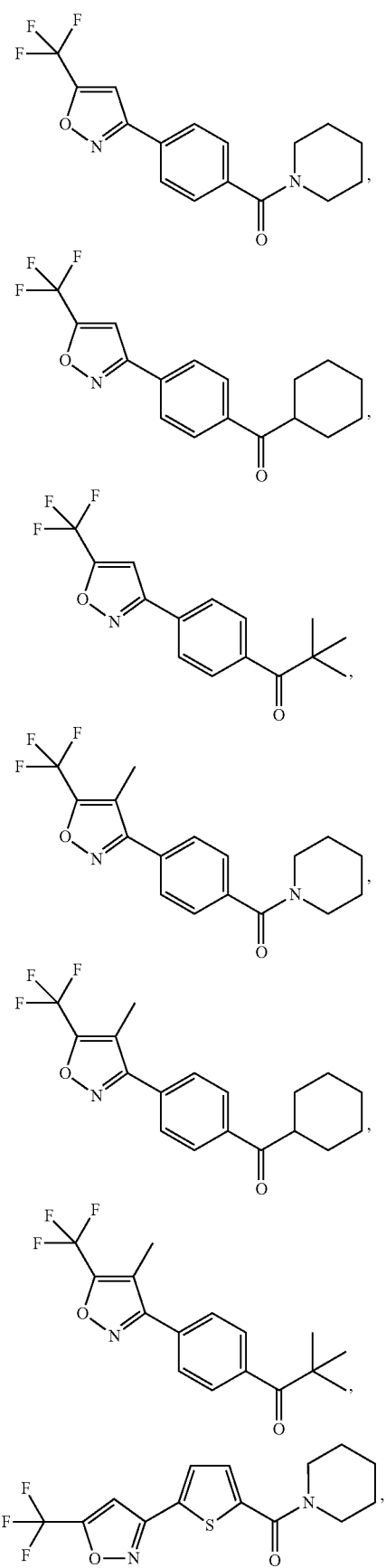
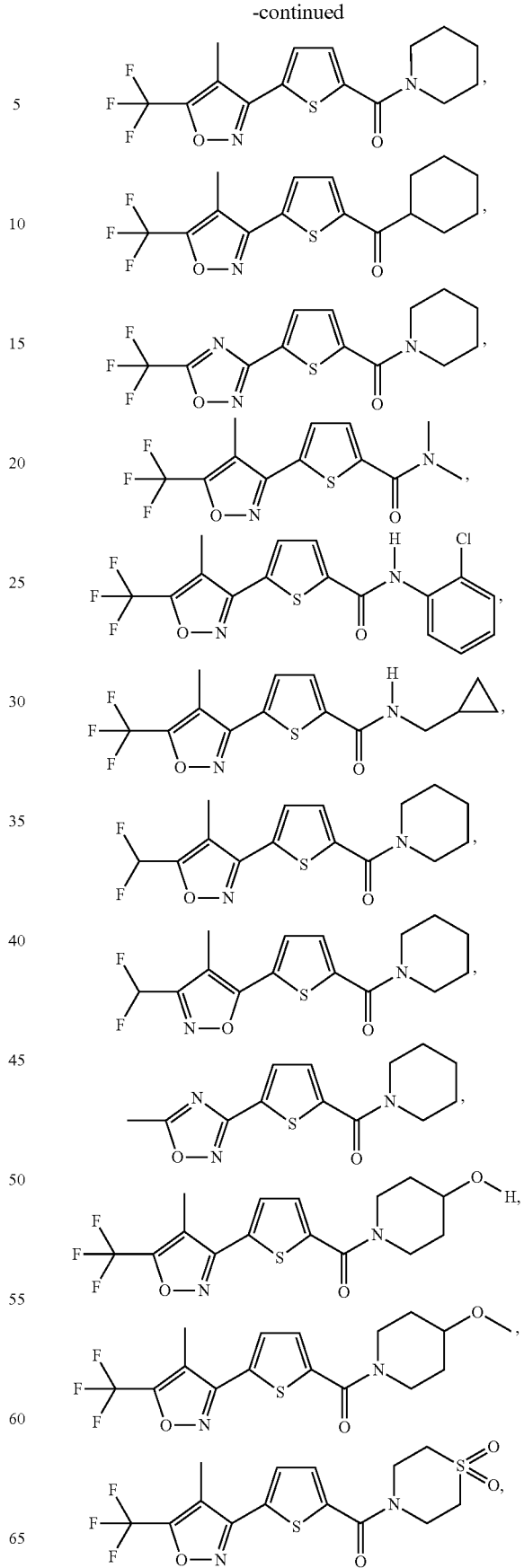

-continued
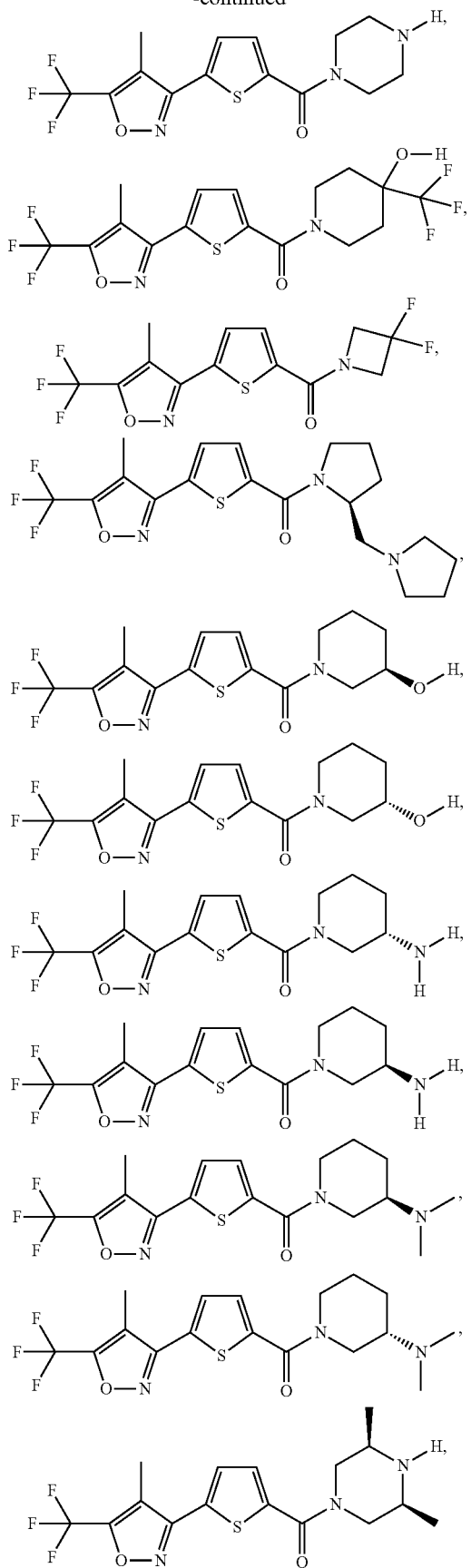
-continued
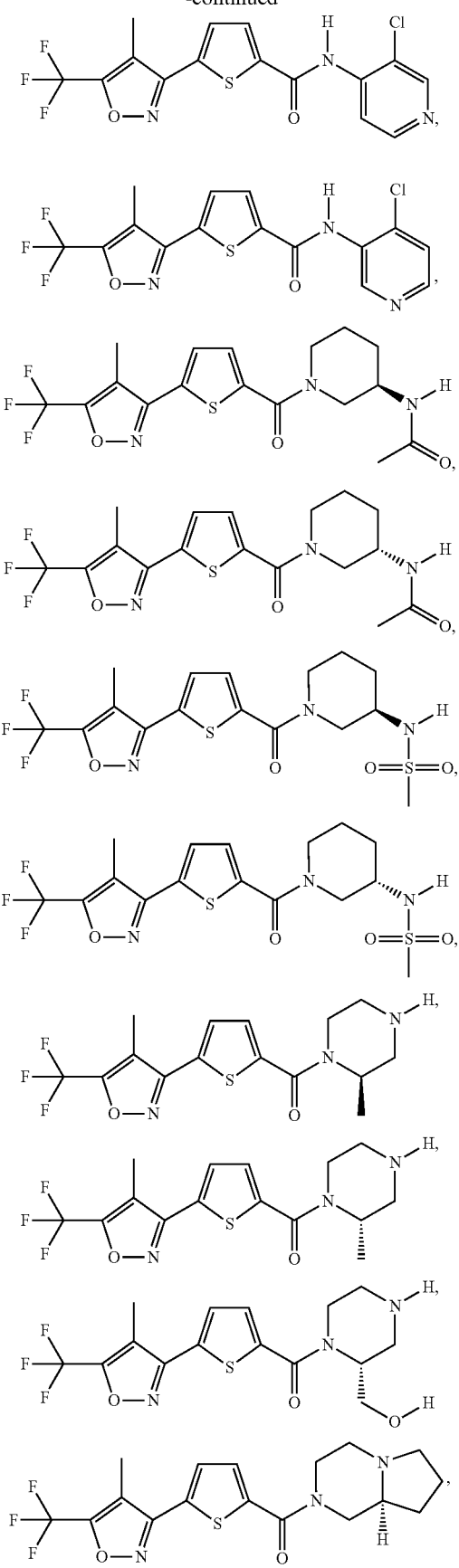

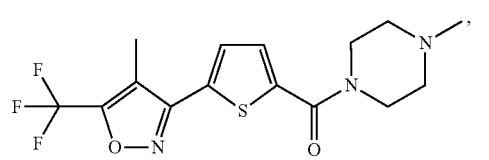
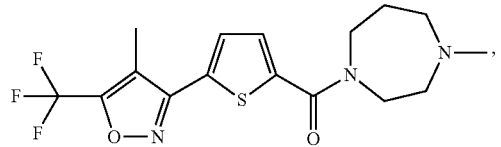
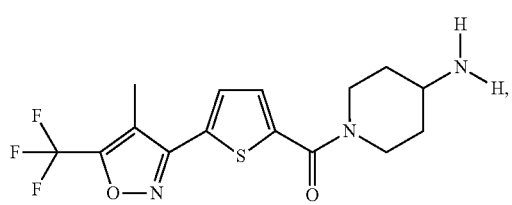
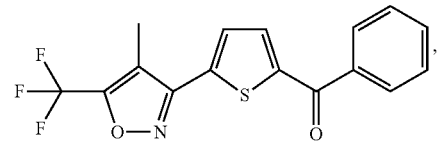
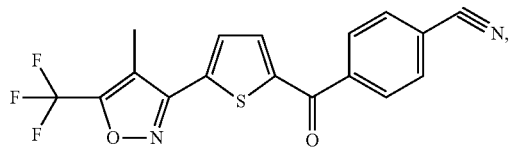
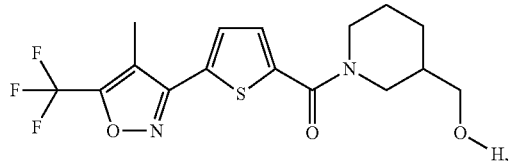
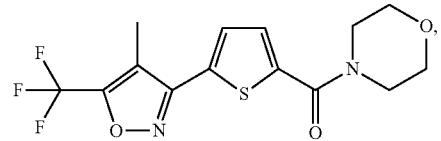
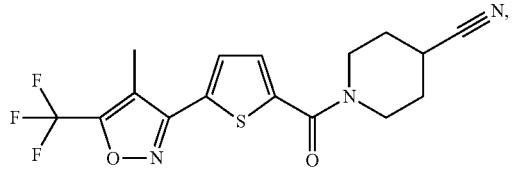
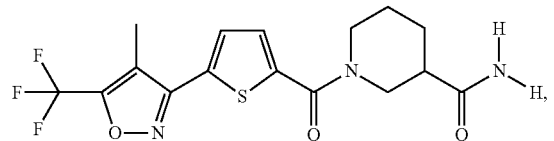
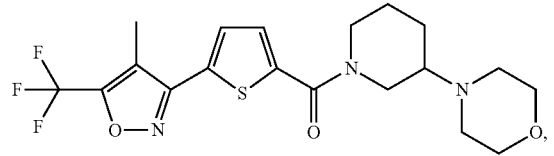
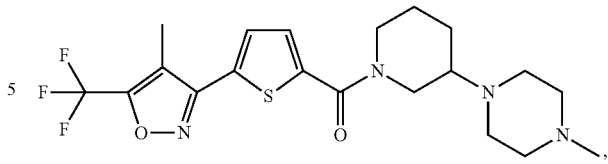
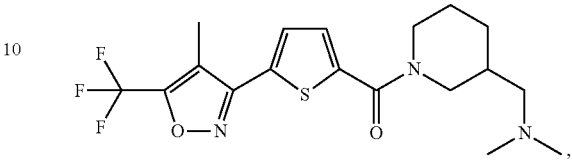
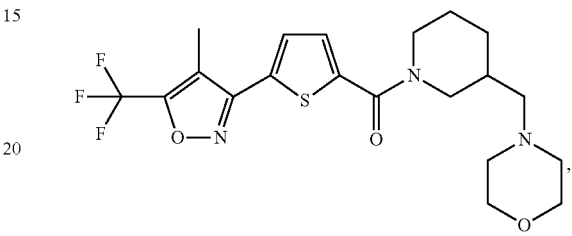
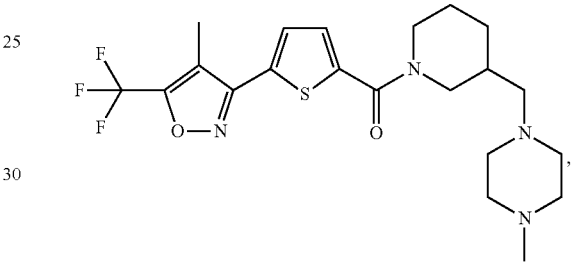
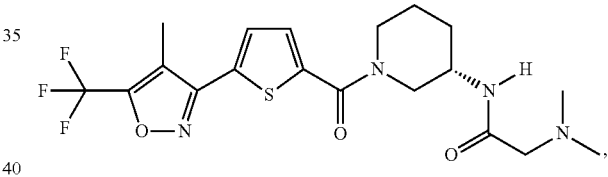
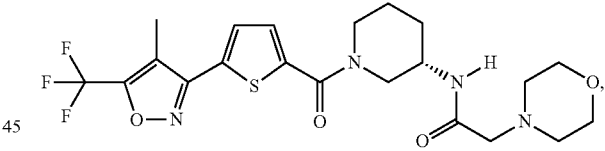
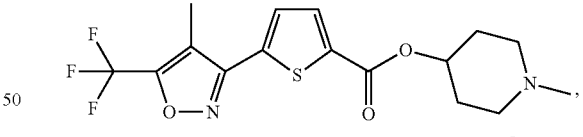
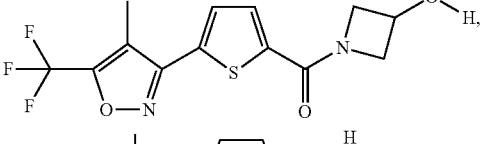
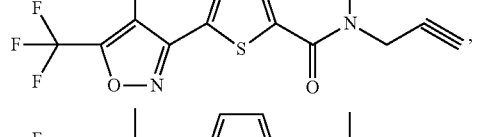
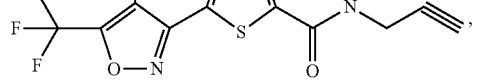

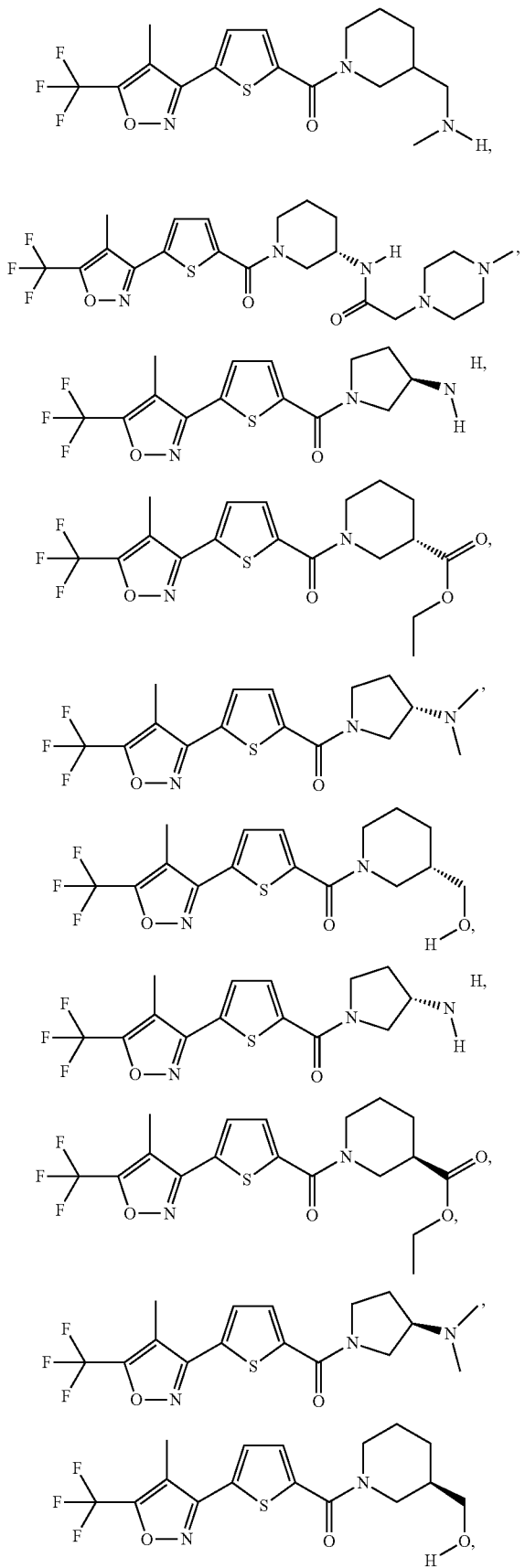
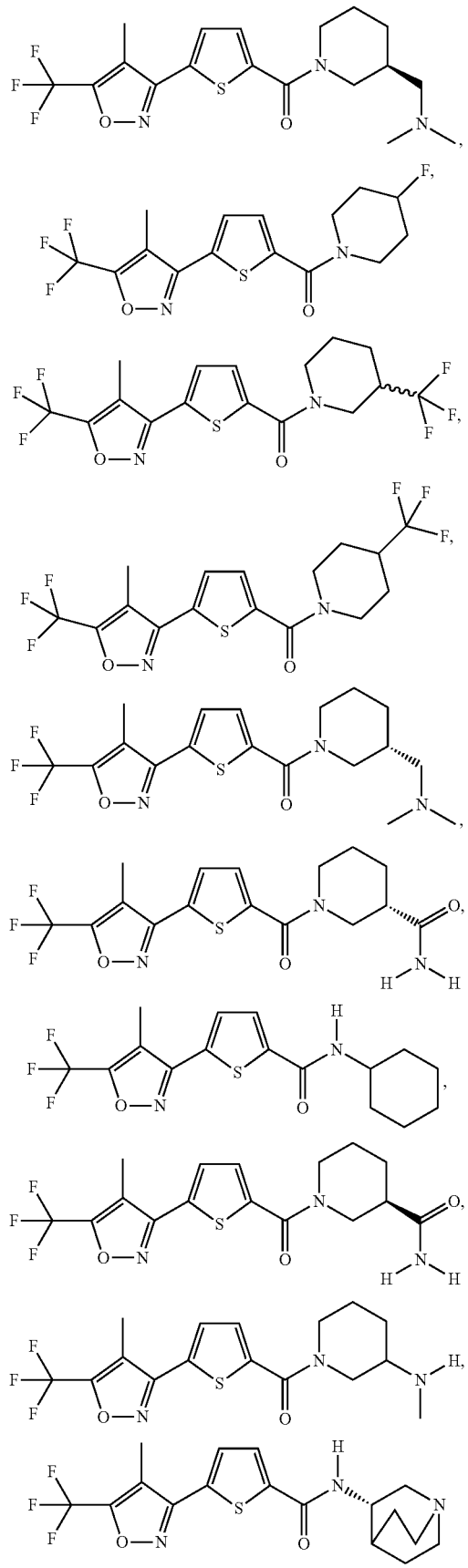

-continued

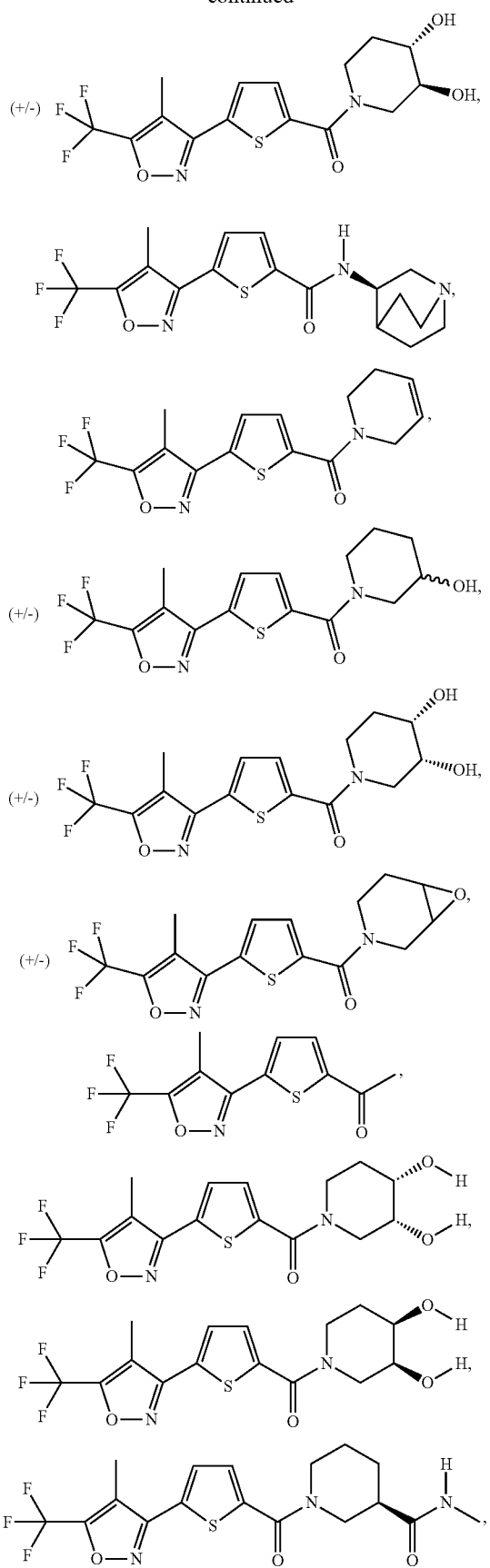

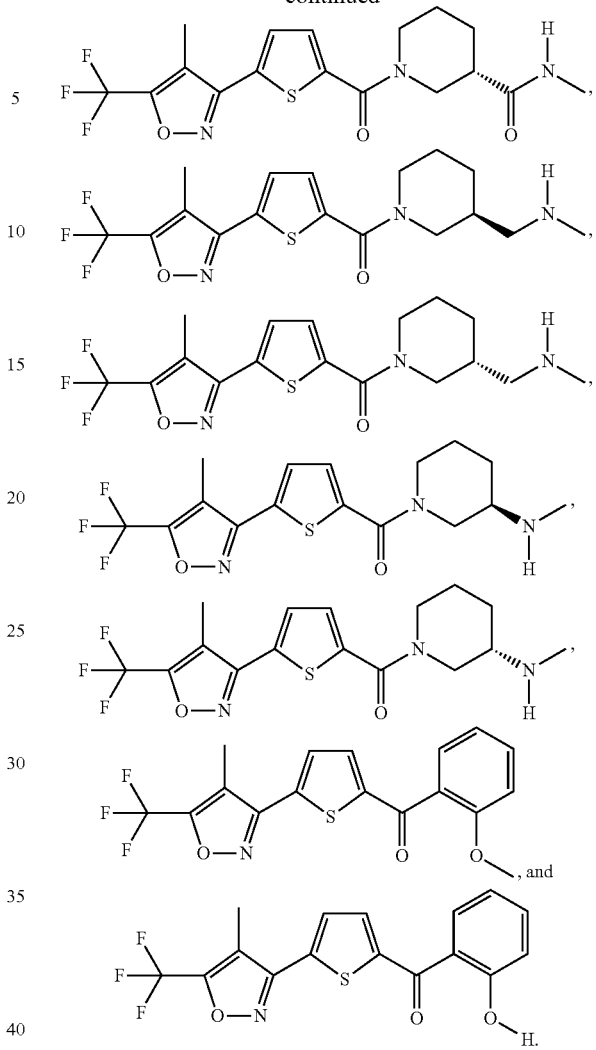

The ability of a compound to modulate cognitive behavior can be evaluated using the following assay to measure memory after contextual fear conditioning.

Contextual Memory Assay: Fear Conditioning

Contextual memory is a form of Pavlovian fear conditioning in which a naïve mouse is placed into a novel chamber (context) containing distinct visual, olfactory and tactile cues. After a couple of minutes of acclimation, the mouse receives a brief, mild electric shock to its feet. From this negative experience, the mouse will remember for months that that chamber is dangerous. When placed back into the same context at some later time after training, the mouse's natural response to danger is to "freeze," sitting stone still for many seconds. This is similar to what happens to humans when they experience fear. The percent of time during an observation period that the mouse spends frozen represents a quantitative measure (memory score) of its memory of the context.

Contextual conditioning has been extensively used to investigate the neural substrates mediating fear-motivated learning (Phillips, R. G., LeDoux, J. E., *Behav Neurosci,* 1992, 106, 274-285; Kim, J. J., et. al., *Behav Neurosci,* 1993, 107, 1093-1098; Bourtchouladze, R., et. al., *Learn Mem,* 1998, 5, 365-374; and Bourtchouladze, R et. al., *Cell,* 1994, 79, 59-68). Contextual conditioning has been also used to study the impact of various mutations on hippocampus-dependent memory (Bourtchouladze, R., et. al., *Learn Mem,* 1998, 5, 365-374; Bourtchouladze, R., et. al., *Cell,* 1994, 79, 59-68; Silva, A. J., et. al., *Curr Biol,* 1996, 6, 1509-1518; Kogan J. L. et al., *Curr Biol,* 1997, 7, 1-11; Abel, T., et. al., *Cell,* 1997, 88, 615-626; and Giese K. P., et al., *Science,* 1998, 279, 870-873); and strain and genetic background differences in mice (Logue, S. F., et. al., *Behav Neurosci,* 1997, 111, 104-113; and Nguyen, P. V., et. al., *Learn Mem,* 2000, 7, 170-179). Because robust memory can be triggered with a few minutes training session, contextual conditioning has been especially useful to study biology of temporally distinct processes of short- and long-term memory (Kim, J. J., et. al., *Behav Neurosci,* 1993, 107, 1093-1098; Bourtchouladze, R., et. al., *Learn Mem,* 1998, 5, 365-374; Bourtchouladze, R., et. al., *Cell,* 1994, 79, 59-68; and Abel, T., et. al., *Cell,* 1997, 88, 615-626). As such, contextual conditioning is an excellent model to evaluate the role of various novel drug-compounds in hippocampus-dependent memory.

Young-adult (10-12 weeks old) C57BL/6 male mice and Sprague Dawley male rats of 250-300 g (Taconic, N.Y.) were used. Mice were group-housed (5 mice) in standard laboratory cages while rats were housed in pairs and maintained on a 12:12 light-dark cycle. The experiments were always conducted during the light phase of the cycle. With the exception of testing times, the mice had ad lib access to food and water. The experiments were conducted according with the Animal Welfare assurance #A3280-01 and animals were maintained in accordance with the animal Welfare Act and Department of Health and Human Services guide.

To assess contextual memory, a modified contextual fear conditioning task originally developed for evaluation of memory in CREB knock-out mice was used (Bourtchouladze, R., et. al., *Cell,* 1994, 79, 59-68). On the training day, the mouse was placed into the conditioning chamber (Med Associates, Inc., VA) for 2 minutes before the onset of unconditioned stimulus (US), 0.5 mA, of 2 sec foot shock. The US was repeated two times with a 1 min inter-trial interval between shocks. Training was performed by automated software package (Med Associates, Inc., VA). After the last training trial, the mice were left in the conditioning chamber for another 30 sec and were then placed back in their home cages. 24 hours after training, the mouse was placed into the same training chamber and contextual memory was assessed by scoring freezing behavior ('freezing' serves as memory score). Freezing was defined as the complete lack of movement in intervals of 5 seconds (Kim, J. J., et. al., *Behav Neurosci,* 1993, 107, 1093-1098; Phillips, R. G., LeDoux, J. E., *Behav Neurosci,* 1992, 106, 274-285; Bourtchouladze, R., et. al., *Learn Mem,* 1998, 5, 365-374; Bourtchouladze, R., et. al., *Cell,* 1994, 79, 59-68; and Abel, T., et. al., *Cell,* 1997, 88, 615-626). Total testing time lasted 3 minutes. After each experimental subject, the experimental apparatus was thoroughly cleaned with 75% ethanol, water, dried, and ventilated for a few minutes.

All experiments were designed and performed in a balanced fashion, meaning that (i) for each experimental condition (e.g. a specific dose-effect) an equal number of experimental and control mice was used; and (ii) each experimental condition was replicated 2-3 independent times, and replicate days were added to generate final number of subjects. The proceeding of each experiment was filmed. In each experiment, the experimenter was unaware (blind) to the treatment of the subjects during training and testing. Data were analyzed by Student's unpaired t test using a software package (Statview 5.0.1; SAS Institute, Inc). All values in the text and figures are expressed as mean±SEM.

Compounds were dissolved in 1% DMSO/PBS and administered intraperitonially (I.P.) in a volume of 8 mL/kg 20 min before training. Control animals received vehicle alone (1% DMSO/PBS). For oral administration the compounds were dissolved in 30% DMSO/70% CMC. Consequently, control animals received 30% DMSO/70% CMC. For each training and drug-injecting procedure, an experimentally naïve group of animals were used.

The ability of a compound to modulate cognitive behavior can also be evaluated using the following Object Recognition Assay.

Object Recognition Assay

Object recognition is an ethologically relevant task for rodents, which does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze, R., et. al., *Proc Natl Acad Sci USA,* 2003, 100, 10518-10522). Recent neuroimaging studies in humans demonstrated that memory in object recognition depends on prefrontal cortex (PFC) (Deibert, et. al., *Neurology,* 1999, 52, 1413-1417). Consistent with these findings, rats with the PFC lesions show poor working memory when they are required to discriminate between familiar and novel objects (Mitchell, J. B., Laiacona, J., *Behav Brain Res,* 1998, 97, 107-113). Other studies on monkeys and rodents suggest that the hippocampus is important for novel object recognition (Teng, E., et. al., *J. Neurosci,* 2000, 20, 3853-3863; and Mumby, D. G., *Brain Res,* 2001, 127, 159-181). Hence, object recognition provides an excellent behavioral model to evaluate drug-compound effects on cognitive task associated with function of hippocampus and cortex.

Prior to initiation of training, animals were handled for 3-5 minutes for 5 days. Training and testing were performed identically for mice and rats with an exception of training apparatus dimensions (for mice: a Plexiglas box of L=48 cm; W=38 cm and H=20 cm; for rats: a Plexiglas box of L=70 cm; W=60 cm and H=35 cm). The day before training, an individual animal was placed into a training apparatus located in a dimly lit room and allowed to habituate to the environment for 15 minutes (also see Pittenger, C., et. al., *Neuron,* 2002, 34, 447-462; and Bourtchouladze, R., et. al., *Proc Natl Acad Sci USA,* 2003, 100, 10518-10522). Training was initiated 24 h hours after habituation. An animal was placed back into the training box, which contained two identical objects (e.g. a small conus-shape object), and was allowed to explore these objects. The objects were placed into the central area of the box and the spatial position of objects (left-right sides) was counterbalanced between subjects. Animals were trained for 15 minutes. To test for memory retention, animals were observed for 10 minutes 24 hours after training. A rodent was presented with two objects, one of which was used during training, and thus was 'familiar' and the other of which was novel (e.g. a small pyramid-shape object). To insure that the discrimination targets do not differ in smell, after each experimental subject, the apparatus and the objects were thoroughly cleaned with 90% ethanol, dried and ventilated for a few minutes.

The experiments were videotaped via an overhead video camera system. Types were then reviewed by a blinded observer and the following behavioral parameters were determined: time of exploration of an each object; the total time of exploration of the objects; number of approaches to the objects; and time (latency) to first approach to an object. The discrimination index—memory score—was determined as described previously (Ennaceur, A., Aggleton, J. P., *Behav Brain Res*, 1997, 88, 181-193; and Bourtchouladze, R., et. al., *Proc Natl Acad Sci USA*, 2003, 100, 10518-10522). This Data was analyzed by Student's unpaired t test using a software package (Statview 5.0.1; SAS Institute, Inc).

The compounds evaluated in the MAO Inhibition Assay can be tested in the Object Recognition Assay to show improvement of cognitive function in the subject animal.

The following Examples illustrate methods that are generally useful for preparing compounds of the invention.

LC Protocol:

Observed, 254 nm. Solvent system, acetonitrile (0.1% formic acid) and water (0.1% formic acid). Column, XTerra MS C-18 3.5 µM (2.1×50 mm), 30° C. oven temperature. Run time, 10 min. Flow rate 0.3 mL/min. Substrate is dissolved in acetonitrile and diluted to equal volume with water for injection.

Inlet Method:

| Time (min) | % acetonitrile (0.1% formic acid) | % water (0.1% formic acid) |
|---|---|---|
| 0 | 10 | 90 |
| 5 | 90 | 10 |
| 7 | 90 | 10 |
| 7.5 | 10 | 90 |
| 10 | 10 | 90 |

PREPARATIVE EXAMPLES

Preparative Example 1

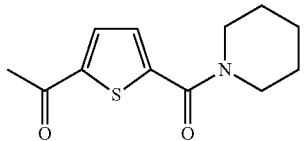 [SMILES: CC(=O)c1ccc(C(=O)N2CCCCC2)s1]

1-[5-(Piperidine-1-carbonyl)-thiophen-2-yl]-ethanone

A solution of 5-acetylthiophene-2-carboxylic acid (34.0 g, 200 mmol) in toluene (800 mL) was treated with DMF (500 µL) followed by oxalyl chloride (22.3 mL, 260 mmol) and allowed to stir 3 hr after which time the reaction was evaporated in vacuo to afford intermediate acid chloride. The intermediate acid chloride was then dissolved in THF (500 mL) and treated with a THF solution (100 mL) of triethylamine (30.7 mL, 220 mmol) and piperdine (20.7 mL, 210 mmol). The reaction was allowed to stir for 3 hr then evaporated to approximately ¼ volume and partitioned between EtOAc (150 mL) and a 1N HCl solution (100 mL). The organic portion was then further washed with a saturated aqeuous solution of NaHCO$_3$ (100 mL) followed by a brine solution (100 mL), then dried over MgSO$_4$, filtered, and evaporated in vacuo to afford product as yellow colored solid which was triturated and filtered with the aid of hexanes to afford product as a solid (43.2 g, 91%). $^1$H NMR (CDCl$_3$) 1.63-1.71 (m, 6H), 2.57 (s, 3H), 3.62 (br s, 4H), 7.24 (d, J=4.0, 1 H), 7.60 (d, J=4.0, 1 H). $^{13}$C NMR 24.7, 26.3 (br), 27.1, 44.5 (br), 48.0 (br), 128.8, 131.6, 144.7, 145.5, 162.7, 190.8. LC/MS 4.92 min, [M+1]$^+$ 238.

Preparative Example 2

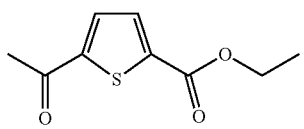

5-Acetyl-thiophene-2-carboxylic acid ethyl ester

A solution of 5-acetylthiophene-2-carboxylic acid (17.0 g, 100 mmol) in ethanol (500 mL) was treated with a concentrated H$_2$SO$_4$ solution (10 mL) and heated at reflux for 3 days after which time the reaction was evaporated to approximately ¼ volume and partitioned between EtOAc (300 mL) and water (100 mL). The organic portion was then further washed with a saturated aqueous solution of NaHCO$_3$ (2×100 mL) followed by a brine solution (100 mL), then dried over MgSO$_4$, filtered, and evaporated in vacuo to afford product as light brown colored solid (25.0 g, 84%). $^1$H NMR (CDCl$_3$) 1.39 (t, J=7.0, 3 H), 2.59 (s, 3H), 4.38 (q, J=7.3, 2 H), 7.64 (d, J=4.0, 1 H), 7.76 (d, J=4.0, 1 H). $^{13}$C NMR 14.3, 27.1, 61.9, 131.8, 133.3, 140.3, 148, 161.7, 190.9. LC/MS 5.47 min, [M+1]$^+$ 199.

Preparative Example 3

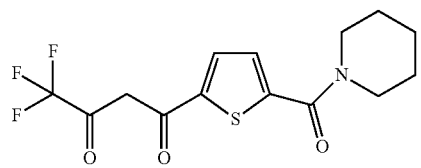 [SMILES: O=C(CC(=O)C(F)(F)F)c1ccc(C(=O)N2CCCCC2)s1]

4,4,4-Trifluoro-1-[5-(piperidine-1-carbonyl)-thiophen-2-yl]-butane-1,3-dione

A suspension of sodium methoxide (8.78, 162.5 mmol) in toluene (300 mL) was treated with ethyl trifluoroacetate and allowed to stir at 30 OC for 30 min after which time solid 1-[5-(Piperidine-1-carbonyl)-thiophen-2-yl]-ethanone (Preparative Example 1, 11.87 g, 50 mmol) was added portionwise. The reaction was heated at 40 OC for 3 hr and allowed to stir at room temperature for a further 16 hr. The reaction was then cooled to 0-5° C. and filtered with the aid of cold toluene. The filtered solids were then partitioned between EtOAc (300 mL) and an aqueous 5% H$_2$SO$_4$ solution (100 mL) and the organic layer further washed with a brine solution (2×50 mL), then dried over MgSO$_4$, filtered, and evaporated in vacuo to afford product as light brown colored solid (15.26 g, 91%). An approx. 2:1 isomer mixture was observed in the NMR spectra of product. $^1$H NMR (CDCl$_3$) 1.65-1.71 (m, 6H), 3.63 (br s, 4H), 7.06 (s, 1H), 5.38 (br s, minor enol, 1H), 6.45 (s, major isomer, 1H), 7.25 (d, minor isomer, J=3.8, 1 H), 7.28 (d, major isomer, J=4.1, 1 H), 7.71 (d, minor isomer, J=4.1, 1 H), 7.74 (d, major isomer, J=3.8, 1 H). $^{19}$F NMR −87.3 (minor isomer), −76.2 (major isomer). LC/MS 5.05 min, [M+1+H$_2$O]$^+$ 352.

Preparative Example 4

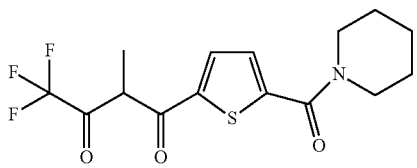 [SMILES: CC(C(=O)c1ccc(C(=O)N2CCCCC2)s1)C(=O)C(F)(F)F]

4,4,4-Trifluoro-2-methyl-1-[5-(piperidine-1-carbonyl)-thiophen-2-yl]-butane-1,3-dione A suspension of 60% sodium hydride (440 mg, 11 mmol) in DMF (15 mL) at 0-5° C. was treated portionwise with 4,4,4-Trifluoro-1-[5-(piperidine-1-carbonyl)-thiophen-2-yl]-butane-1,3-dione (Preparative Example 3, 3.34 g, 10 mmol) and allowed to stir until all hydrogen evolution had ceased. The reaction mixture was then treated with iodomethane (1.25 mL, 20 mmol) and heated at 60 OC for 16 hr. The reaction mixture was then cooled and partitioned between EtOAc (25 mL) and an aqueous 5% H$_2$SO$_4$ solution (50 mL) and the organic layer further washed with a brine solution (2×25 mL), then dried over MgSO$_4$, filtered, and evaporated in vacuo to afford product as light brown oil. The residue was chromatographed on silica gel with EtOAc/hexanes (50%) as eluant to afford product as an oil (2.70 g, 78%). An approximately 1:1 mixture of isomers was observed in the NMR spectra of product. $^1$H NMR (CDCl$_3$) 1.40 (d, isomer, J=7.0, 3 H), 1.58 (d, isomer, J=7.0, 3 H), 1.65-1.71 (m, 6H), 3.63 (br s, 4H), 3.83 (q, isomer, J=7.0, 1 H), 4.78 (q, isomer, J=6.7, 1 H), 5.06 (s, isomer, 1H), 5.67 (s, isomer, 1H), 7.27 (d, isomer, J=4.0, 1 H), 7.29 (d, isomer, J=4.0, 1 H), 7.71 (d, isomer, J=4.0, 1 H), 7.74 (d, isomer, J=4.0, 1 H). $^{19}$F NMR −83.7 (isomer), −77.6 (isomer). LC/MS 5.05 min, [M+1+H$_2$O]$^+$ 366.

Preparative Example 5

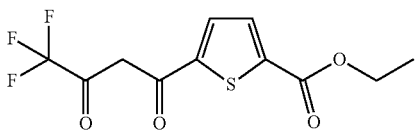 [SMILES: CCOC(=O)c1ccc(C(=O)CC(=O)C(F)(F)F)s1]

5-(4,4,4-Trifluoro-3-oxo-butyryl)-thiophene-2-carboxylic acid ethyl ester

Prepared from 5-Acetyl-thiophene-2-carboxylic acid ethyl ester as described in Preparative Example 3. Sodium methoxide was substituted with sodium ethoxide. Product was not chromatographed, but obtained as a yellow solid (11.5 g, 78%). $^1$H NMR (CDCl$_3$) 1.41 (t, J=7.0, 3 H), 4.41 (q, J=7.0, 2 H), 6.48 (s, 1H), 7.77 (d, J=7.0, 1 H), 7.81 (d, J=4.0, 1 H). $^{13}$C NMR 14.4, 62.3, 93.8, 117.5 (q, J=281), 132.0, 133.7, 141.5, 143.7, 161.4, 174.0 (q, J=37), 181.4. $^{19}$F NMR −76.4. LC/MS 5.44 min, [M+1]$^{+295}$, [M+1+H$_2$O]$^+$ 313.

Preparative Example 6

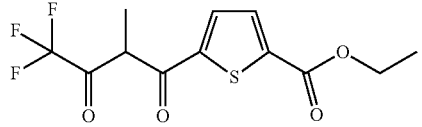 [SMILES: CCOC(=O)c1ccc(C(=O)C(C)C(=O)C(F)(F)F)s1]

5-(4,4,4-Trifluoro-2-methyl-3-oxo-butyryl)-thiophene-2-carboxylic acid ethyl ester Prepared from 5-(4,4,4-Trifluoro-3-oxo-butyryl)-thiophene-2-carboxylic acid ethyl ester as described in Preparative Example 4. Product was not chromatographed, but obtained as a brown oil (12.2 g, 113%) and used as such. LC/MS 5.81 min, [M+1+H$_2$O]$^+$ 327.

Preparative Example 7

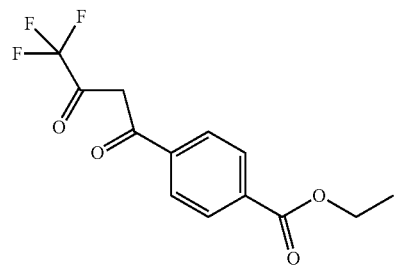 [SMILES: CCOC(=O)c1ccc(C(=O)CC(=O)C(F)(F)F)cc1]

4-(4,4,4-Trifluoro-3-oxo-butyryl)-benzoic acid ethyl ester

Prepared from 4-Acetyl-benzoic acid ethyl ester as described in Preparative Example 3. Sodium methoxide was substituted with sodium ethoxide. Product was not chromatographed, but obtained as an off-white solid (10.4 g, 90%). $^1$H NMR (CDCl$_3$) 1.43 (t, J=7.0, 3 H), 4.43 (q, J=7.3, 2 H), 6.61 (s, 1H), 8.00 (d, J=8.8, 2 H), 8.40 (d, J=8.4, 2 H). $^{19}$F NMR −77.1. LC/MS 5.51 min, [M+1]$^+$ 289, [M+1+H$_2$O]$^+$ 307.

Preparative Example 8

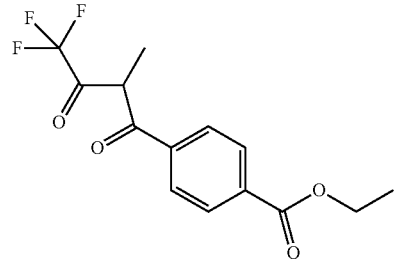 [SMILES: CCOC(=O)c1ccc(C(=O)C(C)C(=O)C(F)(F)F)cc1]

4-(4,4,4-Trifluoro-2-methyl-3-oxo-butyryl)-benzoic acid ethyl ester

Prepared from 4-(4,4,4-Trifluoro-3-oxo-butyryl)-benzoic acid ethyl ester as described in Preparative Example 4. Sodium methoxide was substituted with sodium ethoxide. Product was chromatographed on silica gel with EtOAc/hexanes (15%) to afford a copper-colored oil (1.14 g, 38%). LC/MS 5.94 min, $[M+1]^+$ 303, $[M+1+H_2O]^+$ 321.

Preparative Example 9

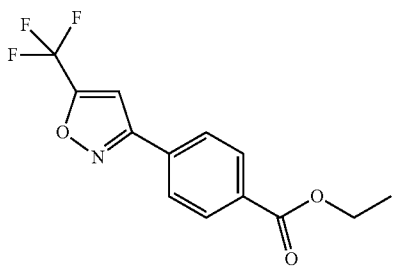 [SMILES: CCOC(=O)c1ccc(-c2cc(C(F)(F)F)on2)cc1]

4-(5-Trifluoromethyl-isoxazol-3-yl)-benzoic acid ethyl ester

A solution of 4-(4,4,4-Trifluoro-3-oxo-butyryl)-benzoic acid ethyl ester (Preparative Example 7, 2.88 g, 10 mmol) in glacial acetic acid (2.5 mL) was treated with hydroxylamine hydrochloride (833 mg, 12 mmol) and heated at 80-90° C. for 16 hr, after which time the reaction was cooled and the resulting solids filtered with the aid of water to afford the 5-hydroxy-4,5,-dihydro-isoxazole intermediate (2.25 g, 74%). The intermediate (2.2 g, 7.25 mmol) was then dissolved in trifluoroacetic acid (10 mL) and heated at reflux for 3 days. The reaction was then evaporated and the residue chromatographed on silica gel with EtOAc/hexanes (20%) as eluant to afford product as a colorless solid (1.30 g, 63%). $^1$H NMR (CDCl$_3$) 1.41 (t, J=7.5, 3 H), 4.41 (q, J=7.0, 2 H), 7.06 (s, 1H), 7.89 (d, J=8.8, 2 H), 8.15 (d, J=8.8, 2 H). $^{13}$C NMR 14.5, 61.7, 103.8, 118.0 (q, J=270), 127.1, 130.6, 131.5, 132.8, ~150 quartet not resolved from baseline noise, 162.0, 166.0. $^{19}$F NMR −63.6. LC/MS 7.15 min, $[M+1]^+$ 286.

Preparative Example 10

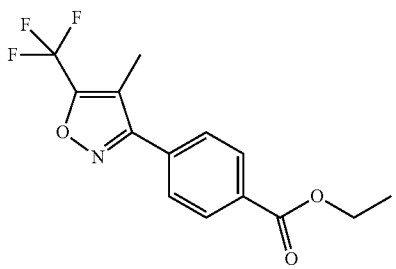 [SMILES: CCOC(=O)c1ccc(-c2noc(C(F)(F)F)c2C)cc1]

4-(4-Methyl-5-trifluoromethyl-isoxazol-3-yl)-benzoic acid ethyl ester

A solution of 4-(4,4,4-Trifluoro-2-methyl-3-oxo-butyryl)-benzoic acid ethyl ester (927 mg, 3.07 mmol) in glacial acetic acid (10 mL) was treated with hydroxylamine hydrochloride (256 mg, 3.68 mmol) and heated at 80-90° C. for 48 hr, after which time the reaction was evaporated in vacuo. The crude material was then chromatographed on silica gel with EtOAc/hexanes (5%) as eluant to afford product as a colorless oil (840 mg, 91%). $^1$H NMR (CDCl$_3$) 1.43 (t, J=7.0, 3 H), 2.29 (q, J=3H), 4.43 (q, J=7.0, 2 H), 7.72 (d, J=8.8, 2 H), 8.19 (d, J=8.3, 2 H). $^{13}$C NMR 7.7, 14.5, 61.6, 115.0, 118.9 (q, J=271), 128.5, 130.3, 132.1, 132.3, ~150 quartet not resolved from baseline noise, 163.0, 166.0. $^{19}$F NMR −63.2. LC/MS 7.28 min, $[M+1]^+$ 300.

Preparative Example 11

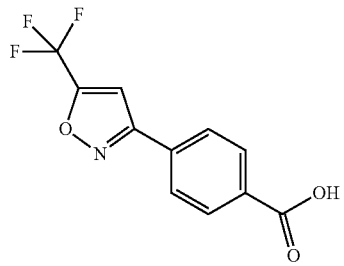 [SMILES: O=C(O)c1ccc(-c2cc(C(F)(F)F)on2)cc1]

4-(5-Trifluoromethyl-isoxazol-3-yl)-benzoic acid

A solution of 4-(5-Trifluoromethyl-isoxazol-3-yl)-benzoic acid ethyl ester (Preparative Example 9, 2.25 g, 7.86 mmol) in THF (20 mL) was treated with an aqueous solution (5 mL) of lithium hydroxide monohydrate (660 mg, 15.72 mmol) and allowed to stir for 16 hr. The reaction was then evaporated to a small volume and treated with a 1 N aqueous hydrochloric acid solution (25 mL) and the resulting solids filtered, washed with water and air dried to afford product as a colorless solid (1.48 g, 73%). $^1$H NMR (DMSO-d6) 8.06 (s, 4H), 8.13 (s, 1H). $^{13}$C NMR 106.5, 118.0 (q, J=270), 127.9, 130.8, 131.2, 132.4, ~150 quartet not resolved from baseline noise, 133.8, 162.8, 167.3. $^{19}$F NMR −63.6. LC/MS 6.04 min, $[M+1]^+$ 258.

Preparative Example 12

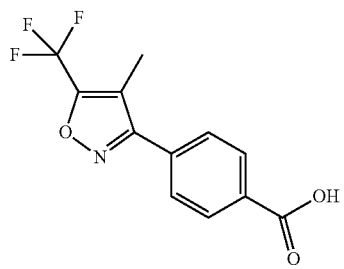 [SMILES: Cc1c(-c2ccc(C(=O)O)cc2)noc1C(F)(F)F]

4-(4-Methyl-5-trifluoromethyl-isoxazol-3-yl)-benzoic acid

Prepared from 4-(4-Methyl-5-trifluoromethyl-isoxazol-3-yl)-benzoic acid ethyl ester as described in Preparative Example 11 to afford product as a colorless solid (3.7 g, 98%). $^1$H NMR (DMSO-d6) 2.25 (s, 3H), 7.81 (d, J=7.9, 2 H), 8.10 (d, J=8.2, 2 H), 13.26 (s, 1H). $^{13}$C NMR 7.8, 116.9, 119.3 (q, J=270), 129.3, 130.6, 131.6, 133.2, 153.6 (q, J=39), 163.6, 167.4. $^{19}$F NMR −62.3. LC/MS 6.14 min, [M+1]$^+$ 272.

Preparative Example 13

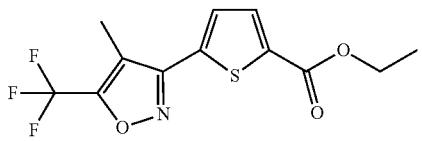 [SMILES: CCOC(=O)c1ccc(-c2noc(C(F)(F)F)c2C)s1]

5-(4-Methyl-5-trifluoromethyl-isoxazol-3-yl)-thiophene-2-carboxylic acid ethyl ester Prepared from crude 5-(4,4,4-Trifluoro-2-methyl-3-oxo-butyryl)-thiophene-2-carboxylic acid ethyl ester as described in Preparative Example 10. Crude material was chromatographed on silica gel with EtOAc/hexanes (25%) as eluant to afford product as a colorless solid (7.4 g, 66%). $^1$H NMR (CDCl$_3$) 1.41 (t, J=7.0, 3 H), 2.38 (s, 3H), 4.43 (q, J=7.5, 2 H), 7.51 (d, J=4.0, 1 H), 7.83 (d, J=4.0, 1 H). $^{13}$C NMR 7.9, 14.5, 61.9, 114.8, 118.7 (q, J=271), 128.4, 133.6, 134.7, 136.6, 155.4 (q, J=41), 157.9, 161.8. $^{19}$F NMR −63.2. LC/MS 7.26 min, [M+1]$^+$ 306.

Preparative Example 14

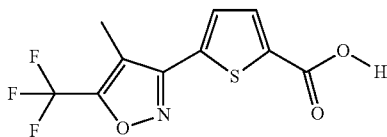 [SMILES: Cc1c(-c2ccc(C(=O)O)s2)noc1C(F)(F)F]

5-(4-Methyl-5-trifluoromethyl-isoxazol-3-yl)-thiophene-2-carboxylic acid

Prepared from 5-(4-Methyl-5-trifluoromethyl-isoxazol-3-yl)-thiophene-2-carboxylic acid ethyl ester as described in Preparative Example 11 to afford product as a colorless solid (6.15 g, 94%). $^1$H NMR (DMSO-d6) 2.33 (s, 3H), 7.64-7.66 (m, 2H). $^{13}$C NMR 8.0, 116.6, 119.1 (q, J=271), 129.3, 130.7, 131.8, 132.4, 142.7, 153.8 (q, J=40), 158.8, 163.6. $^{19}$F NMR −62.3. LC/MS 6.02 min, [M+1]$^+$ 278.

Preparative Example 15

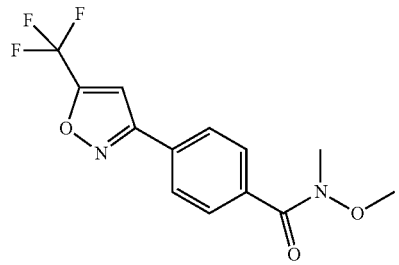 [SMILES: CON(C)C(=O)c1ccc(-c2cc(C(F)(F)F)on2)cc1]

N-Methoxy-N-methyl-4-(5-trifluoromethyl-isoxazol-3-yl)-benzamide

A solution of 4-(5-Trifluoromethyl-isoxazol-3-yl)-benzoic acid (Preparative Example 11, 1.024 g, 4.0 mmol) in dichloromethane (14 mL) at 0-5 OC was treated with DMF (2 mL) followed by DMAP (50 mg), hydroxylamine hydrochloride (468 mg, 4.8 mmol), triethylamine (458 µL, 4.8 mmol), and DCC (990 mg, 4.8 mmol). The reaction was allowed to warm to room temperature and stirred 16 hr then evaporated in vacuo. The crude material was then chromatographed on silica gel with EtOAc/hexanes (40%) as eluant to afford product as a colorless solid (890 mg, 74%). $^1$H NMR (CDCl$_3$) 3.40 (s, 3H), 3.57 (s, 3H), 7.06 (s, 3), 7.82 (d, J=8.3, 2 H), 7.88 (d, J=8.8, 2 H). $^{13}$C NMR 33.7, 61.4, 103.7, 118.0 (q, J=460), 127.1, 129.3, 129.4, 136.6, 159.7 (q, J=42), 162.2, 169.0. $^{19}$F NMR −64.6. LC/MS 6.01 min, [M+1]$^+$ 301.

Preparative Example 16

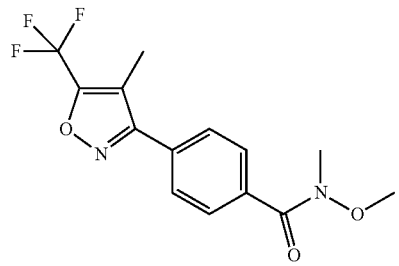 [SMILES: CON(C)C(=O)c1ccc(-c2noc(C(F)(F)F)c2C)cc1]

N-Methoxy-N-methyl-4-(4-methyl-5-trifluoromethyl-isoxazol-3-yl)-benzamide

Prepared from 4-(4-Methyl-5-trifluoromethyl-isoxazol-3-yl)-benzoic acid as described in Preparative Example 15. Crude material was chromatographed on silica gel with EtOAc/hexanes (30 then 40%) as eluant to afford product as a colorless solid (1.41 g, 75%). $^1$H NMR (CDCl$_3$) 2.26 (s, 3H), 3.36 (s, 3H), 3.55 (s, 3H), 7.65 (d, J=7.9, 2 H), 7.80 (d, J=7.9, 2 H). $^{13}$C NMR 7.7, 33.7, 61.4, 117.1, 117.9 (q, J=428), 128.2, 129.0, 130.0, 136.1, 155 (obs q), 163.1, 169.1. $^{19}$F NMR −63.2. LC/MS 6.27 min, [M+1]$^+$ 315.

Preparative Example 17

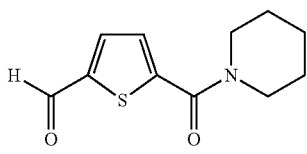 [SMILES: O=Cc1ccc(C(=O)N2CCCCC2)s1]

5-(Piperidine-1-carbonyl)-thiophene-2-carbaldehyde

A solution of 5-formylthiophenecarboxylic acid (9.0 g, 57.6 mmol) in toluene (100 mL) was treated with DMF (100 μL) followed by oxalyl chloride (9.9 mL, 115 mmol) and stirred at room temperature for 3 hr then evaporated in vacuo. The crude acid chloride was then dissolved in THF (100 mL), cooled in an ice bath, and treated with a THF solution (50 mL) containing triethylamine (10 mL, 72 mmol) and piperdine (6.3 mL, 63.4 mmol). The reaction was placed in a 5° C. refrigerator for 16 hr and then treated with a 1N HCl solution (200 mL) and EtOAc (200 mL). The organic portion was further washed with a saturated aqueous solution of $NaHCO_3$ (100 mL) followed by a brine solution (100 mL), then dried over $MgSO_4$, filtered, and evaporated in vacuo to afford product as an oil (12.87 g, 100%). $^1$H NMR (CDCl$_3$) 1.64-1.71 (m, 6H), 3.62 (br s, 4H), 7.31 (d, J=4.0, 1 H), 7.71 (d, J=3.5, 1 H), 9.94 (s, 1H). $^{13}$C NMR 24.6, 26.3 (br), 44.2 (br), 49.0 (br), 128.8, 135.4, 144.8, 146.1, 162.5, 183.3. LC/MS 4.78 min, [M+1]$^+$ 224.

Preparative Example 18

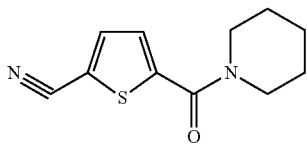 [SMILES: N#Cc1ccc(C(=O)N2CCCCC2)s1]

5-(Piperidine-1-carbonyl)-thiophene-2-carbonitrile

A solution of 5-(Piperidine-1-carbonyl)-thiophene-2-carbaldehyde (Preparative Example 17, 2.23 g, 10 mmol) in EtOH (50 mL) was treated with pyridine (971 L, 12 mmol, 1.2 eq) followed by hydroxylamine hydrochloride (833 mg, 12 mmol, 1.2 eq) and heated at reflux for 2 hr then evaporated in vacuo. The crude intermediate oxime was then dissolved in acetic anhydride and heated at 145° C. for 16 hr then evaporated in vacuo to a small volume which was partitioned between EtOAc (50 mL) and water (200 mL). The organic layer was further washed with a brine solution (50 mL), dried over $MgSO_4$, filtered, evaporated in vacuo and the residue chromatographed on silica gel with EtOAc/hexanes (30 then 50%) as eluant to afford product as a yellow-tinted oil (1.43 g, 65%). $^1$H NMR (CDCl$_3$) 1.65-1.76 (m, 6H), 3.64 (br s, 4H), 7.23 (d, J=4.0, 1 H), 7.56 (d, J=4.0, 1 H). $^{13}$C NMR 24.5, 26.2, 44.3 (br), 48.5 (br), 111.9, 113.7, 128.0, 137.0, 144.7, 161.3. LC/MS 5.09 min, [M+1]$^+$ 221.

Preparative Example 19

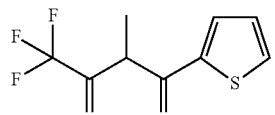

4,4,4-Trifluoro-2-methyl-1-thiophen-2-yl-butane-1,3-dione

Prepared from 2-Thenoyltrifluoroacetone as described in Preparative Example 4. Product was not chromatographed, but obtained as a brown oil (13.6 g, 115%) and used as such. LC/MS 4.99 min, [M+1+H$_2$O]$^+$ 255.

Preparative Example 20

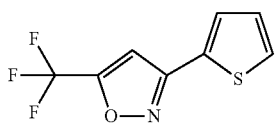 [SMILES: FC(F)(F)c1cc(-c2cccs2)no1]

3-Thiophen-2-yl-5-trifluoromethyl-isoxazole

Prepared from 2-Thenoyltrifluoroacetone as described in Preparative Example 9. Product was chromatographed on silica gel with EtOAc/hexanes (5%) as eluant to afford product as a colorless solid (2.57 g, 59%). Intermediate: LC/MS 5.23 min, [M+1+H$_2$O]$^+$ 255. Product: $^1$H NMR (CDCl$_3$) 6.93 (s, 1H), 7.14 (dd, J=3.5 and 4.8, 1 H), 7.47-7.52 (m, 2H). $^{13}$C NMR 103.7, 118.0 (q, J=271), 128.2, 128.9, 129.1, 158.0, 159.3 (q, J=43). $^{19}$F NMR −64.7. LC/MS 6.62 min, [M+1]$^+$ 220.

Preparative Example 21

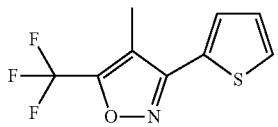

4-Methyl-3-thiophen-2-yl-5-trifluoromethyl-isoxazole

Prepared from crude 4,4,4-Trifluoro-2-methyl-1-thiophen-2-yl-butane-1,3-dione as described in Preparative Example 10. Product was not chromatographed, but obtained as a colorless solid after filtration with aid of water (3.05 g, 65%). $^1$H NMR (CDCl$_3$) 2.35 (s, 3H), 7.16-7.19 (m, 1H), 7.49-7.52 (m, 2H). $^{13}$C NMR 7.9, 114.6, 118.9 (q, J=271), 128.1, 128.6, 128.7, 154.9 (q, J=40), 158.5. $^{19}$F NMR −63.2. LC/MS 6.79 min, [M+1]$^+$ 234.

Preparative Example 22

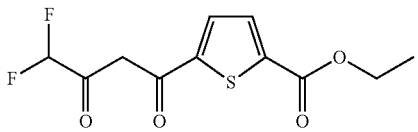 [SMILES: CCOC(=O)c1ccc(C(=O)CC(=O)C(F)F)s1]

5-(4,4-Difluoro-3-oxo-butyryl)-thiophene-2-carboxylic acid ethyl ester

Prepared from 5-Acetyl-thiophene-2-carboxylic acid ethyl ester and ethyl difluoroacetate by the method described in Preparative Example 3. Sodium methoxide was substituted with sodium ethoxide. The product was obtained as a crude oil (5.4 g, 85%). An approx. 5:1 isomer mixture was observed in the NMR spectra of product. $^1$H NMR (CDCl$_3$) 1.41 (t, J=7.0, 3 H), 3.63 (q, J=7.0, 2 H), 5.98 (t, minor isomer, J=53.2, 1 H), 6.05 (t, major isomer, J=54.0, 1 H), 6.45 (s, 1H), 7.74 (d, J=4.0, 1 H), 7.80 (d, J=4.0, 1 H). $^{19}$F NMR −127.8 (minor isomer, J=53.5), −127.1 (major isomer, J=55.5). LC/MS 5.18 min, [M+1]$^+$ 277.

Preparative Example 23

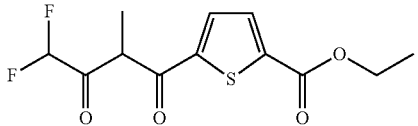 [SMILES: CCOC(=O)c1ccc(C(=O)C(C)C(=O)C(F)F)s1]

5-(4,4-Difluoro-2-methyl-3-oxo-butyryl)-thiophene-2-carboxylic acid ethyl ester

Prepared from 5-(4,4-Difluoro-3-oxo-butyryl)-thiophene-2-carboxylic acid ethyl ester by the method described in Preparative Example 4 to afford product as a crude oil (5.5 g, 108%). LC/MS 5.37 min, [M+1]$^+$ 291.

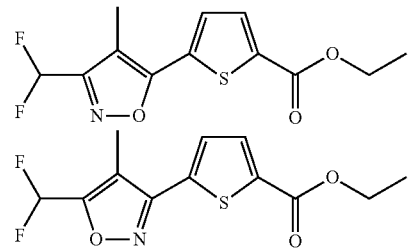

Preparative Example 24 and 25

5-(3-Difluoromethyl-4-methyl-isoxazol-5-yl)-thiophene-2-carboxylic acid ethyl ester and 5-(5-Difluoromethyl-4-methyl-isoxazol-3-yl)-thiophene-2-carboxylic acid ethyl ester Prepared from 5-(4,4-Difluoro-2-methyl-3-oxo-butyryl)-thiophene-2-carboxylic acid ethyl ester by the method described in Preparative Example 10. The crude material was chromatographed on silica gel with EtOAc/hexanes (10%) as eluant and the pure fractions isolated to afford products as colorless solids. High Rf material (Rf=0.40, 440 mg, 9%), low Rf material (Rf=0.24, 1.1 g, 22%), as well as an approximately 1:1 mixture of isomers (1.5 g, 30%).

Higher Rf Product: 5-(3-Difluoromethyl-4-methyl-isoxazol-5-yl)-thiophene-2-carboxylic acid ethyl ester: $^1$H NMR (CDCl$_3$) 1.41 (t, J=7.0, 3 H), 2.38 (s, 3H), 4.38 (q, J=7.0, 2 H), 6.80 (t, J=53.2, 1 H), 7.51 (d, J=4.4, 1 H), 7.82 (d, J=4.4, 1 H). $^{13}$C NMR 7.7, 14.5, 61.9, 109.5, 110.3 (t, J=236), 127.5, 133.7, 134.1, 136.3, 158.7 (t, J=29), 161.9. $^{19}$F NMR −118.2 (J=53.5). LC/MS 6.60 min, [M+1]$^+$ 288.

Lower Rf Product: 5-(5-Difluoromethyl-4-methyl-isoxazol-3-yl)-thiophene-2-carboxylic acid ethyl ester. $^1$H NMR (CDCl$_3$) 1.41 (t, J=7.0, 3 H), 2.37 (s, 3H), 4.39 (q, J=7.0, 2 H), 6.81 (t, J=52.7, 1 H), 7.50 (d, J=4.0, 1 H), 7.82 (d, J=4.0, 1 H). $^{13}$C NMR 7.7, 14.5, 61.8, 108.1 (t, J=238), 113.5, 128.4, 133.6, 135.4, 136.2, 157.7, 159.8 (t, J=29), 161.9. $^{19}$F NMR −118.2 (J=53.5). LC/MS 6.85 min, [M+1]$^+$ 288.

Preparative Example 26

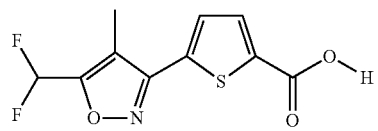 [SMILES: Cc1c(-c2ccc(C(=O)O)s2)noc1C(F)F]

5-(5-Difluoromethyl-4-methyl-isoxazol-3-yl)-thiophene-2-carboxylic acid

A solution of 5-(5-Difluoromethyl-4-methyl-isoxazol-3-yl)-thiophene-2-carboxylic acid ethyl ester (Preparative Example 25, 1.0 g, 3.48 mmol) in THF (20 mL) was treated with an aqueous solution (5 mL) of lithium hydroxide monohydrate (292 mg, 6.96 mmol) and allowed to stir for 20 hr. The reaction was then evaporated to a small volume and treated with a 1 N aqueous hydrochloric acid solution to a pH of ~2 and the resulting solids filtered, washed with water and air dried to afford product as a colorless solid (900 mg, 99%). $^1$H NMR (DMSO-d6) 2.29 (s, 3H), 7.44 (t, J=51.9, 1 H), 7.66 (d, J=2.6, 1 H), 7.78 (d, J=2.6, 1 H). $^{13}$C NMR 7.7, 108.1 (t, J=236), 115.0, 130.3, 134.3, 134.5, 137.4, 157.8, 159.6 (t, J=26), 163.1. $^{19}$F NMR −118.8 (J=51.5). LC/MS 5.41 min, [M+1]$^+$ 260.

Preparative Example 27

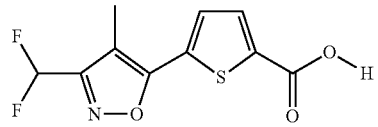 [SMILES: Cc1c(C(F)F)noc1-c1ccc(C(=O)O)s1]

5-(3-Difluoromethyl-4-methyl-isoxazol-5-yl)-thiophene-2-carboxylic acid

Prepared from 5-(3-Difluoromethyl-4-methyl-isoxazol-5-yl)-thiophene-2-carboxylic acid ethyl ester by the method described in Preparative Example 26 to afford product as a colorless solid (355 mg, 99%). $^1$H NMR (DMSO-d6) 2.27 (s, 3H), 7.33 (t, J=51.9, 1 H), 7.67 (d, J=4.0, 1 H), 7.80 (d, J=4.0, 1 H). $^{19}$F NMR −118.8 (J=51.5). LC/MS 5.90 min, [M+1]$^+$ 260.

Preparative Example 28

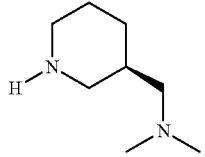

Dimethyl-(R)-1-piperidin-3-ylmethyl-amine, dihydrochloride

A solution of (S)-1-Boc-3-(aminomethyl)piperdine (429 mg, 2.0 mmol, CAS [140645-24-5], CHN Technologies, Woburn Mass., USA) in dichloromethane (10 mL) was treated with a 37% aqueous formaldehyde solution (551 µL, 20.0 mmol) followed by sodium triacetoxyborohydride (4.23 g, 20.0 mmol). The mixture was stirred for 4 h then quenched with dichloromethane (10 mL) and saturated aqueous solution of NaHCO$_3$ (50 mL). The organic portion was further washed with a brine solution (10 mL), then dried over MgSO$_4$, filtered, and evaporated in vacuo to afford product as an oil. LC/MS 1.10 min, [M+1]$^+$ 243. The methylated intermediate was dissolved in 1,4-dioxane (5 mL) and treated with a 4 N solution of hydrogen chloride in 1,4,-dioxane (5 mL) and stirred for 2 hr, after which time product had precipitated out of solution. The reaction mixture was evaporated in vacuo and filtered with the aid of ethyl ether. The resulting solids were air dried to afford product as a colorless solid (290 mg, 67% overall). LC/MS 0.60 min, [M+1]$^+$ 143.

Preparative Example 29

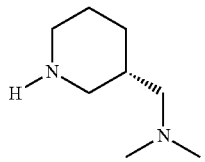

Dimethyl-(S)-1-piperidin-3-ylmethyl-amine, dihydrochloride

Prepared from (R)-1-Boc-3-(aminomethyl)piperidine (429 mg, 2.0 mmol, CAS [140645-23-4], CHN Technologies, Woburn Mass., USA) in the same manner as the R isomer described in Preparative Example 28. Colorless solid (306 mg, 71% overall). LC/MS 0.60 min, [M+1]$^+$ 143.

Preparative Example 30

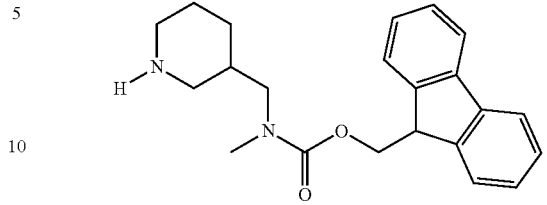

Methyl-piperidin-3-ylmethyl-carbamic acid 9H-fluoren-9-ylmethyl ester, hydrochloride A solution of 9-fluorenylmethoxycarbonyl chloride (259 mg, 1.0 mmol) in THF (3 mL), at 0-5° C., was treated with a THF solution (2 mL) containing 1-Boc-3-methylaminopiperdine (214 mg, 1.0 mmol, CAS [392331-89-4], CHN Technologies, Woburn Mass., USA) and diisopropylethylamine (174 µL, 1.0 mmol). The reaction mixture was allowed to stir for 1 h then placed in a 0-5° C. refrigerator for 16 h. After this time the reaction mixture was evaporated in vacuo, partitioned between EtOAc (10 mL) and a 1N aqueous HCl solution (10 mL), and the organic portion further washed with a saturated aqueous solution of NaHCO$_3$ (10 mL) followed by a brine solution (10 mL). The organic portion was then dried over MgSO$_4$, filtered, and evaporated in vacuo to afford crude oil. The oil was chromatographed on silica gel with EtOAc/hexane (40%) to afford the Fmoc/Boc-protected intermediate as a colorless foam (409 mg, 94%). The intermediate was then dissolved in 1,4-dioxane (5 mL) and treated with a 4 N solution of hydrogen chloride in 1,4,-dioxane (5 mL), stirred for 2 hr, then evaporated in vacuo to afford product as a colorless solid. LC/MS 4.42 min, [M+1]$^+$ 337.

Preparative Example 31

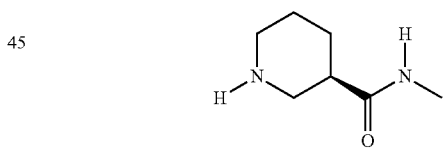

(3R)—N-methylpiperidine-3-carboxamide

A solution of D-Cbz-Nipecotic acid ((R)-Piperdine-1,3,-dicarboxylic acid 1-benzyl ester) (1.32 g, 5.0 mmol) in toluene (25 mL) was treated with DMF (20 µL) followed by oxalyl chloride (646 µL, 7.5 mmol). The reaction mixture was stirred for 3 hr and evaporated to an oil. The crude acid chloride was then dissolved in THF (20 mL), cooled to 0-5° C., and treated with a 2 M THF solution of methylamine (7.5 mL, 15 mmol). The reaction mixture was stirred for 2 hr, allowed to warm to room temperature and evaporated in vacuo to afford solids which were filtered with the aid of water to afford Cbz-protected intermediate as a colorless solid (1.2 5 g, 91%). LC/MS 5.05 min, [M+1]$^+$ 277. The CbZ-protected intermediate (1.0 g, 3.62 mmol) was dissolved in EtOH (50 mL), treated with a 10% palladium on carbon (50% water content) catalyst (750 mg) and hydrogenated at 60-70 psi hydrogen for 5 hr. The crude reaction mixture was then filtered through Celite, evaporated in vacuo, and redissolved in EtOH (10 mL) which was filtered through a nylon syringe filter to remove residual catalyst. Evaporation of the solution afforded crude product as a tacky solid (581 mg, 113%). LC/MS 0.68 min, [M+1]+ 143.

Preparative Example 32

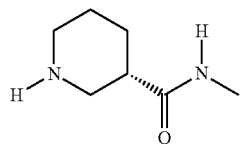

(3S)—N-methylpiperidine-3-carboxamide

Prepared from L-Cbz-Nipecotic acid in the same manner as the D/(R) isomer described in Preparative Example 31. CBz-protected intermediate as a colorless solid (1.22 g, 88%). LC/MS 4.96 min, [M+1]+ 277. Evaporation of the mixture afforded crude product as a tacky solid (571 mg, 111%). LC/MS 0.64 min, [M+1]+ 143.

Preparative Example 33

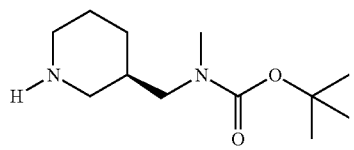 [SMILES: CN(C[C@@H]1CCCNC1)C(=O)OC(C)(C)C]

tert-butyl methyl[(3R)-piperidin-3-ylmethyl]carbamate

A solution of (3R)—N-methylpiperidine-3-carboxamide (Preparative Example 31, 430 mg, 3.0 mmol) in acetonitrile (3 mL) was treated with triethylamine (836 L, 6.0 mmol) followed by benzylbromide (449 µL, 3.75 mmol). The reaction mixture was allowed to stir for 24 hr then partitioned between EtOAc (20 mL) and a saturated aqueous solution of NaHCO₃ (20 mL). The organic portion was washed with an additional portion of NaHCO₃ solution followed by a brine solution (10 mL), then dried over MgSO₄, filtered, and evaporated in vacuo to afford N-benzylated intermediate as a waxy solid (459 mg, 66%). The intermediate (450 mg, 1.94 mmol) was then dissolved in THF (20 mL) and treated with a 1M THF solution of lithium aluminum hydride (2.9 mL, 2.91 mmol) followed by heating at 60° C. for 8 hr. After this time the reaction mixture was cooled in an ice bath and quenched sequentially with water (0.5 mL), a 1 M NaOH solution (1 mL), and solid MgSO₄. The reaction mixture was allowed to stir for 30 min followed by filtration with the aid of THF. Evaporation of the filtrate in vacuo afforded the N-benzylated amine intermediate as a clear liquid (403 mg, 95%). LC/MS 0.66 min, [M+1]+ 219. The amine intermediate (400 mg, 1.83 mmol) was then dissolved in THF (10 mL) and treated with triethylamine (510 µL, 3.66 mmol) followed by di-tert-butyl dicarbonate (600 mg, 1.83 mmol) and allowed to stir for 16 hr. After this time the reaction mixture was partitioned between EtOAc (20 mL) and a saturated aqueous solution of NaHCO₃ (20 mL). The organic portion was washed with an additional portion of NaHCO₃ solution followed by a brine solution (10 mL), then dried over MgSO₄, filtered, and evaporated in vacuo to afford and oil that was chromatographed on silica gel with EtOAc/hexanes (30%) then MeOH/EtOAc (10%) as eluant to afford N-benzylated-N—BOC-protected product as colorless oil (442 mg, 76%). LC/MS 4.42 min, [M+1]+ 319. The differentially protected intermediate (440 mg, 1.38 mmol) was dissolved in EtOH (50 mL), treated with palladium hydroxide on carbon (Pearlman's catalyst, 500 mg) and hydrogenated at 60-70 psi hydrogen for 8 hr. The crude reaction mixture was then filtered through Celite, evaporated in vacuo, and redissolved in EtOH (10 mL) which was filtered through a nylon syringe filter to remove residual catalyst. Evaporation of the mixture afforded crude product a clear colorless oil (298 mg, 94%, 45% overall). LC/MS 3.71 min, [M+1]+ 229.

Preparative Example 34

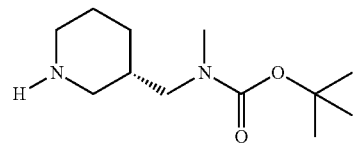 [SMILES: CN(C[C@H]1CCCNC1)C(=O)OC(C)(C)C]

tert-butyl methyl[(3S)-piperidin-3-ylmethyl]carbamate

Prepared from (3S)—N-methylpiperidine-3-carboxamide (Preparative Example 32) in the same manner as the (3R) isomer described in Preparative Example 33. Product obtained as a colorless oil (340 mg, 51% overall). LC/MS 1.76 min, [M+1]+ 229

Preparative Example 35

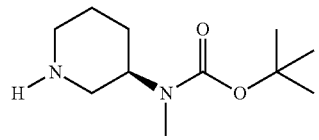

(tert-butyl methyl[(3R)-piperidin-3-yl]carbamate

A solution of (R)-3-(tert-butoxycarbonylamino)piperdine (2.0 g, 10.0 mmol) in THF (25 mL), at 0-5 OC, was treated with triethylamine (1.67 mL, 12.0 mmol) followed by benzyl chloroformate (1.55 mL, 11.0 mmol) and allowed to stir at that temperature for 24 hr. The reaction mixture was then evaporated in vacuo to ~¼ volume and partitioned between EtOAc (20 mL) and a 1 M HCl solution (20 mL). The organic portion was then sequentially washed with another portion of 1 M HCl (10 mL), a saturated aqueous solution of NaHCO₃ (10 mL), and a brine solution (10 mL). The organic portion was then dried over MgSO₄, filtered, and evaporated in vacuo to afford the N-Cbz protected intermediate as a colorless solid (3.2 g, 96%). LC/MS 6.58 min, [M+1]+ 335. The differentially protected intermediate (1.67 g, 5.0 mmol) was then dissolved in DMF (20 mL) at 0-5° C. and treated with a 60% suspension of sodium hydride (240 mg, 6.0 mmol). The reaction mixture was allowed to warm to room temperature for 10 min then recooled and iodomethane (374 μL, 6.0 mmol) added. After 2 hr, and warming to room temperature, an additional amount (40 μL, 1.0 mmol) of iodomethane was added and the reaction mixture allowed to stir 16 hr. After this time the reaction mixture was evaporated in vacuo to ~¼ volume and partitioned between EtOAc (50 mL) and a water (50 mL). The organic portion was then washed with a brine solution (50 mL), dried over MgSO₄, filtered, and evaporated in vacuo to afford a residue which was chromatographed on silica gel with EtOAc/hexanes (20% then 30%) to afford the N-methylated intermediate as a colorless oil (1.59 g, 93%). LC/MS 6.92 min, [M+1]+ 349. The N-methylated intermediate (1.56 g, 4.48 mmol) was dissolved in EtOH (50 mL), treated with 10% palladium on carbon (250 mg) and hydrogenated at 60-70 psi hydrogen for 6 hr. The crude reaction mixture was then filtered through Celite, evaporated in vacuo, and redissolved in EtOH (5 mL) which was filtered through a nylon syringe filter to remove residual catalyst. Evaporation of the mixture afforded crude product as a clear colorless oil. Product yield was treated as quantitative for last step and used as reagent in a further reaction (Example 93). LC/MS 1.49 min, [M+1]+ 215.

Preparative Example 36

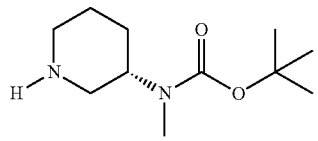

tert-butyl methyl[(3S)-piperidin-3-yl]carbamate

Prepared from (S)-3-(tert-butoxycarbonylamino)piperdine in the same scale and manner as the (3R) isomer described in Preparative Example 35. Yields were 96% and 93% for the first two steps. Product yield was treated as quantitative for last step and used as reagent in a further reaction (Example 94). LC/MS 1.30 min, [M+1]+ 215.

Compound Preparations

Example 1

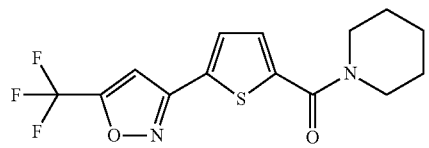 [SMILES: O=C(c1ccc(-c2cc(C(F)(F)F)on2)s1)N1CCCCC1]

Piperidin-1-yl-[5-(5-trifluoromethyl-isoxazol-3-yl)-thiophen-2-yl]-methanone

A solution of 4,4,4-Trifluoro-1-[5-(piperidine-1-carbonyl)-thiophen-2-yl]-butane-1,3-dione (Preparative Example 3, 333 mg, 1 mmol) in glacial acetic acid (2.5 mL) was treated with hydroxylamine hydrochloride (73 mg, 1.05 mol) and heated at 80-90° C. for 24 hr, after which time the reaction was evaporated and filtered with the aid of 30% EtOAc/hexanes to afford the 5-hydroxy-4,5,-dihydro-isoxazole intermediate (225 mg). The intermediate was then dissolved in trifluoroacetic acid (2.5 mL) and heated at reflux for 3 days. The reaction was then evaporated and the residue chromatographed on silica gel with EtOAc/hexanes (30 then 50%) as eluant to afford product as a colorless solid (105 mg, 32%). ¹H NMR (CDCl₃) 1.65-1.73 (m, 6H), 3.66-3.69 (m, 4H), 6.95 (s, 1H), 7.28 (d, J=4.0, 1 H), 7.44 (d, J=4.0, 1 H). ¹³C NMR 24.7, 26.4, 47.0 (br), 103.7, 110.0, 114.3 (q, J=267), 128.0, 129.0, 131.0, 140.9, 155.1 (q, J=40), 157.5, 162.5. ¹⁹F NMR −64.6. LC/MS 6.63 min, [M+1]+ 331.

Example 2

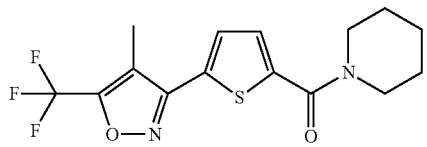 [SMILES: Cc1c(-c2ccc(C(=O)N3CCCCC3)s2)noc1C(F)(F)F]

[5-(4-Methyl-5-trifluoromethyl-isoxazol-3-yl)-thiophen-2-yl]-piperidin-1-yl-methanone Method A Prepared from 4,4,4-Trifluoro-2-methyl-1-[5-(piperidine-1-carbonyl)-thiophen-2-yl]-butane-1,3-dione as described in Example 1. Chromatographed on silica gel with EtOAc/hexanes (40%) as eluant to afford product as a colorless solid (90 mg, 26%). ¹H NMR (CDCl₃) 1.62-1.68 (m, 6H), 2.33 (d, J=1.3, 3 H), 3.64-3.67 (m, 4H), 7.28 (d, J=4.0, 1 H), 7.41 (d, J=3.5, 1 H). ¹³C NMR 7.9, 24.7, 26.3, 46.0 (br), 114.7, 118.8 (q, J=271), 128.0, 129.0, 131.0, 140.3, 155.1 (q, J=40), 158.0, 162.3. ¹⁹F NMR −63.2. LC/MS 7.92 min, [M+1]+ 344.

Method B

A solution of 5-(4-Methyl-5-trifluoromethyl-isoxazol-3-yl)-thiophene-2-carboxylic acid (Preparative Example 14, 139 mg, 0.5 mmol) in toluene (5 mL) was treated with DMF (~5 μL) followed by oxalyl chloride (85 μL, 1.0 mmol). The reaction was allowed to stir for 2 hr at room temperature and 1 hr at 40 OC. The reaction was then concentrated in vacuo to afford crude acid chloride which was dissolved in THF (5 mL) and treated with a THF solution (2 mL) of triethylamine (84 μL, 0.6 mmol) and piperdine (54 μL, 0.55 mmol). The reaction was allowed to stir for 2 hr and concentrated to approximately ¼ volume and partitioned between EtOAc (10 mL) and an aqueous 1N hydrochloric acid solution (10 mL). The organic portion was then washed with a second portion of 1N hydrochloric acid solution followed by a saturated aqueous solution of NaHCO₃ (10 mL) and brine (10 mL). The organic solution was then dried over MgSO₄, filtered, and concentrated in vacuo to afford product which required no further purification.

Example 3

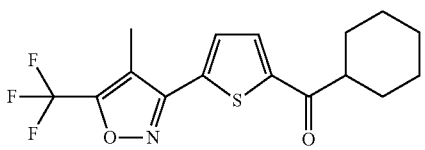 [SMILES: Cc1c(-c2ccc(C(=O)C3CCCCC3)s2)noc1C(F)(F)F]

Cyclohexyl-[5-(4-methyl-5-trifluoromethyl-isoxazol-3-yl)-thiophen-2-yl]-methanone A solution of 4-Methyl-3-thiophen-2-yl-5-trifluoromethyl-isoxazole (Preparative Example 21, 468 mg, 2.0 mmol) in dichloromethane (20 mL) was treated with FeCl₃ (324 mg, 2.0 mmol) followed by cyclohexylcarbonyl chloride (268 μL, 05. mmol). The reaction was heated at reflux for 20 hours followed by evaporation and partitioning between EtOAc (25 mL) and an aqueous 1N hydrochloric acid solution (25 mL). The organic portion was then washed with a second portion of 1N hydrochloric acid solution and brine, dried over MgSO₄, filtered, and concentrated in vacuo to afford crude product. The crude product was then chromatographed on silica gel with EtOAc/hexanes (3%) as eluant to afford product as a colorless solid (240 mg, 35%). $^1$H NMR (CDCl₃) 1.24-1.76 (m, 6H), 1.84-1.94 (m, 4H), 2.37 (d, J=1.3, 3 H), 3.05-3.15 (m, 1H), 7.54 (d, J=4.0, 1 H), 7.74 (d, J=4.0, 1 H). $^{13}$C NMR 7.9, 25.9, 26.0, 29.7, 47.8, 114.8, 118.7 (q, J=271), 129.1, 131.6, 135.5, 146.0, 155.4 (q, J=41), 158.0, 196.8. $^{19}$F NMR −63.1. LC/MS 7.92 min, [M+1]⁺ 344.

Example 4

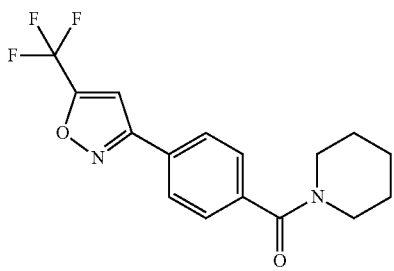 [SMILES: O=C(c1ccc(-c2cc(C(F)(F)F)on2)cc1)N1CCCCC1]

Piperidin-1-yl-[4-(5-trifluoromethyl-isoxazol-3-yl)-phenyl]-methanone

A solution of 4-(5-Trifluoromethyl-isoxazol-3-yl)-benzoic acid (Preparative Example 11, 256 mg, 1.0 mmol) in toluene (10 mL) was treated with DMF (~5 L) followed by oxalyl chloride (112 μL, 1.3 mmol). The reaction was allowed to stir for 3 hr then concentrated in vacuo to afford crude acid chloride which was dissolved in THF (5 mL) and treated with a THF solution (2 mL) of triethylamine (174 μL, 1.25 mmol) and piperdine (109 μL, 1.1 mmol). The reaction was allowed to stir for 3 hr and concentrated in vacuo to afford crude product which was filtered with the aid of water and solids air dried to afford product as a colorless solid (295 mg, 91%). $^1$H NMR (CDCl₃) 1.55-1.70 (m, 6H), 3.35 (br s, 2H), 3.73 (br s, 2H), 7.04 (s, 1H), 7.52 (d, J=8.3, 2 H), 7.86 (d, J=7.9, 2 H). $^{13}$C NMR 24.7, 25.8, 26.8, 43.4, 49.0, 103.7, 118.0 (q, J=270), 127.3, 127.9, 128.4, 139.2, 162.2, 169.4. $^{19}$F NMR −64.6. LC/MS 6.49 min, [M+1]⁺ 325.

Example 5

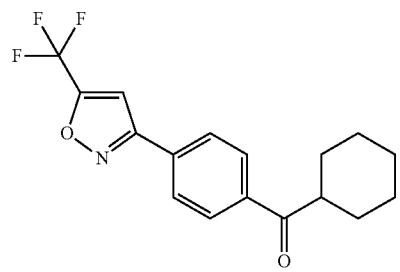 [SMILES: O=C(c1ccc(-c2cc(C(F)(F)F)on2)cc1)C1CCCCC1]

Cyclohexyl-[4-(5-trifluoromethyl-isoxazol-3-yl)-phenyl]-methanone

A solution of N-Methoxy-N-methyl-4-(5-trifluoromethyl-isoxazol-3-yl)-benzamide (Preparative Example 15, 300 mg, 1.0 mmol) in THF (10 mL) was treated with a 1 N THF solution of cyclohexylmagnesium bromide (4 mL, 4 mmol) and stirred for 2 hr then quenched with a saturated ammonium chloride solution (2 mL) and diluted with EtOAc (10 mL). The organic layer was then washed with brine (2×10 mL), dried over MgSO₄, filtered, evaporated in vacuo and the residue chromatographed on silica gel with EtOAc/hexanes (5 then 10%) as eluant to afford product as a colorless solid (81 mg, 25%). $^1$H NMR (CDCl₃) 1.26-1.58 (m, 5H), 1.74-1.94 (m, 5H), 3.23-3.32 (m, 1H), 7.09 (s, 1H), 7.79 (d, J=8.3, 2 H), 7.87 (d, J=8.3, 2 H). $^{19}$F NMR −64.6. LC/MS 7.79 min, [M+1]⁺ 324.

Example 6

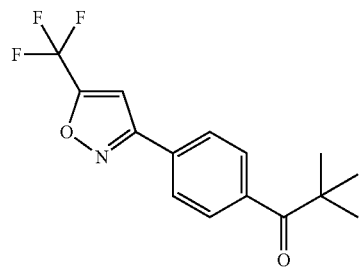 [SMILES: CC(C)(C)C(=O)c1ccc(-c2cc(C(F)(F)F)on2)cc1]

2,2-Dimethyl-1-[4-(5-trifluoromethyl-isoxazol-3-yl)-phenyl]-propan-1-one

Prepared from N-Methoxy-N-methyl-4-(5-trifluoromethyl-isoxazol-3-yl)-benzamide and a 1.7 N THF solution of tert-butylmagnesium bromide as described in Example 5. Chromatographed on silica gel with EtOAc/hexanes (5 then 10%) as eluant to afford product as a colorless solid (21 mg, 7%). $^1$H NMR (CDCl$_3$) 1.37 (s, 9H), 7.05 (s, 1H), 7.79 (d, J=8.4, 2 H), 7.87 (d, J=7.9, 2 H). $^{19}$F NMR −64.6. LC/MS 7.28 min, [M+1]$^+$ 298.

Example 7

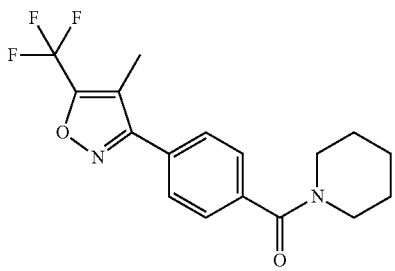 [SMILES: Cc1c(-c2ccc(C(=O)N3CCCCC3)cc2)noc1C(F)(F)F]

[4-(4-Methyl-5-trifluoromethyl-isoxazol-3-yl)-phenyl]-piperidin-1-yl-methanone

Prepared from 4-(4-Methyl-5-trifluoromethyl-isoxazol-3-yl)-benzoic acid as described in Example 4. Chromatographed on silica gel with EtOAc/hexanes (20 then 25%) as eluant to afford product as a colorless solid (136 mg, 80%). $^1$H NMR (CDCl$_3$) 1.49-1.64 (m, 6H), 2.21 (d, J=1.8, 3 H), 3.31 (br s, 2H), 3.67 (br s, 2H), 7.47 (d, J=7.9, 2 H), 7.60 (d, J=7.9, 2 H). $^{13}$C NMR 7.6, 24.7, 25.8, 26.7, 43.3, 48.9, 115.0, 118.9 (q, J=271), 127.6, 128.7, 128.8, 138.6, 154.8 (q, J=40), 163.2, 169.4. $^{19}$F NMR −63.3. LC/MS 6.65 min, [M+1]$^+$ 339.

Example 8

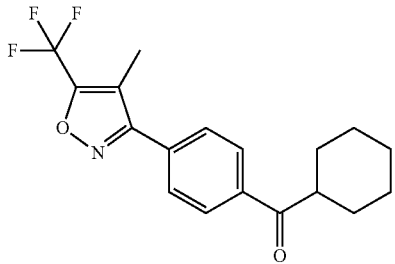 [SMILES: Cc1c(-c2ccc(C(=O)C3CCCCC3)cc2)noc1C(F)(F)F]

Cyclohexyl-[4-(4-methyl-5-trifluoromethyl-isoxazol-3-yl)-phenyl]-methanone

Prepared from N-Methoxy-N-methyl-4-(4-methyl-5-trifluoromethyl-isoxazol-3-yl)-benzamide as described in Example 5. Chromatographed on silica gel with EtOAc/hexanes (5%) as eluant to afford product as a colorless solid (130 mg, 19%). $^1$H NMR (CDCl$_3$) 1.23-1.56 (m, 5H), 1.71-1.91 (m, 5H), 2.27 (d, J=0.9, 3 H), 3.22-3.30 (m, 1H), 7.71 (d, J=7.9, 2 H), 8.04 (d, J=8.3, 2 H). $^{19}$F NMR −63.3. LC/MS 7.88 min, [M+1]$^{+338}$.

Example 9

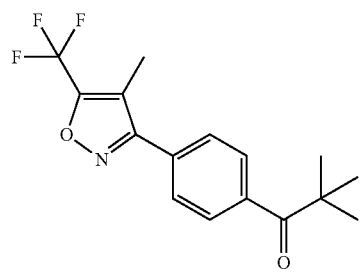 [SMILES: Cc1c(-c2ccc(C(=O)C(C)(C)C)cc2)noc1C(F)(F)F]

2,2-Dimethyl-1-[4-(4-methyl-5-trifluoromethyl-isoxazol-3-yl)-phenyl]-propan-1-one Prepared from N-Methoxy-N-methyl-4-(4-methyl-5-trifluoromethyl-isoxazol-3-yl)-benzamide and tert-butylmagnesium bromide as described in Example 5. Chromatographed on silica gel with EtOAc/hexanes (5%) as eluant to afford product as a colorless solid (53 mg, 9%). $^1$H NMR (CDCl$_3$) 1.37 (s, 9H), 2.29 (d, J=1.3, 3 H), 7.68 (d, J=7.9, 2 H), 7.81 (d, J=8.3, 2 H). $^{19}$F NMR −63.2. LC/MS 7.42 min, [M+1]$^+$ 312.

Example 10

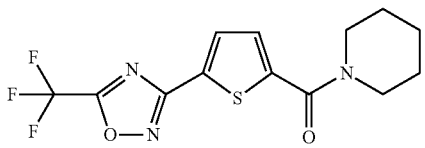 [SMILES: O=C(c1ccc(-c2noc(C(F)(F)F)n2)s1)N1CCCCC1]

Piperidin-1-yl-[5-(5-trifluoromethyl-[1,2,4]oxadiazol-3-yl)-thiophen-2-yl]-methanone A solution of 5-(Piperidine-1-carbonyl)-thiophene-2-carbonitrile (Preparative Example 18, 1.27 g, 5.77 mmol) in EtOH/water (20 mL/4 mL) was treated with sodium acetate (638 mg, 6.92 mmol) followed by hydroxylamine hydrochloride (481 mg, 6.92 mmol) and the resulting mixture heated at reflux for 2 hr then evaporated in vacuo. The resulting solids were filtered with the aid of water and air dried for 1.25 g (86%) of intermediate amidoxime. The intermediate amidoxime (1.15 g, 4.54 mmol) was dissolved in toluene (30 mL), treated with trifluoroacetic anhydride (1.89 mL, 13.62 mmol), and heated at reflux for 3 hr. The reaction was allowed to cool to room temperature and stir 16 hr then evaporated in vacuo and the residue chromatographed on silica gel with EtOAc/hexanes (20 then 40%) as eluant to afford product as a colorless solid (953 mg, 63%). $^1$H NMR (CDCl$_3$) 1.66-1.73 (m, 6H), 3.66-3.70 (m, 4H), 7.32 (d, J=4.0, 1 H), 7.80 (d, J=4.0, 1 H). $^{13}$C NMR 24.6, 26.3, 45.5 (br), 48.3 (br), 116.0 (q, J=274), 128.2, 129.2, 130.7, 142.5, 162.4, 165.0, 166.1 (q, J=45). $^{19}$F NMR −65.8. LC/MS 6.50 min, [M+1]$^+$ 332.

Example 11

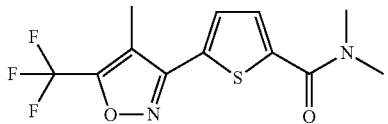 [SMILES: Cc1c(-c2ccc(C(=O)N(C)C)s2)noc1C(F)(F)F]

5-(4-Methyl-5-trifluoromethyl-isoxazol-3-yl)-thiophene-2-carboxylic acid dimethylamide Prepared from 5-(4-Methyl-5-trifluoromethyl-isoxazol-3-yl)-thiophene-2-carboxylic acid and dimethylamine hydrochloride by the method described in Example 2 Method B utilizing an additional equivalent of triethylamine. The reaction mixture was evaporated to a solid then triturated and filtered with the aid of water to afford product as a colorless solid (110 mg, 72%). $^1$H NMR (CDCl$_3$) 2.37 (s, 3H), 3.22 (br s, 6H), 7.41 (d, J=4.0, 1 H), 7.47 (d, J=4.0, 1 H). $^{13}$C NMR 7.9, 37.0 (br), 39.8 (br), 114.7, 118.8 (q, J=271), 128.0, 129.7, 131.6, 140.9, 155.7 (q, J=41), 158.0, 163.7. $^{19}$F NMR −63.2. LC/MS 6.03 min, [M+1]$^+$ 305.

Example 12

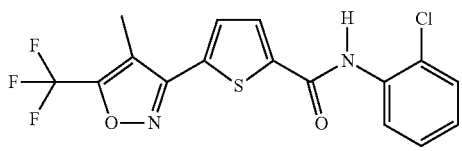 [SMILES: Cc1c(-c2ccc(C(=O)Nc3ccccc3Cl)s2)noc1C(F)(F)F]

5-(4-Methyl-5-trifluoromethyl-isoxazol-3-yl)-thiophene-2-carboxylic acid (2-chloro-phenyl)-amide Prepared from 5-(4-Methyl-5-trifluoromethyl-isoxazol-3-yl)-thiophene-2-carboxylic acid and 2-chloroaniline by the method described in Example 2 Method B. The reaction mixture was evaporated in vacuo, triturated and filtered with the aid of water, then washed with an aqueous 1 N hydrochloric acid solution followed by water. The crude solid was then chromatographed on silica gel with EtOAc/hexanes (10 then 15%) as eluant to afford product as a colorless solid (42 mg, 43%). $^1$H NMR (CDCl$_3$) 2.39 (d, J=1.3, 3 H), 7.10 (td, J=7.9, 1.3, 1 H), 7.33 (td, J=7.9, 1.3, 1 H), 7.42 (dd, J=8.3, 1.8, 1 H), 7.56 (d, J=4.0, 1 H), 7.69 (d, J=4.0, 1 H), 8.34 (s, 1H), 8.46 (dd, J=1.3, 1 H). $^{13}$C NMR 8.0, 114.8, 118.7 (q, J=271), 123.2, 125.4, 128.2, 129.0, 129.3, 134.0, 134.3, 141.7, 155.5 (q, J=40), 157.8, 159.0. $^{19}$F NMR −63.1. LC/MS 7.19 min, [M+1]$^+$ 387.

Example 13

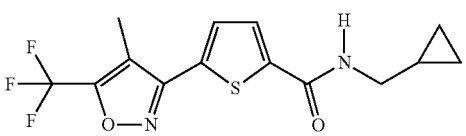 [SMILES: Cc1c(-c2ccc(C(=O)NCC3CC3)s2)noc1C(F)(F)F]

5-(4-Methyl-5-trifluoromethyl-isoxazol-3-yl)-thiophene-2-carboxylic acid cyclopropylmethyl-amide Prepared from 5-(4-Methyl-5-trifluoromethyl-isoxazol-3-yl)-thiophene-2-carboxylic acid and cyclopropylmethylamine by the method described in Example 2 Method B. The reaction mixture was evaporated in vacuo, triturated and filtered with the aid of water, then washed with an aqueous 1 N hydrochloric acid solution followed by water. The crude solid was then triturated with a 25% EtOAc/hexanes solution (3×1 mL) and air dried to afford product as a colorless solid (110 mg, 67%). $^1$H NMR (CDCl$_3$) 0.27-0.32 (m, 2H), 0.55-0.61 (m, 2H), 1.03-1.12 (m, 1H), 2.37 (d, J=0.9, 3 H), 3.31 (d, J=5.7, 1 H), 3.33 (d, J=5.7, 1 H), 6.23 (br s, 1H), 7.50 (d, J=4.0, 1 H), 7.56 (d, J=4.0, 1 H). $^{19}$F NMR −63.1. LC/MS 6.5 min, [M+1]$^+$ 331.

Example 14

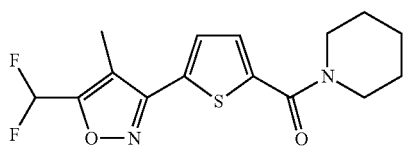 [SMILES: Cc1c(-c2ccc(C(=O)N3CCCCC3)s2)noc1C(F)F]

[5-(5-Difluoromethyl-4-methyl-isoxazol-3-yl)-thiophen-2-yl-piperidin]-1-yl-methanone Prepared from 5-(5-Difluoromethyl-4-methyl-isoxazol-3-yl)-thiophene-2-carboxylic acid (Preparative Example 26) and piperdine by the method described in Example 2 Method B. The reaction mixture was evaporated in vacuo, then chromatographed on silica gel with EtOAc/hexanes (30 then 40%) as eluant to afford product as a colorless solid (54 mg, 66%). $^1$H NMR (CDCl$_3$) 1.65-1.72 (6, 3 H), 2.34 (s, 3H), 3.67-3.70 (m, 4H), 6.80 (t, J=53.2, 1 H), 7.30 (d, J=4.0, 1 H), 7.43 (d, J=3.5, 1 H). $^{13}$C NMR 7.7, 24.7, 26.3, ~46 (br), 39.8 (br), 108.1 (t, J=238), 113.5, 127.6, 128.9, 131.6, 140.1, 157.8, 159.5 (q, J=29), 162.7. $^{19}$F NMR −118.2 (J=53.5). LC/MS 6.18 min, [M+1]$^+$ 327.

Example 15

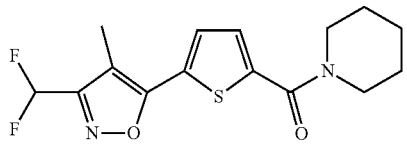 [SMILES: Cc1c(C(F)F)noc1-c1ccc(C(=O)N2CCCCC2)s1]

[5-(3-Difluoromethyl-4-methyl-isoxazol-5-yl)-thiophen-2-yl-piperidin]-1-yl-methanone Prepared from 5-(3-Difluoromethyl-4-methyl-isoxazol-5-yl)-thiophene-2-carboxylic acid (Preparative Example 27) and piperdine by the method described in Example 2 Method B. The reaction mixture was evaporated in vacuo, then chromatographed on silica gel with EtOAc/hexanes (30 then 40%) as eluant to afford product as a colorless solid (110 mg, 72%). $^1$H NMR (CDCl$_3$) 1.66-1.72 (6, 3 H), 2.35 (s, 3H), 3.67-3.71 (m, 4H), 6.79 (t, J=53.2, 1 H), 7.31 (d, J=4.0, 1 H), 7.45 (d, J=4.0, 1 H). $^{13}$C NMR 7.7, 24.7, 26.3, ~46 (br), 39.8 (br), 108.7, 110.3 (t, J=236), 126.8, 128.8, 130.6, 140.6, 158.6 (q, J=30), 162.1, 162.5. $^{19}$F NMR −117.4 (J=53.5). LC/MS 6.36 min, [M+1]$^+$ 327.

Example 16

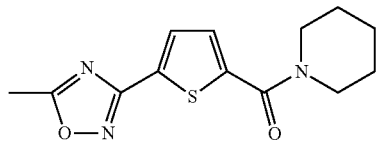 [SMILES: Cc1nc(-c2ccc(C(=O)N3CCCCC3)s2)no1]

[5-(5-Methyl-[1,2,4]oxadiazol-3-yl)-thiophen-2-yl]-piperidin-1-yl-methanone

Prepared from 5-(5-Methyl-[1,2,4]oxadiazol-3-yl)-thiophene-2-carboxylic acid (CAS [133380-64-0]) as described in Example 4. Product was obtained as a colorless solid (80 mg, 77%). $^1$H NMR 1.60 (br m, 6H), 2.59 (s, 3H), 3.61 (br m, 4H), 7.22 (d, J=4.0, 1 H), 7.61 (d, J=3.5, 1 H). $^{13}$C NMR 12.5, 24.7, 26.3, 46.5 (br), 128.7, 129.1, 130.6, 141.0, 162.7, 164.2, 177.0. LC/MS 5.51 min, [M+1]$^+$ 278.

Example 17

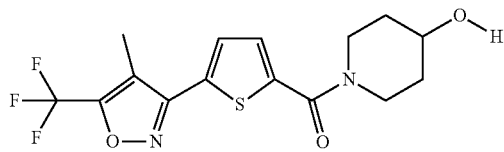 [SMILES: Cc1c(-c2ccc(C(=O)N3CCC(O)CC3)s2)noc1C(F)(F)F]

(4-Hydroxy-piperidin-1-yl)-[5-(4-methyl-5-trifluoromethyl-isoxazol-3-yl)-thiophen-2-yl]-methanone Prepared from 5-(4-Methyl-5-trifluoromethyl-isoxazol-3-yl)-thiophene-2-carboxylic acid and 4-hydroxypiperdine by the method described in Example 2 Method B. The reaction mixture was evaporated to a solid, triturated and filtered with the aid of water, then washed with a 1 N aqueous hydrochloric acid solution followed by water. The solid was air dried to afford product as a colorless solid (141 mg, 78%). $^1$H NMR (CDCl$_3$) 1.58-1.69 (m, 2H), 1.93-2.00 (m, 2H), 2.26 (br s, 1H), 2.37 (s, 3H), 3.44-3.52 (m, 2H), 4.00-4.12 (m, 3H), 7.33 (d, J=4.0, 1 H), 7.46 (d, J=3.5, 1 H). $^{13}$C NMR 7.9, 34.4, 42 (br), 66.9, 114.8, 118.7 (q, J=271), 128.0, 129.2, 131.2, 140.1, 155.2 (q, J=40), 158.1, 162.8. $^{19}$F NMR −63.1. LC/MS 5.71 min, [M+1]$^+$ 361.

Example 18

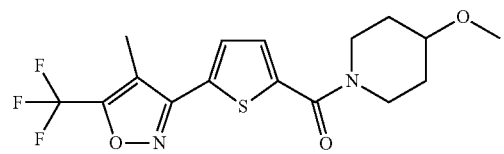 [SMILES: COC1CCN(C(=O)c2ccc(-c3noc(C(F)(F)F)c3C)s2)CC1]

(4-Methoxy-piperidin-1-yl)-[5-(4-methyl-5-trifluoromethyl-isoxazol-3-yl)-thiophen-2-yl]-methanone Prepared from 5-(4-Methyl-5-trifluoromethyl-isoxazol-3-yl)-thiophene-2-carboxylic acid and 4-methoxypiperdine by the method described in Example 2 Method B. The reaction mixture was evaporated to a solid, triturated and filtered with the aid of water, then washed with a 1 N aqueous hydrochloric acid solution followed by water. The solid was air dried to afford product as a colorless solid (151 mg, 81%). $^1$H NMR (CDCl$_3$) 1.64-1.72 (m, 2H), 1.86-1.93 (m, 2H), 2.33 (d, J=1.3, 3 H), 3.36 (s, 3H), 3.47-3.58 (m, 3H), 3.87-3.95 (m, 2H), 7.29 (d, J=3.5, 1 H), 7.42 (d, J=4.0, 1 H). $^{13}$C NMR 7.9, 30.9, 42 (br), 56.1, 75.2, 114.7, 118.7 (q, J=271), 128.0, 129.1, 131.1, 140.3, 155.2 (q, J=40), 158.0, 162.7. $^{19}$F NMR −63.2. LC/MS 6.31 min, [M+1]$^+$ 375.

Example 19

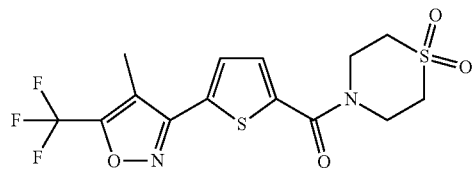 [SMILES: Cc1c(-c2ccc(C(=O)N3CCS(=O)(=O)CC3)s2)noc1C(F)(F)F]

(1,1-Dioxo-1lambda~6~-thiomorpholin-4-yl)-[5-(4-methyl-5-trifluoromethyl-isoxazol-3-yl)-thiophen-2-yl]-methanone Prepared from 5-(4-Methyl-5-trifluoromethyl-isoxazol-3-yl)-thiophene-2-carboxylic acid and thiomopholine 1,1-dioxide by the method described in Example 2 Method B. The reaction mixture was evaporated to a solid, triturated and filtered with the aid of water, then washed with a 1 N aqueous hydrochloric acid solution followed by water. The solid was air dried to afford product as a colorless solid (157 mg, 80%). $^1$H NMR (DMSO-d6) 2.34 (d, J=1.7, 3 H), 3.27 (obs m, 4H), 4.00 (m, 4H), 7.58 (d, J=3.5, 1 H), 7.68 (d, J=4.0, 1 H). $^{13}$C NMR (incomplete, F-coupled carbons obscured by baseline noise due to poor solubility) 8.0, ~44 (br), 51.5, 116.6, 128.0, 130.0, 130.8, 139.6, 158.5, 162.7. $^{19}$F NMR −62.2. LC/MS 5.80 min, [M+1]$^+$ 395.

Example 20

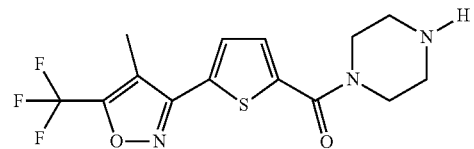 [SMILES: Cc1c(-c2ccc(C(=O)N3CCNCC3)s2)noc1C(F)(F)F]

[5-(4-Methyl-5-trifluoromethyl-isoxazol-3-yl)-thiophen-2-yl]-piperazin-1-yl-methanone, hydrochloride Prepared from 5-(4-Methyl-5-trifluoromethyl-isoxazol-3-yl)-thiophene-2-carboxylic acid and N-Boc-piperazine by the method described in Example 2 Method B. The reaction mixture was evaporated to a solid, triturated and filtered with the aid of water, then washed with a 1 N aqueous hydrochloric acid solution followed by water. The solid was air dried then chromatographed on silica gel with EtOAc/hexanes (50%) as eluant to afford intermediate N-Boc protected product as a colorless solid (165 mg, 74%). The Boc-protected intermediate was dissolved in 1,4-dioxane (5 mL) and treated with a 4 N solution of hydrogen chloride in 1,4-dioxane and stirred for 12 hr, after which time the reaction mixture was evaporated to approximately ½ volume and diluted with ethyl ether (20 mL). The resulting solids were filtered and air dried to afford product as a colorless solid (131 mg, 69% overall). $^1$H NMR (D$_2$O) 2.16 (s, 3H), 3.22 (m, 4H), 3.87 (m, 4H), 7.34 (d, J=4.0, 1 H), 7.42 (d, J=4.0, 1 H). $^{19}$F NMR −63.6. LC/MS 4.34 min, [M+1]$^+$ 346.

Example 21

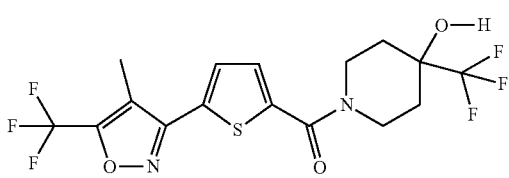 [SMILES: Cc1c(-c2ccc(C(=O)N3CCC(O)(C(F)(F)F)CC3)s2)noc1C(F)(F)F]

(4-Hydroxy-4-trifluoromethyl-piperidin-1-yl)-[5-(4-methyl-5-trifluoromethyl-isoxazol-3-yl)-thiophen-2-yl]-methanone Prepared from 5-(4-Methyl-5-trifluoromethyl-isoxazol-3-yl)-thiophene-2-carboxylic acid and 4-hydroxy-4-trifluoromethyl-piperdine by the method described in Example 2 Method B reversing the order of addition such that solid acid chloride was added to a THF solution of triethylamine and piperdine derivative. The reaction mixture was evaporated to a solid, triturated and filtered with the aid of water, then washed with a 1 N aqueous hydrochloric acid solution followed by water. The solid was air dried and then chromatographed on silica gel with EtOAc/hexanes (50%) as eluant to afford product as a colorless solid (53 mg, 49%). $^1$H NMR (DMSO-d6) 1.70-1.72 (m, 4H), 2.34 (d, J=1.8, 3 H), 3.24 (br, 2H), 4.19 (br, 2H), 6.17 (s, 1H), 7.56 (d, J=4.0, 1 H), 7.65 (d, J=4.0, 1 H). 19F NMR −83.5, −63.1. LC/MS 6.40 min, [M+1]+ 429.

Example 22

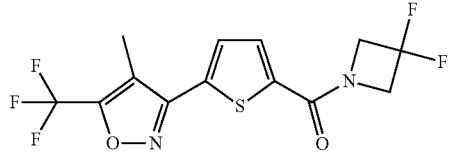 [SMILES: Cc1c(-c2ccc(C(=O)N3CC(F)(F)C3)s2)noc1C(F)(F)F]

(3,3-Difluoro-azetidin-1-yl)-[5-(4-methyl-5-trifluoromethyl-isoxazol-3-yl)-thiophen-2-yl]-methanone Prepared from 5-(4-Methyl-5-trifluoromethyl-isoxazol-3-yl)-thiophene-2-carboxylic acid and 3,3-difluoroazetidine hydrochloride by the method described in Example 2 Method B reversing the order of addition such that solid acid chloride was added to a THF solution of triethylamine (containing and additional 1.1 eq to neutralize the azetadinyl hydrochloride salt) and azetidine derivative. The reaction mixture was evaporated to a solid, triturated and filtered with the aid of water, then washed with a 1 N aqueous hydrochloric acid solution followed by water. The solid was air dried and then chromatographed on silica gel with EtOAc/hexanes (25 then 50%) as eluant to afford product as a colorless solid (43 mg, 49%). $^1$H NMR (CDCl$_3$) 2.37 (s, 3H), 4.68 (br, 4H), 4.19 (br, 2H), 7.53 (s, 2H). $^{19}$F NMR −100.6, −63.1. LC/MS 6.42 min, [M+1]$^+$ 353.

Example 23

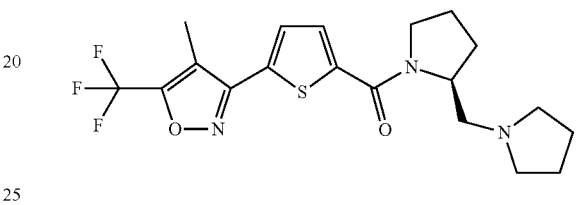

[5-(4-Methyl-5-trifluoromethyl-isoxazol-3-yl)-thiophen-2-yl]-((S)-2-pyrrolidin-1-ylmethyl-pyrrolidin-1-yl)-methanone Prepared from 5-(4-Methyl-5-trifluoromethyl-isoxazol-3-yl)-thiophene-2-carboxylic acid and (S)-(+)-1-(2-pyrrolidinylmethyl)-pyrrolidine by the method described in Example 2 Method B reversing the order of addition such that solid acid chloride was added to a THF solution of triethylamine and piperdine derivative. The reaction mixture was evaporated to a solid, triturated and filtered with the aid of water, then washed with a saturated aqueous NaHCO$_3$ solution followed by water to afford product as a pale yellow solid (88 mg, 85%). $^1$H NMR (CDCl$_3$) 1.76 (m, 4H), 1.96-2.10 (m, 4H), 2.37 (d, J=1.3, 3 H), 2.56-2.64 (m, 6H), 3.80 (m, 2H), 4.48 (m, 1H), 7.50 (d, J=4.0, 1 H), 7.57 (br, 1H). $^{19}$F NMR −63.2. LC/MS 4.66 min, [M+1]$^+$ 414.

Example 24

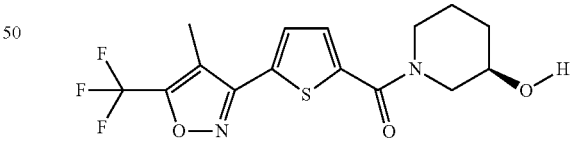

((R)-3-Hydroxy-piperidin-1-yl)-[5-(4-methyl-5-trifluoromethyl-isoxazol-3-yl)-thiophen-2-yl]-methanone Prepared from 5-(4-Methyl-5-trifluoromethyl-isoxazol-3-yl)-thiophene-2-carboxylic acid and (R)-(+)-3-hydroxypiperidine hydrochloride by the method described in Example 2 Method B reversing the order of addition such that solid acid chloride was added to a THF solution of triethylamine (containing and additional 1.1 eq. to neutralize the piperdinyl hydrochloride salt) and piperidine derivative. The reaction mixture was evaporated to an oil and partitioned between EtOAc (5 mL) and water (5 mL). The organic fraction was further washed with brine (2×5 mL), dried over MgSO₄, filtered, and evaporated to an oil. The crude product was then chromatographed on silica gel with EtOAc/hexanes (50 then 75 then 100%) as eluant to afford product as a colorless solid (41 mg, 45%). ¹H NMR (CDCl₃) 1.56-1.62 (m, 1H), 1.62-1.80 (m, 1H), 1.83-2.10 (m, 2H), 2.36 (d, J=1.3, 3 H), 2.86 (br, 1H), 3.50-3.76 (m, 4H), 3.82-3.98 (m, 2H), 7.39 (br d, J=4.0, 1 H), 7.44 (d, J=4.0, 1 H). ¹³C NMR 7.9, 22.6, 32.5, ~48 (br), ~52 (br), 66.2, 114.7, 118.7 (q, J=271), 128.0, 129.6, 131.3, 140.1, 155.2 (q, J=40), 157.9, 163.5. ¹⁹F NMR −63.2. LC/MS 5.65 min, [M+1]⁺ 361.

Example 25

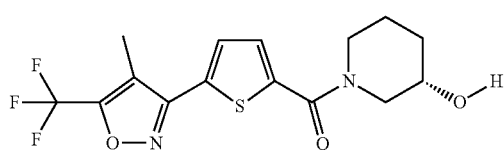

((S)-3-Hydroxy-piperidin-1-yl)-[5-(4-methyl-5-trifluoromethyl-isoxazol-3-yl)-thiophen-2-yl]-methanone Prepared in the same manner as the R isomer. Colorless solid (27 mg, 30%). LC/MS 5.68 min, [M+1]⁺ 361.

Example 26

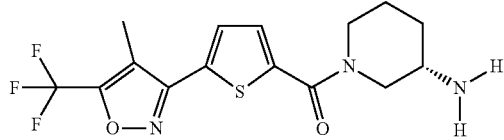 [SMILES: Cc1c(-c2ccc(C(=O)N3CCC[C@H](N)C3)s2)noc1C(F)(F)F]

((S)-3-Amino-piperidin-1-yl)-[5-(4-methyl-5-trifluoromethyl-isoxazol-3-yl)-thiophen-2-yl]-methanone, hydrochloride Prepared from 5-(4-Methyl-5-trifluoromethyl-isoxazol-3-yl)-thiophene-2-carboxylic acid and N-Boc-3-(S)-aminopiperdine by the method described in Example 2 Method B. The reaction mixture was evaporated to a solid, triturated and filtered with the aid of water, then washed with a 1 N aqueous hydrochloric acid solution followed by water. The solid was air dried then chromatographed on silica gel with EtOAc/hexanes (50 then 75%) as eluant to afford intermediate N-Boc protected product as a colorless solid (87 mg, 76%). The Boc-protected intermediate was dissolved in 1,4-dioxane (5 mL) and treated with a 4 N solution of hydrogen chloride in 1,4-dioxane and stirred for 12 hr, after which time the reaction mixture was evaporated to approximately ½ volume and diluted with ethyl ether (20 mL). The resulting solids were filtered and air dried to afford product as a colorless solid (70 mg, 71% overall). ¹H NMR (D₂O) 1.36 (m, 1H), 1.58 (m, 2H), 1.90 (s, 3H), 1.96 (m, 1H), 3.08 (m, 3H), 3.21 (m, 1H), 3.65 (m, 1H), 4.18 (br d, J=11.4, 1 H), 7.06 (br d, 1H), 7.09 (br d, 1H). ¹⁹F NMR −64.6. LC/MS 4.40 min, [M+1]⁺ 360.

Example 27

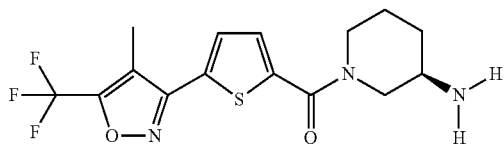 [SMILES: Cc1c(-c2ccc(C(=O)N3CCC[C@@H](N)C3)s2)noc1C(F)(F)F]

((R)-3-Amino-piperidin-1-yl)-[5-(4-methyl-5-trifluoromethyl-isoxazol-3-yl)-thiophen-2-yl]-methanone, hydrochloride Prepared in the same manner as the S isomer. Colorless solid (15 mg, 20% overall). LC/MS 4.49 min, [M+1]⁺ 360.

Example 28

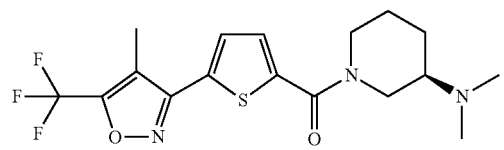 [SMILES: Cc1c(-c2ccc(C(=O)N3CCC[C@@H](N(C)C)C3)s2)noc1C(F)(F)F]

((R)-3-Dimethylamino-piperidin-1-yl)-[5-(4-methyl-5-trifluoromethyl-isoxazol-3-yl)-thiophen-2-yl]-methanone A suspension of ((R)-3-Amino-piperidin-1-yl)-[5-(4-methyl-5-trifluoromethyl-isoxazol-3-yl)-thiophen-2-yl]-methanone, hydrochloride (Example 26, 40 mg, 0.1 mmol) in dichloromethane (2 mL) was treated with a 37% aqueous formaldehyde solution (14 µL, 0.5 mmol) followed by sodium triacetoxyborohydride (128 mg, 0.6 mmol) and allowed to stir 24 hr. The reaction was then quenched by pouring onto a mixture of dichloromethane (5 mL) and a saturated aqueous NaHCO₃ solution (5 mL). The organic layer was separated, dried over MgSO₄, filtered, and evaporated to afford product as a colorless oil which solidified on standing (34 mg, 87%). ¹H NMR (CDCl₃) 1.46-1.60 (m, 2H), 1.83-1.90 (m, 1H), 2.02-2.12 (m, 1H), 2.31 (s, 3H), 2.34 (d, J=1.3, 3 H), 2.80-3.00 (m, 2H), 4.28 (br s, 1H), 4.50 (br s, 1H), 7.31 (d, J=4.0, 1 H), 7.43 (d, J=4.0, 1 H). ¹³C NMR 7.9, 24.9, 42.4, ~48 (br), 61.5, 115.0, 118.8 (q, J=271), 128.0, 129.0, 131.2, 140.4 (q, J=41), 158.0, 162.8. ¹⁹F NMR −63.1. LC/MS 4.51 min, [M+1]⁺ 388.

Example 29

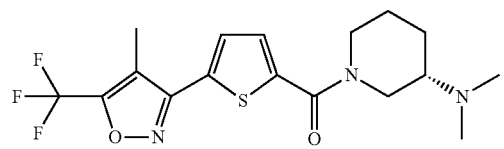 [SMILES: Cc1c(-c2ccc(C(=O)N3CCC[C@H](N(C)C)C3)s2)noc1C(F)(F)F]

((S)-3-Dimethylamino-piperidin-1-yl)-[5-(4-methyl-5-trifluoromethyl-isoxazol-3-yl)-thiophen-2-yl]-methanone Prepared in the same manner as the R isomer. Colorless solid (32 mg, 83%). LC/MS 4.34 min, [M+1]+ 388.

Example 30

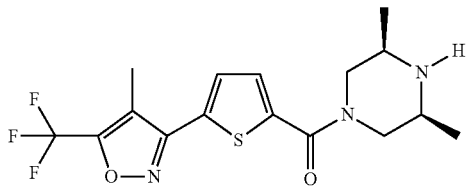 [SMILES: Cc1c(-c2ccc(C(=O)N3C[C@@H](C)N[C@@H](C)C3)s2)noc1C(F)(F)F]

(3,5-Dimethyl-piperazin-1-yl)-[5-(4-methyl-5-trifluoromethyl-isoxazol-3-yl)-thiophen-2-yl]-methanone Prepared from 5-(4-Methyl-5-trifluoromethyl-isoxazol-3-yl)-thiophene-2-carboxylic acid and 2,6-cis-dimethylpiperazine by the method described in Example 2 Method B reversing the order of addition such that solid acid chloride was added to a THF solution of triethylamine and piperazine derivative. The reaction mixture was evaporated to an oil and partitioned between EtOAc (5 mL) and water (5 mL). The organic fraction was further washed with brine (2×5 mL), dried over MgSO$_4$, filtered, and evaporated to a colorless solid (79 mg, 85%). $^1$H NMR (CDCl$_3$) 1.03 (d, J=4.8, 6 H), 1.72-2.20 (m, 1H), 2.29 (s, 3H), 2.58 (br, 1H), 2.78-2.90 (m, 2H), 4.25 (br, 2H), 7.24-7.26 (m, 1H), 7.37-7.39 (m, 1H). $^{13}$C NMR 7.9, 19.4, ~50 (br obsc), 51.3, 114.7, 118.7 (q, J=271), 128.0, 129.3, 131.2, 140.2, 155.1 (q, J=40), 157.9, 162.4. $^{19}$F NMR −63.2. LC/MS 4.43 min, [M+1]+ 374.

Example 31

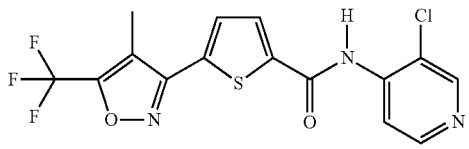 [SMILES: Cc1c(-c2ccc(C(=O)Nc3ccncc3Cl)s2)noc1C(F)(F)F]

5-(4-Methyl-5-trifluoromethyl-isoxazol-3-yl)-thiophene-2-carboxylic acid (3-chloro-pyridin-4-yl)-amide Prepared from 5-(4-Methyl-5-trifluoromethyl-isoxazol-3-yl)-thiophene-2-carboxylic acid and 4-amino-3-chloropyridine by the method described in Example 2 Method B reversing the order of addition such that solid acid chloride was added to a THF solution of triethylamine and pyridine derivative. The reaction mixture was evaporated to a solid, triturated and filtered with the aid of water, then washed with a saturated aqueous NaHCO$_3$ solution followed by water to afford product as a colorless solid (80 mg, 83%). $^1$H NMR (CDCl$_3$) 2.40 (s, 3H), 7.59 (d, J=4.0, 1 H), 7.73 (d, J=4.0, 1 H), 8.46 (s, 3H), 8.59 (s, 1H). $^{13}$C NMR 7.9, 114.5, 114.7, 118.6 (q, J=271), 129.0, 129.7, 135.2, 140.4, 141.0, 149.4, 149.6, 155.6 (q, J=40), 157.6, 159.3. $^{19}$F NMR −63.1. LC/MS 6.68 min, [M+1]+ 388.

Example 32

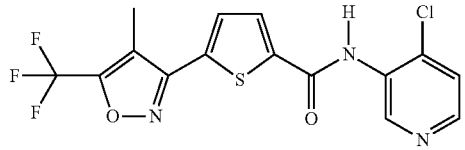 [SMILES: Cc1c(-c2ccc(C(=O)Nc3cnccc3Cl)s2)noc1C(F)(F)F]

5-(4-Methyl-5-trifluoromethyl-isoxazol-3-yl)-thiophene-2-carboxylic acid (4-chloro-pyridin-3-yl)-amide A solution of 3-amino-4-chloropyridine (129 mg, 1.0 mmol) in THF (2 mL) was treated with solid 5-(4-methyl-5-trifluoromethyl-isoxazol-3-yl)-thiophene-2-carbonyl chloride (148 mg, 0.5 mmol, as prepared in Example 2 Method B) and allowed to stir for 1 hr. The reaction was then evaporated and the residue chromatographed on silica gel with EtOAc/hexanes (70%) as eluant to afford product as a colorless solid (31 mg, 16%). $^1$H NMR (CDCl$_3$) 2.39 (d, J=1.5, 3 H), 7.39 (d, J=5.3, 1 H), 7.56 (d, J=7.56, 4.1, 1 H), 7.72 (d, J=4.1, 1 H), 8.22 (s, 1H), 8.33 (d, J=4.7, 1 H), 9.61 (s, 1H). $^{13}$C NMR 8.0, 114.8, 118.7 (q, J=271), 129.0, 129, 7, 132.9, 134.6, 140.5, 143.8, 146.1, 157.7, 159.0, $^{19}$F NMR −63.1. LC/MS 6.34 min, [M+1]+ 388.

Example 33

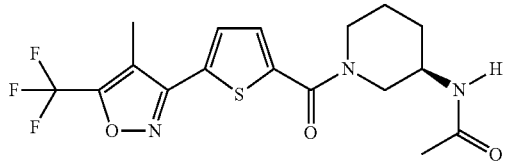 [SMILES: CC(=O)N[C@@H]1CCCN(C(=O)c2ccc(-c3noc(C(F)(F)F)c3C)s2)C1]

N—{(R)-1-[5-(4-Methyl-5-trifluoromethyl-isoxazol-3-yl)-thiophene-2-carbonyl]-piperidin-3-yl}-acetamide A suspension of ((R)-3-Amino-piperidin-1-yl)-[5-(4-methyl-5-trifluoromethyl-isoxazol-3-yl)-thiophen-2-yl]-methanone, hydrochloride (Example 27, 79 mg, 0.2 mmol) in THF (2 mL) was treated with triethylamine (70 μL, 0.5 mmol) followed by acetyl chloride (22 μL, 0.3 mmol). The reaction mixture was allowed to stir 48 hr, evaporated and chromatographed on silica gel with EtOAc then MeOH/EtOAc (10%) as eluant to afford product as a colorless solid (66 mg, 83%). $^1$H NMR (CDCl$_3$) 1.65 (m, 2H), 1.81 (m, 1H), 1.95 (s, 3H), 2.00 (obs m, 1H), 2.33 (d, J=1.3, 3 H), 3.30 (m, 2H), 3.98 (m, 2H), 4.10 (br d, J=11.0, 1 H), 6.10 (br d, J=6.6, 1 H), 7.43 (d, J=4.0, 1 H), 7.49 (br s, 1H). $^{13}$C NMR 7.9, 23.5, 30.1, 46.5, 51.0 (br), 114.8, 118.7 (q, J=271), 128.3, 129.7, 131.7, 140.1, 155.2 (J=40), 157.9, 163.3, 170.3 $^{19}$F NMR −63.1. LC/MS 5.72 min, [M+1]+ 402.

Example 34

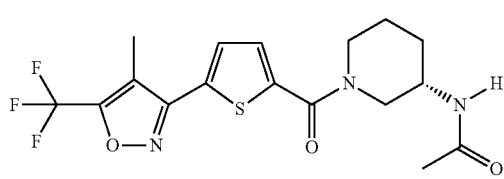 [SMILES: CC(=O)N[C@H]1CCCN(C(=O)c2ccc(-c3noc(C(F)(F)F)c3C)s2)C1]

N—{(S)-1-[5-(4-Methyl-5-trifluoromethyl-isoxazol-3-yl)-thiophene-2-carbonyl]-piperidin-3-yl}-acetamide Prepared in the same manner as the R isomer. Colorless solid (66 mg, 83%). LC/MS 5.60 min, [M+1]$^+$ 402.

Example 35

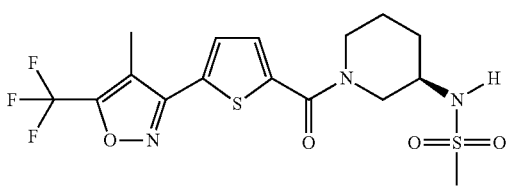 [SMILES: Cc1c(-c2ccc(C(=O)N3CCC[C@@H](NS(C)(=O)=O)C3)s2)noc1C(F)(F)F]

N—{(R)-1-[5-(4-Methyl-5-trifluoromethyl-isoxazol-3-yl)-thiophene-2-carbonyl]-piperidin-3-yl}-methanesulfonamide A suspension of ((R)-3-Amino-piperidin-1-yl)-[5-(4-methyl-5-trifluoromethyl-isoxazol-3-yl)-thiophen-2-yl]-methanone, hydrochloride (Example 27, 79 mg, 0.2 mmol) in THF (2 mL) was treated with triethylamine (63 μL, 0.45 mmol) followed by methanesulfonyl chloride (19 μL, 0.24 mmol). The reaction mixture was allowed to stir 48 h, evaporated, and chromatographed on silica gel with EtOAc as eluant to afford product as a colorless foam (61 mg, 70%). $^1$H NMR (CDCl$_3$) 1.68 (m, 2H), 1.88 (m, 2H), 2.02 (m, 1H), 2.33 (d, J=1.8, 3 H), 2.98 (s, 3H), 3.46 (m, 2H), 3.57 (m, 1H), 3.84 (m, 1H), 4.05 (d, J=12.7, 1 H), 5.45 (d, J=7.5, 1 H), 7.39 (d, J=4.0, 1 H), 7.43 (d, J=3.5, 1 H). $^{13}$C NMR 7.9, 23.4, 31.6, 41.9, 47 (br), 52 (br), 49.9, 114.8, 118.7 (q, J=271), 128.2, 129.8, 131.8, 139.6, 155.2 (q, 40), 157.9, 163.5. $^{19}$F NMR −63.1. LC/MS 5.82 min, [M+1]$^+$ 438.

Example 36

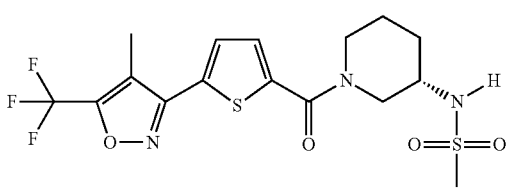 [SMILES: Cc1c(-c2ccc(C(=O)N3CCC[C@H](NS(C)(=O)=O)C3)s2)noc1C(F)(F)F]

N—{(S)-1-[5-(4-Methyl-5-trifluoromethyl-isoxazol-3-yl)-thiophene-2-carbonyl]-piperidin-3-yl}-methanesulfonamide Prepared in the same manner as the R isomer. Colorless foam (57 mg, 65%). LC/MS 5.82 min, [M+1]$^+$ 438.

Example 37

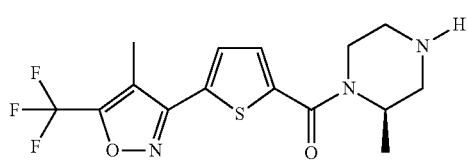 [SMILES: Cc1c(-c2ccc(C(=O)N3CCNC[C@H]3C)s2)noc1C(F)(F)F]

((R)-2-Methyl-piperazin-1-yl)-[5-(4-methyl-5-trifluoromethyl-isoxazol-3-yl)-thiophen-2-yl]-methanone, hydrochloride Prepared from 5-(4-Methyl-5-trifluoromethyl-isoxazol-3-yl)-thiophene-2-carboxylic acid and 4-N-Boc-2-(R)-methyl-piperazine by the method described in Example 2 Method B. The reaction mixture was evaporated to a solid, triturated and filtered with the aid of water, then washed with a 1 N aqueous hydrochloric acid solution followed by water. The solid was air dried to afford intermediate N-Boc protected product as a colorless solid (106 mg, 92%). The Boc-protected intermediate was dissolved in a 4 N solution of hydrogen chloride in 1,4,-dioxane (2 mL) and stirred for 2 hr, after which time the reaction mixture was evaporated to approximately ¼ volume and diluted with ethyl ether (4 mL). The resulting solids were filtered and air dried to afford product as a colorless solid (85 mg, 86% overall). $^1$H NMR (D$_2$O) 1.27 (d, J=7.5, 3 H), 2.02 (s, 3H), 3.04 (dt, J=12.7, 3.1, 1 H), 3.12-3.18 (m, 2H), 3.30-3.50 m (m, 2H), 4.21 (d, J=14.5, 1 H), 7.23 (s, 2H). $^{19}$F NMR −64.1. LC/MS 4.50 min, [M+1]$^+$ 360.

Example 38

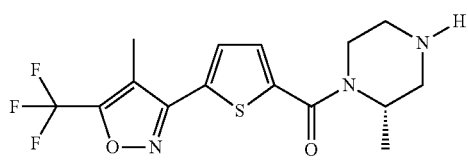 [SMILES: Cc1c(-c2ccc(C(=O)N3CCNC[C@@H]3C)s2)noc1C(F)(F)F]

((S)-2-Methyl-piperazin-1-yl)-[5-(4-methyl-5-trifluoromethyl-isoxazol-3-yl)-thiophen-2-yl]-methanone, hydrochloride Prepared in the same manner as the R isomer. Colorless solid (81 mg, 79%). LC/MS 4.37 min, [M+1]$^+$ 360.

Example 39

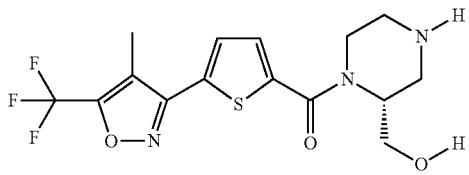 [SMILES: Cc1c(-c2ccc(C(=O)N3CCNC[C@@H]3CO)s2)noc1C(F)(F)F]

((R)-2-Hydroxymethyl-piperazin-1-yl)-[5-(4-methyl-5-trifluoromethyl-isoxazol-3-yl)-thiophen-2-yl]-methanone, hydrochloride Prepared from 5-(4-Methyl-5-trifluoromethyl-isoxazol-3-yl)-thiophene-2-carboxylic acid and 4-N-Boc-2-(R)-hydroxymethyl-piperazine by the method described in Example 2 Method B. The reaction mixture was evaporated to a solid, triturated and filtered with the aid of water, then washed with a 1 N aqueous hydrochloric acid solution followed by water. The solid was air dried afford intermediate N-Boc protected product as a colorless solid (102 mg, 86%). The Boc-protected intermediate was dissolved in a 4 N solution of hydrogen chloride in 1,4,-dioxane (2 mL) and stirred for 2 hr, after which time the reaction mixture was evaporated to approximately ¼ volume and diluted with ethyl ether (4 mL). The resulting solids were filtered and air dried to afford product as a colorless solid (85 mg, 83% overall). $^1$H NMR (D$_2$O) 2.17 (s, 3H), 3.26-3.46 (m, 3H), 3.60-3.80 (m, 3H), 4.00-4.04 (m, 1H), 4.48 (dd, J=12.7, 5.3, 1 H), 4.60 (obs dd, J=13.2, 3.5, 1 H), 7.46 (d, J=4.3, 1 H), 7.82 (d, J=4.0, 1 H). $^{19}$F NMR −63.5. LC/MS 3.89 min, [M+1]$^+$ 376.

Example 40

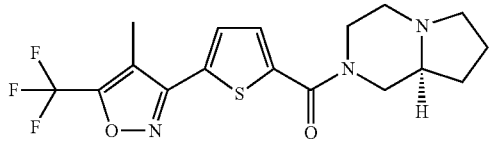 [SMILES: Cc1c(-c2ccc(C(=O)N3CCN4CCC[C@H]4C3)s2)noc1C(F)(F)F]

(S)-Hexahydro-pyrrolo[1,2-a]pyrazin-2-yl-[5-(4-methyl-5-trifluoromethyl-isoxazol-3-yl)-thiophen-2-yl]-methanone Prepared from 5-(4-Methyl-5-trifluoromethyl-isoxazol-3-yl)-thiophene-2-carboxylic acid and 4-amino-3-chloropyridine by the method described in Example 2 Method B reversing the order of addition such that solid acid chloride was added to a THF solution of triethylamine and (S)-1,4-diazabicyclo[4.3.0]nonane. The reaction mixture was evaporated to a solid, triturated and filtered with the aid of water, then washed with a saturated aqueous NaHCO$_3$ solution followed by water to afford product as a yellow colored solid (82 mg, 85%). $^1$H NMR (CDCl$_3$) 1.34-1.48 (m, 1H), 1.70-1.90 (m, 3H), 1.92-2.20 (m, 1H), 2.10-2.26 (m, 2H), 2.32 (d, J=1.3, 3 H), 2.80 (br s, 1H), 3.03-3.11 (m, 2H), 3.20 (obs br s, 1H), 4.40 (br s, 2H), 7.29 (d, J=4.0, 1 H), 7.41 (d, J=3.5, 1 H). $^{13}$C NMR 7.9, 21.3, 27.5, 30.0, ~48 (br), 51.8, 53.5, 62.8, 114.7, 118.7 (q, J=271), 128.0, 129.3, 131.2, 140.2, 155.2 (q, J=40), 157.9, 162.9. $^{19}$F NMR −63.1. LC/MS 4.34 min, [M+1]$^+$ 386.

Example 41

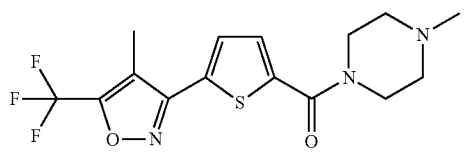 [SMILES: Cc1c(-c2ccc(C(=O)N3CCN(C)CC3)s2)noc1C(F)(F)F]

(4-Methyl-piperazin-1-yl)-[5-(4-methyl-5-trifluoromethyl-isoxazol-3-yl)-thiophen-2-yl]-methanone A suspension of 5-(4-Methyl-5-trifluoromethyl-isoxazol-3-yl)-thiophene-2-carboxylic acid (90 mg, 0.33 mmol) in dichloromethane (2 mL) was treated with 4-dimethylaminopyridine (100 mg, 0.82 mmol), 1-(3-dimethylaminopropyl)-3-ethylcarbodiimide hydrochloride (157 mg, 0.82 mmol), and N-methylpiperazine (0.1 mL, 0.90 mmol). A further portion of dichloromethane (2 mL) and DMF (5 drops) was added and the reaction stirred at room temperature for 20 hr. The reaction mixture was partitioned between dichloromethane (20 mL) and a 1 N aqueous hydrochloric acid solution (20 mL). The organic layer was further washed with a 1 N aqueous hydrochloric acid solution (20 mL), then a 5% aqueous sodium hydroxide solution (2×20 mL) followed by brine (20 mL). The organic layer was dried over Na$_2$SO$_4$, filtered, and concentrated in vacuo to afford a yellow colored oil (66.5 mg). Gradient column chromatography on silica with MeOH/EtOAc (10 to 50%) as eluant to afford product as a colorless solid (26 mg, 22%). $^1$H NMR (CD$_3$OD) 2.40 (s, 3H), 2.42 (d, J=1.4, 3 H), 2.59 (t, J=5.0, 4 H), 3.84 (t, J=5.0, 4 H), 7.52 (d, J=3.8, 1 H), 7.64 (d, J=3.8, 1 H). $^{19}$F NMR −64.8. LC/MS 4.48 min, [M+1]$^+$ 360.

Example 42

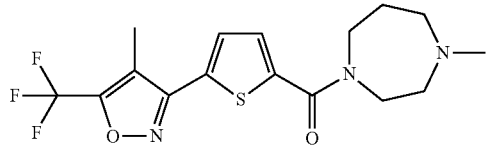 [SMILES: Cc1c(-c2ccc(C(=O)N3CCCN(C)CC3)s2)noc1C(F)(F)F]

(4-Methyl-[1,4]diazepan-1-yl)-[5-(4-methyl-5-trifluoromethyl-isoxazol-3-yl)-thiophen-2-yl]-methanone Prepared from 5-(4-Methyl-5-trifluoromethyl-isoxazol-3-yl)-thiophene-2-carboxylic acid and 1-methyl-[1,4]diazepane by the method described in Example 41. Yellow colored solid (49 mg, 37%). $^1$H NMR (CDCl$_3$) 1.97-2.05 (m, 2H), 2.36 (d, J=1.4, 3H), 2.40 (s, 3H), 2.62 (br s, 2H), 2.74 (br s, 2H), 3.80 (br s, 2H), 7.37 (br s, 1H), 7.45 (d, J=3.8, 1 H). $^{19}$F NMR −63.1. LC/MS 4.43 min, [M+1]$^+$ 374.

Example 43

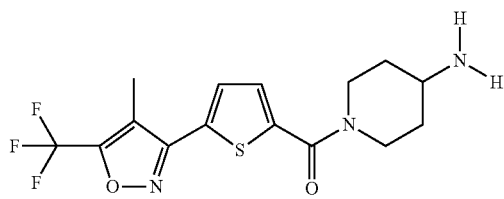 [SMILES: Cc1c(-c2ccc(C(=O)N3CCC(N)CC3)s2)noc1C(F)(F)F]

(4-Amino-piperidin-1-yl)-[5-(4-methyl-5-trifluoromethyl-isoxazol-3-yl)-thiophen-2-yl]-methanone Prepared from 5-(4-Methyl-5-trifluoromethyl-isoxazol-3-yl)-thiophene-2-carboxylic acid and piperidin-4-yl-carbamic acid tert-butyl ester by the method described in Example 41. N-Boc intermediate. The crude product was chromatographed on silica with EtOAc/hexanes (25 then 50%) as eluant to afford intermediate as a colorless solid (110 mg, 68%): LC/MS 6.70 min, [M+1]$^+$ 460. The N-Boc intermediate (84.8 mg, 0.18 mmol) in EtOAc (4 mL) was treated with a 4 N solution of hydrogen chloride in 1,4-dioxane (2 mL) and stirred for 22 hr. The resulting precipitate was filtered and washed with EtOAc (2×10 mL). The solids were then partitioned between a 2.5% aqueous sodium hydroxide solution (40 mL) and dichlormethane (20 mL). The aqueous phase was further extracted with dichlormethane (2×20 mL) and the combined organics dried over Na$_2$SO$_4$, filtered, and concentrated in vacuo to afford product as a colorless solid (56 mg, 57% overall). $^1$H NMR (CD$_3$OD) 1.36-1.50 (m, 2H), 1.98 (d, J=11.8, 2 H), 2.43 (s, 3H), 3.02 (m, 1H), 3.18 (br s, 2H), 4.40 (br s, 2H), 7.49 (d, J=3.6, 1 H), 7.64 (d, J=3.8, 1 H). $^{19}$F NMR −64.8. LC/MS 4.51 min, [M+1]$^+$ 360.

Example 44

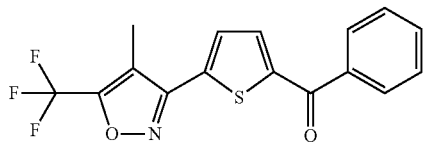 [SMILES: Cc1c(-c2ccc(C(=O)c3ccccc3)s2)noc1C(F)(F)F]

[5-(4-Methyl-5-trifluoromethyl-isoxazol-3-yl)-thiophen-2-yl]-phenyl-methanone

Prepared from 4-Methyl-3-thiophen-2-yl-5-trifluoromethyl-isoxazole and benzoyl chloride by the method described in Example 3. Crude product was chromatographed on silica gel with EtOAc/hexanes (10 then 20%) as eluant to afford product as a colorless solid (118 mg, 70%). $^1$H NMR (CDCl$_3$) 2.33 (d, J=1.3, 3 H), 7.43-7.59 (m, 4H), 7.62 (d, J=4.0, 1 H), 7.80-7.83 (m, 2H). $^{13}$C NMR 7.9, 118.7 (q, J=271), 128.8, 128.9, 129.4, 133.0, 134.8, 136.3, 137.7, 145.8, 155.5 (q, J=40), 157.9, 188.0. $^{19}$F NMR −63.1. LC/MS 7.29 min, [M+1]$^+$ 338.

Example 45

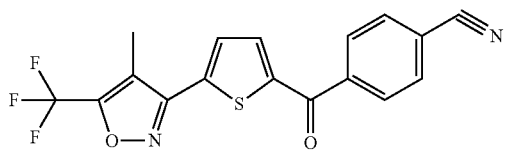 [SMILES: Cc1c(-c2ccc(C(=O)c3ccc(C#N)cc3)s2)noc1C(F)(F)F]

4-[5-(4-Methyl-5-trifluoromethyl-isoxazol-3-yl)-thiophene-2-carbonyl]-benzonitrile Prepared from 4-Methyl-3-thiophen-2-yl-5-trifluoromethyl-isoxazole and 4-cyanobenzoyl chloride by the method described in Example 3. Crude product was chromatographed on silica gel with EtOAc/hexanes (10 then 20%) as eluant to afford product as a colorless solid (130 mg, 36%). $^1$H NMR (CDCl$_3$) 2.42 (d, J=1.3, 3 H), 7.62 (d, J=4.0, 1 H), 7.67 (d, J=4.0, 1 H), 7.85 (d, J=8.3, 1 H), 7.98 (d, J=7.9, 1 H). $^{13}$C NMR 8.0, 114.9, 116.3, 118.7 (q, J=271), 118.0, 129.1, 129.8, 132.7, 135.3, 137.6, 141.1, 144.6, ~155 (q, obscured due to baseline noise), 157.7, 186.4. $^{19}$F NMR −63.1. LC/MS 7.08 min, [M+1]$^+$ 363.

Example 46

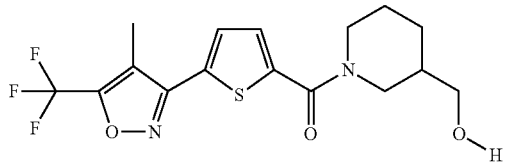 [SMILES: Cc1c(-c2ccc(C(=O)N3CCCC(CO)C3)s2)noc1C(F)(F)F]

(3-Hydroxymethyl-piperidin-1-yl)-[5-(4-methyl-5-trifluoromethyl-isoxazol-3-yl)-thiophen-2-yl]-methanone Prepared from 5-(5-Trifluoromethyl-4-methyl-isoxazol-3-yl)-thiophene-2-carboxylic acid and 3-piperdinemethanol by the method described in Example 2 Method B reversing the order of addition such that solid acid chloride was added to a THF solution of triethylamine and piperdine derivative. The reaction mixture was evaporated to an oil then partitioned between EtOAc (5 mL) and water (5 mL). The organic fraction was further washed with brine (2×5 mL), dried over MgSO$_4$, filtered, and evaporated to an oil. The crude product was then chromatographed on silica gel with EtOAc/hexanes (75%) as eluant to (190 mg, 75%). $^1$H NMR (CDCl$_3$) 1.28-1.35 (m, 1H), 1.44-1.56 (m, 1H), 1.67-1.82 (m, 3H), 2.28 (d, J=0.9, 3 H), 2.99 (dd, J=13.2, 9.7, 1 H), 3.32 (br s, 1H), 3.41-3.52 (m, 2H), 4.10 (br s, 1H), 4.21 (d, J=11.4, 1 H), 7.29 (d, J=4.0, 1 H), 7.37 (d, J=4.0, 1 H). $^{13}$C NMR 7.8, 24.9, 27.2, 39.1, ~49 (br), 64.5, 114.8, 118.7 (q, J=271), 128.1, 129.3, 131.2, 140.3, 155.0 (q, J=40), 157.9, 162.9. $^{19}$F NMR −63.2. LC/MS 5.91 min, [M+1]$^+$ 375.

Example 47

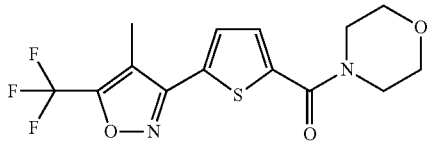 [SMILES: Cc1c(-c2ccc(C(=O)N3CCOCC3)s2)noc1C(F)(F)F]

[5-(4-Methyl-5-trifluoromethyl-isoxazol-3-yl)-thiophen-2-yl]-morpholin-4-yl-methanone Prepared from 5-(5-Trifluoromethyl-4-methyl-isoxazol-3-yl)-thiophene-2-carboxylic acid and morpholine by the method described in Example 2 Method B reversing the order of addition such that solid acid chloride was added to a THF solution of triethylamine and piperdine derivative. The reaction mixture was evaporated to a solid, triturated and filtered with the aid of water, then washed with a 1 N aqueous hydrochloric acid solution followed by water. The solid was air dried to afford product as a colorless solid (66 mg, 95%). $^1$H NMR (CDCl$_3$) 2.34 (d, J=1.3, 3 H), 3.71-3.77 (m, 8H), 7.32 (d, J=4.0, 1 H), 7.43 (d, J=4.0, 1 H). $^{13}$C NMR 7.9, ~48 (br), 67.0, 114.7, 118.7 (q, J=271), 128.0, 129.5, 131.7, 139.5, 157.9, 162.8. $^{19}$F NMR −63.2. LC/MS 5.93 min, [M+1]$^+$ 347.

Example 48

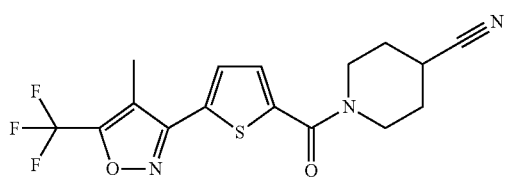 [SMILES: Cc1c(-c2ccc(C(=O)N3CCC(C#N)CC3)s2)noc1C(F)(F)F]

1-[5-(4-Methyl-5-trifluoromethyl-isoxazol-3-yl)-thiophene-2-carbonyl]-piperidine-4-carbonitrile Prepared from 5-(5-Trifluoromethyl-4-methyl-isoxazol-3-yl)-thiophene-2-carboxylic acid and 4-cyanopiperdine by the method described in Example 2 Method B reversing the order of addition such that solid acid chloride was added to a THF solution of triethylamine and piperdine derivative. The reaction mixture was evaporated to a solid, triturated and filtered with the aid of water, then washed with a 1 N aqueous hydrochloric acid solution followed by water. The solid was air dried then chromatographed on a short column of silica gel with EtOAc as eluant to afford product as a colorless solid (91 mg, 61%). $^1$H NMR (CDCl$_3$) 1.91-2.06 (m, 4H), 2.37 (d, J=1.3, 3 H), 2.97-3.03 (m, 1H), 3.71-3.79 (m, 2H), 3.90-3.98 (m, 2H), 7.34 (d, J=4.0, 1 H), 7.47 (d, J=4.0, 1 H). $^{13}$C NMR 7.9, 26.5, 28.9, 43.6, 114.8, 118.7 (q, J=271), 120.8, 128.1, 129.5, 131.7, 139.4, 155.2 (q, J=40), 157.8, 162.9. $^{19}$F NMR −63.2. LC/MS 6.18 min, [M+1]$^+$ 370.

Example 49

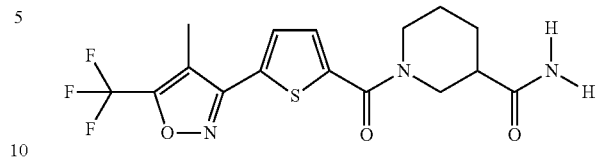

1-[5-(4-Methyl-5-trifluoromethyl-isoxazol-3-yl)-thiophene-2-carbonyl]-piperidine-3-carboxylic acid amide Prepared from 5-(5-Trifluoromethyl-4-methyl-isoxazol-3-yl)-thiophene-2-carboxylic acid and 3-piperidinecarboxamide by the method described in Example 2 Method B reversing the order of addition such that solid acid chloride was added to a THF solution of triethylamine and piperdine derivative. The reaction mixture was evaporated to a solid, triturated and filtered with the aid of water, then washed with a 1 N aqueous hydrochloric acid solution followed by water. The solid was air dried to afford product as a colorless solid (120 mg, 97%). $^1$H NMR (DMSO-d6) 1.36-1.49 (m, 1H), 1.55-1.75 (m, 2H), 1.89-1.93 (m, 1H), 2.35 (d, J=1.8, 3 H), 3.03 (br s, 2H), 4.10 (br s, 2H), 6.90 (s, 1H), 7.37 (s, 1H), 7.51 (d, J=4.0, 1 H), 7.67 (d, J=4.0, 1 H). $^{19}$F NMR −62.2. LC/MS 5.54 min, [M+1]$^+$ 388.

Example 50

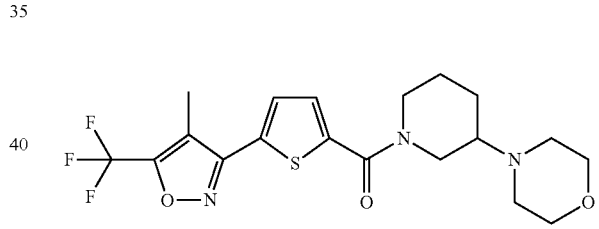

[5-(4-Methyl-5-trifluoromethyl-isoxazol-3-yl)-thiophen-2-yl]-(3-morpholin-4-yl-piperidin-1-yl)-methanone, hydrochloride Prepared from 5-(5-Trifluoromethyl-4-methyl-isoxazol-3-yl)-thiophene-2-carboxylic acid and 4-piperidin-3-yl-morpholine, di-hydrochloride by the method described in Example 2 Method B reversing the order of addition such that solid acid chloride was added to a THF solution of triethylamine and piperdine derivative. An additional 2 equivalents of triethylamine was used. The reaction mixture was evaporated to an oil, triturated and filtered with the aid of water, then with a saturated aqueous NaHCO$_3$ solution. The residual oil was then dissolved in EtOAc (2 mL), dried over MgSO$_4$, filtered, and evaporated to an oil. The crude oil was then dissolved in diethyl ether (1 mL) and treated with a 4 N solution of hydrogen chloride in 1,4,-dioxane to precipitate product as a colorless solid. The solid was filtered with the aid of diethyl ether and air dried to afford product as a colorless solid (61 mg, 65%). LC/MS 4.66 min, [M+1]$^+$ 430.

Example 51

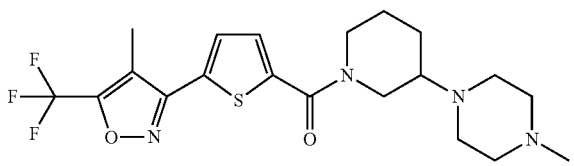 [SMILES: Cc1c(-c2ccc(C(=O)N3CCCC(N4CCN(C)CC4)C3)s2)noc1C(F)(F)F]

[3-(4-Methyl-piperazin-1-yl)-piperidin-1-yl]-[5-(4-methyl-5-trifluoromethyl-isoxazol-3-yl)-thiophen-2-yl]-methanone, hydrochloride Prepared from 5-(5-Trifluoromethyl-4-methyl-isoxazol-3-yl)-thiophene-2-carboxylic acid and 1-Methyl-4-piperidin-3-yl-piperazine, tri-hydrochloride by the method described in Example 2 Method B reversing the order of addition such that solid acid chloride was added to a THF solution of triethylamine and piperdine derivative. An additional 3 equivalents of triethylamine was used. The reaction mixture was evaporated to an oil, triturated and filtered with the aid of water, then with a saturated aqueous NaHCO$_3$ solution. The residual oil was then dissolved in EtOAc (2 mL), dried over MgSO$_4$, filtered, and evaporated to an oil. The crude oil was then dissolved in diethyl ether (1 mL) and treated with a 4 N solution of hydrogen chloride in 1,4,-dioxane to precipitate product as a colorless solid. The solid was filtered with the aid of diethyl ether and air dried to afford product as a colorless solid (47 mg, 53%). LC/MS 4.62 min, [M+1]$^+$ 443.

Example 52

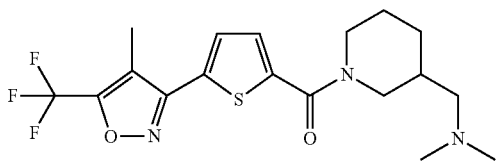 [SMILES: Cc1c(-c2ccc(C(=O)N3CCCC(CN(C)C)C3)s2)noc1C(F)(F)F]

(3-Dimethylaminomethyl-piperidin-1-yl)-[5-(4-methyl-5-trifluoromethyl-isoxazol-3-yl)-thiophen-2-yl]-methanone, hydrochloride A solution of (3-Hydroxymethyl-piperidin-1-yl)-[5-(4-methyl-5-trifluoromethyl-isoxazol-3-yl)-thiophen-2-yl]-methanone (Example 46, 170 mg, 0.454 mmol) and triethylamine (111 µL, 0.795 mmol) in CH$_2$Cl$_2$ (4 mL) at −10 to −5 OC, was treated with methanesulfonyl chloride (53 µL, 0.681 mmol) and allowed to stir for 1 hr. The reaction mixture was then quenched with CH$_2$Cl$_2$ (4 mL) and water (4 mL), and the organic portion further washed with a 1 N aqueous hydrochloric acid solution (2×3 mL) followed by a saturated aqueous NaHCO$_3$ solution (2×3 mL) and brine (3 mL). The organic layer was then dried over MgSO$_4$, filtered, and evaporated to the Methanesulfonic acid 1-[5-(4-methyl-5-trifluoromethyl-isoxazol-3-yl)-thiophene-2-carbonyl]-piperidin-3-ylmethyl ester intermediate as an oil (180 mg, 88%). A solution of the intermediate sulfonate (60 mg, 0.1326 mmol) in acetonitrile (2 mL) was treated with a 2 N THF solution of dimethylamine (265 µL, 0.5304 mmol) and heated at 45° C. in a sealed tube for 2 weeks. The reaction was then evaporated and the resulting oil triturated with water (3×2 mL) then dissolved in EtOAc (2 mL), dried over MgSO$_4$, filtered, and evaporated. The crude oil product was then dissolved in diethyl ether (2 mL) and treated with a 4 N solution of hydrogen chloride in 1,4,-dioxane to precipitate product as a colorless solid. The solid was filtered with the aid of diethyl ether and air dried to afford product as a colorless solid (30 mg, 52%). $^1$H NMR (CDCl$_3$) 1.12-1.29 (m, 1H), 1.44-1.58 (m, 1H), 1.67-1.79 (m, 2H), 1.80-1.90 (m, 1H), 2.05-2.15 (m, 8H), 2.29 (d, J=1.3, 3 H), 2.70 (br s, 1H), 3.00 (br s, 1H), 4.10-4.40 (br m, 2H), 7.28 (d, J=3.5, 1 H), 7.38 (d, J=3.5, 1 H). $^{13}$C NMR 7.9, 25.2, 29.7, 34.9, 46.1, 63.3, 114.7, 118.8 (q, J=271), 128.0, 129.1, 131.0, 140.8, 155.1 (q, J=40), 158.0, 162.8. $^{19}$F NMR −63.1. LC/MS 4.52 min, [M+1]$^+$ 402.

Example 53

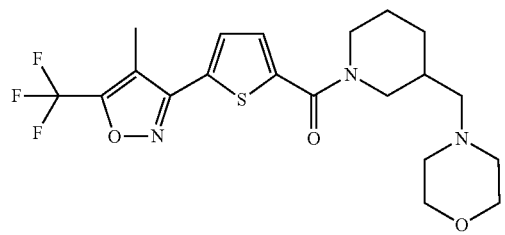 [SMILES: Cc1c(-c2ccc(C(=O)N3CCCC(CN4CCOCC4)C3)s2)noc1C(F)(F)F]

[5-(4-Methyl-5-trifluoromethyl-isoxazol-3-yl)-thiophen-2-yl]-(3-morpholin-4-ylmethyl-piperidin-1-yl)-methanone Prepared from Methanesulfonic acid 1-[5-(4-methyl-5-trifluoromethyl-isoxazol-3-yl)-thiophene-2-carbonyl]-piperidin-3-ylmethyl (60 mg, 0.1326 mmol) and morpholine (46 µL, 0.530 mmol) by the method described in Example 52. The reaction mixture was heated at 65° C. for 10 days and isolated as the free-base oil (51 mg, 86%). $^1$H NMR (CDCl$_3$) 1.12-1.29 (m, 1H), 1.44-1.58 (m, 1H), 1.68-1.90 (m, 3H), 2.12-2.16 (m, 2H), 2.20-2.32 (m, 5H), 2.34-2.42 (m, 2H), 2.76 (br s, 1H), 3.04 (br t, J=11.4, 1 H), 3.57 (s, 4H), 4.18 (br s, 1H), 4.32 (br s, 1H), 7.29 (d, J=4.0, 1 H), 7.37 (d, J=3.5, 1 H). $^{19}$F NMR −63.1. LC/MS 4.62 min, [M+1]$^+$ 444.

Example 54

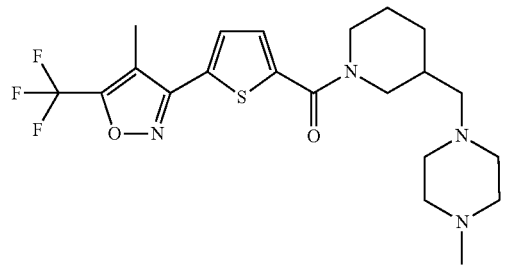 [SMILES: Cc1c(-c2ccc(C(=O)N3CCCC(CN4CCN(C)CC4)C3)s2)noc1C(F)(F)F]

[3-(4-Methyl-piperazin-1-ylmethyl)-piperidin-1-yl]-[5-(4-methyl-5-trifluoromethyl-isoxazol-3-yl)-thiophen-2-yl]-methanone Prepared from Methanesulfonic acid 1-[5-(4-methyl-5-trifluoromethyl-isoxazol-3-yl)-thiophene-2-carbonyl]-piperidin-3-ylmethyl (60 mg, 0.1326 mmol) and N-Methylpiperazine (58 µL, 0.530 mmol) by the method described in Example 52. The reaction mixture was heated at 65° C. for 10 days and isolated as the free-base oil (44 mg, 73%). $^1$H NMR (CDCl$_3$) 1.14-1.30 (m, 1H), 1.42-1.58 (m, 1H), 1.66-1.90 (m, 3H), 2.10-2.45 (m, 16H), 2.34-2.42 (m, 2H), 2.76 (br s, 1H), 3.02 (br t, J=10.5, 1 H), 4.18 (br s, 1 H), 4.28 (br s, 1H), 7.31 (br d, J=3.5, 1 H), 7.38 (d, J=4.0, 1 H). $^{19}$F NMR −63.1. LC/MS 4.64 min, [M+1]$^+$ 457.

Example 55

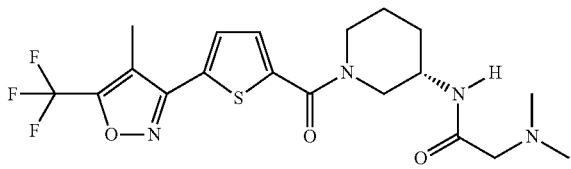 [SMILES: Cc1c(-c2ccc(C(=O)N3CCC[C@H](NC(=O)CN(C)C)C3)s2)noc1C(F)(F)F]

2-Dimethylamino-N—{(S)-1-[5-(4-methyl-5-trifluoromethyl-isoxazol-3-yl)-thiophene-2-carbonyl]-piperidin-3-yl}-acetamide A solution of ((S)-3-Amino-piperidin-1-yl)-[5-(4-methyl-5-trifluoromethyl-isoxazol-3-yl)-thiophen-2-yl]-methanone, hydrochloride (Example 26, 79 mg, 0.20 mmol) in THF (3 mL) was treated with dimethylaminoacetyl chloride hydrochloride (40 mg, 0.24 mmol) followed by triethylamine (62 µL, 0.44 mmol). The resulting mixture was stirred for 16 hr, evaporated to an oil, and dissolved in water (3 mL). The solution was then basified with a saturated aqueous K$_2$CO$_3$ solution and the precipitated product filtered, washed with water, and air dried to afford product as a colorless solid (69 mg, 78%). $^1$H NMR (CDCl$_3$) 1.62-1.72 (m, 2H), 1.78-1.84 (m, 1H), 1.94-2.04 (m, 1H), 2.25 (s, 6H), 2.32 (d, J=1.3, 3 H), 2.49 (s, 2H), 3.24-3.40 (m, 2H), 3.94-4.04 (m, 2H), 4.12 (br d, J=13.2, 1 H), 7.23 (br d, J=7.5, 1 H), 7.44 (d, J=4.0, 1 H), 7.47 (br s, 1H). $^{13}$C NMR 7.9, 23.5, 30.4, 45.6, 46.2, ~51 (br), 63.2, 114.8, 118.8 (q, J=271), 128.3, 129.5, 131.6, 140.2, 155.1 (q, J=40), 157.9, 163.1, 170.7. $^{19}$F NMR −63.1. LC/MS 4.59 min, [M+1]$^+$ 445.

Example 56

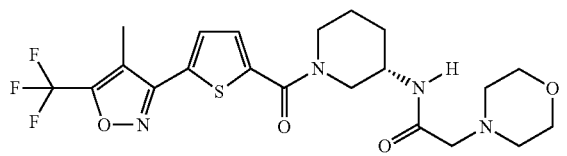 [SMILES: Cc1c(-c2ccc(C(=O)N3CCC[C@H](NC(=O)CN4CCOCC4)C3)s2)noc1C(F)(F)F]

N—{(S)-1-[5-(4-Methyl-5-trifluoromethyl-isoxazol-3-yl)-thiophene-2-carbonyl]-piperidin-3-yl}-2-morpholin-4-yl-acetamide A solution of ((S)-3-Amino-piperidin-1-yl)-[5-(4-methyl-5-trifluoromethyl-isoxazol-3-yl)-thiophen-2-yl]-methanone, hydrochloride (Example 26, 79 mg, 0.20 mmol) and triethylamine (69 µL, 0.42 mmol) in THF (3 mL) was treated with chloroacetyl chloride (18 µL, 0.22 mmol), stirred for 1 hr and evaporated to a solid. The solid was triturated and filtered with the aid of water, then air dried to provide the 2-Chloro-N—{(S)-1-[5-(4-methyl-5-trifluoromethyl-isoxazol-3-yl)-thiophene-2-carbonyl]-piperidin-3-yl}-acetamide intermediate as a colorless solid (75 mg, 86%). LC/MS 6.13 min, [M+1]$^+$ 436. The chloroacetyl intermediate (35 mg, 0.08 mmol) was dissolved in acetonitrile (3 mL) containing anhydrous K$_2$CO$_3$, treated with morpholine (14 µL, 0.16 mmol), and stirred for 3 days. The reaction mixture was then evaporated and treated with water to provide an oil which was then triturated with water (3×2 mL), dissolved in EtOAc (4 mL), dried over MgSO$_4$, filtered, and evaporated to afford product as an oil (34 mg, 87%). $^1$H NMR (CDCl$_3$) 1.62-1.76 (m, 3H), 1.88-1.98 (m, 1H), 2.29 (d, J=1.3, 3 H), 2.45-2.48 (m, 4H), 2.93 (s, 2H), 3.52 (br s, 1H), 3.63-3.67 (m, 4H), 3.72-3.92 (m, 2H), 3.98-4.08 (m, 1H), 7.32 (br s, 1H), 7.41 (s, 2H). $^{19}$F NMR −63.1. LC/MS 4.68 min, [M+1]$^+$ 487.

Example 57

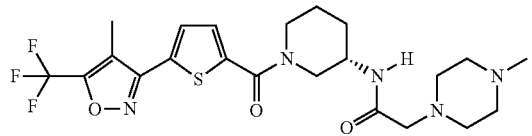 [SMILES: Cc1c(-c2ccc(C(=O)N3CCC[C@H](NC(=O)CN4CCN(C)CC4)C3)s2)noc1C(F)(F)F]

2-(4-Methyl-piperazin-1-yl)-N—{(S)-1-[5-(4-methyl-5-trifluoromethyl-isoxazol-3-yl)-thiophene-2-carbonyl]-piperidin-3-yl}-acetamide 2-Chloro-N—{(S)-1-[5-(4-methyl-5-trifluoromethyl-isoxazol-3-yl)-thiophene-2-carbonyl]-piperidin-3-yl}-acetamide (35 mg, 0.08 mmol, as prepared in Example 56) was dissolved in acetonitrile (3 mL) containing anhydrous K$_2$CO$_3$, treated with N-methylpiperazine (18 µL, 0.16 mmol), and stirred for 3 days. The reaction mixture was then evaporated and treated with water to provide a homogeneous solution which was extracted with EtOAc (2×4 mL), dried over MgSO$_4$, filtered, and evaporated to afford product as an foam (34 mg, 85%). $^1$H NMR (CDCl$_3$) 1.60-1.76 (m, 3H), 1.88-1.98 (m, 1H), 2.22 (s, 3H), 2.29 (d, J=1.3, 3 H), 2.32-2.52 (m, 8H), 2.92 (s, 2H), 3.52 (br s, 1H), 3.48 (br s, 2H), 3.72-4.46 (m, 3H), 7.32-7.44 (br m, 3H). $^{19}$F NMR −63.1. LC/MS 4.59 min, [M+1]$^+$ 500.

Example 58

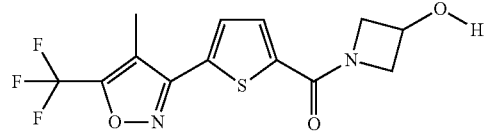 [SMILES: Cc1c(-c2ccc(C(=O)N3CC(O)C3)s2)noc1C(F)(F)F]

(3-Hydroxy-azetidin-1-yl)-[5-(4-methyl-5-trifluoromethyl-isoxazol-3-yl)-thiophen-2-yl]-methanone Prepared from 5-(5-Trifluoromethyl-4-methyl-isoxazol-3-yl)-thiophene-2-carboxylic acid and 3-hydroxyazetidine hydrochloride by the method described in Example 41. Colorless solid (78 mg, 73%). ¹H NMR (DMSO-d6) 2.38 (s, 3H), 3.77-3.90 (m, 1H), 4.19-4.38 (m, 2H), 4.52-4.63 (m, 1H), 4.65-4.78 (m, 1H), 5.88 (d, J=5.9, 1H), 7.62 (d, J=4.0, 1H), 7.73 (d, J=4.0, 1H). ¹³C NMR 7.4, 58.9, 60.6, 62.5, 116.0 (q, J=2), 118.5 (q, J=271), 130.3, 130.5, 131.0, 140.2, 153.2 (q, J=40), 157.9, 160.8. ¹⁹F NMR −62.3. LC/MS 5.42 min, [M+1]⁺ 333.

Example 59

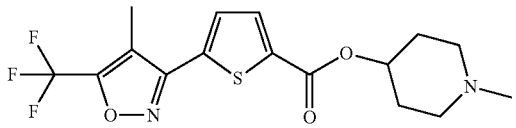 [SMILES: Cc1c(-c2ccc(C(=O)OC3CCN(C)CC3)s2)noc1C(F)(F)F]

5-(4-Methyl-5-trifluoromethyl-isoxazol-3-yl)-thiophene-2-carboxylic acid 1-methyl-piperidin-4-yl ester Prepared from 5-(5-Trifluoromethyl-4-methyl-isoxazol-3-yl)-thiophene-2-carboxylic acid and 1-methyl-piperidin-4-ol by the method described in Example 41. Colorless solid (51 mg, 75%). ¹H NMR (CD₃OD) 1.85-1.98 (m, 2H), 2.03-2.15 (m, 2H), 2.38 (s, 3H), 2.43 (br q, J=1.3, 3H), 2.40-2.56 (m, 2H), 2.73-2.86 (m, 2H), 5.02-5.14 (m, 1H), 7.69 (d, J=4.0, 1H), 7.90 (d, J=4.0, 1H). ¹³C NMR 7.9, 31.4, 46.2, 53.5 (br), 71.9 (br), 116.8 (br), 120.3 (q, J=270), 130.7, 135.1, 136.0, 137.5, 159.4, 162.3. ¹⁹F NMR −64.8. LC/MS 4.75 min, [M+1]⁺ 375.

Example 60

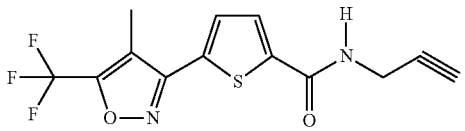 [SMILES: C#CCNC(=O)c1ccc(-c2noc(C(F)(F)F)c2C)s1]

5-(4-Methyl-5-trifluoromethyl-isoxazol-3-yl)-thiophene-2-carboxylic acid prop-2-ynylamide Prepared from 5-(5-Trifluoromethyl-4-methyl-isoxazol-3-yl)-thiophene-2-carboxylic acid and propragylamine by the method described in Example 2 Method B. Pale yellow solid (122 mg, 97%). ¹H NMR (DMSO-d₆) 2.41 (d, J=1.3, 3H), 3.25 (t, J=2.6, 1H), 4.13 (dd, J=5.7, 2.6, 2H), 7.79 (d, J=4.0, 1H), 7.97 (d, J=4.0, 1H), 9.29 (t, J=5.7, 1H). ¹⁹F NMR −62.30. LC/MS 6.07 min, [M+1]⁺ 315.

Example 61

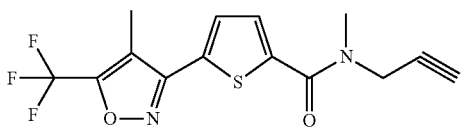 [SMILES: C#CCN(C)C(=O)c1ccc(-c2noc(C(F)(F)F)c2C)s1]

5-(4-Methyl-5-trifluoromethyl-isoxazol-3-yl)-thiophene-2-carboxylic acid methyl-prop-2-ynyl-amide Prepared from 5-(5-Trifluoromethyl-4-methyl-isoxazol-3-yl)-thiophene-2-carboxylic acid and N— methyl propragylamine by the method described in Example 2 method B. Colorless solid (128 mg, 98%). ¹H NMR (CDCl₃) 2.37 (d, J=1.8, 3H), 3.28 (br s, 3H), 4.34 (br s, 2H), 7.48 (d, J=3.5, 1H), 7.51 (br d, 1H). ¹⁹F NMR −63.13. LC/MS 6.36 min, [M+1]⁺ 329.

Example 62

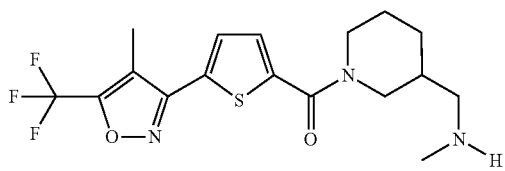 [SMILES: CNCC1CCCN(C(=O)c2ccc(-c3noc(C(F)(F)F)c3C)s2)C1]

(3-Methylaminomethyl-piperidin-1-yl)-[5-(4-methyl-5-trifluoromethyl-isoxazol-3-yl)-thiophen-2-yl]-methanone, hydrochloride Prepared from 5-(5-Trifluoromethyl-4-methyl-isoxazol-3-yl)-thiophene-2-carboxylic acid and 3-(tert-butoxycarbonylamino)piperidine (CAS [172603-05-3], CHN Technologies, Woburn Mass., USA) by the method described in Example 2 method B. The intermediate Boc-protected adduct was chromatographed on silica gel with EtOAc to afford product as a colorless solid (54 mg, 44%). LC/MS 7.26 min, [M+1]⁺ 488. The Boc-protected intermediate was dissolved in 1,4-dioxane (1 mL) and treated with a 4 N solution of hydrogen chloride in 1,4,-dioxane (4 mL) and stirred for 4 hr, after which time the reaction mixture was evaporated to approximately ½ volume and diluted with ethyl ether (10 mL). The resulting solids were filtered and air dried to afford product as a colorless solid (47 mg, 100%, 44% overall). LC/MS 4.58 min, [M+1]⁺ 388.

Example 63

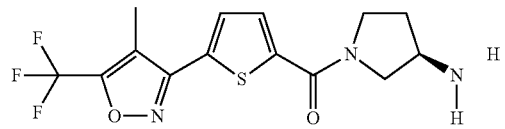

((R)-3-Amino-pyrrolidin-1-yl)-[5-(4-methyl-5-trifluoromethyl-isoxazol-3-yl)-thiophen-2-yl]-methanone, hydrochloride Prepared from 5-(5-Trifluoromethyl-4-methyl-isoxazol-3-yl)-thiophene-2-carboxylic acid and (R)-(+)-3-(Boc-amino)pyrrolidine (CAS [122536-77-0], CHN Technologies, Woburn Mass., USA) by the method described in Example 2 Method B. The intermediate Boc-protected adduct was chromatographed on silica gel with EtOAc to afford product as a colorless solid (66 mg, 30%). LC/MS 6.54 min, [M+1]⁺ 446. The Boc-protected intermediate was dissolved in 1,4-dioxane (1 mL) and treated with a 4 N solution of hydrogen chloride in 1,4,-dioxane (4 mL) and stirred for 24 hr, after which time the reaction mixture was evaporated to approximately ½ volume and diluted with ethyl ether (10 mL). The resulting solids were filtered and air dried to afford product as a colorless solid (45 mg, 80%, 24% overall). LC/MS 4.29 min, [M+1]+ 346.

Example 64

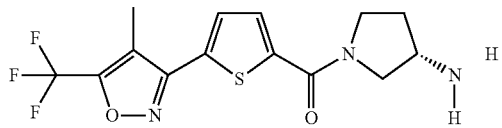

((S)-3-Amino-pyrrolidin-1-yl)-[5-(4-methyl-5-trifluoromethyl-isoxazol-3-yl)-thiophen-2-yl]-methanone Prepared from 5-(5-Trifluoromethyl-4-methyl-isoxazol-3-yl)-thiophene-2-carboxylic acid and (S)-(−)-3-(Boc-amino)pyrrolidine (CAS [122536-76-9], CHN Technologies, Woburn Mass., USA) by the method described in Example 2 Method B. The intermediate Boc-protected adduct was chromatographed on silica gel with EtOAc to afford product as a colorless solid (145 mg, 65%). LC/MS 6.54 min, [M+1]+ 446. The Boc-protected intermediate was dissolved in 1,4-dioxane (1 mL) and treated with a 4 N solution of hydrogen chloride in 1,4,-dioxane (4 mL) and stirred for 24 hr, after which time the reaction mixture was evaporated to approximately ½ volume and diluted with ethyl ether (10 mL). The resulting solids were filtered and air dried to afford product as a colorless solid (90 mg, 72%, 47% overall). LC/MS 4.29 min, [M+1]+ 346.

Example 65

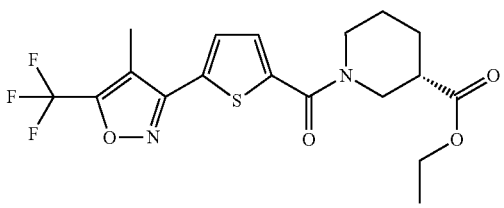 [SMILES: CCOC(=O)[C@H]1CCCN(C(=O)c2ccc(-c3noc(C(F)(F)F)c3C)s2)C1]

(S)-1-[5-(4-Methyl-5-trifluoromethyl-isoxazol-3-yl)-thiophene-2-carbonyl]-piperidine-3-carboxylic acid ethyl ester Prepared from 5-(5-Trifluoromethyl-4-methyl-isoxazol-3-yl)-thiophene-2-carboxylic acid and (S)-(+)-nipecotic acid, ethyl ester (TCI America, Portland Oreg., USA) by the method described in Example 2 Method B. Colorless solid (415 mg, 91%). $^1$H NMR (CDCl$_3$) 1.19 (t, J=7.0, 3H), 1.50-1.60 (m, 1H), 1.66-1.82 (m, 2H), 2.02-2.12 (m, 1H), 2.29 (d, J=1.4, 3H), 2.46-2.56 (m, 1H), 3.13 (t, J=11.0, 1H), 3.28 (br s, 1H), 4.08 (q, J 7.0, 3H), 4.10 (obs m, 1H), 4.34 (br s, 1H), 7.28 (d, J=4.0, 1H), 7.39 (d, J=3.5, 1H). $^{19}$F NMR −63.12. LC/MS 6.74 min, [M+1]+ 417.

Example 66

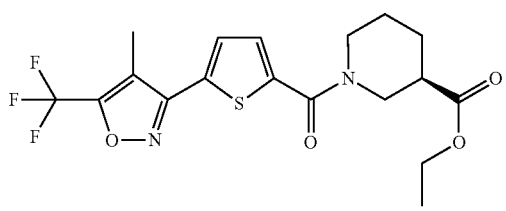

(R)-1-[5-(4-Methyl-5-trifluoromethyl-isoxazol-3-yl)-thiophene-2-carbonyl]-piperidine-3-carboxylic acid ethyl ester Prepared from 5-(5-Trifluoromethyl-4-methyl-isoxazol-3-yl)-thiophene-2-carboxylic acid and (R)-(−)-nipecotic acid, ethyl ester (TCI America, Portland Oreg., USA) in the same manner as the R isomer. Colorless solid (220 mg, 70%). LC/MS 6.76 min, [M+1]+417.

Example 67

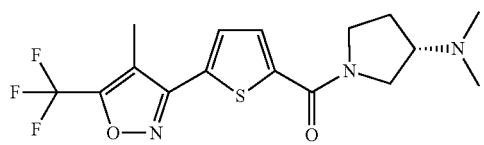 [SMILES: Cc1c(-c2ccc(C(=O)N3CC[C@H](N(C)C)C3)s2)noc1C(F)(F)F]

((S)-3-Dimethylamino-pyrrolidin-1-yl)-[5-(4-methyl-5-trifluoromethyl-isoxazol-3-yl)-thiophen-2-yl]-methanone A solution of ((S)-3-amino-pyrrolidin-1-yl)-[5-(4-methyl-5-trifluoromethyl-isoxazol-3-yl)-thiophen-2-yl]-methanone, hydrochloride (Example 64, 80 mg, 0.21 mmol) in dichloromethane (10 mL) was treated with a 37% aqueous formaldehyde solution (58 μL, 2.10 mmol) followed by sodium triacetoxyborohydride (445 mg, 2.10 mmol). The mixture was stirred for 24 h then quenched with saturated aqueous solution of NaHCO$_3$ (10 mL) and stirred for 30 min. The organic portion was further washed with an additional portion of NaHCO$_3$ solution (10 mL) followed by a brine solution (10 mL), then dried over MgSO$_4$, filtered, and evaporated in vacuo to afford product as a colorless solid. $^1$H NMR (CDCl$_3$) 1.70-2.00 (m, 1H), 2.06-2.20 (m, 1H), 2.23 (s, 6H), 2.29 (s, 3H), 2.62-2.80 (m, 1H), 3.32-4.00 (m, 4H), 7.42 (d, J=4.0, 1H), 7.47 (br d, 1H). LC/MS 4.25 min, [M+1]+ 374.

Example 68

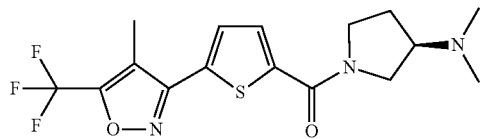 [SMILES: Cc1c(-c2ccc(C(=O)N3CC[C@@H](N(C)C)C3)s2)noc1C(F)(F)F]

((R)-3-Dimethylamino-pyrrolidin-1-yl)-[5-(4-methyl-5-trifluoromethyl-isoxazol-3-yl)-thiophen-2-yl]-methanone Prepared from ((R)-3-amino-pyrrolidin-1-yl)-[5-(4-methyl-5-trifluoromethyl-isoxazol-3-yl)-thiophen-2-yl]-methanone, hydrochloride (Example 63, 40 mg, 0.105) in the same manner as the S isomer. LC/MS 4.27 min, [M+1]+ 374.

Example 69

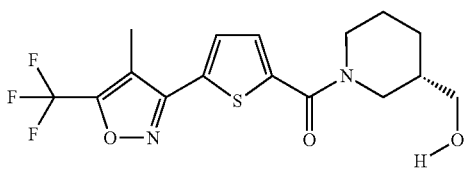 [SMILES: Cc1c(-c2ccc(C(=O)N3CCC[C@H](CO)C3)s2)noc1C(F)(F)F]

((S)-3-Hydroxymethyl-piperidin-1-yl)-[5-(4-methyl-5-trifluoromethyl-isoxazol-3-yl)-thiophen-2-yl]-methanone Prepared from 5-(5-Trifluoromethyl-4-methyl-isoxazol-3-yl)-thiophene-2-carbonyl chloride (74 mg, 0.25 mmol, as prepared in Example 2 Method B) and (S)-1-piperidin-3-yl-methanol, hydrochloride (76 mg, 0.5 mmol) by the method used in Example 46 for the achiral isomer. Gummy solid (70 mg, 74%). LC/MS 5.85 min, [M+1]+ 375.

Example 70

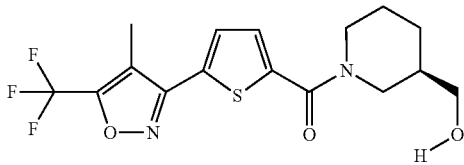 [SMILES: Cc1c(-c2ccc(C(=O)N3CCC[C@@H](CO)C3)s2)noc1C(F)(F)F]

((R)-3-Hydroxymethyl-piperidin-1-yl)-[5-(4-methyl-5-trifluoromethyl-isoxazol-3-yl)-thiophen-2-yl]-methanone Prepared from 5-(5-Trifluoromethyl-4-methyl-isoxazol-3-yl)-thiophene-2-carbonyl chloride (74 mg, 0.25 mmol, as prepared in Example 2 Method B) and (S)-1-piperidin-3-yl-methanol, hydrochloride (76 mg, 0.5 mmol) in the same manner as the S isomer (Example 69). Gummy solid (56 mg, 60%). LC/MS 5.86 min, [M+1]+ 375.

Example 71

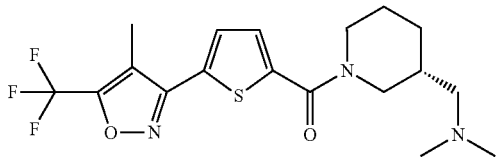 [SMILES: Cc1c(-c2ccc(C(=O)N3CCC[C@H](CN(C)C)C3)s2)noc1C(F)(F)F]

((R)-3-Dimethylaminomethyl-piperidin-1-yl)-[5-(4-methyl-5-trifluoromethyl-isoxazol-3-yl)-thiophen-2-yl]-methanone A solution of dimethyl-(S)-1-piperidin-3-ylmethyl-amine, dihydrochloride (Preparative Example 29, 108 mg, 0.5 mmol) in THF/DMF (3 mL/500 µL) was treated with triethylamine (95 µL, 1.0 mmol) followed by 5-(5-Trifluoromethyl-4-methyl-isoxazol-3-yl)-thiophene-2-carbonyl chloride (74 mg, 0.25 mmol, as prepared in Example 2 Method B). The reaction mixture was vigorously stirred or 16 h then evaporated and diluted with water (5 mL). The crude reaction mixture was extracted with EtOAc (2×3 mL) which was then washed with a 1 N NaOH solution (2×3 mL), dried over MgSO4, filtered, and evaporated in vacuo to afford product as a colorless solid. The solid was dissolved in a EtOAc/hexanes (1:1) mixture (1 mL), filtered through a PTFE syringe filter, and again evaporated in vacuo to afford product as a colorless solid (31 mg, 31%). LC/MS 5.13 min, [M+1]+ 402.

Example 72

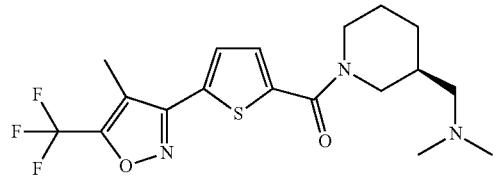 [SMILES: Cc1c(-c2ccc(C(=O)N3CCC[C@@H](CN(C)C)C3)s2)noc1C(F)(F)F]

((S)-3-Dimethylaminomethyl-piperidin-1-yl)-[5-(4-methyl-5-trifluoromethyl-isoxazol-3-yl)-thiophen-2-yl]-methanone Prepared from dimethyl-(R)-1-piperidin-3-ylmethyl-amine, dihydrochloride (Preparative Example 28, 108 mg, 0.5 mmol) and 5-(5-Trifluoromethyl-4-methyl-isoxazol-3-yl)-thiophene-2-carbonyl chloride (74 mg, 0.25 mmol, as prepared in Example 2 Method B) as described for the R isomer (Example 70). Colorless solid (41 mg, 41%). LC/MS 5.28 min, [M+1]+ 402.

Example 73

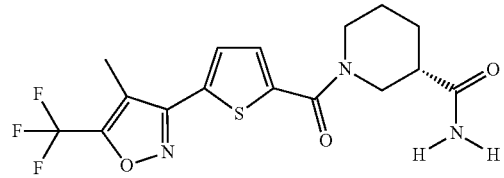 [SMILES: Cc1c(-c2ccc(C(=O)N3CCC[C@H](C(N)=O)C3)s2)noc1C(F)(F)F]

(S)-1-[5-(4-Methyl-5-trifluoromethyl-isoxazol-3-yl)-thiophene-2-carbonyl]-piperidine-3-carboxylic acid amide A solution of (S)-1-[5-(4-Methyl-5-trifluoromethyl-isoxazol-3-yl)-thiophene-2-carbonyl]-piperidine-3-carboxylic acid ethyl ester (Example 65, 88 mg, 0.20 mmol) in 7N methanolic ammonia (5 mL) was heated at 60 OC in a sealed vial for 48 hr. After this time the reaction mixture was evaporated and triturated and filtered with the aid of water. The filtered solids were air dried to afford product as a colorless solid (67 mg, 86%). LC/MS 5.52 min, [M+1]+ 388.

Example 74

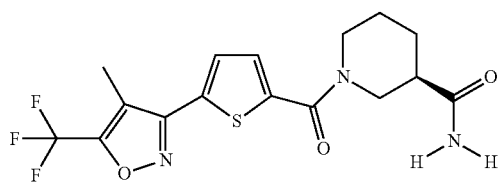 [SMILES: Cc1c(-c2ccc(C(=O)N3CCC[C@@H](C(N)=O)C3)s2)noc1C(F)(F)F]

(R)-1-[5-(4-Methyl-5-trifluoromethyl-isoxazol-3-yl)-thiophene-2-carbonyl]-piperidine-3-carboxylic acid amide Prepared from (R)-1-[5-(4-Methyl-5-trifluoromethyl-isoxazol-3-yl)-thiophene-2-carbonyl]-piperidine-3-carboxylic acid ethyl ester (Example 66, 88 mg, 0.20 mmol) in the same manner as the S isomer (Example 72). Colorless solid (68 mg, 88%). LC/MS 5.52 min, [M+1]+ 388.

Example 75

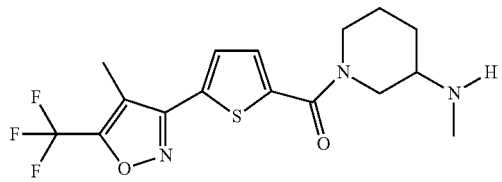 [SMILES: CNC1CCCN(C(=O)c2ccc(-c3noc(C(F)(F)F)c3C)s2)C1]

(3-Methylamino-piperidin-1-yl)-[5-(4-methyl-5-trifluoromethyl-isoxazol-3-yl)-thiophen-2-yl]-methanone A solution of 5-(5-Trifluoromethyl-4-methyl-isoxazol-3-yl)-thiophene-2-carbonyl chloride (74 mg, 0.25 mmol, as prepared in Example 2 Method B) in THF (2 mL) was treated with a THF solution (2 mL) of methyl-piperidin-3-ylmethyl-carbamic acid 9H-fluoren-9-ylmethyl ester, hydrochloride (112 mg, 0.30 mmol, Preparative Example 30) and diisopropylethylamine (52 μL, 0.30 mmol). The reaction mixture was allowed to stir for 2 hr then evaporated to ~1 mL volume and diluted with EtOAc (10 mL). The resulting solution was then washed with a 1N aqueous HCl solution (10 mL), then a saturated aqueous solution of NaHCO₃ (10 mL) followed by a brine solution (10 mL). The organic portion was then dried over MgSO₄, filtered, and evaporated in vacuo to afford crude oil. The oil was chromatographed on silica gel with EtOAc/hexane (75%) to afford the Fmoc-protected intermediate as a colorless oil (103 mg, 69%). LC/MS 7.63 min, [M+1]+ 596. The intermediate was then dissolved in DMF (2.5 mL), treated with morpholine (200 μL), and stirred for 4 h resulting in precipitated colorless solids. The reaction mixture was cooled to 0° C. and filtered through a glass wool plug to remove solids, then evaporated in vacuo to afford crude product which was chromatographed on a small silica gel column with EtOAc then MeOH/EtOAc (10%) containing 2% triethylamine to afford product as a copper colored oil (59 mg, 89%, 61% overall). ¹H NMR (CDCl₃) 1.54-1.64 (m, 2H), 1.84-1.92 (m, 1H), 2.05-2.14 (m, 1H), 2.37 (d, J=1.8, 3H), 2.51 (br s, 3H), 2.70-2.80 (m, 1H), 3.13 (dd, J=13.2, 9.2, 1H), 3.22-3.30 (m, 1H), 4.10 (br, 1H), 4.34 (br d, J=11.0, 1H), 5.05 (br s, 1H), 7.37 (d, J=4.0, 1H), 7.46 (d, J=4.0, 1H). ¹⁹F NMR -63.11. LC/MS 4.46 min, [M+1]+ 374.

Example 76

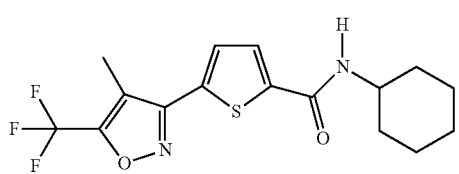 [SMILES: Cc1c(-c2ccc(C(=O)NC3CCCCC3)s2)noc1C(F)(F)F]

5-(4-Methyl-5-trifluoromethyl-isoxazol-3-yl)-thiophene-2-carboxylic acid cyclohexylamide Prepared from 5-(5-Trifluoromethyl-4-methyl-isoxazol-3-yl)-thiophene-2-carboxylic acid and cyclohexylamine by the method described in Example 2 Method B reversing the order of addition such that intermediate solid acid chloride was added to a THF solution of triethylamine and piperdine derivative. Colorless solid (80 mg, 89%). ¹H NMR (CDCl₃) 1.18-1.36 (m, 1H), 1.36-1.50 (m, 1H), 1.60-1.82 (m, 4H), 1.98-2.10 (m, 2H), 2.37 (d, J=0.9, 3H), 3.90-4.04 (m, 1H), 5.88 (br d, J=7.0, 1H), 7.49 (d, J=4.0, 1H), 7.51 (d, J=3.5, 1H). ¹⁹F NMR -63.36. LC/MS 7.18 min, [M+1]+ 359.

Example 77

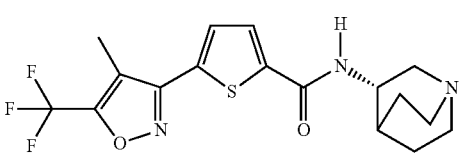 [SMILES: Cc1c(-c2ccc(C(=O)N[C@@H]3CN4CCC3CC4)s2)noc1C(F)(F)F]

(S)-5-(4-Methyl-5-trifluoromethyl-isoxazol-3-yl)-thiophene-2-carboxylic acid (1-aza-bicyclo[2.2.2]oct-3-yl)-amide A suspension of (S)-(-)-aminoquinuclidine dihydrochloride (55 mg, 0.275 mmol) in dichloromethane (1 mL) as treated with triethylamine (53 μL, 0.55 mmol) followed by 5-(5-Trifluoromethyl-4-methyl-isoxazol-3-yl)-thiophene-2-carbonyl chloride (74 mg, 0.25 mmol) and the reaction mixture allowed to stir for 20 hr. After this time, the reaction mixture was evaporated and the residue partitioned between EtOAc (5 mL) and a 1 N HCl solution (10 mL). The aqueous portion was then basified to pH ~10-12 with a 1N NaOH solution. The aqueous portion was then extracted with EtOAc (10 mL) which was then washed with a brine solution (10 mL), dried over MgSO₄, filtered, and evaporated in vacuo to afford product as a colorless solid (38 mg, 40%). ¹H NMR (CDCl₃) 1.50-1.62 (m, 1H), 1.70-1.88 (m, 3H), 2.08-2.12 (m, 2H), 2.37 (d, J=1.3, 3H), 2.72-3.10 (m, 5H), 3.44 (ddd, J=14.0, 9.7, 2.2, 1H), 4.14-4.22 (m, 1H), 6.56 (br d, J=7.0, 1H), 7.49 (d, J=4.0, 1H), 7.56 (d, J=4.0, 1H). $^{19}$F NMR −63.13. LC/MS 4.63 min, [M+1]$^+$ 386.

Example 78

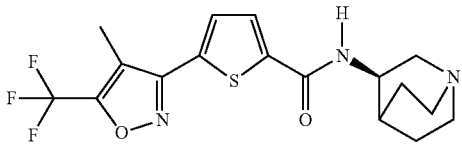

(R)-5-(4-Methyl-5-trifluoromethyl-isoxazol-3-yl)-thiophene-2-carboxylic acid (1-aza-bicyclo[2.2.2]oct-3-yl)-amide Prepared from (R)-(+)-aminoquinuclidine dihydrochloride in the same manner as the R isomer (Example 77). Colorless solid (40 mg, 42%). LC/MS 4.58 min, [M+1]$^+$ 386.

Example 79

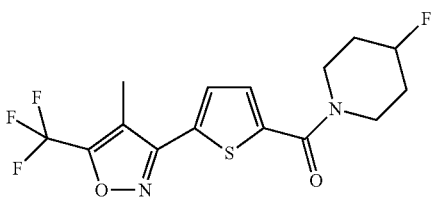 [SMILES: Cc1c(-c2ccc(C(=O)N3CCC(F)CC3)s2)noc1C(F)(F)F]

(4-Fluoro-piperidin-1-yl)-[5-(4-methyl-5-trifluoromethyl-isoxazol-3-yl)-thiophen-2-yl]-methanone Prepared from 5-(5-Trifluoromethyl-4-methyl-isoxazol-3-yl)-thiophene-2-carboxylic acid and 4-fluoromethylpiperidine hydrochloride by the method described in Example 41. Colorless solid (116 mg, 89%). $^1$H NMR (CDCl$_3$) 1.85-2.03 (m, 4H), 2.37 (s, 3H), 3.63-3.76 (m, br, 2H), 3.89-4.03 (m, br, 2H), 4.95 (dm, J$_{H-F}$=48, 1H), 7.34 (d, J=3.6, 1H), 7.46 (d, J=3.6, 1H). $^{13}$C NMR 7.7, 31.3 (J=20), 41.2 (br), 87.2 (d, J=171), 114.5 (q, J=2), 118.3 (q, J=271), 127.8, 129.0, 131.1, 139.6, 155.0 (q, J=40), 157.7, 162.6. $^{19}$F NMR −63.1. LC/MS 6.42 min, [M+1]$^+$ 363.

Example 80

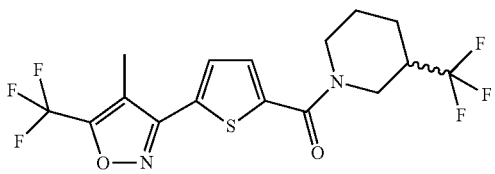 [SMILES: Cc1c(-c2ccc(C(=O)N3CCCC(C(F)(F)F)C3)s2)noc1C(F)(F)F]

[5-(4-Methyl-5-trifluoromethyl-isoxazol-3-yl)-thiophen-2-yl]-(3-trifluoromethyl-piperidin-1-yl)-methanone Prepared from 5-(5-Trifluoromethyl-4-methyl-isoxazol-3-yl)-thiophene-2-carboxylic acid and (±)-3-trifluoromethylpiperidine hydrochloride by the method described in Example 41. Colorless solid (123 mg, 82%). $^1$H NMR (CDCl$_3$) 1.53-1.76 (m, br, 2H), 1.84-1.95 (m, br, 1H), 2.10-2.22 (m, br, 1H), 2.31-2.43 (m, br, 4H), 2.92-3.16 (m, br, 2H), 4.28-4.45 (m, br, 1H), 4.54-4.72 (m, br, 1H), 7.34 (d, J=4.0, 1H), 7.47 (d, J=4.0, 1H). $^{13}$C NMR 7.7, 23.5, 24.2, 40.5 (q, J=27), 44.0 (br), 46.3 (br), 114.5 (q, J=2), 118.5 (q, J=271), 126.1 (q, J=283), 127.8, 129.1, 131.4, 139.3, 155.0 (q, J=41), 157.6, 162.8. $^{19}$F NMR −72.8, −63.2. LC/MS 6.99 min, [M+1]$^+$ 413.

Example 81

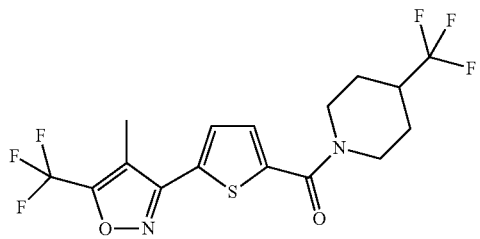 [SMILES: Cc1c(-c2ccc(C(=O)N3CCC(C(F)(F)F)CC3)s2)noc1C(F)(F)F]

(4-Methyl-5-trifluoromethyl-isoxazol-3-yl)-thiophen-2-yl]-(4-trifluoromethyl-piperidin-1-yl)-methanone Prepared from 5-(5-trifluoromethyl-4-methyl-isoxazol-3-yl)-thiophene-2-carboxylic acid and 4-trifluoromethylpiperidine hydrochloride by the method described in Example 41. Colorless solid (135 mg, 90%). $^1$H NMR (CDCl$_3$) 1.54-1.73 (m, br, 2H), 2.00 (d, br, J=12.7, 2H), 2.31-2.42 (m, br, 4H), 2.89-3.12 (m, br, 2H), 4.43-4.68 (m, br, 2H), 7.33-7.37 (m, br, 1H), 7.44-7.50 (m, br, 1H). $^{13}$C NMR 7.7, 24.7, 40.5 (q, J=28), 44.4 (br), 114.5 118.5 (q, J=271), 126.8 (q, J=278), 127.8, 129.1, 131.3, 139.4, 155.0 (q, J=41), 157.6, 162.6. $^{19}$F NMR −74.2, −63.2. LC/MS 7.01 min, [M+1]$^+$ 413.

Example 82

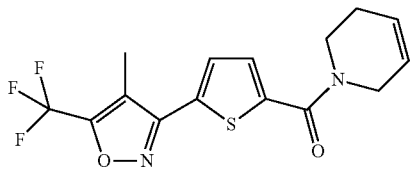 [SMILES: Cc1c(-c2ccc(C(=O)N3CC=CCC3)s2)noc1C(F)(F)F]

6-Dihydro-2H-pyridin-1-yl)-[5-(4-methyl-5-trifluoromethyl-isoxazol-3-yl)-thiophen-2-yl]-methanone Prepared from 5-(5-trifluoromethyl-4-methyl-isoxazol-3-yl)-thiophene-2-carboxylic acid and 1,2,3,6-tetrahydropyridine hydrochloride by the method described in Example 41.

Colorless solid (59 mg, 89%). $^1$H NMR (CDCl$_3$) 2.26-2.34 (m, br, 2H), 2.36 (s, 3H), 3.81 (t, br, J=5.9, 2H), 4.20-4.25 (m, br, 2H), 5.67-5.77 (m, 1H), 5.88-5.97 (m, 1H), 7.37 (d, J=3.9, 1H), 7.47 (d, J=3.9, 1H). $^{13}$C NMR 7.7, 25.5 (br), 29.7, 44.5 (br), 114.5 (q, J=2), 118.5 (q, J=271), 123.8, 125.7, 127.8, 128.9, 131.1, 140.3, 155.0 (q, J=41), 157.7, 162.7. $^{19}$F NMR −63.1. LC/MS 6.61 min, [M+1]$^+$ 343.

Example 83

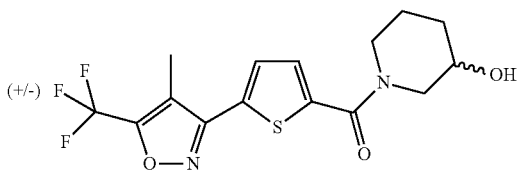 [SMILES: Cc1c(-c2ccc(C(=O)N3CCCC(O)C3)s2)noc1C(F)(F)F]

(3-Hydroxy-piperidin-1-yl)-[5-(4-methyl-5-trifluoromethyl-isoxazol-3-yl)-thiophen-2-yl]-methanone Prepared from 5-(5-trifluoromethyl-4-methyl-isoxazol-3-yl)-thiophene-2-carboxylic acid and (±)-3-hydroxypiperidine hydrochloride by the method described in Example 41. Colorless solid (101 mg, 85%). $^1$H NMR (CD$_3$OD) 1.51-1.71 (m, 2H), 1.84-2.05 (m, 2H), 2.39 (q, J$_{H-F}$=1.5, 3H), 3.34-3.65 (m, 2H), 3.68-3.85 (m, 2H), 3.86-4.14 (m, 1H), 7.49 (d, br, J=3.9, 1H), 7.60 (d, br, J=3.9, 1H). $^{13}$C NMR 8.0, 23.6 (br), 33.5, 45.1 (br), 55.1 (br), 67.0, 116.7 (q, J=2), 120.3 (q, J=270), 129.8, 130.9, 132.4, 141.1, 155.8 (q, J=40), 159.4, 165.0. $^{19}$F NMR −64.8. LC/MS 6.00 min, [M+1]$^+$ 361.

Example 84

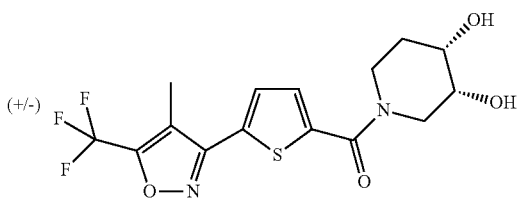 [SMILES: Cc1c(-c2ccc(C(=O)N3CC[C@H](O)[C@H](O)C3)s2)noc1C(F)(F)F]

(±) ((cis)-3,4-Dihydroxy-piperidin-1-yl)-[5-(4-methyl-5-trifluoromethyl-isoxazol-3-yl)-thiophen-2-yl]-methanone A solution of (3,6-Dihydro-2H-pyridin-1-yl)-[5-(4-methyl-5-trifluoromethyl-isoxazol-3-yl)-thiophen-2-yl]-methanone (31 mg, 0.09 mmol) in acetone (2 mL) and water (1 mL) was treated with N-methylmorpholine-N-oxide (17 mg, 0.14 mmol) followed by K$_2$OsO$_4$·2H$_2$O (catalytic). The resulting mixture was stirred at room temperature for 16 hr, at which time LC/MS analysis showed full conversion of starting material (6.91 min, MH$^+$=343) to product (5.57 min, MH$^+$=377).

A saturated aqueous Na$_2$SO$_3$ solution (10 mL) was then added and the reaction stirred vigorously for 10 minutes. The mixture was then partitioned between CH$_2$Cl$_2$ (10 mL) and water (10 mL) and the aqueous portion further extracted with CH$_2$Cl$_2$ (3×20 mL). The combined organic extract was dried over Na$_2$SO$_4$, filtered, and concentrated in vacuo to crude product (32 mg).

Gradient column chromatography on silica eluting with 75% EtOAc/hexanes, 100% EtOAc, 5% then 10% MeOH/EtOAc gave the title compound as a colorless solid (29 mg, 0.77 mmol, 85%). $^1$H NMR (CD$_3$OD) 1.69-1.81 (m, 1H), 1.85-1.99 (m, 1H), 2.39 (s, 3H), 3.37-3.72 (m, br, 2H), 3.75-3.84 (m, 1H), 3.84-4.16 (m, br, 3H), 7.53 (s, br, 1H), 7.60 (d, br, J=3.8, 1H). $^{13}$C NMR 8.0, 30.9 (br), 41.6 (br), 52.1 (br), 69.5, 70.0, 116.7 (q, J=2), 120.3 (q, J=270), 129.8, 131.1, 132.4, 141.1, 155.8 (q, J=40), 159.4, 165.3. $^{19}$F NMR −64.8. LC/MS 5.57 min, [M+1]$^+$ 377.

Example 85

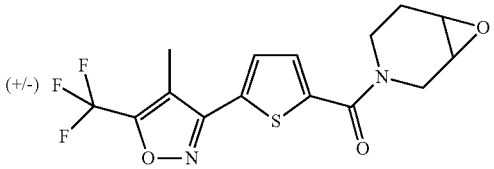 [SMILES: Cc1c(-c2ccc(C(=O)N3CCC4OC4C3)s2)noc1C(F)(F)F]

[5-(4-Methyl-5-trifluoromethyl-isoxazol-3-yl)-thiophen-2-yl]-(7-oxa-3-aza-bicyclo[4.1.0]hept-3-yl)-methanone A solution of (3,6-Dihydro-2H-pyridin-1-yl)-[5-(4-methyl-5-trifluoromethyl-isoxazol-3-yl)-thiophen-2-yl]-methanone (177 mg, 0.52 mmol) in CH$_2$Cl$_2$ (5 mL) was treated with MCPBA (presumed 50% purity, 356 mg, 1.03 mmol). The reaction was stirred at room temperature for 16 hr at which time LC/MS analysis showed full conversion of starting material (6.93 min, MH$^+$=343) to product (6.29 min, MH$^+$=359).

The reaction mixture was then treated with a 5% NaOH solution (10 mL) with vigorous mixing. The mixture was partitioned between CH$_2$Cl$_2$ (10 mL) and water (10 mL) and the aqueous portion further extracted with CH$_2$Cl$_2$ (3×20 mL). The combined organic extract was dried over Na$_2$SO$_4$, filtered, and concentrated in vacuo to afford crude product (192 mg).

Gradient column chromatography on silica eluting with 75% EtOAc/hexanes, 100% EtOAc then 10% MeOH/EtOAc gave the title compound as a colorless solid (177 mg, 0.49 mmol, 95%). $^1$H NMR (CDCl$_3$) 1.98-2.26 (m, br, 2H), 2.34 (s, br, 3H), 3.18-3.73 (m, br, 4H), 3.82-4.30 (m, br, 2H), 7.33 (s, br, 1H), 7.43 (s, br, 1H). $^{13}$C NMR 7.6, 24.6 (br), 37.1-47.2 (br), 50.1, 50.5, 114.5 (br), 118.4 (q, J=271), 127.8, 129.2, 131.2, 139.5, 154.9 (q, J=40), 157.6, 162.9. $^{19}$F NMR −63.2. LC/MS 6.29 min, [M+1]$^+$ 359.

Example 86

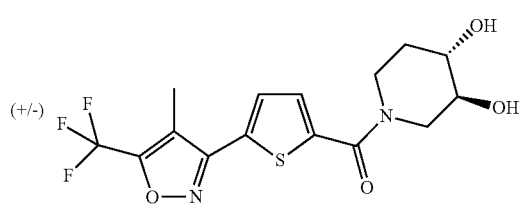 [SMILES: Cc1c(-c2ccc(C(=O)N3CC[C@H](O)[C@@H](O)C3)s2)noc1C(F)(F)F]

(±)((trans)-3,4-Dihydroxy-piperidin-1-yl)-[5-(4-methyl-5-trifluoromethyl-isoxazol-3-yl)-thiophen-2-yl]-methanone A solution of [5-(4-Methyl-5-trifluoromethyl-isoxazol-3-yl)-thiophen-2-yl]-(7-oxa-3-aza-bicyclo[4.1.0]hept-3-yl)-methanone (93 mg, 0.26 mmol) in CH$_3$CN (4 mL) and H$_2$O (2 mL) was treated with cerium (IV) ammonium nitrate (cat.). The resulting solution was stirred at room temperature for 40 hr, at which time LC/MS analysis confirmed full conversion of starting material (6.29 min, MH$^+$=359) to product (5.53 mins, MH$^+$=377).

The mixture was then partitioned between CH$_2$Cl$_2$ (10 mL) and water (10 mL) and aqueous portion further extracted with CH$_2$Cl$_2$ (3×20 mL), dried over Na$_2$SO$_4$, filtered, and concentrated in vacuo to afford crude product.

Gradient column chromatography on silica eluting with 100% EtOAc, then 5% MeOH/EtOAc gave the title compound as a colorless solid (72 mg, 0.19 mmol, 73%). $^1$H NMR (CD$_3$OD) 1.48-1.63 (m, br, 1H), 1.99-2.14 (m, br, 1H), 2.39 (s, br, 3H), 3.32-3.72 (m, br, 4H), 3.87-4.19 (m, br, 2H), 7.50 (s, br, 1H), 7.59 (s, br, 1H). $^{13}$C NMR 8.0, 30.3-33.0 (br), 40.5-43.8 (br), 71.7, 72.1 (br), 116.6 (br), 120.2 (q, J=270), 129.8, 131.0, 132.5, 140.8, 155.8 (q, J=41), 159.3, 164.9. $^{19}$F NMR −64.7. LC/MS 5.53 min, [M+1]$^+$ 377.

Example 87

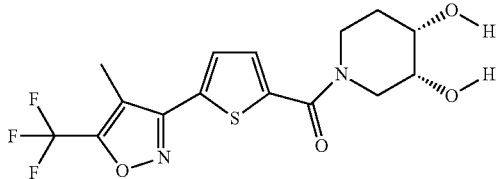 [SMILES: Cc1c(-c2ccc(C(=O)N3CC[C@H](O)[C@H](O)C3)s2)noc1C(F)(F)F]

(3R,4S)-1-({5-[4-methyl-5-(trifluoromethyl)isoxazol-3-yl]thien-2-yl}carbonyl)piperidine-3,4-diol Prepared from 5-(5-Trifluoromethyl-4-methyl-isoxazol-3-yl)-thiophene-2-carboxylic acid and (3R,4S)-3,4-Piperidinediol (CAS [135501-61-0]) by the method described in Example 2 Method B reversing the order of addition such that solid acid chloride was added to a THF/DMF (4 mL/1 mL) solution of triethylamine and (3R,4S)-3,4-Piperidinediol (2 mmol). After 30 min the reaction mixture was quenched with the addition of water. The resulting solids were then filtered and washed with a 1 N aqueous HCl solution followed by water. The material was air dried to afford product as a colorless solid (304 mg, 81%). $^1$H NMR (DMSO-d6) 1.53-1.60 (m, 1H), 1.65-1.71 (m, 1H), 2.34 (d, J=1.3, 3 H), 3.10-4.00 (br m, 6H), 4.70 (d, J=4.4, 1 H), 4.81 (d, J=4.0, 1 H), 7.54 (br s, 1H), 7.65 (d, J=4.0, 1 H). $^{19}$F NMR −62.2. LC/MS 5.44 min, [M+1]$^+$ 377.

Example 88

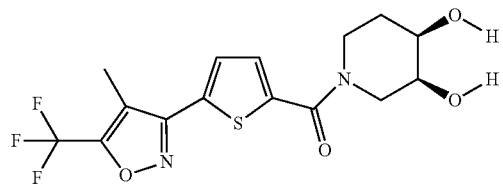 [SMILES: Cc1c(-c2ccc(C(=O)N3CC[C@@H](O)[C@@H](O)C3)s2)noc1C(F)(F)F]

(3S,4R)-1-({5-[4-methyl-5-(trifluoromethyl)isoxazol-3-yl]thien-2-yl}carbonyl)piperidine-3,4-diol Prepared from 5-(5-Trifluoromethyl-4-methyl-isoxazol-3-yl)-thiophene-2-carboxylic acid and (3S,4R)-3,4-Piperidinediol (CAS [868051-84-7]) in the same manner as the (3R,4S) isomer (Example 87) to afford product as a colorless solid (303 mg, 81%). LC/MS 5.43 min, [M+1]$^+$ 377.

Example 89

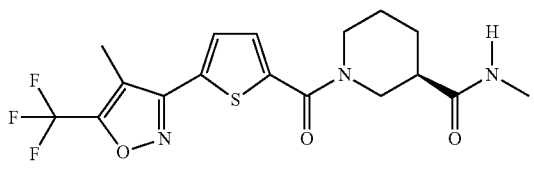 [SMILES: CNC(=O)[C@@H]1CCCN(C(=O)c2ccc(-c3noc(C(F)(F)F)c3C)s2)C1]

(3R)—N-methyl-1-({5-[4-methyl-5-(trifluoromethyl)isoxazol-3-yl]thien-2-yl}carbonyl)piperidine-3-carboxamide Prepared from 5-(5-Trifluoromethyl-4-methyl-isoxazol-3-yl)-thiophene-2-carboxylic acid and (3R)—N-methylpiperidine-3-carboxamide (Preparative Example 31) by the method described in Example 2 Method B reversing the order of addition such that solid acid chloride was added to a THF solution of triethylamine and (3R)—N-methylpiperidine-3-carboxamide. After 3 hr the reaction mixture was evaporated in vacuo and filtered with the aid of water. The resulting solids were then washed with a 1 N aqueous HCl solution followed by water. The material was air dried to afford product as a colorless solid (157 mg, 86%). LC/MS 6.00 min, [M+1]$^+$ 402.

Example 90

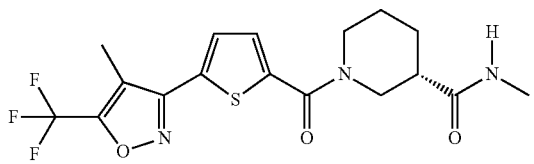 [SMILES: CNC(=O)[C@H]1CCCN(C(=O)c2ccc(-c3noc(C(F)(F)F)c3C)s2)C1]

(3S)—N-methyl-1-({5-[4-methyl-5-(trifluoromethyl)isoxazol-3-yl]thien-2-yl}carbonyl)piperidine-3-carboxamide Prepared from 5-(5-Trifluoromethyl-4-methyl-isoxazol-3-yl)-thiophene-2-carboxylic acid and (3S)—N-methylpiperidine-3-carboxamide (Preparative Example 32) in the same manner as the 3R isomer (Example 89) to afford product as a colorless solid (303 mg, 81%). LC/MS 5.88 min, [M+1]$^+$ 402.

Example 91

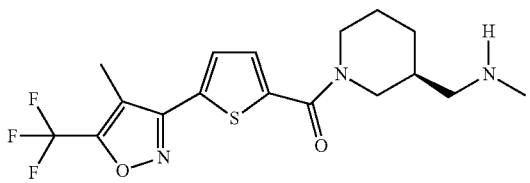 [SMILES: CNC[C@@H]1CCCN(C(=O)c2ccc(-c3noc(C(F)(F)F)c3C)s2)C1]

N-methyl-N-{[(3S)-1-({5-[4-methyl-5-(trifluoromethyl)isoxazol-3-yl]thien-2-yl}carbonyl)piperidin-3-yl]methyl}amine, hydrochloride Prepared from 5-(5-Trifluoromethyl-4-methyl-isoxazol-3-yl)-thiophene-2-carboxylic acid and tert-butyl methyl [(3R)-piperidin-3-ylmethyl]carbamate (Preparative Example 33, 298 mg, 1.30 mmol) by the method described in Example 2 Method B reversing the order of addition such that solid acid chloride (0.90 eq) was added to a THF solution of triethylamine and tert-butyl methyl[(3R)-piperidin-3-ylmethyl]carbamate. The reaction was allowed to stir 4 hr then partitioned between EtOAc (10 mL) and a 1 N aqueous HCl solution (10 mL). The organic portion was washed with a further portion of 1N HCl solution (10 mL) followed by a saturated aqueous NaHCO$_3$ solution (10 mL) and brine (10 mL). The organic layer was then dried over MgSO$_4$, filtered, and evaporated to a residue that was chromatographed on silica gel with EtOAc/hexane (40% then 60%) as eluant to afford Boc-protected intermediate as a yellow-tinted oil (423 mg, 67%). LC/MS 7.44 min, [M+1]$^+$ 487. The intermediate was then treated with a 4 N solution of hydrogen chloride in 1,4-dioxane (4 mL) and stirred for 24 hr, after which time the reaction mixture was evaporated in vacuo to afford a free-flowing colorless powder (320 mg, 88%). LC/MS 4.91 min, [M+1]$^+$ 388.

Example 92

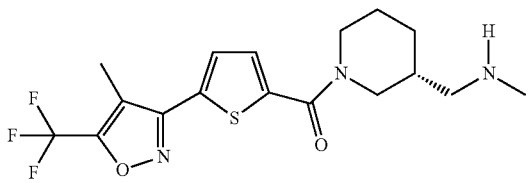 [SMILES: CNC[C@H]1CCCN(C(=O)c2ccc(-c3noc(C(F)(F)F)c3C)s2)C1]

N-methyl-N-{[(3R)-1-({5-[4-methyl-5-(trifluoromethyl)isoxazol-3-yl]thien-2-yl}carbonyl)piperidin-3-yl]methyl}amine, hydrochloride Prepared from 5-(5-Trifluoromethyl-4-methyl-isoxazol-3-yl)-thiophene-2-carboxylic acid and tert-butyl methyl [(3S)-piperidin-3-ylmethyl]carbamate (Preparative Example 34, 340 mg, 1.48 mmol) in the same manner as the 3S isomer (Example 91) to afford Boc-protected intermediate as a colorless oil (547 mg, 76%). LC/MS 7.36 min, [M+1]$^+$ 487. The product was obtained as a colorless free-flowing powder (440 mg, 93%). LC/MS 4.82 min, [M+1]$^+$ 388.

Example 93

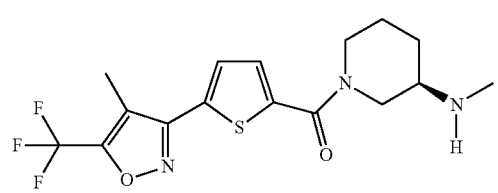 [SMILES: CN[C@@H]1CCCN(C(=O)c2ccc(-c3noc(C(F)(F)F)c3C)s2)C1]

(3R)—N-methyl-1-({5-[4-methyl-5-(trifluoromethyl)isoxazol-3-yl]thien-2-yl}carbonyl)piperidin-3-amine, hydrochloride Prepared from 5-(5-Trifluoromethyl-4-methyl-isoxazol-3-yl)-thiophene-2-carboxylic acid and (tert-butyl methyl [(3R)-piperidin-3-yl]carbamate (Preparative Example 35, presumed quantitative yield, 4.48 mmol) by the method described in Example 2 Method B reversing the order of addition such that solid acid chloride (0.90 eq) was added to a THF solution of triethylamine and (tert-butyl methyl[(3R)-piperidin-3-yl]carbamate (presumed quantitative yield, 4.48 mmol). The reaction was allowed to stir 4 hr, evaporated in vacuo, and the solids filtered with the aid of water. The air-dried solids were then chromatographed on a short silica gel column with EtOAc/hexane (75%) to afford Boc-protected intermediate as a colorless solid (1.61 g, 76%). LC/MS 7.33 min, [M+1]$^+$ 474. The intermediate was then treated with a 4 N solution of hydrogen chloride in 1,4,-dioxane (20 mL) and stirred for 24 hr, after which time the reaction mixture was evaporated in vacuo to afford a free-flowing colorless powder (1.14 g, 82%, some loss of material had occurred on rotary evaporation). LC/MS 4.57 min, [M+1]$^+$ 374.

Example 94

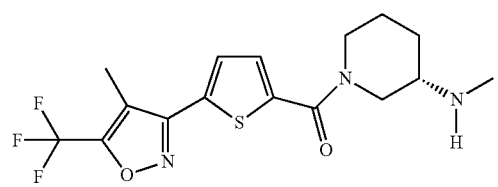 [SMILES: CN[C@H]1CCCN(C(=O)c2ccc(-c3noc(C(F)(F)F)c3C)s2)C1]

(3S)—N-methyl-1-({5-[4-methyl-5-(trifluoromethyl)isoxazol-3-yl]thien-2-yl}carbonyl)piperidin-3-amine, hydrochloride Prepared from 5-(5-Trifluoromethyl-4-methyl-isoxazol-3-yl)-thiophene-2-carboxylic acid and tert-butyl methyl [(3S)-piperidin-3-ylmethyl]carbamate (Preparative Example 36, presumed quantitative yield, 4.48 mmol) in the same manner as the 3R isomer (Example 93) to afford Boc-protected intermediate as a colorless oil (1.51 g, 71%). LC/MS 7.32 min, [M+1]$^+$ 474. The product was obtained as a colorless free-flowing powder (1.06 g, 81%, some loss of material had occurred on rotary evaporation). LC/MS 4.55 min, [M+1]$^{+374}$.

Example 95

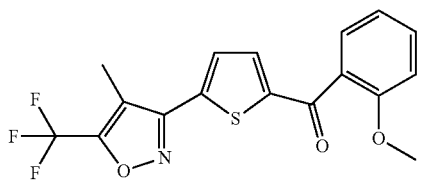 [SMILES: COc1ccccc1C(=O)c1ccc(-c2noc(C(F)(F)F)c2C)s1]

(2-methoxyphenyl) {5-[4-methyl-5-(trifluoromethyl)isoxazol-3-yl]thien-2-yl}methanone Prepared from 4-Methyl-3-thiophen-2-yl-5-trifluoromethyl-isoxazole and 2-methoxybenzoyl chloride by the method described in Example 3. Crude product was chromatographed on silica gel with EtOAc/hexanes (15 then 25%) as eluant to afford product as a yellow-tinted oil (100 mg, 54%). $^1$H NMR (CDCl$_3$) 2.39 (d, J=1.3, 3 H), 3.82 (s, 3H), 7.01-7.08 (m, 2H), 7.27-7.54 (m, 4H). $^{13}$C NMR 8.0, 55.9, 111.9, 115.9 (q, J=151), 120.7, 128.2, 129.0, 129.6, 132.7, 135.0, 136.3, 147.1, 155.4 (q, J=41), 157.3, 158.0, 188.2. $^{19}$F NMR -63.1. LC/MS 7.50 min, [M+1]$^+$ 368.

Example 96

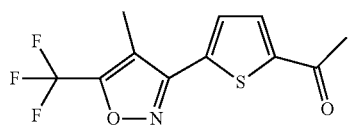 [SMILES: CC(=O)c1ccc(-c2noc(C(F)(F)F)c2C)s1]

1-{5-[4-methyl-5-(trifluoromethyl)isoxazol-3-yl]thien-2-yl}ethanone

Prepared from 4-Methyl-3-thiophen-2-yl-5-trifluoromethyl-isoxazole and 2-acetoxybenzoyl chloride by the method described in Example 3. Crude product was chromatographed on silica gel with EtOAc/hexanes (15 then 25%) as eluant to afford product as a tan colored solid (80 mg, 58%). $^1$H NMR (CDCl$_3$) 2.39 (d, J=1.3, 3 H), 3.62 (s, 3H), 7.57 (d, J=4.0, 1 H), 7.74 (d, J=4.0, 1 H). $^{19}$F NMR -63.1. LC/MS 7.82 min, [M+1]$^+$ 276.

Example 97

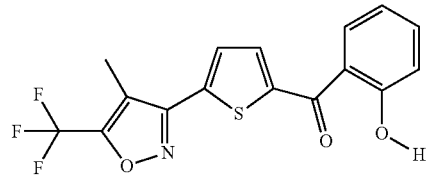 [SMILES: Cc1c(-c2ccc(C(=O)c3ccccc3O)s2)noc1C(F)(F)F]

(2-hydroxyphenyl) {5-[4-methyl-5-(trifluoromethyl)isoxazol-3-yl]thien-2-yl}methanone A solution of (2-methoxyphenyl) {5-[4-methyl-5-(trifluoromethyl)isoxazol-3-yl]thien-2-yl}methanone (Example 95, 37 mg, 0.1 mmol) in dichloromethane (2 mL) at -78° C. was treated with boron tribromide (100 μL of a 1 M dichloromethane solution, 0.1 mol) and allowed to warm to 0 OC and stir at that temperature for 16 h. After that time the reaction was quenched with water (3 mL) and partitioned between water (10 mL) and EtOAc (10 mL). The organic extract was washed with a brine solution (10 mL) then dried over Na$_2$SO$_4$, filtered, and concentrated in vacuo to afford crude product. The crude product was chromatographed on silica gel with EtOAc/hexanes (20%) as eluant to afford product as a yellow colored solid (29 mg, 82%). $^1$H NMR (CDCl$_3$) 2.92 (d, J=1.8, 3 H), 7.46-7.76 (m, 2H), 8.03-8.08 (m, 1H), 8.12 (d, J=4.0, 1 H), 8.28 (d, J=4.0, 1 H), 8.46 (dd, J=8.4, 1.8, 1 H), 11.50 (s, 1H). $^{19}$F NMR -63.1.

What is claimed is:

1. A method for improving cognitive function in an animal in need of such treatment comprising administering to the animal an effective amount of a compound of formula Ia:

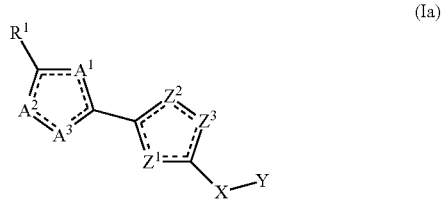

(Ia)

or a pharmaceutically acceptable salt or prodrug ester thereof,
wherein:
R$^1$ is H (hydrogen), or is selected from the group consisting of aryl and (C$_1$-C$_6$)alkyl, each optionally substituted with one or more R$_h$;
each R$_h$ is independently selected from the group consisting of halo, cyano, nitro, and —OH;
A$^1$ is N (nitrogen), or CR$^2$;
A$^2$ and A$^3$ are each independently O (oxygen) or N (nitrogen) with the proviso that when A$^2$ is O (oxygen), A$^3$ is N (nitrogen) and when A$^2$ is N (nitrogen), A$^3$ is O (oxygen);
R$^2$ is H (hydrogen), (C$_1$-C$_6$)alkyl, aryl(C$_1$-C$_6$)alkyl, (C$_2$-C$_6$)alkenyl, (C$_2$-C$_6$)alkynyl, or aryl optionally substituted with one or more halo;
X is —C(=O)—, —C(=S)—, —S—, or —S(O)—;
Y is —N(R$^4$)$_2$ where the two R$^4$ groups are taken together with the nitrogen to which they are attached to form a 3-8 membered monocyclic or a 7-12 membered bicyclic ring system, each optionally comprising one or more additional heteroatom groups selected from O (oxygen), $S(O)_z$, and $NR_c$ wherein each ring system is optionally substituted with one or more $R_d$;

each $R_c$ is independently selected from the group consisting of hydrogen, $(C_1-C_6)$alkyl, aryl, heteroaryl, $(C_1-C_6)$alkyl sulfonyl, aryl sulfonyl, $(C_1-C_6)$alkylC(O)—, arylC(O)—, hydroxy$(C_1-C_6)$alkyl, alkoxy$(C_1-C_6)$alkyl, heterocycle, $(C_1-C_6)$alkylOC(O)—, $(C_1-C_6)$alkylaminocarbonyl, and arylaminocarbonyl;

each $R_d$ is independently halo, cyano, nitro, oxo, $R_fR_gN$ $(C_1-C_6)$alkyl, —$(CH_2)_nNR_fR_g$, —$C(O)NR_fR_g$, —$NR_eC(O)R_g$, arylC(O)$NR_fR_g$, —C(O)OH, $(C_1-C_6)$alkyl, $(C_3-C_8)$cycloalkyl, —$(CH_2)_nOH$, $(C_1-C_6)$alkoxy, halo$(C_1-C_6)$alkoxy, heterocycle, aryl, heterocycle$(C_1-C_6)$alkyl, aryl$(C_1-C_6)$alkyl, —$NR_eS(O)_z(C_1-C_6)$alkyl, —$NR_eS(O)_z$aryl, —$NR_eC(O)NR_fR_g$, —$NR_eC(O)OR_f$, or —$OC(O)NR_fR_g$;

each n is independently an integer selected from 0, 1, and 2;

each z is independently an integer selected from 0, 1, and 2;

$Z^1$ is S (sulfur);

$Z^2$, and $Z^3$ are each independently O (oxygen), N (nitrogen), S (sulfur), or $CR^5$;

each $R^5$ is independently H (hydrogen), $(C_1-C_6)$alkyl, or aryl$(C_1-C_6)$alkyl;

each $R_e$ is independently hydrogen, $(C_1-C_6)$alkyl, aryl or heteroaryl;

each $R_f$ and $R_g$ is independently hydrogen, $(C_1-C_6)$alkyl, aryl or heteroaryl, or $R_f$ and $R_g$ are optionally taken together with the nitrogen to which they are attached to form a 3-8 membered monocyclic or a 7-12 membered bicyclic ring system, each optionally comprising one or more additional heteroatom groups selected from O (oxygen), $S(O)_z$, and $NR_c$ wherein each ring system is optionally substituted with one or more $R_q$;

each $R_q$ is independently halo, cyano, nitro, oxo, $R_iR_jN$ $(C_1-C_6)$alkyl, —$(CH_2)_nNR_iR_j$, —$C(O)NR_iR_j$, —$NR_kC(O)R_j$, arylC(O)$NR_iR_j$, —C(O)OH, $(C_1-C_6)$alkyl, $(C_3-C_8)$cycloalkyl, —$(CH_2)_nOH$, $(C_1-C_6)$alkoxy, halo$(C_1-C_6)$alkoxy, heterocycle, aryl, heterocycle$(C_1-C_6)$alkyl, aryl$(C_1-C_6)$alkyl, —$NR_eS(O)_z(C_1-C_6)$alkyl, —$NR_kS(O)_z$aryl, —$NR_kC(O)NR_iR_j$, —$NR_kC(O)OR_i$, or —$OC(O)NR_iR_j$;

each $R_k$ is independently hydrogen, $(C_1-C_6)$alkyl, aryl or heteroaryl;

each $R_i$ and $R_j$ is independently hydrogen, $(C_1-C_6)$alkyl, aryl or heteroaryl; and the dashed line represents an optional double bond wherein the ring comprising $Z^1$, $Z^2$, and $Z^3$ is heteroaromatic.

2. The method of claim 1, wherein X is —C(=O).

3. The method of claim 1, wherein Y is —$N(R^4)_2$; and the two $R^4$ groups are taken together with the nitrogen to which they are attached to form a 3-8 membered monocyclic or a 7-12 membered bicyclic ring system, each optionally comprising one or more additional heteroatom groups selected from O (oxygen), $S(O)_z$, and $NR_c$ wherein each ring system is optionally substituted with one or more $R_d$.

4. The method of claim 1, wherein the compound is selected from the group consisting of:

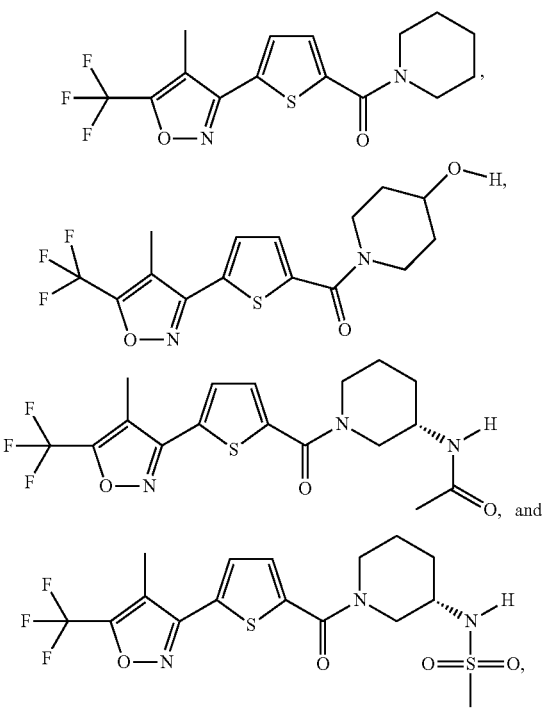

or a pharmaceutically acceptable salt thereof.

5. The method of claim 1, wherein the compound is selected from the group consisting of:

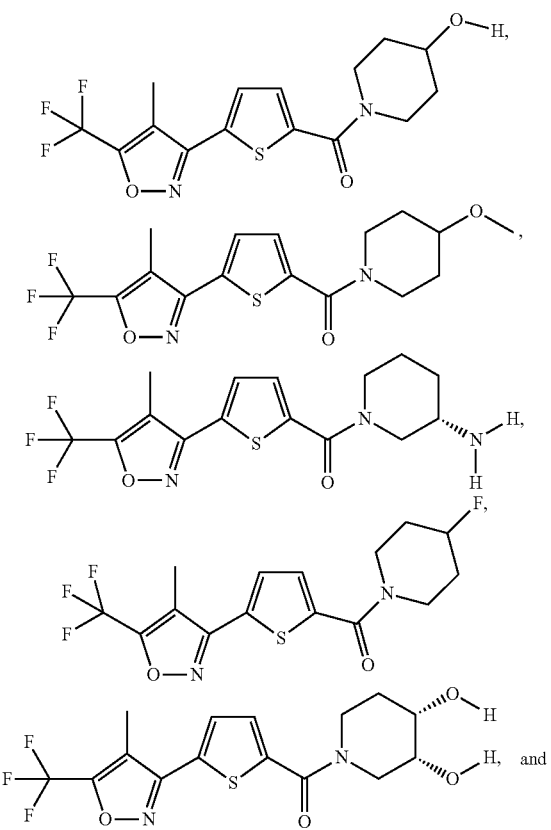

-continued

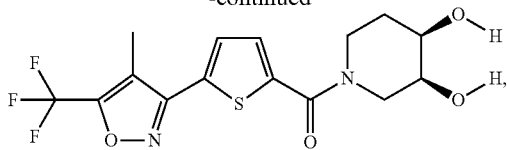

or a pharmaceutically acceptable salt thereof.

6. A method for treating a psychiatric disorder in an animal comprising administering to an animal in need thereof an effective amount of a compound of formula Ia:

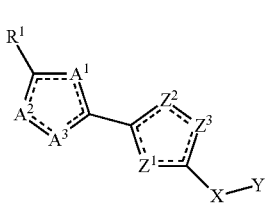

(Ia)

or a pharmaceutically acceptable salt or prodrug ester thereof,
wherein:
$R^1$ is H (hydrogen), or is selected from the group consisting of aryl and ($C_1$-$C_6$)alkyl, each optionally substituted with one or more $R_h$;
each $R_h$ is independently selected from the group consisting of halo, cyano, nitro, and —OH;
$A^1$ is N (nitrogen), or $CR^2$;
$A^2$ and $A^3$ are each independently O (oxygen) or N (nitrogen) with the proviso that when $A^2$ is O (oxygen), $A^3$ is N (nitrogen) and when $A^2$ is N (nitrogen), $A^3$ is O (oxygen);
$R^2$ is H (hydrogen), ($C_1$-$C_6$)alkyl, aryl($C_1$-$C_6$)alkyl, ($C_2$-$C_6$)alkenyl, ($C_2$-$C_6$)alkynyl, or aryl optionally substituted with one or more halo;
X is —C(=O)—, —C(=S)—, —S—, or —S(O)—;
Y is —N($R^4$)$_2$ where the two $R^4$ groups are taken together with the nitrogen to which they are attached to form a 3-8 membered monocyclic or a 7-12 membered bicyclic ring system, each optionally comprising one or more additional heteroatom groups selected from O (oxygen), S(O)$_z$, and $NR_c$ wherein each ring system is optionally substituted with one or more $R_d$;
each $R_c$ is independently selected from the group consisting of hydrogen, ($C_1$-$C_6$)alkyl, aryl, heteroaryl, ($C_1$-$C_6$)alkyl sulfonyl, aryl sulfonyl, ($C_1$-$C_6$)alkylC(O)—, arylC(O)—, hydroxy($C_1$-$C_6$)alkyl, alkoxy($C_1$-$C_6$)alkyl, heterocycle, ($C_1$-$C_6$)alkylOC(O)—, ($C_1$-$C_6$)alkylaminocarbonyl, and arylaminocarbonyl;
each $R_d$ is independently halo, cyano, nitro, oxo, $R_fR_gN$($C_1$-$C_6$)alkyl, —(CH$_2$)$_n$NR$_f$R$_g$, —C(O)NR$_f$R$_g$, —NR$_c$C(O)R$_g$, arylC(O)NR$_f$R$_g$, —C(O)OH, ($C_1$-$C_6$)alkyl, ($C_3$-$C_8$)cycloalkyl, —(CH$_2$)$_n$OH, ($C_1$-$C_6$)alkoxy, halo($C_1$-$C_6$)alkoxy, heterocycle, aryl, heterocycle($C_1$-$C_6$)alkyl, aryl($C_1$-$C_6$)alkyl, —NR$_e$S(O)$_z$($C_1$-$C_6$)alkyl, —NR$_e$S(O)$_z$aryl, —NR$_e$C(O)NR$_f$R$_g$, —NR$_e$C(O)OR$_f$, or —OC(O)NR$_f$R$_g$;
each n is independently an integer selected from 0, 1, and 2;
each z is independently an integer selected from 0, 1, and 2;
$Z^1$ is S (sulfur);

$Z^2$, and $Z^3$ are each independently O (oxygen), N (nitrogen), S (sulfur), or $CR^5$;
each $R^5$ is independently H (hydrogen), ($C_1$-$C_6$)alkyl, or aryl($C_1$-$C_6$)alkyl;
each $R_e$ is independently hydrogen, ($C_1$-$C_6$)alkyl, aryl or heteroaryl;
each $R_f$ and $R_g$ is independently hydrogen, ($C_1$-$C_6$)alkyl, aryl or heteroaryl, or $R_f$ and $R_g$ are optionally taken together with the nitrogen to which they are attached to form a 3-8 membered monocyclic or a 7-12 membered bicyclic ring system, each optionally comprising one or more additional heteroatom groups selected from O (oxygen), S(O)$_z$, and $NR_c$ wherein each ring system is optionally substituted with one or more $R_q$;
each $R_q$ is independently halo, cyano, nitro, oxo, $R_iR_jN$($C_1$-$C_6$)alkyl, —(CH$_2$)$_n$NR$_i$R$_j$, —C(O)NR$_i$R$_j$, —NR$_k$C(O)R$_j$, arylC(O)NR$_i$R$_j$, —C(O)OH, ($C_1$-$C_6$)alkyl, ($C_3$-$C_8$)cycloalkyl, —(CH$_2$)$_n$OH, ($C_1$-$C_6$)alkoxy, halo($C_1$-$C_6$)alkoxy, heterocycle, aryl, heterocycle($C_1$-$C_6$)alkyl, aryl($C_1$-$C_6$)alkyl, —NR$_e$S(O)$_z$($C_1$-$C_6$)alkyl, —NR$_k$S(O)$_z$aryl, —NR$_k$C(O)NR$_i$R$_j$, —NR$_k$C(O)OR$_i$, or —OC(O)NR$_i$R$_j$;
each $R_k$ is independently hydrogen, ($C_1$-$C_6$)alkyl, aryl or heteroaryl;
each $R_i$ and $R_j$ is independently hydrogen, ($C_1$-$C_6$)alkyl, aryl or heteroaryl; and
the dashed line represents an optional double bond wherein the ring comprising $Z^1$, $Z^2$, and $Z^3$ is heteroaromatic.

7. The method of claim 6, wherein the psychiatric disorder is a disorder of the central nervous system.

8. The method of claim 7, wherein the disorder of the central nervous system is age-associated memory impairment, mild cognitive impairment, Alzheimer's disease or Parkinson's disease.

9. The method of claim 6, wherein the psychiatric disorder is associated with head trauma, brain trauma or cerebrovascular disease.

10. The method of claim 6, wherein the psychiatric disorder is attention deficit disorder.

11. The method of claim 6, wherein the compound is selected from the group consisting of:

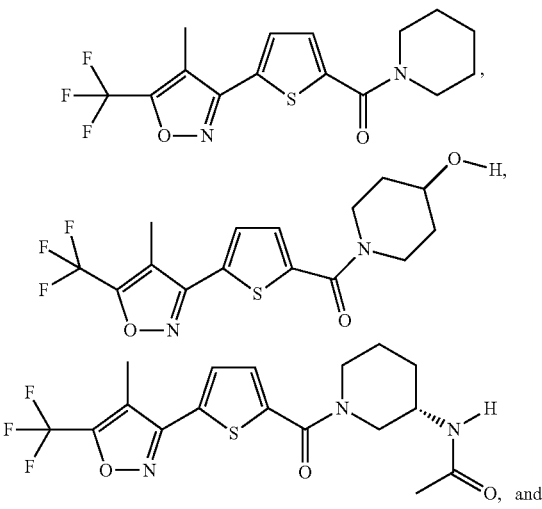

-continued

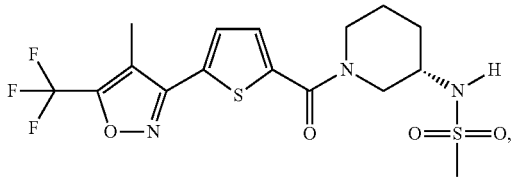

or a pharmaceutically acceptable salt thereof.

12. The method of claim 6, wherein the compound is selected from the group consisting of:

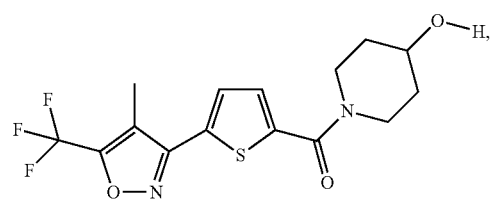

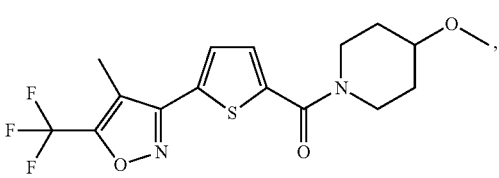

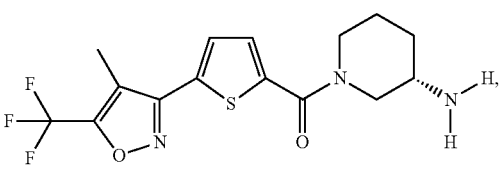

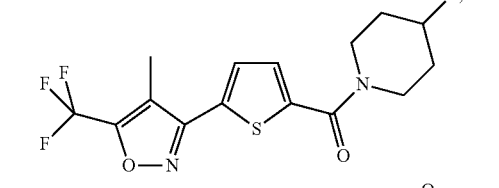

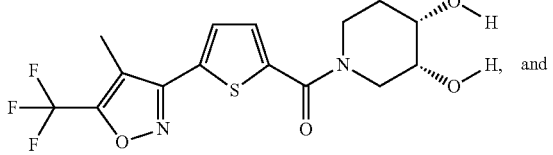

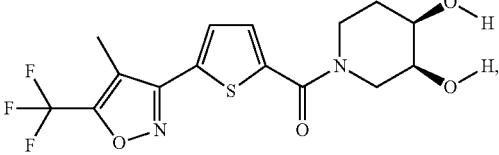

or a pharmaceutically acceptable salt thereof.

13. A method for treating memory impairment in an animal with a psychiatric disorder comprising administering to the animal an effective amount of a compound of formula Ia:

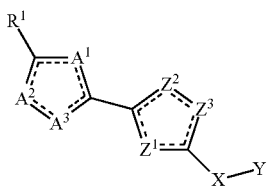

or a pharmaceutically acceptable salt or prodrug ester thereof, wherein:

$R^1$ is H (hydrogen), or is selected from the group consisting of aryl and ($C_1$-$C_6$)alkyl, each optionally substituted with one or more $R_h$;

each $R_h$ is independently selected from the group consisting of halo, cyano, nitro, and —OH;

$A^1$ is N (nitrogen), or $CR^2$;

$A^2$ and $A^3$ are each independently O (oxygen) or N (nitrogen) with the proviso that when $A^2$ is O (oxygen), $A^3$ is N (nitrogen) and when $A^2$ is N (nitrogen), $A^3$ is O (oxygen);

$R^2$ is H (hydrogen), ($C_1$-$C_6$)alkyl, aryl($C_1$-$C_6$)alkyl, ($C_2$-$C_6$)alkenyl, ($C_2$-$C_6$)alkynyl, or aryl optionally substituted with one or more halo;

X is —C(=O)—, —C(=S)—, —S—, or —S(O)—;

Y is —N($R^4$)$_2$ where the two $R^4$ groups are taken together with the nitrogen to which they are attached to form a 3-8 membered monocyclic or a 7-12 membered bicyclic ring system, each optionally comprising one or more additional heteroatom groups selected from O (oxygen), S(O)$_z$, and $NR_c$ wherein each ring system is optionally substituted with one or more $R_d$;

each $R_c$ is independently selected from the group consisting of hydrogen, ($C_1$-$C_6$)alkyl, aryl, heteroaryl, ($C_1$-$C_6$)alkylsulfonyl, aryl sulfonyl, ($C_1$-$C_6$)alkylC(O)—, arylC(O)—, hydroxy($C_1$-$C_6$)alkyl, alkoxy($C_1$-$C_6$)alkyl, heterocycle, ($C_1$-$C_6$)alkylOC(O)—, ($C_1$-$C_6$)alkylaminocarbonyl, and arylaminocarbonyl;

each $R_d$ is independently halo, cyano, nitro, oxo, $R_fR_gN$($C_1$-$C_6$)alkyl, —(CH$_2$)$_n$NR$_f$R$_g$, —C(O)NR$_f$R$_g$, —NR$_e$C(O)R$_g$, arylC(O)NR$_f$R$_g$, —C(O)OH, ($C_1$-$C_6$)alkyl, ($C_3$-$C_8$)cycloalkyl, —(CH$_2$)$_n$OH, ($C_1$-$C_6$)alkoxy, halo($C_1$-$C_6$)alkoxy, heterocycle, aryl, heterocycle($C_1$-$C_6$)alkyl, aryl($C_1$-$C_6$)alkyl, —NR$_e$S(O)$_z$($C_1$-$C_6$)alkyl, —NR$_e$S(O)$_z$aryl, —NR$_e$C(O)NR$_f$R$_g$, —NR$_e$C(O)OR$_f$, or —OC(O)NR$_f$R$_g$;

each n is independently an integer selected from 0, 1, and 2;

each z is independently an integer selected from 0, 1, and 2;

$Z^1$ is S (sulfur);

$Z^2$, and $Z^3$ are each independently O (oxygen), N (nitrogen), S (sulfur), or $CR^5$;

each $R^5$ is independently H (hydrogen), ($C_1$-$C_6$)alkyl, or aryl($C_1$-$C_6$)alkyl;

each $R_e$ is independently hydrogen, ($C_1$-$C_6$)alkyl, aryl or heteroaryl;

each $R_f$ and $R_g$ is independently hydrogen, ($C_1$-$C_6$)alkyl, aryl or heteroaryl, or $R_f$ and $R_g$ are optionally taken together with the nitrogen to which they are attached to form a 3-8 membered monocyclic or a 7-12 membered bicyclic ring system, each optionally comprising one or more additional heteroatom groups selected from O (oxygen), S(O)$_z$, and NR$_c$ wherein each ring system is optionally substituted with one or more R$_q$;

each R$_q$ is independently halo, cyano, nitro, oxo, R$_i$R$_j$N (C$_1$-C$_6$)alkyl, —(CH$_2$)$_n$NR$_i$R$_j$, —C(O)NR$_i$R$_j$, —NR$_k$C(O)R$_j$, arylC(O)NR$_i$R$_j$, —C(O)OH, (C$_1$-C$_6$)alkyl, (C$_3$-C$_8$)cycloalkyl, —(CH$_2$)$_n$OH, (C$_1$-C$_6$)alkoxy, halo(C$_1$-C$_6$)alkoxy, heterocycle, aryl, heterocycle(C$_1$-C$_6$)alkyl, aryl(C$_1$-C$_6$)alkyl, —NR$_e$S(O)$_z$(C$_1$-C$_6$)alkyl, —NR$_k$S(O)$_z$aryl, —NR$_k$C(O)NR$_i$R$_j$, —NR$_k$C(O)OR$_i$, or —OC(O)NR$_i$R$_j$;

each R$_k$ is independently hydrogen, (C$_1$-C$_6$)alkyl, aryl or heteroaryl;

each R$_i$ and R$_j$ is independently hydrogen, (C$_1$-C$_6$)alkyl, aryl or heteroaryl; and the dashed line represents an optional double bond wherein the ring comprising Z$^1$, Z$^2$, and Z$^3$ is heteroaromatic.

14. The method of claim 13, wherein the psychiatric disorder is a psychotic disorder, a neurological disorder, or a neurotic disorder.

15. The method of claim 13, wherein X is —C(=O).

16. The method of claim 13, wherein Y is —N(R$^4$)$_2$; and the two R$^4$ groups are taken together with the nitrogen to which they are attached to form a 3-8 membered monocyclic or a 7-12 membered bicyclic ring system, each optionally comprising one or more additional heteroatom groups selected from O (oxygen), S(O)$_z$, and NR$_c$ wherein each ring system is optionally substituted with one or more R$_d$.

17. The method of claim 13, wherein the compound is selected from the group consisting of:

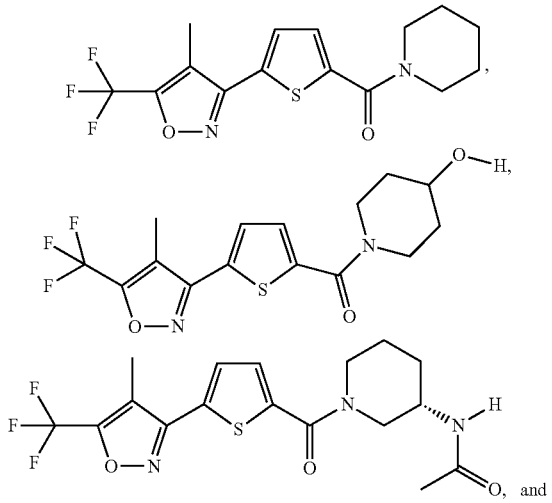

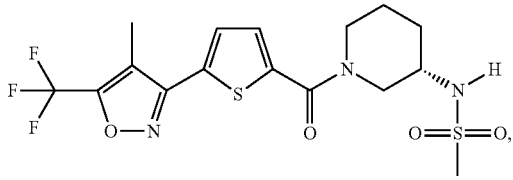

or a pharmaceutically acceptable salt thereof.

18. The method of claim 13, wherein the compound is selected from the group consisting of:

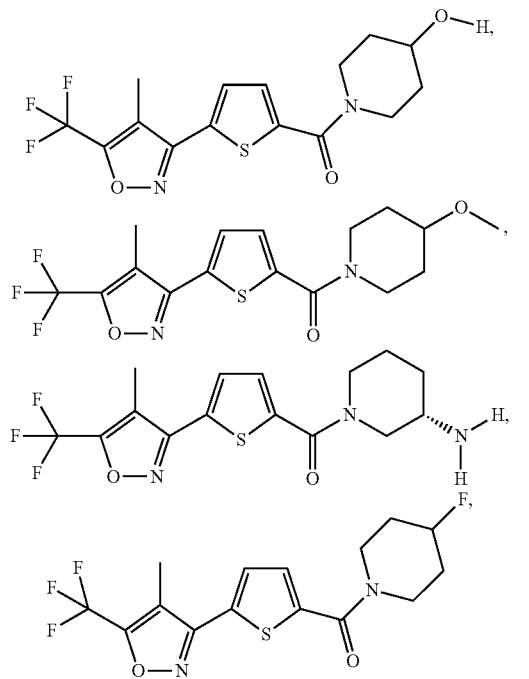

or a pharmaceutically acceptable salt thereof.

* * * * *